(12) United States Patent
Ootawara et al.

(10) Patent No.: US 7,087,010 B2
(45) Date of Patent: Aug. 8, 2006

(54) ENDOSCOPE AND ENDOSCOPE SYSTEM THEREOF

(75) Inventors: Takashi Ootawara, Hachioji (JP); Akira Suzuki, Kitatsuru-gun (JP); Hiroaki Kubokawa, Sagamihara (JP); Hidenobu Kimura, Hachioji (JP); Osamu Tamada, Hachioji (JP); Mamoru Nakada, Hachioji (JP); Masayuki Iwasaka, Hachioji (JP)

(73) Assignee: Olympus Corporation, Tokyo (JP)

( * ) Notice: Subject to any disclaimer, the term of this patent is extended or adjusted under 35 U.S.C. 154(b) by 684 days.

(21) Appl. No.: 10/017,743

(22) Filed: Dec. 14, 2001

(65) Prior Publication Data

US 2002/0091303 A1    Jul. 11, 2002

Related U.S. Application Data

(63) Continuation of application No. PCT/JP01/03286, filed on Apr. 17, 2001.

(30) Foreign Application Priority Data

| Apr. 17, 2000 | (JP) | ............................. 2000-115355 |
| Apr. 27, 2000 | (JP) | ............................. 2000-128262 |
| May 17, 2000 | (JP) | ............................. 2000-145530 |

(51) Int. Cl.
*A61B 1/00* (2006.01)

(52) U.S. Cl. ...................... 600/104; 600/106; 600/107; 600/127; 600/129

(58) Field of Classification Search ................ 600/101, 600/104, 106, 107, 127, 129, 153
See application file for complete search history.

(56) References Cited

U.S. PATENT DOCUMENTS

| 4,407,273 | A | * | 10/1983 | Ouchi | ........................ | 600/107 |
| 4,841,949 | A | * | 6/1989 | Shimizu et al. | .............. | 600/107 |
| 5,343,853 | A | * | 9/1994 | Komi | ........................ | 600/107 |
| 5,868,663 | A | * | 2/1999 | Katsurada et al. | .......... | 600/107 |
| 5,921,971 | A | | 7/1999 | Agro et al. | | |
| 6,582,357 | B1 | * | 6/2003 | Ouchi et al. | ................. | 600/107 |
| 6,605,033 | B1 | * | 8/2003 | Matsuno | ..................... | 600/107 |
| 2003/0040657 | A1 | * | 2/2003 | Yamaya et al. | ............. | 600/107 |

FOREIGN PATENT DOCUMENTS

| JP | 56-23501 | 3/1981 |
| JP | 59-37923 | 3/1984 |
| JP | 59-93502 | 6/1984 |
| JP | 60-184506 | 12/1985 |
| JP | 62-87604 | 6/1987 |
| JP | 63-46107 | 3/1988 |

(Continued)

OTHER PUBLICATIONS

Tajiri, H., et al., "Practical Endoscopic Cholangiopancreatography to Establish a Safer Endoscopic Technique", published by Nihon Medical Center, together with a partial English translation.

(Continued)

*Primary Examiner*—Beverly M. Flanagan
(74) *Attorney, Agent, or Firm*—Scully, Scott, Murphy & Presser, P.C.

(57) ABSTRACT

Guide wire fixing means is provided for an insertion portion of an endoscope, and a guide wire is releasably engaged when inserting/removing a therapeutic instrument running on the guide wire with a distal end portion of the guide wire inserted into a therapeutic instrument insertion channel of the endoscope being led out from a distal end opening portion of the channel.

144 Claims, 64 Drawing Sheets

FOREIGN PATENT DOCUMENTS

| | | |
|---|---|---|
| JP | 64-25833 | 1/1989 |
| JP | 2-103009 | 4/1990 |
| JP | 5-76478 | 3/1993 |
| JP | 5-103757 | 4/1993 |
| JP | 5-146397 | 6/1993 |
| JP | 6-64609 | 9/1994 |
| JP | 6-66609 | 9/1994 |
| JP | 6-285014 | 10/1994 |
| JP | 7-303 | 1/1995 |
| JP | 7-148104 | 6/1995 |
| JP | 7-194524 | 8/1995 |
| JP | 7-313441 | 12/1995 |
| JP | 7-327918 | 12/1995 |
| JP | 8-38612 | 2/1996 |
| JP | 8-243076 | 9/1996 |
| JP | 9-10220 | 1/1997 |
| JP | 9-66109 | 3/1997 |
| JP | 9-75296 | 3/1997 |
| JP | 9-234182 | 9/1997 |
| JP | 9-253036 | 9/1997 |
| JP | 10-118014 | 5/1998 |
| JP | 11-4804 | 1/1999 |
| JP | 11-47080 | 2/1999 |
| JP | 2000-23904 | 1/2000 |
| JP | 2001-37710 | 2/2001 |
| WO | WO 01/58360 A2 | 8/2001 |

OTHER PUBLICATIONS

Tatsuta, M., et al., "Digestive Endoscopy Technical Manual", published by Nankodo Co., Ltd., together with a partial English translation.

* cited by examiner

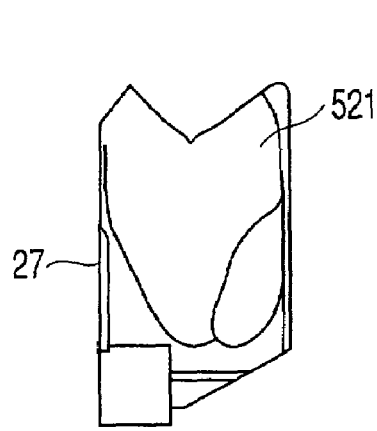
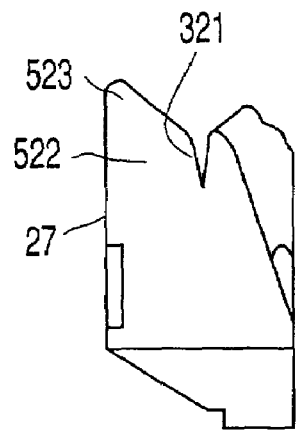
FIG. 15A  FIG. 15B
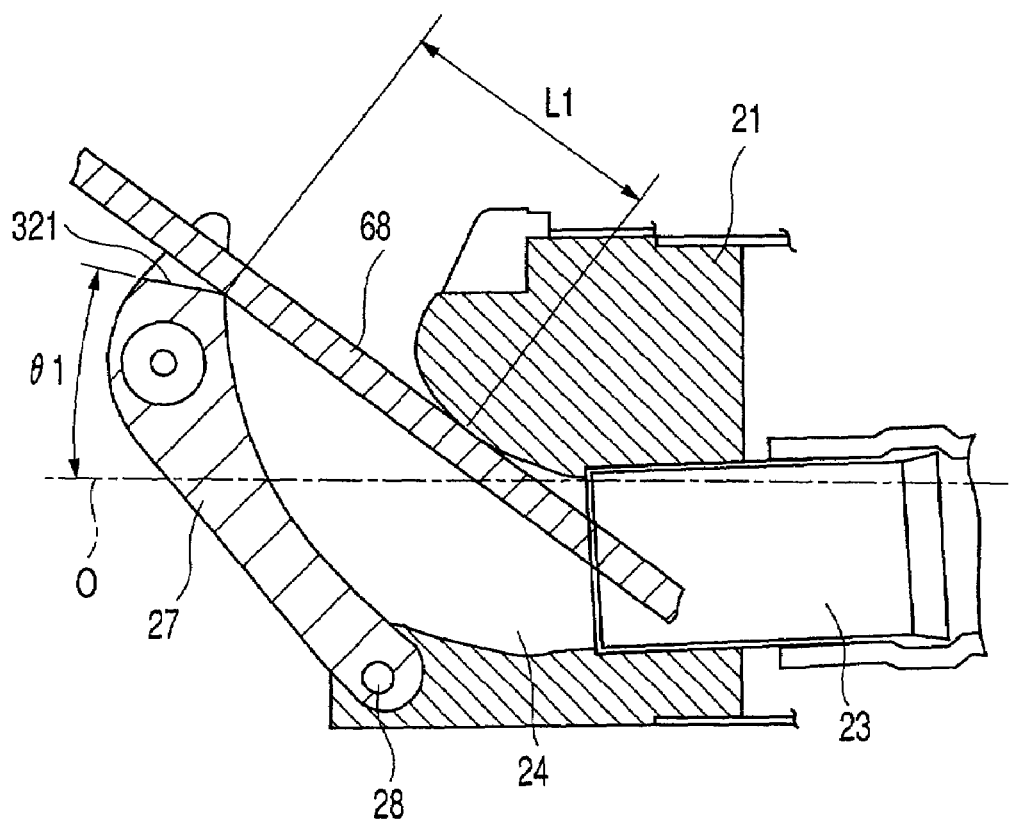
FIG. 16

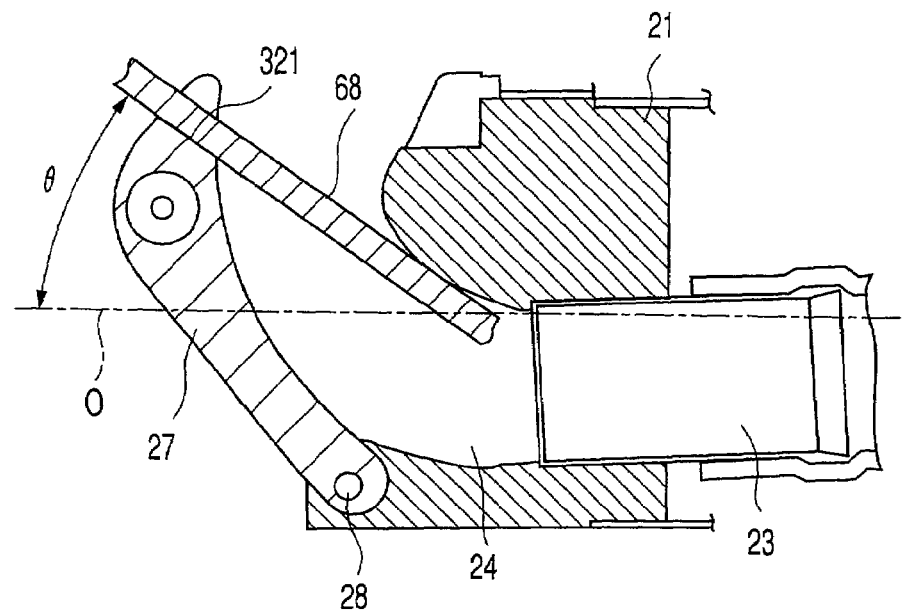
F I G. 17
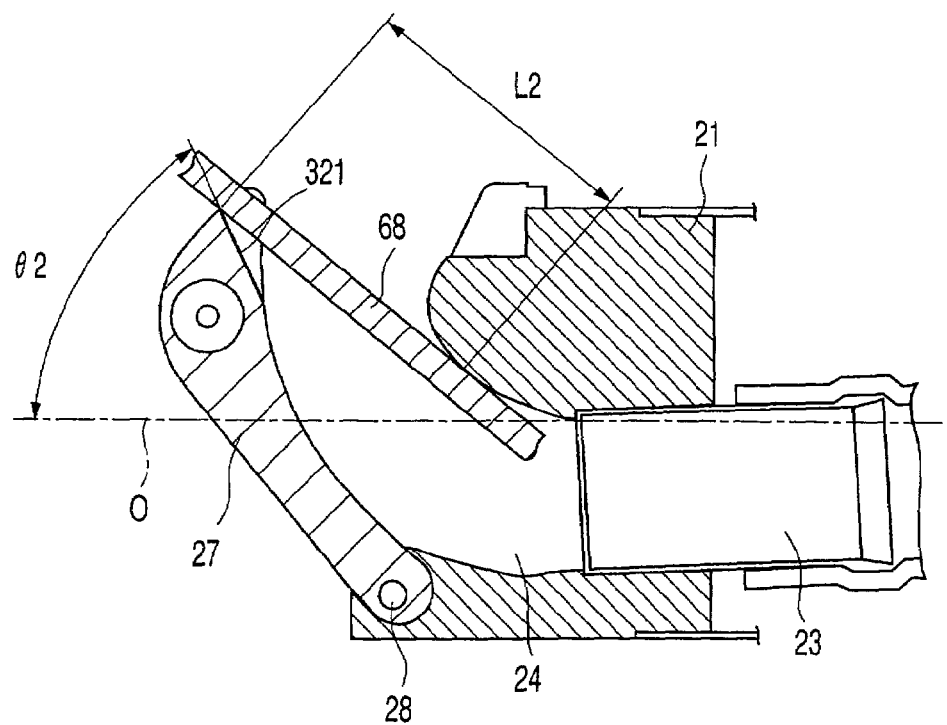
F I G. 18

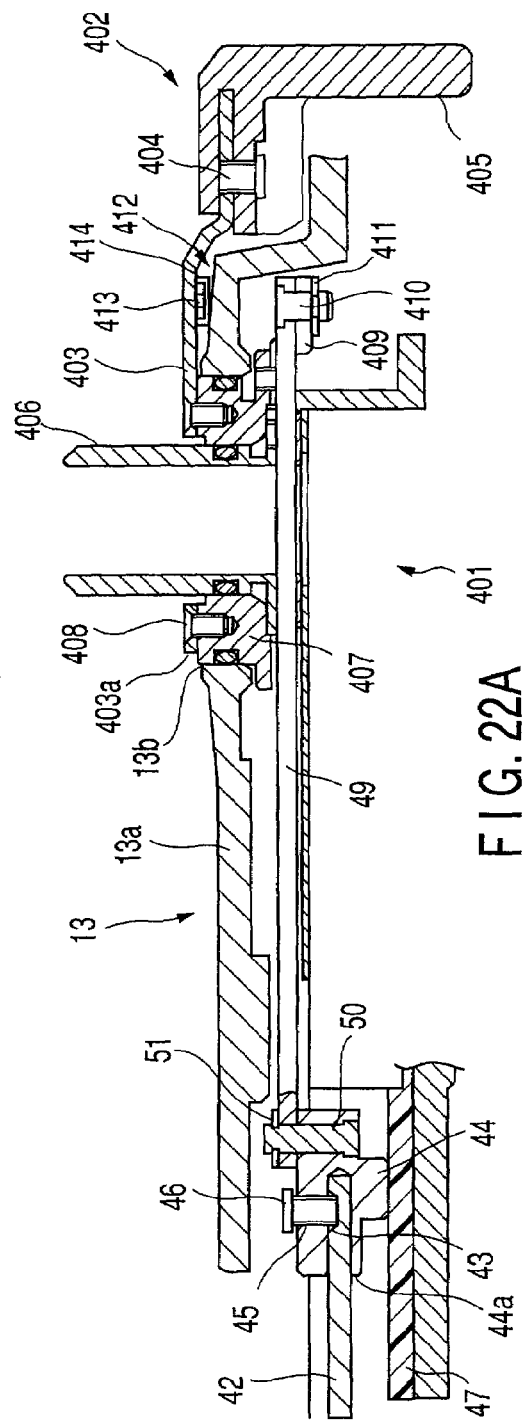
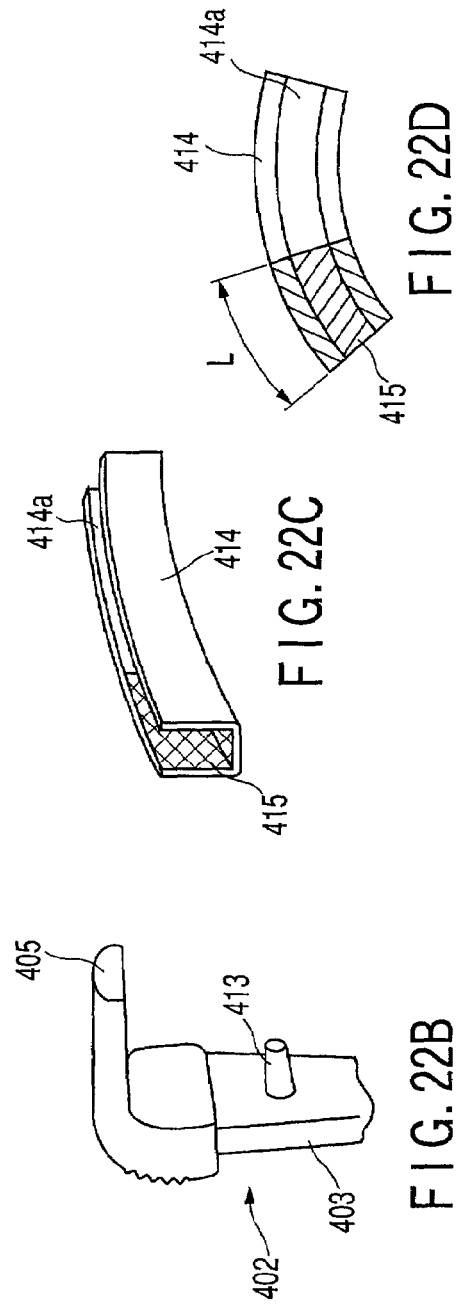
FIG. 22A
FIG. 22B
FIG. 22C
FIG. 22D

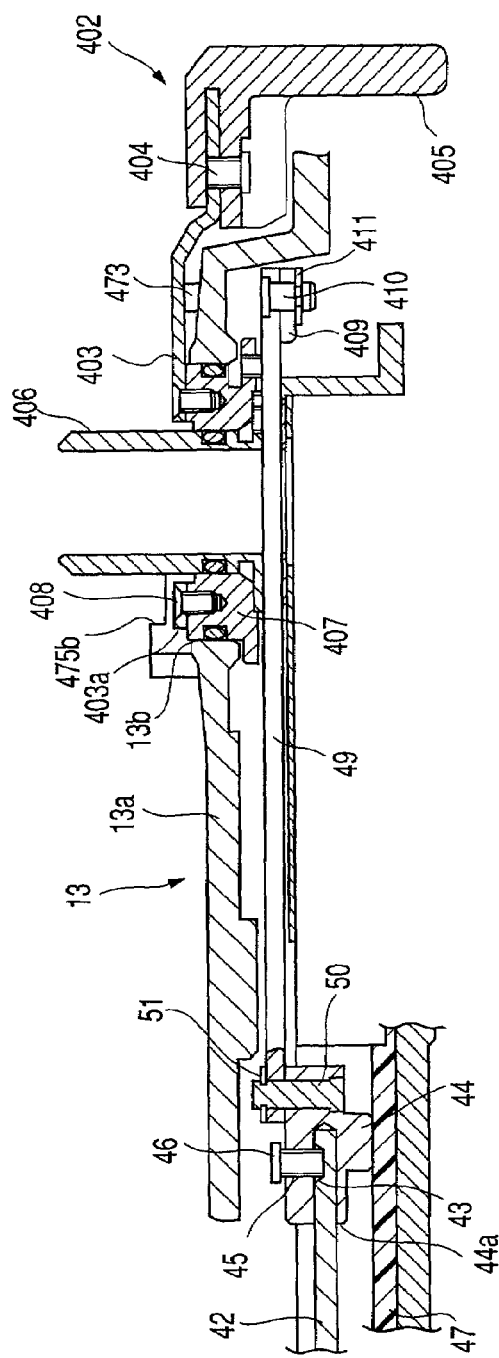
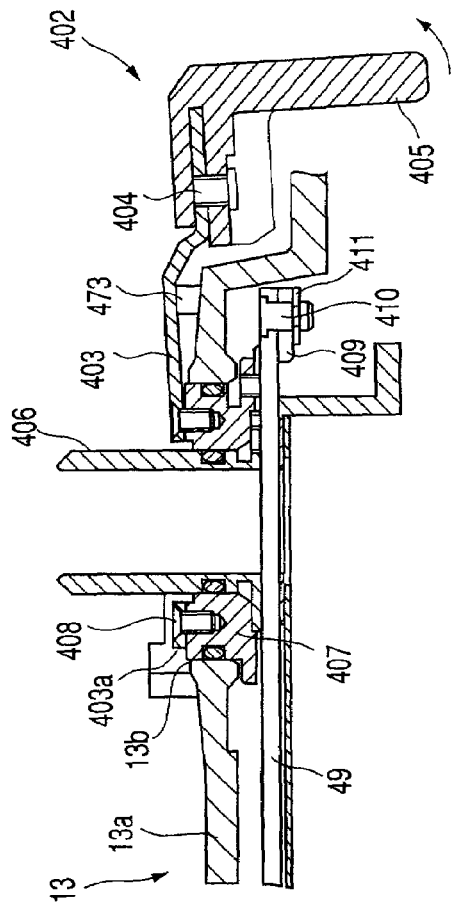
FIG. 25A
FIG. 25B

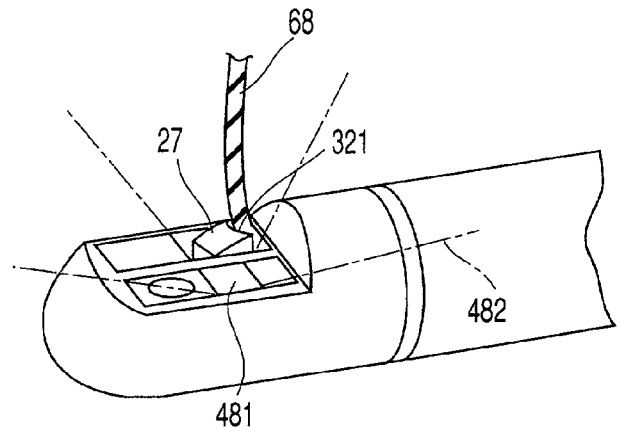
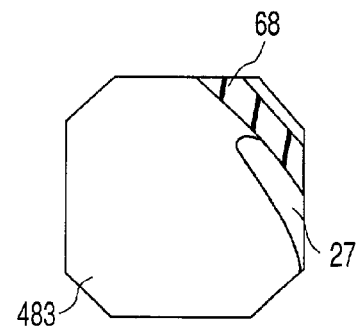
FIG. 29A             FIG. 29B
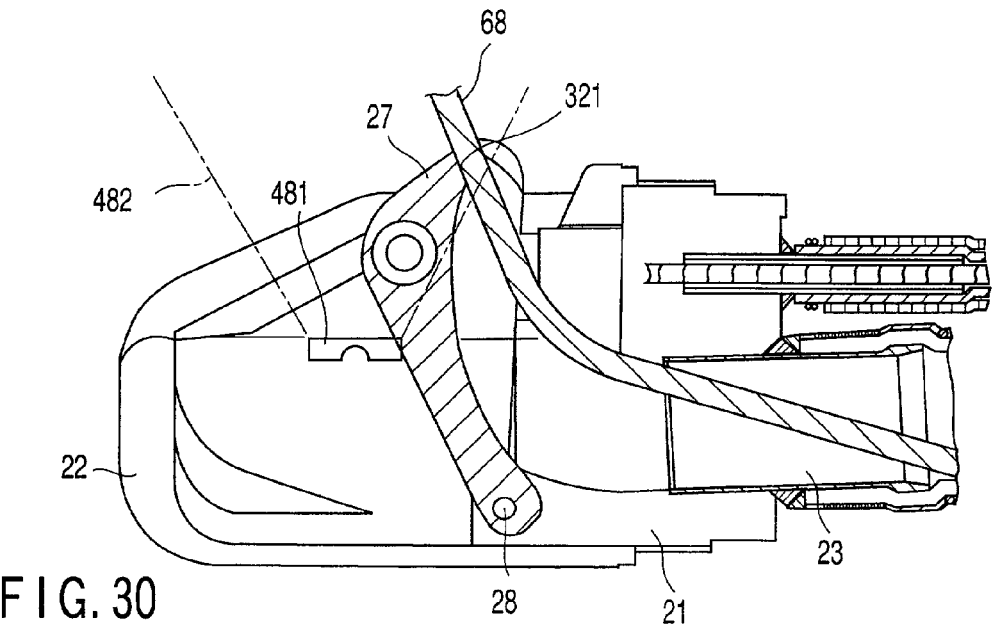
FIG. 30
FIG. 31A
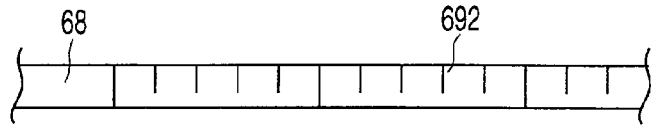
FIG. 31B
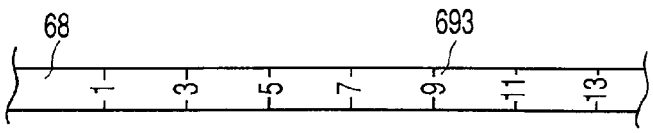
FIG. 31C

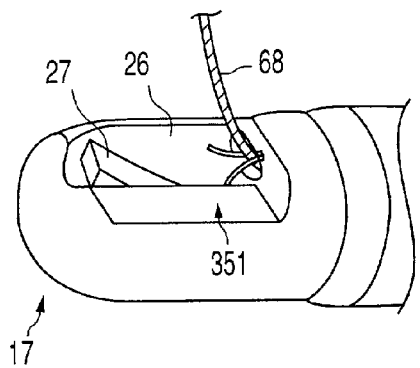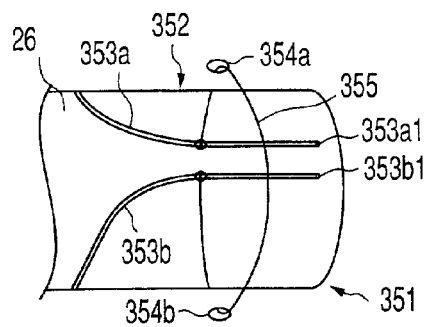
FIG. 41A  FIG. 41B
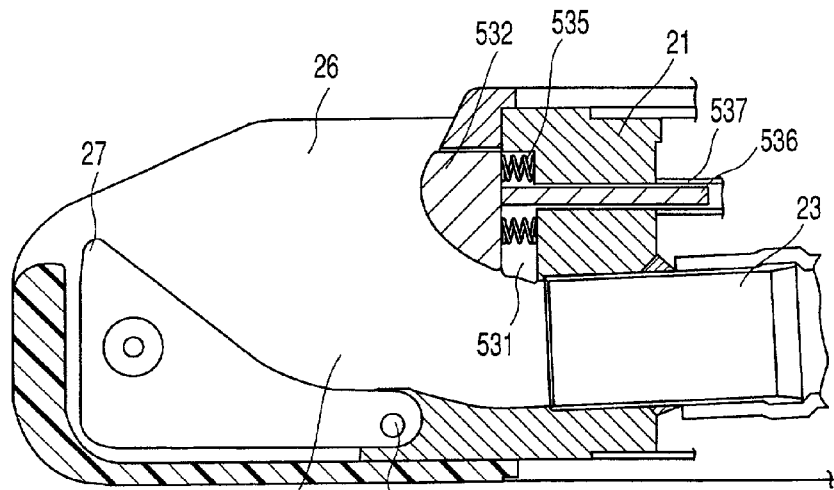
FIG. 42
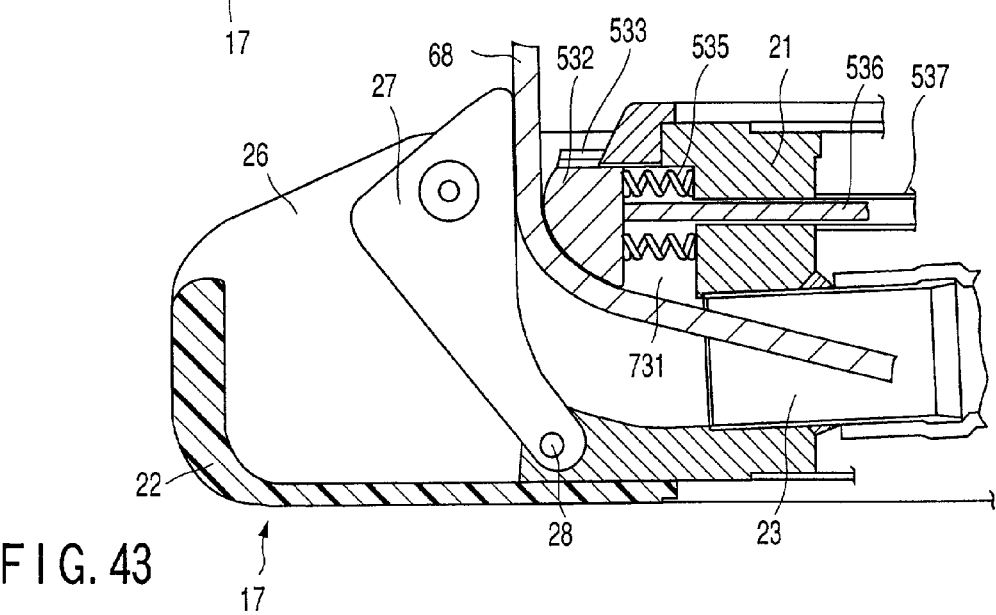
FIG. 43

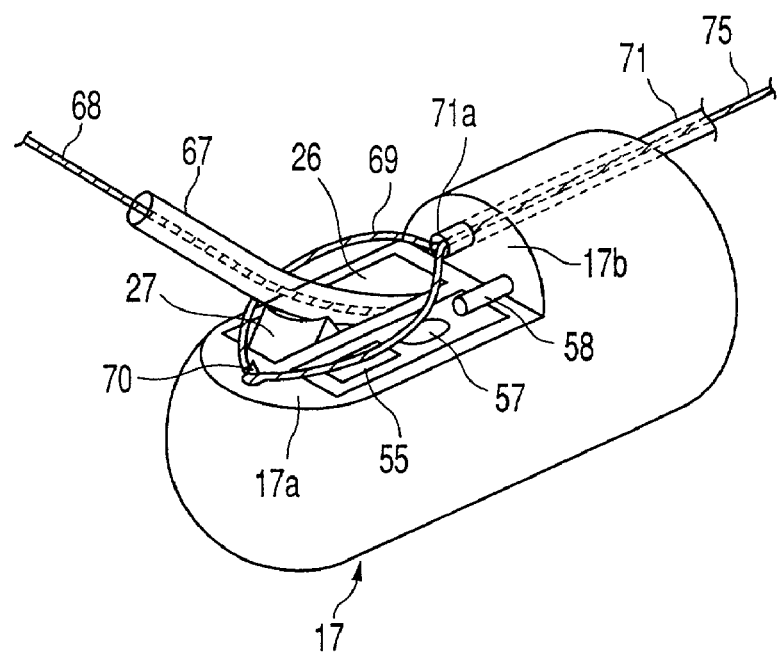
F I G. 46A
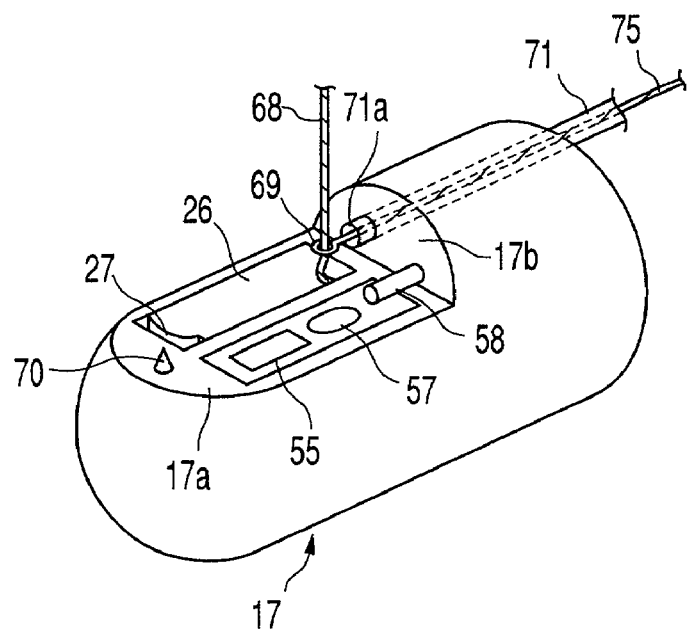
F I G. 46B

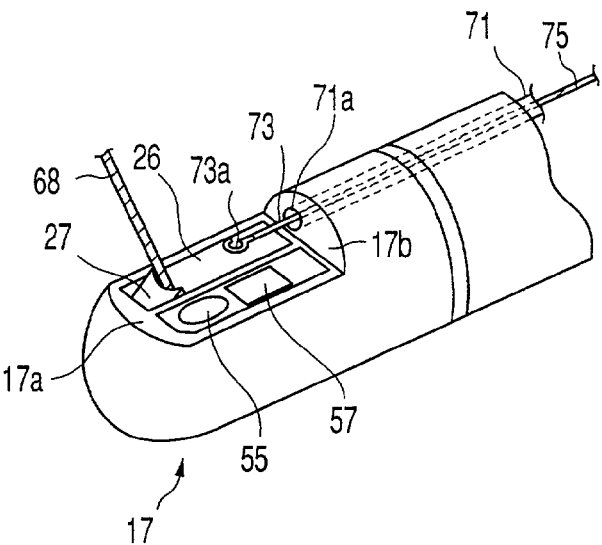
F I G. 47A
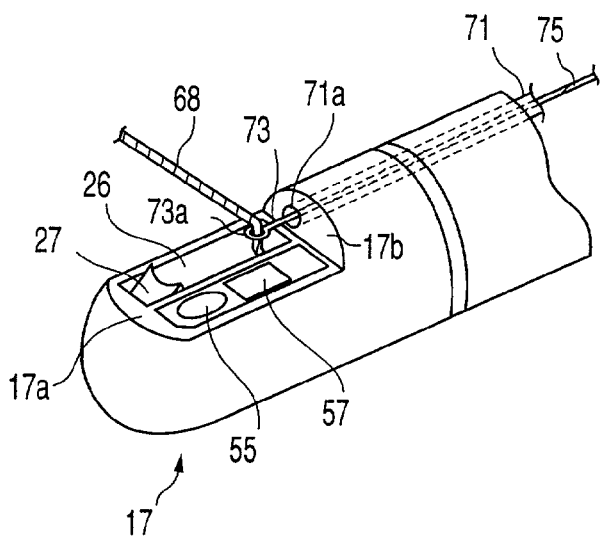
F I G. 47B
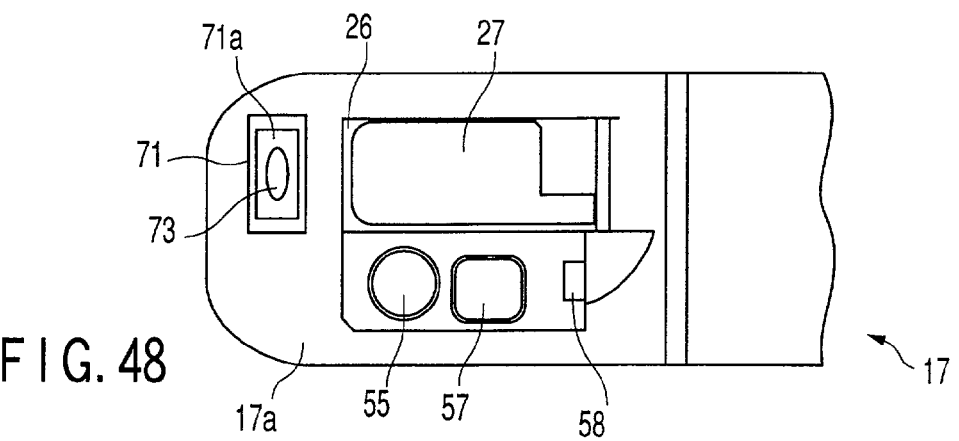
F I G. 48

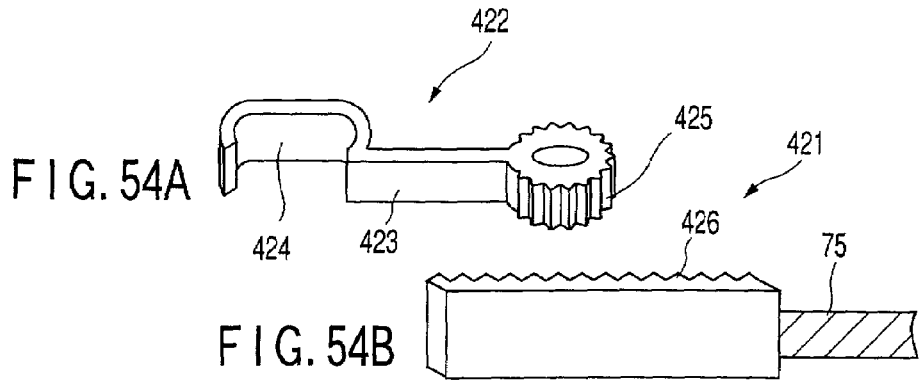
FIG. 54A
FIG. 54B
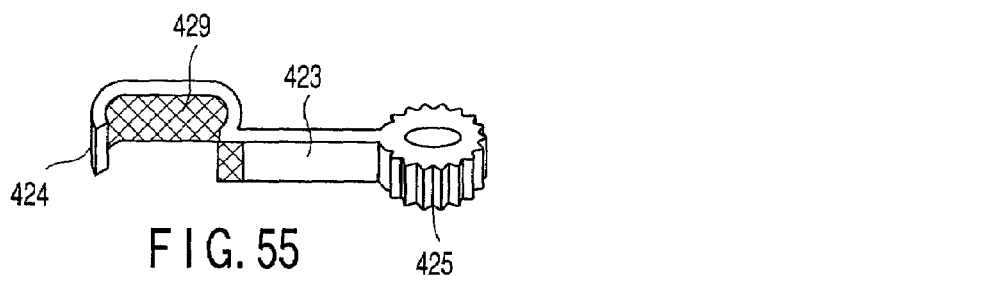
FIG. 55
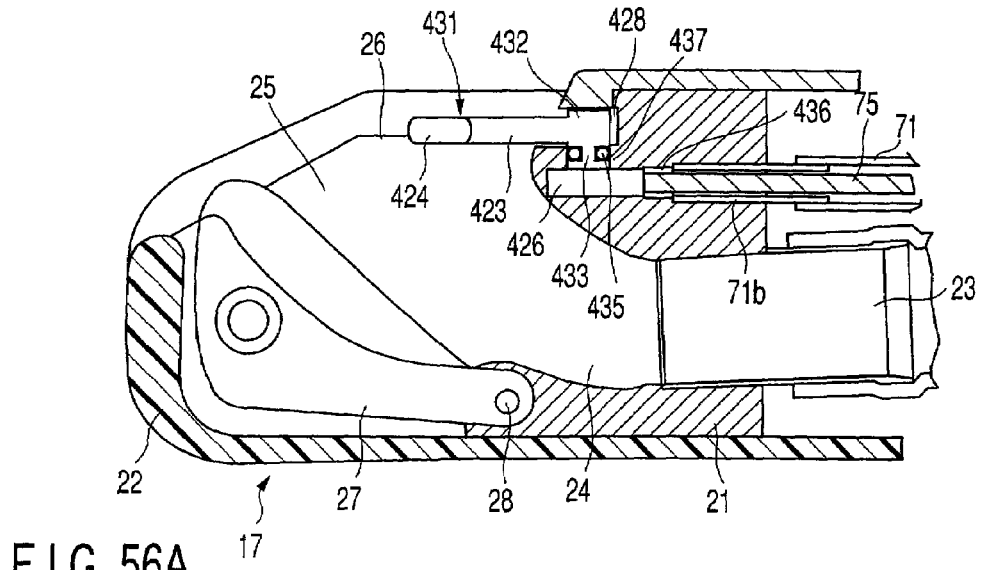
FIG. 56A
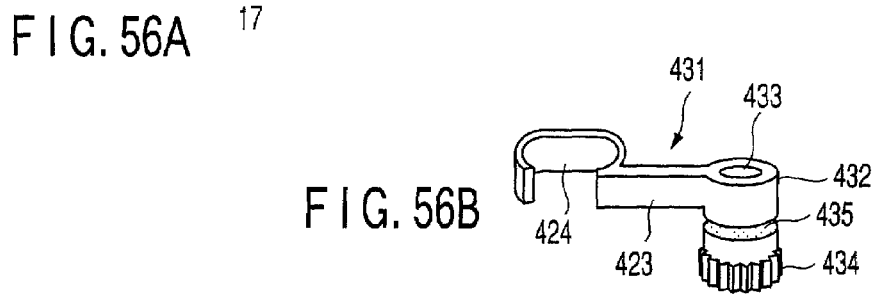
FIG. 56B

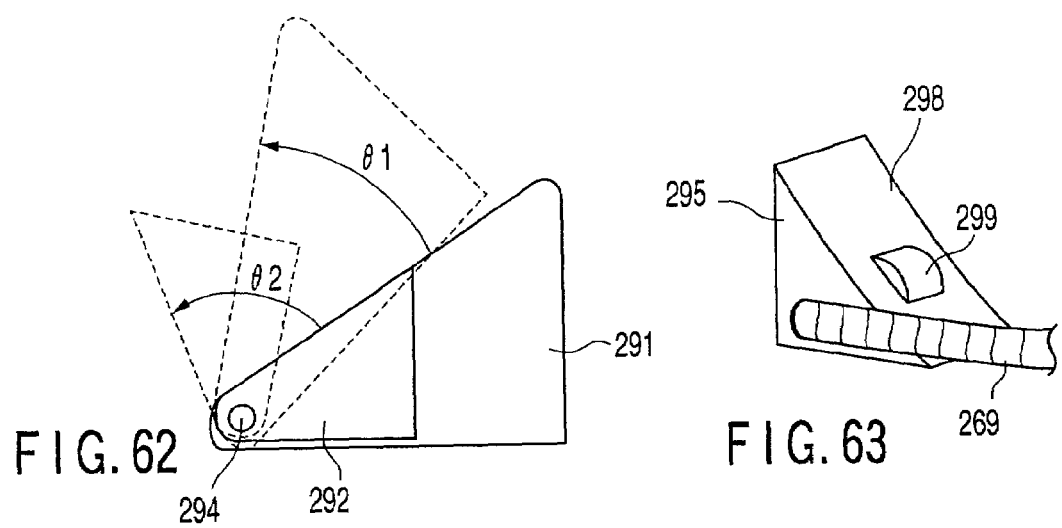
FIG. 62
FIG. 63
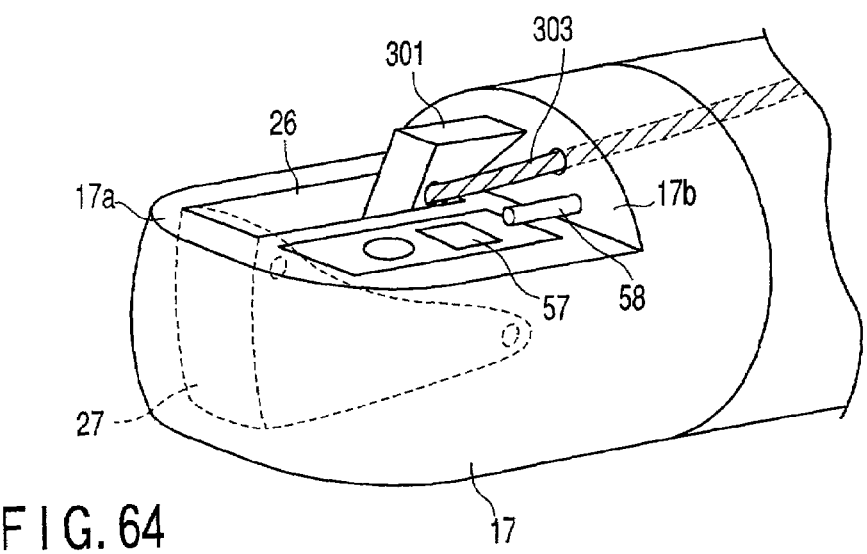
FIG. 64
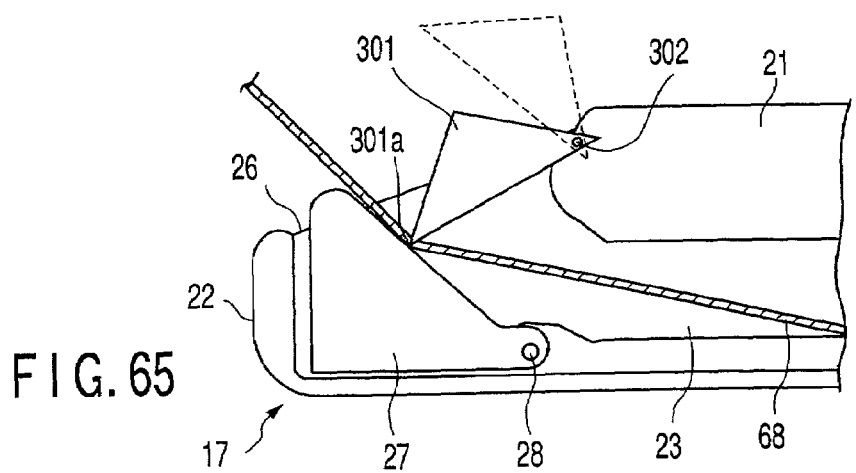
FIG. 65

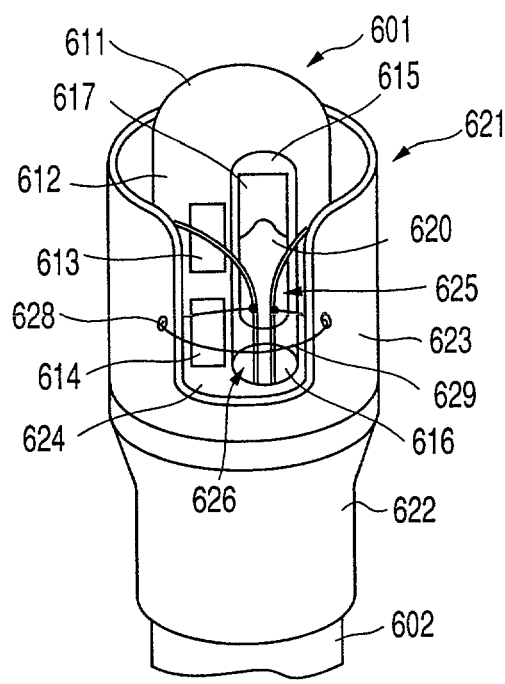
F I G. 81
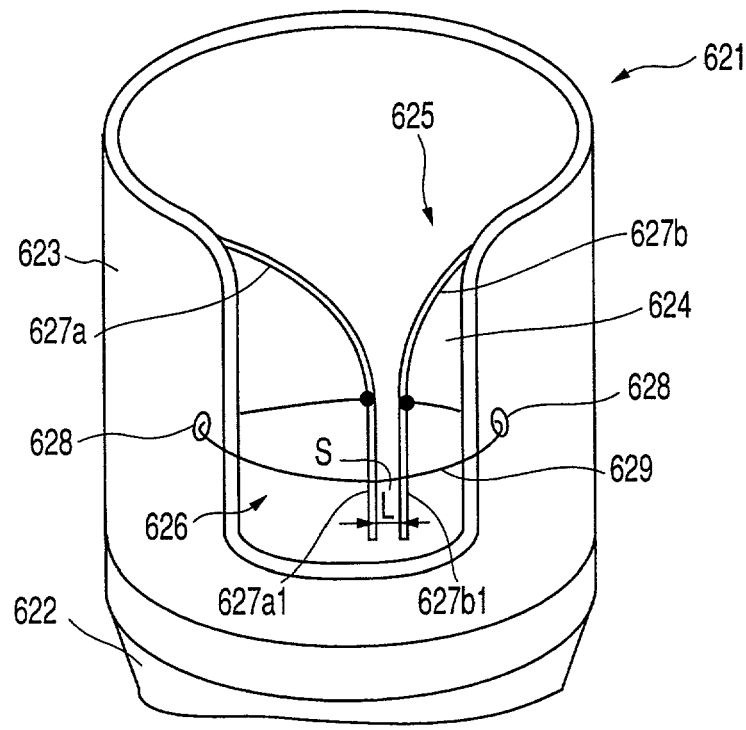
F I G. 82

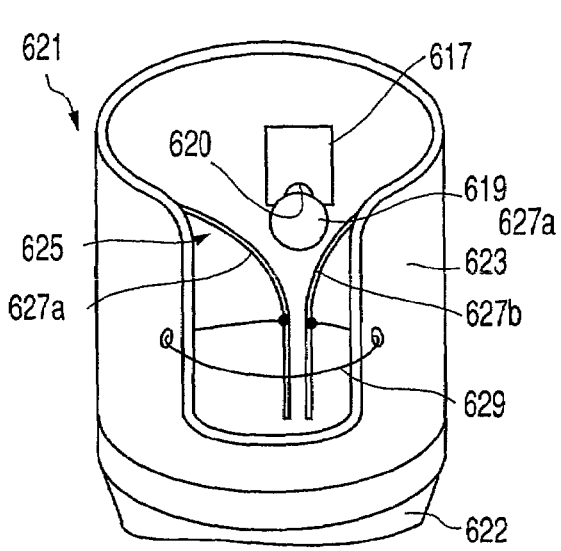
F I G. 83A
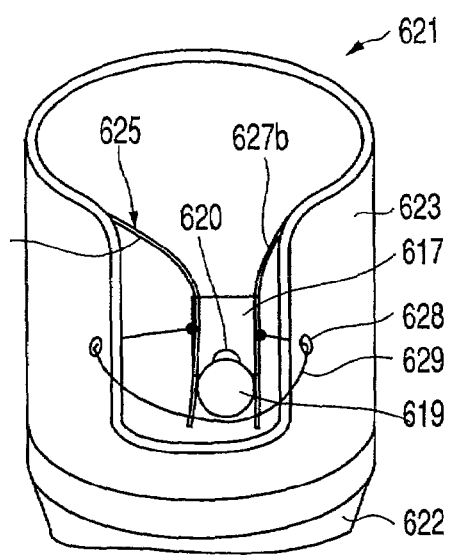
F I G. 83B
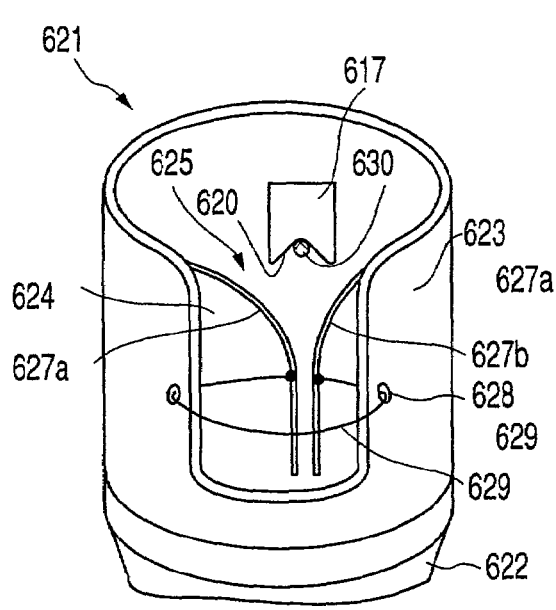
F I G. 84A
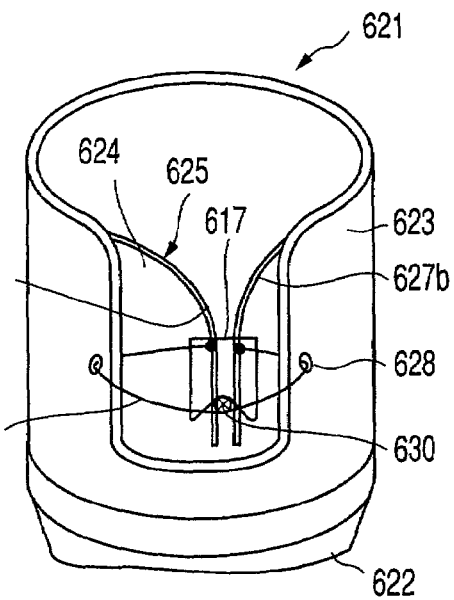
F I G. 84B

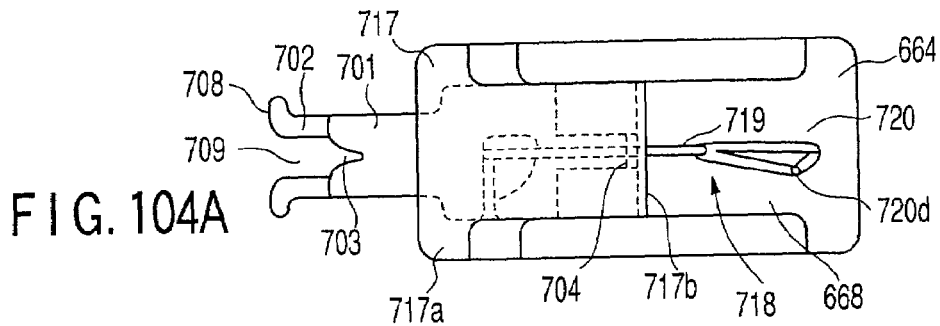
FIG. 104A
FIG. 104B
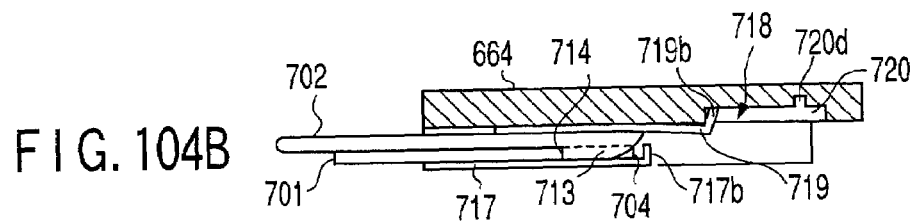
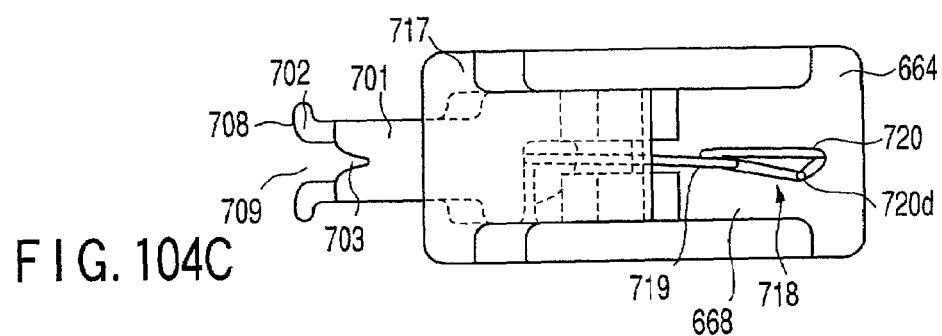
FIG. 104C
FIG. 104D
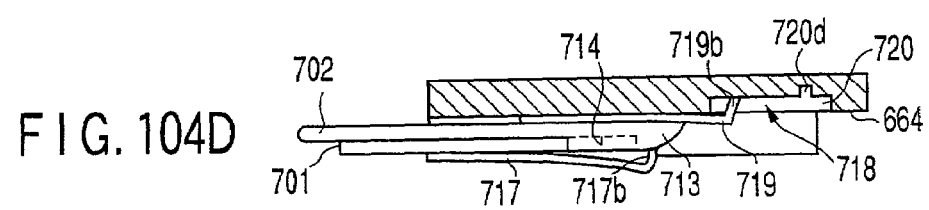
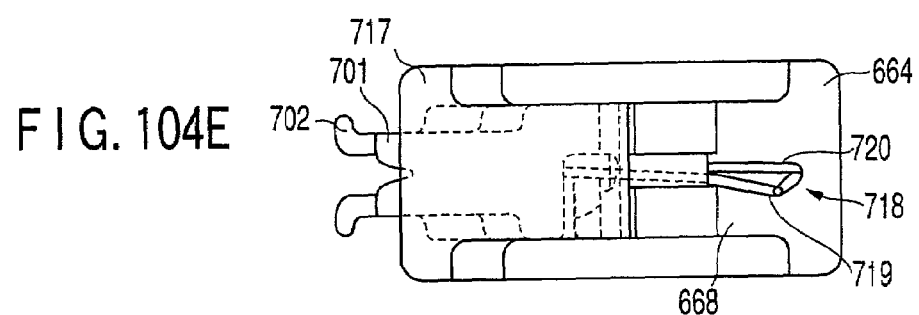
FIG. 104E
FIG. 104F
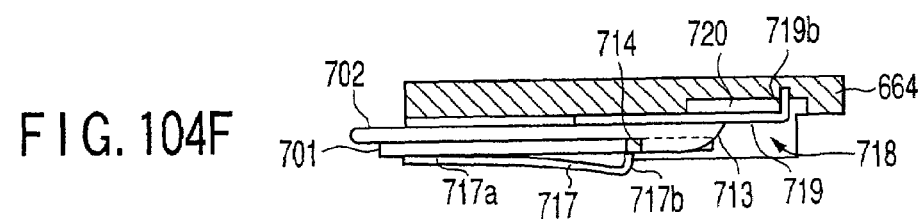

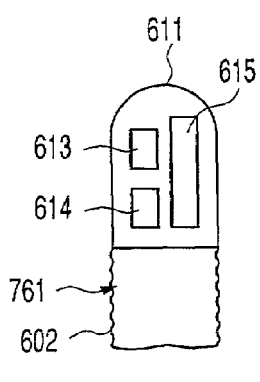 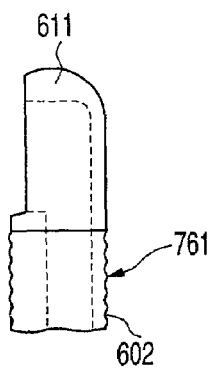 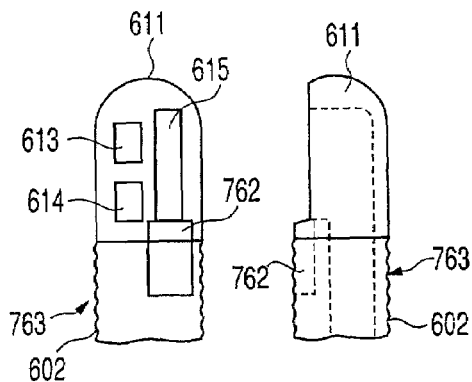
FIG. 112A    FIG. 112B    FIG. 112C    FIG. 112D
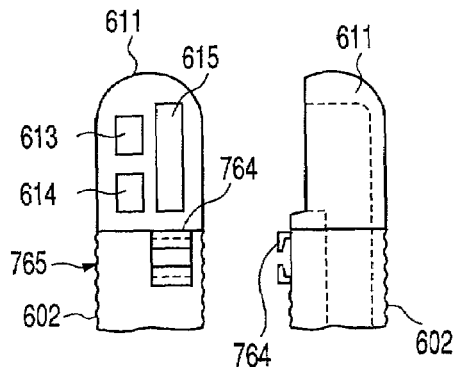 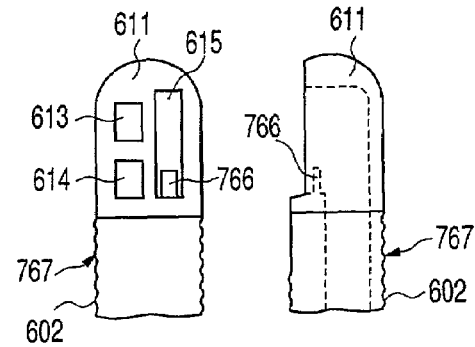
FIG. 112E    FIG. 112F    FIG. 112G    FIG. 112H
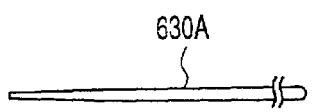 
FIG. 113A    FIG. 113B
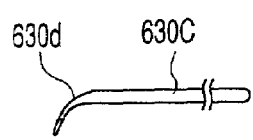
FIG. 113C

ENDOSCOPE AND ENDOSCOPE SYSTEM THEREOF

CROSS-REFERENCE TO RELATED APPLICATIONS

This is a Continuation Application of PCT Application No. PCT/JP01/03286, filed Apr. 17, 2001, which was not published under PCT Article 21(2) in English.

This application is based upon and claims the benefit of priority from the prior Japanese Patent Applications No. 2000-115355, filed Apr. 17, 2000, No. 2000-128262, filed Apr. 27, 2000, No. 2000-145530, filed May 17, 2000; and No. 2001-104390, filed Apr. 3, 2001, the entire contents of all of which are incorporated herein by reference.

BACKGROUND OF THE INVENTION

1. Field of the Invention

The present invention relates to an endoscope and an endoscope system with which can be replaced a therapeutic instrument by using a guide wire in endoscopy or endoscopic surgery of pancreaticobiliary ducts in particular.

2. Description of the Related Art

In recent years, use of an endoscopic treatment for treatment of a disorder in an alimentary canal system and a pancreaticobiliary duct system is increasing. As the current treatment for the pancreaticobiliary duct system using an endoscope, there is a diagnostic treatment for endoscopically imaging a bile duct or a pancreatic duct as well as therapeutic treatment for collecting a bile stone existing in a choledoch duct by a balloon or a gripping therapeutic instrument.

Further, in the endoscopic treatment for a pancreatic duct, a bile duct or a hepatic duct, an end of an insertion portion of the endoscope is inserted to the vicinity of the duodenal papilla, and a therapeutic instrument such as a catheter is then selectively inserted into the pancreatic duct or the bile duct with a guide wire as a guide in radioscopy.

Furthermore, when performing endoscopic treatment for a pancreatic duct, a bile duct or a hepatic duct by using the endoscope, the end of the insertion portion of the endoscope is usually inserted to the vicinity of the duodenal papilla, and a therapeutic instrument such as a catheter is then generally selectively inserted into the pancreatic duct or the bile duct with the guide wire as a guide, in radioscopy.

Specifically, the following operation is carried out. At first, after an end portion 903 of an insertion portion 902 of an endoscope 901 shown in FIGS. 114A and 114B is inserted to the vicinity of duodenal papilla in advance, a catheter 904 is inserted into a therapeutic instrument insertion channel of the endoscope 901, and an end portion 904a of the catheter 904 is endoscopically inserted into the pancreatic duct or the bile duct. Then, a guide wire 905 is inserted from a mouth ring 904b of the inserted catheter 904 on the base end side.

Thereafter, in radioscopy, it is confirmed that the guide wire 905 is correctly inserted into the pancreatic duct or the bile duct, and the operation for pulling out the catheter 904 from the therapeutic instrument insertion channel of the endoscope 901 is carried out while gripping the base end side of the guide wire 905 by hand as shown in FIG. 114A. During this operation, as shown in FIG. 114B, when the end portion 904a of the catheter 904 protrudes from a channel opening portion 907 on an operation portion 906 side of the endoscope 901, the guide wire 905 in the vicinity of the channel opening portion 907 of the endoscope 901 is gripped, and the catheter 904 is completely pulled out of the endoscope 901.

Subsequently, the base end side of the guide wire 905 is inserted into an insertion hole of another therapeutic instrument, and this therapeutic instrument is inserted into the therapeutic instrument insertion channel of the endoscope 901 so as to be guided by the guide wire 905. Thereafter, the above-described operation is repeated in accordance with a number of times of replacement of the therapeutic instrument.

The therapeutic instrument used for such treatment is generally set to have a length which is not less than 190 cm by taking a length of the endoscope 901 into consideration.

Furthermore, since a length which exceeds a combination of a length of the endoscope 901 and that of the therapeutic instrument is required for the guide wire 905, at least approximately 400 cm is necessary.

Moreover, for example, U.S. Pat. No. 5,921,971 discloses a bile duct catheter which can be rapidly replaced by providing an opening portion in the longitudinal direction between an end portion of a guide wire lumen and a base end portion in a catheter shaft.

Meanwhile, in case of observing/treating the pancreaticobiliary duct system by using the endoscope 901, when a therapeutic instrument such as the catheter 904 is inserted into the therapeutic instrument insertion channel of the endoscope 901 and used, the guide wire 905 is inserted into the therapeutic instrument. Therefore, when the therapeutic instrument is moved with respect to the endoscope 901, the guide wire 905 also simultaneously moves. Thus, for example, when replacing the therapeutic instrument with the guide wire 905 as a guide in the state where the end of the guide wire 905 is inserted into the papilla, the guide wire 905 must be constantly gripped on the operation portion 906 side of the endoscope 901 in order to maintain the end of the guide wire 905 being inserted into the papilla.

In addition, during use of the conventional endoscope 901, it is necessary to simultaneously carry out the two operations, i.e., pulling out the therapeutic instrument with respect to the therapeutic instrument insertion channel of the endoscope 901 while inserting the guide wire 905 by the same amount in the operation for replacing the therapeutic instrument, or similarly inserting the therapeutic instrument into the therapeutic instrument insertion channel while pulling out the guide wire 905 by the same movement amount. Therefore, that operation is complicated and troublesome.

Additionally, since the guide wire 905 has a length of approximately 400 cm, it is difficult to handle the guide wire 905 in such a manner that the guide wire 905 does not come into contact with an unclean area such as the floor in a small endoscope room.

Further, since the therapeutic instrument can not be replaced unless the entire length of the guide wire 905 is moved, the time required for replacement of the therapeutic instrument itself may possibly be prolonged. Therefore, there is a drawback that the operation for replacing the therapeutic instrument takes longer.

Furthermore, it is difficult for one operator to carry out the operation for replacing the therapeutic instrument, and at least two assistants are required in an operating room. Therefore, there occurs a problem that the personnel cost increases and the pecuniary burden on a hospital or a patient thereby increases.

Moreover, as in U.S. Pat. No. 5,921,971, in the case of the catheter having the opening portion in the longitudinal direction being provided between the end portion and the base end portion of the guide wire lumen in the catheter shaft, the operation for providing the opening portion in the longitudinal direction to the conventional contrasting catheter. Thus, there is a drawback that the manufacturing cost is higher than that of the conventional contrasting catheter.

In addition, an outside diameter of the shaft must be increased in order to compensate for a reduction in rigidity of the catheter shaft caused due to provision of a slit, or a material of the shaft must be hardened. Therefore, an increase in diameter of the shaft may possibly lead to deterioration of the working property of an operator since the insertion ability in the channel of the endoscope is degraded.

Additionally, since the treatment for the pancreaticobiliary duct system requires specialist techniques, preference of the operator with respect to therapeutic instruments is divided in particular. Further, changing the therapeutic instruments depending on conditions of a patient is frequently carried out. However, usable therapeutic instruments are restricted in this prior art by itself, and the selection range of the operator is disadvantageously lost.

In view of the above-described problems, it is an object of the present invention to provide an endoscope apparatus by which a therapeutic instrument can be replaced in a shorter time and the replacement operation can be performed by one operator without impairing the conventional operation method of a therapeutic instrument or the operation sense.

BRIEF SUMMARY OF THE INVENTION

According to the present invention, there is provided an endoscope in which a therapeutic instrument insertion channel is provided in an insertion portion which is inserted into a celom and an end opening portion of the therapeutic instrument insertion channel is arranged in the vicinity of an end of the insertion portion, wherein, when inserting/removing a therapeutic instrument traveling on a guide wire with an end portion of the guide wire inserted through the therapeutic instrument insertion channel being led out from the end opening portion of the therapeutic instrument insertion channel, guide wire fixing means for releasably engaging the guide wire is provided in the vicinity of the end portion of the insertion portion.

Further, according to the present invention, there is provided an endoscope comprising: an insertion portion inserted into a celom; an operation portion connected to an end portion of the insertion portion on a front side; and a therapeutic instrument elevator base which is arranged at an end portion of the insertion portion and can be operated by the operation portion, wherein a slit enabling engagement of only a guide wire by raising the guide wire by operating the therapeutic instrument elevator base is provided at a top portion on a guide plane of the therapeutic instrument elevator base.

Furthermore, according to the present invention, there is provided an endoscope system comprising: an endoscope in which a therapeutic instrument insertion channel is provided in an insertion portion inserted into a celom and an end opening portion of the therapeutic instrument insertion channel is provided in the vicinity of an end of the insertion portion and a therapeutic instrument insertion port as an opening portion of the therapeutic instrument insertion channel is provided on a front side of the operation portion; a guide wire which can pass through the therapeutic instrument insertion channel; and a therapeutic instrument which has a duct through which the guide wire can be inserted and which can be inserted through the therapeutic instrument insertion channel, wherein the therapeutic instrument has a protrusion length from the end opening portion which is required for the treatment in the state where the therapeutic instrument is inserted into the therapeutic instrument insertion channel and a protrusion length from the therapeutic instrument insertion port required for the operation on the front side, guide wire fixing means which releasably engaging the guide wire when inserting/removing the therapeutic instrument traveling on the guide wire with an end portion of the guide wire inserted through the therapeutic instrument insertion channel being led out from the end opening portion is provided in the vicinity of the end portion of the insertion portion, and the guide wire pulls the therapeutic instrument end portion toward the operation portion front side from a position of the engagement and has a length protruding from the end portion of the therapeutic instrument on the front side when being engaged by the guide wire fixing means.

BRIEF DESCRIPTION OF THE SEVERAL VIEWS OF THE DRAWING

FIG. 15A is a front view of the therapeutic instrument elevator base according to the seventh embodiment;

FIG. 15B is a rear view of the therapeutic instrument elevator base according to the seventh embodiment;

FIG. 16 is a vertical cross-sectional view of a primary part showing a structure of a therapeutic instrument elevator base of an endoscope according to an eighth embodiment of the present invention;

FIG. 17 is a vertical cross-sectional view of a primary part showing an ideal guide wire fixed state in the therapeutic instrument elevator base in the endoscope according to the eighth embodiment;

FIG. 18 is a vertical cross-sectional view showing the guide wire fixed state when irregularities occurred due to processing in the therapeutic instrument elevator base in the endoscope according to the eighth embodiment;

FIG. 22A is a vertical cross-sectional view of the elevator base actuation mechanism according to the 11th embodiment;

FIG. 22B is a perspective view of a primary part showing an elevator base operation knob of the elevator base actuation mechanism according to the 11th embodiment;

FIG. 22C is a perspective view showing a deterrence reinforcement member of a braking mechanism of the elevator base actuation mechanism according to the 11th embodiment;

FIG. 22D is a plane view of the deterrence reinforcement member showing the embedded state of a friction resistance member of the elevator base actuation mechanism according to the 11th embodiment;

FIG. 25A is a vertical cross-sectional view of the elevator base actuation mechanism showing the tenth embodiment;

FIG. 25B is a vertical cross-sectional view of a primary part showing the state in which an operation lever of the set-up actuation mechanism of the elevator base actuation mechanism according to the tenth embodiment is elastically deformed;

FIG. 29A is a perspective view showing an end portion of an insertion portion of an endoscope according to a 12th embodiment of the present invention;

FIG. 29B is a plane view showing an actual endoscopic screen when a guide wire of the endoscope is fixed according to the 12th embodiment;

FIG. 30 is a vertical cross-sectional view showing an inner structure of an end portion in the insertion portion of the endoscope according to the 12th embodiment;

FIG. 31A is a plane view showing a guide wire according to a 13th embodiment of the present invention;

FIG. 31B is a plane view showing a first modification of the guide wire according to the 13th embodiment;

FIG. 31C is a plane view showing a second modification of the guide wire according to the 13th embodiment;

FIG. 41A is a perspective view showing a schematic structure of an end portion of an insertion portion in an endoscope according to a 21st embodiment of the present invention;

FIG. 41B is a perspective view showing a guide wire fixture in the endoscope according to the 21st embodiment;

FIG. 42 is a vertical cross-sectional view showing the set-down state of a therapeutic instrument elevator base according to a 22nd embodiment of the present invention;

FIG. 43 is a vertical cross-sectional view showing the set-up state of the therapeutic instrument elevator base according to the 22nd embodiment;

FIG. 46A is a perspective view of a primary part showing the state in which a guide wire fixture is held in a standby position in an endoscope according to a 24th embodiment;

FIG. 46B is a perspective view of a primary part showing a fixed state of a guide wire;

FIG. 47A is a perspective view of a primary part showing the state in which a guide wire fixture is held at a standby position in an endoscope according to a 25th embodiment of the present invention;

FIG. 47B is a perspective view of a primary part showing the fixed state of the guide wire;

FIG. 48 is a plane view of an end portion of an insertion portion in an endoscope according to a 26th embodiment of the present invention;

FIG. 54A is a perspective view showing a guide wire engagement member according to the 27th embodiment;

FIG. 54B is a perspective view showing a rack gear at an end of a tow wire in the endoscope according to the 27th embodiment;

FIG. 55 is a perspective view showing a modification of the guide wire engagement member in the 27th embodiment;

FIG. 56A is a vertical cross-sectional view of a primary part showing an inner structure of an end portion of an insertion portion in an endoscope according to a 28th embodiment of the present invention;

FIG. 56B is a perspective view showing a guide wire engagement member in the endoscope according to the 28th embodiment;

FIG. 62 is a relational view showing the relationship between a set-up angle of the therapeutic instrument elevator base and a set-up angle of the guide wire fixing elevator base in the endoscope according to the 31st embodiment;

FIG. 63 is a perspective view showing a modification of the guide wire fixing elevator base in the endoscope according to the 31st embodiment;

FIG. 64 is a perspective view of an end portion of an insertion portion in an endoscope according to a 32nd embodiment of the present invention;

FIG. 65 is a vertical cross-sectional view of a primary part showing the state in which a guide wire fixing elevator base of an elevator base actuation mechanism is moved to an engagement position of a guide wire according to the 32nd embodiment;

FIG. 74A is a perspective view of a primary part showing a schematic structure of an end portion of an insertion portion in an endoscope according to a 38th embodiment of the present invention;

FIG. 74B is a perspective view of a primary part showing a structure of a guide wire fixture in the endoscope according to the 38th embodiment;

FIG. 74C is a vertical cross-sectional view of a primary part showing the structure of the guide wire fixture in the endoscope according to the 38th embodiment;

FIG. 75 is a vertical cross-sectional view of a primary part showing a modification of the endoscope according to the 38th embodiment;

FIG. 76 is a perspective view showing an operation portion on the front side in an endoscope according to a 39th embodiment of the present invention;

FIG. 77A is a perspective view showing the state before fixing the guide wire in the endoscope according to the 39th embodiment;

FIG. 77B is a perspective view showing the state after fixing the guide wire in the endoscope according to the 39th embodiment;

FIG. 78 is a vertical cross-sectional view showing the inner structure of the end portion of the insertion portion in the endoscope according to the 39th embodiment;

FIG. 79A is a perspective view showing the state in which a snare is closed according to the 39th embodiment;

FIG. 79B is a perspective view showing the state in which the snare is opened in the endoscope according to the 39th embodiment;

FIG. 80 is an exploded perspective view showing a guide wire fixing member according to the 39th embodiment;

FIG. 81 is a perspective view showing the state in which a guide wire fixing member is attached to an end portion of an insertion portion of an endoscope in an endoscope apparatus according to a 40th embodiment of the present invention;

Figure 85:
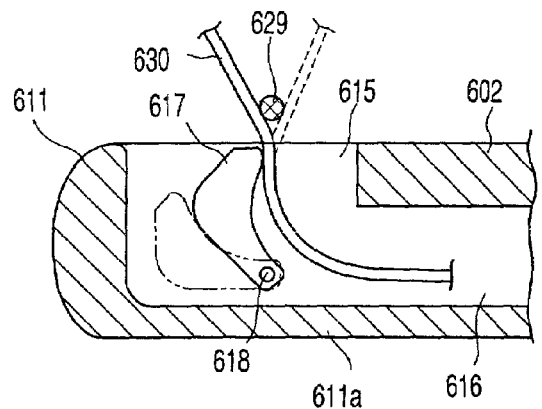
Figure 86A:
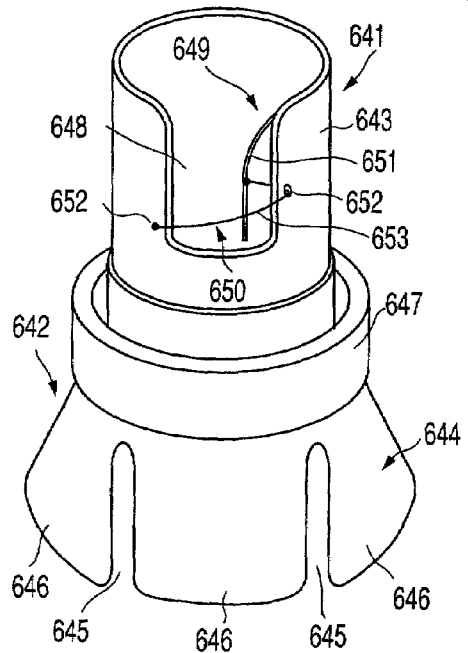
Figure 86B:
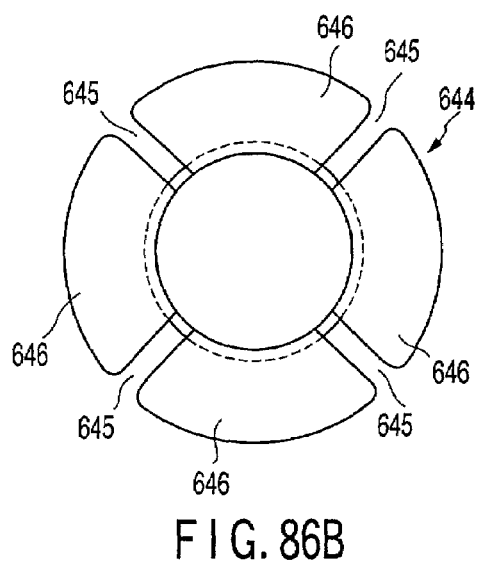
Figure 87A:
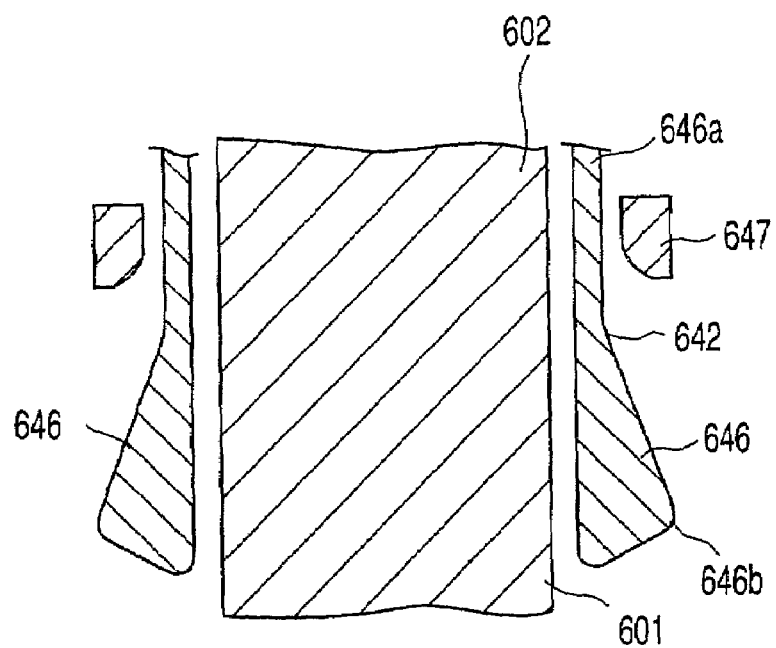
Figure 87B:
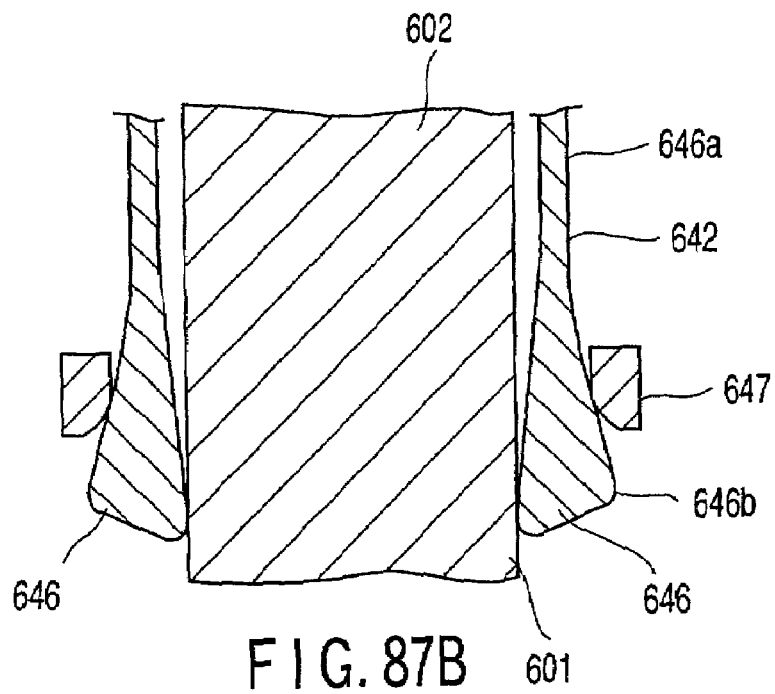
Figure 88A:
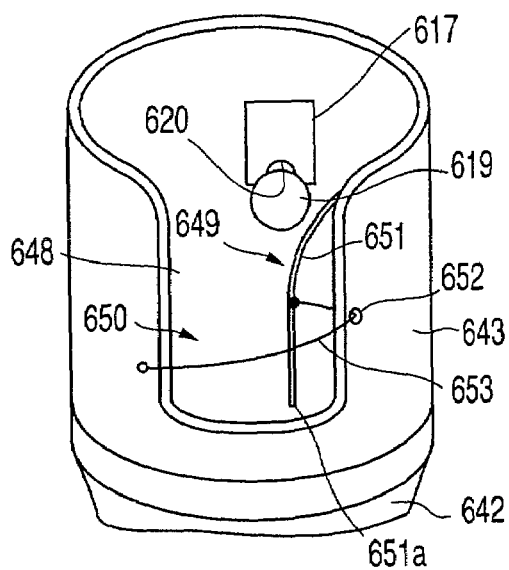
Figure 88B:
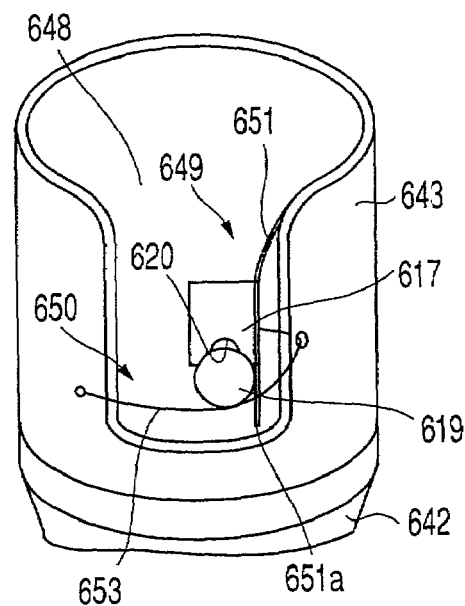
Figure 89A:
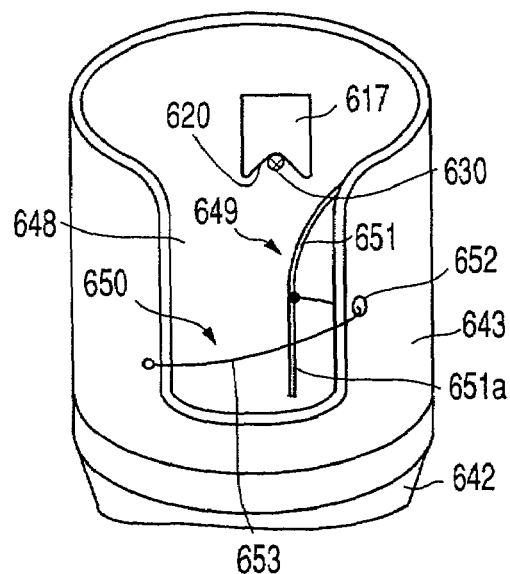
Figure 89B:
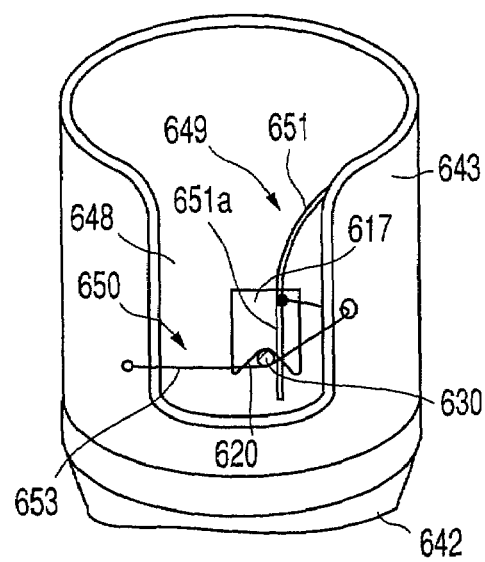
Figure 90:
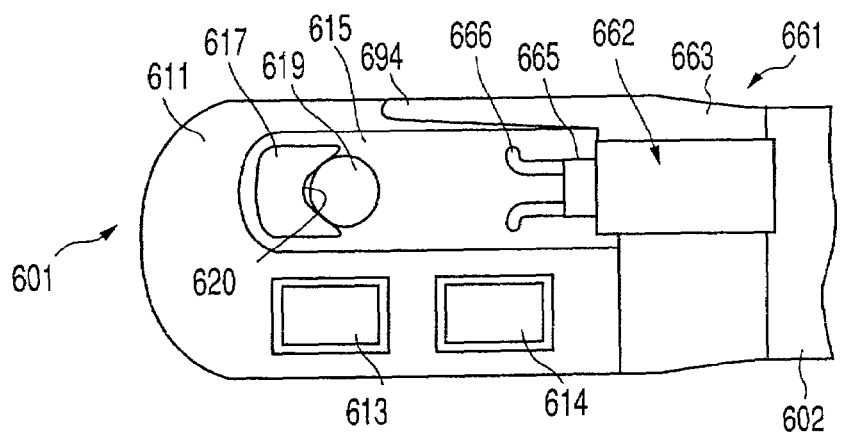
Figure 91:
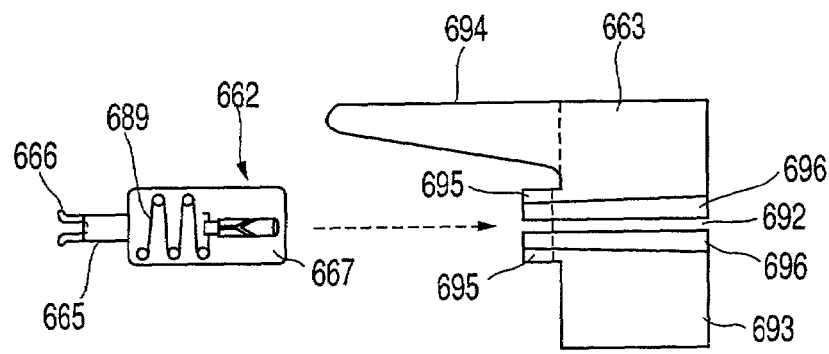
Figures 92A, 92B:
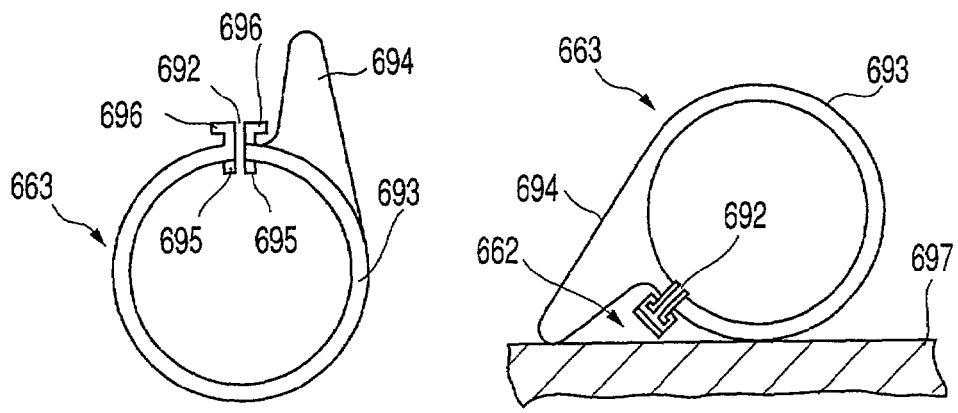
Figure 93A:
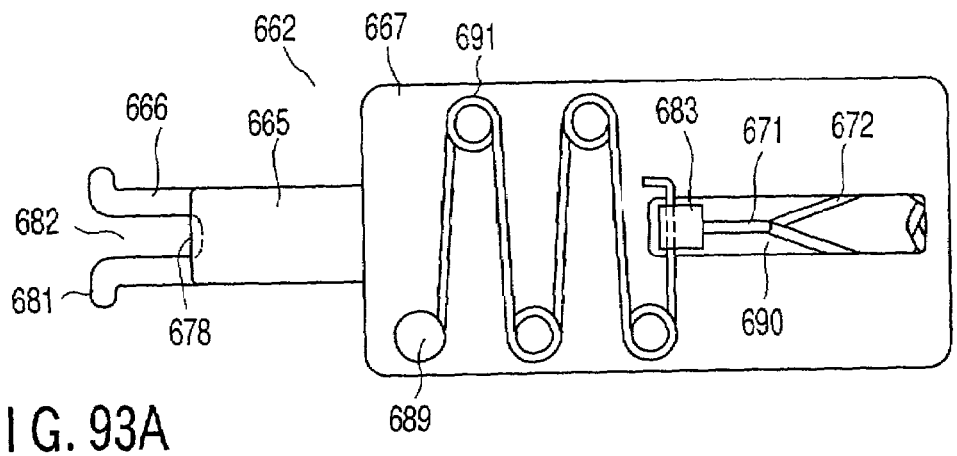
Figure 93B:
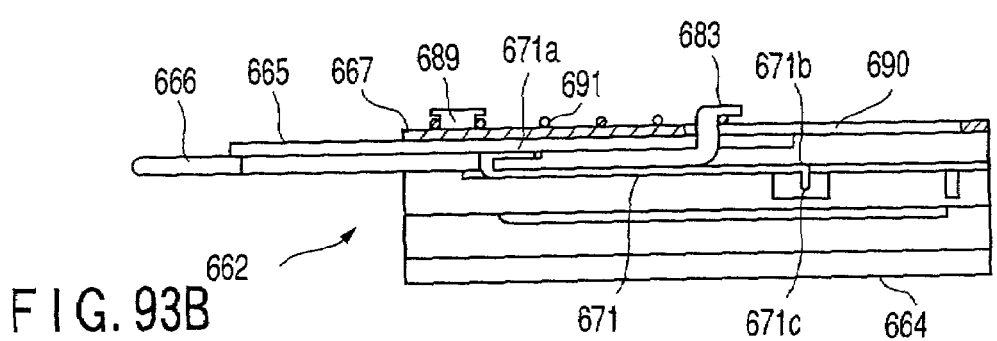
Figure 93C:
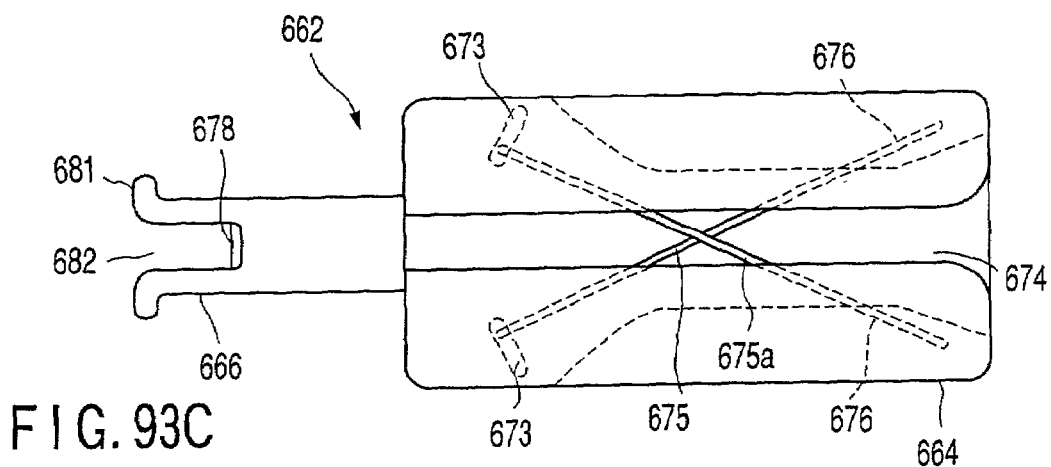
Figure 93D:
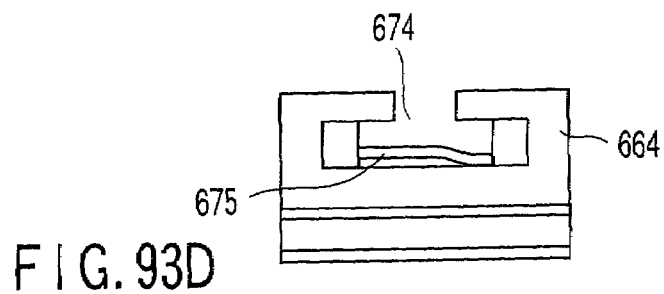
Figure 94A:
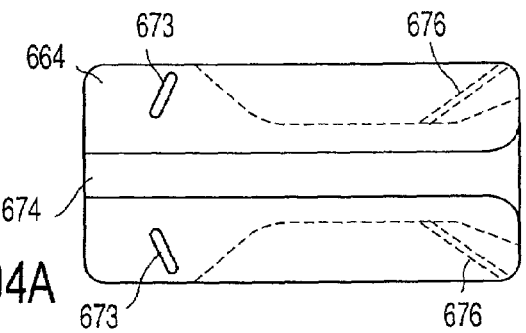
Figure 94C:
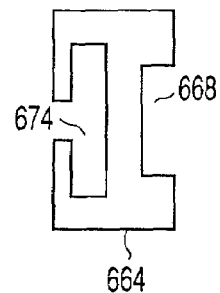
Figure 94B:
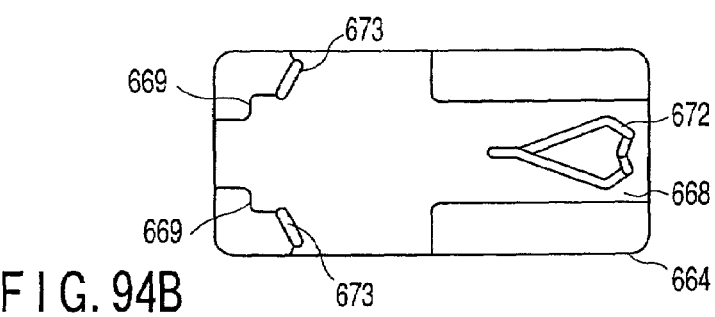
Figure 95A:
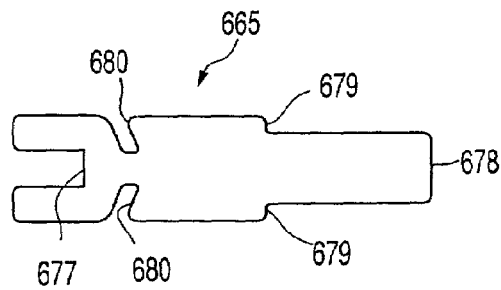
Figure 95B:
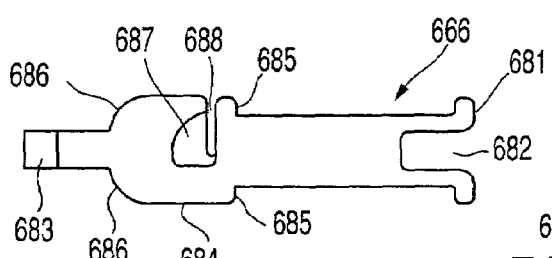
Figure 95D:
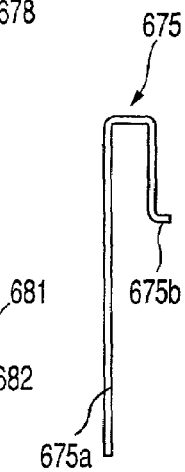
Figure 95E:
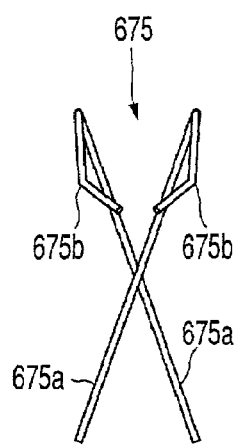
Figure 95C:
Figure 96:
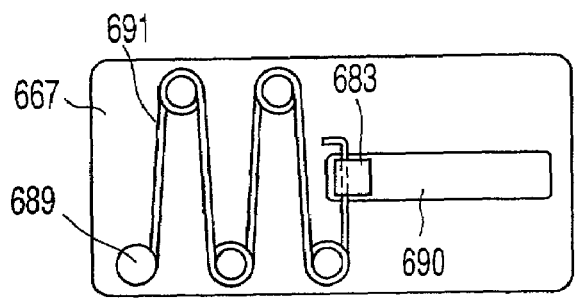
Figure 97A:
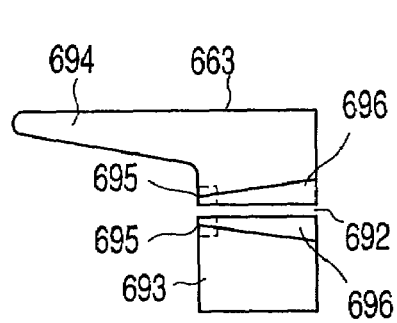
Figure 97B:
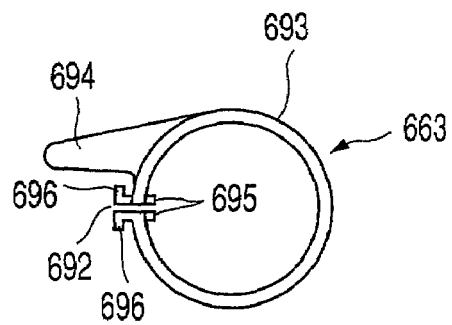
Figure 98A:
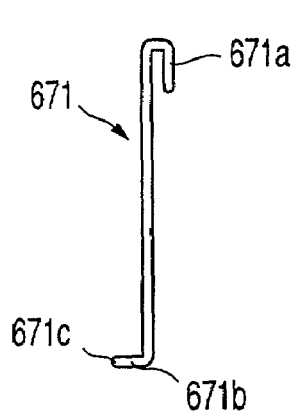
Figure 98B:
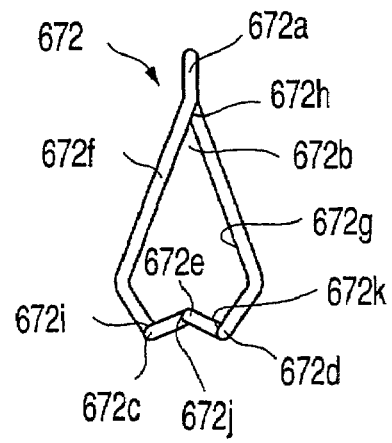
Figure 99A:
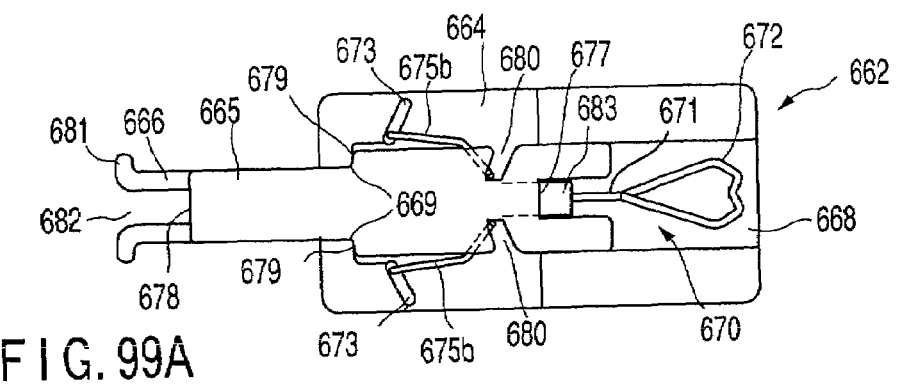
Figure 99B:
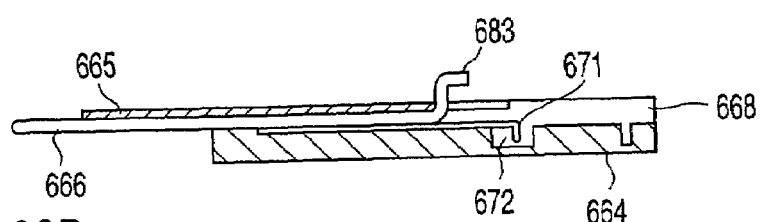
Figure 99C:
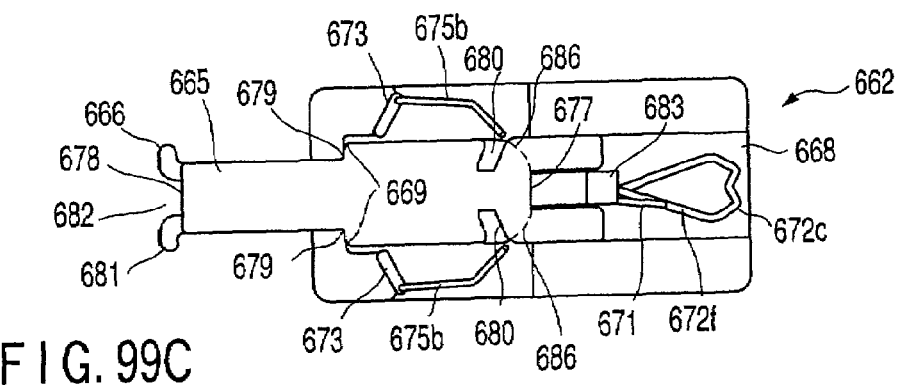
Figure 99D:
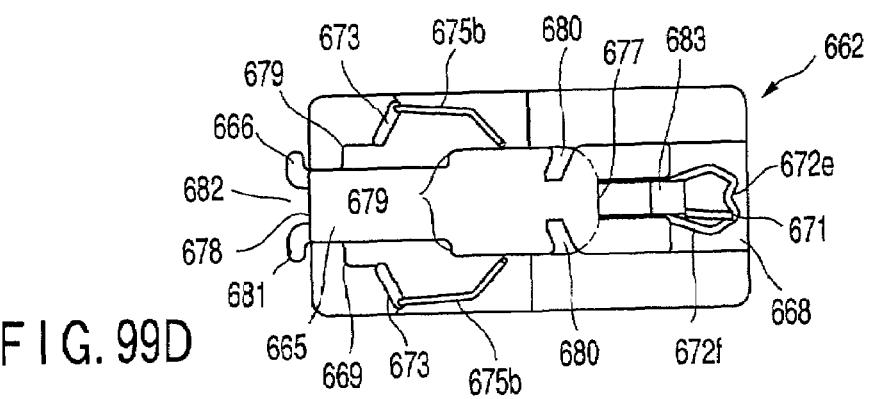
Figure 100A:
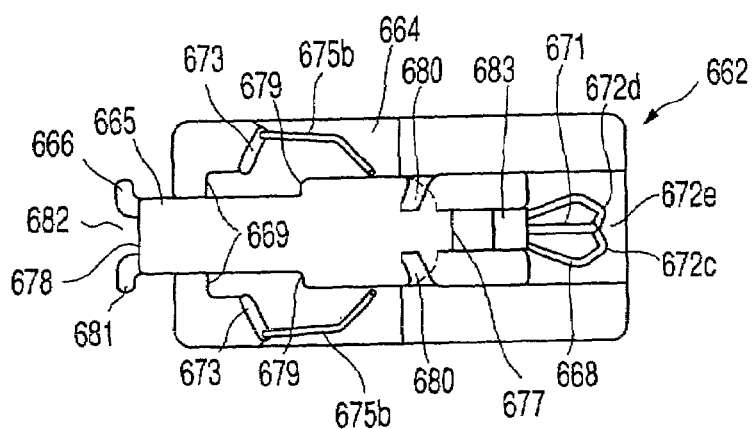
Figure 100B:
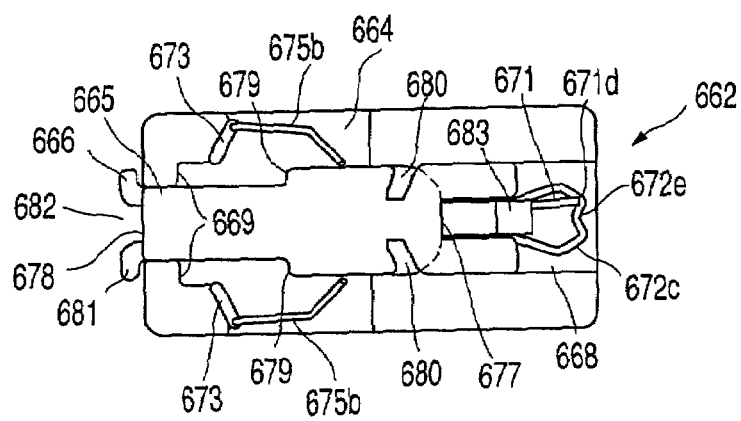
Figure 100C:
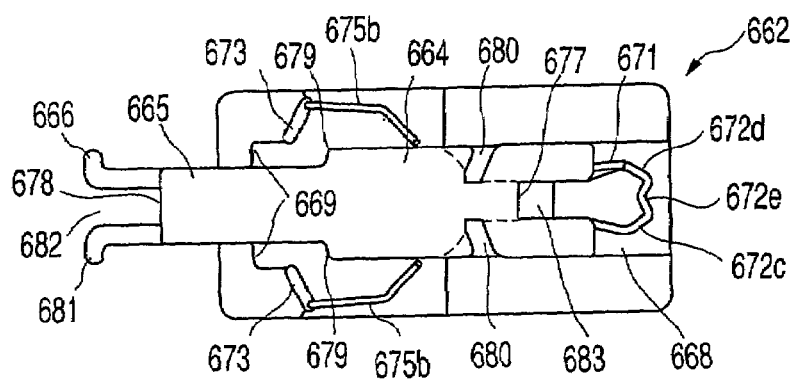
Figure 101A:
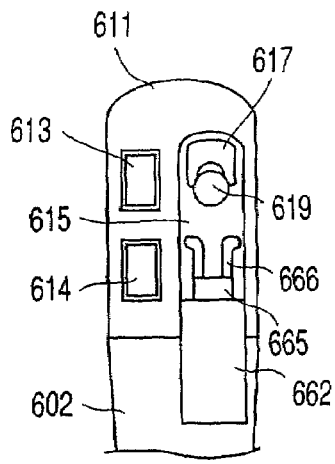
Figure 101B:
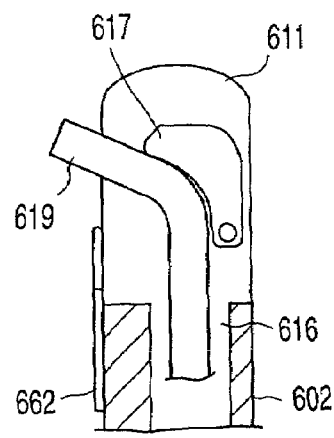
Figure 101C:
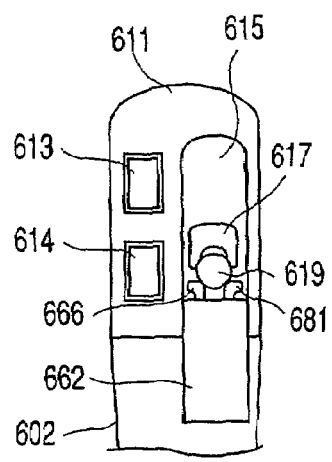
Figure 101D:
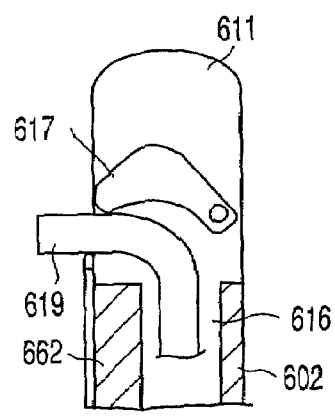
Figure 101E:
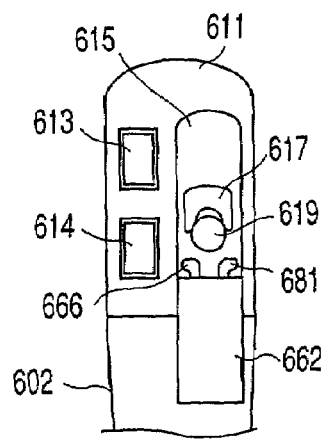
Figure 101F:
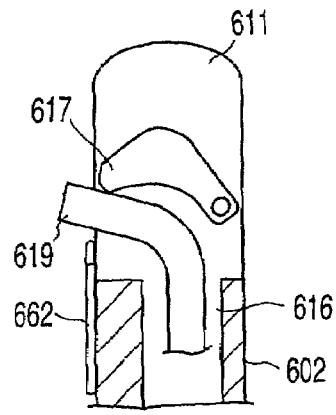
Figure 102A:
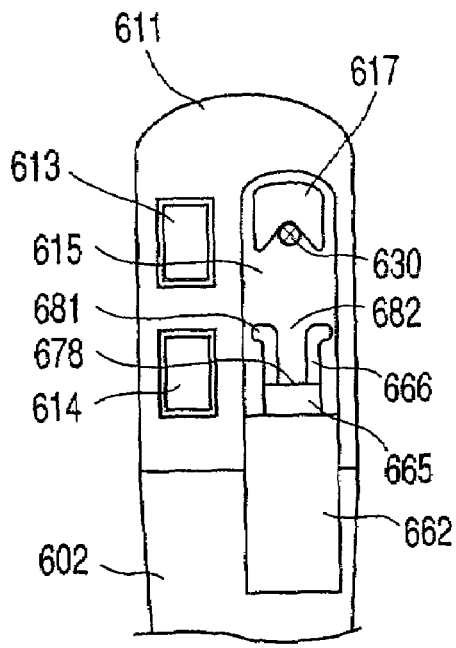
Figure 102B:
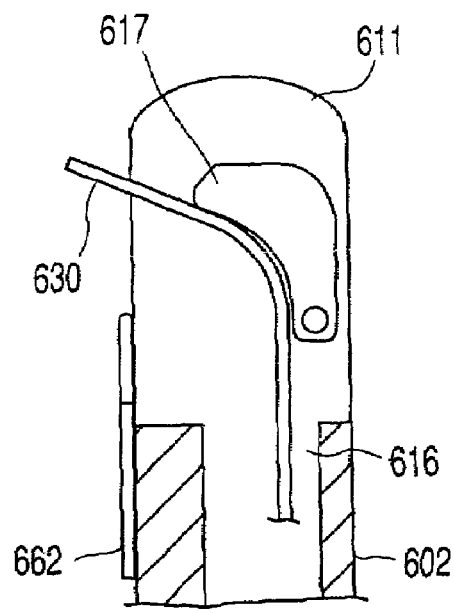
Figure 102C:
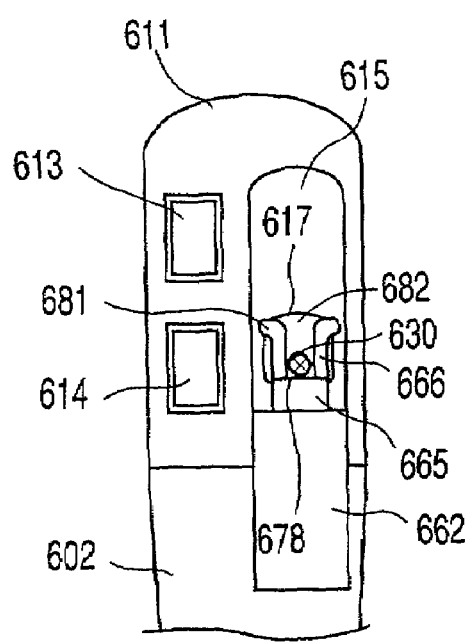
Figure 102D:
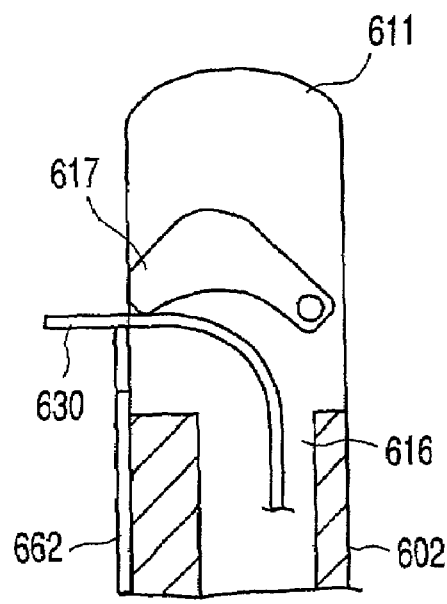
Figure 103A:
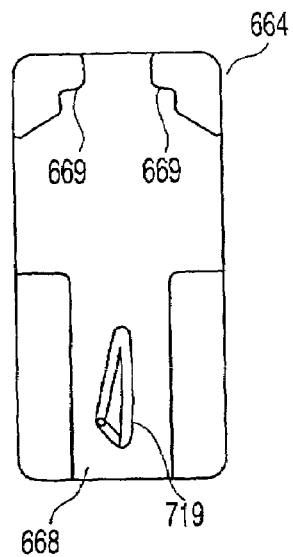
Figure 103B:
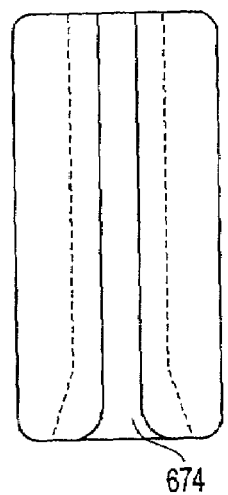
Figure 103D:
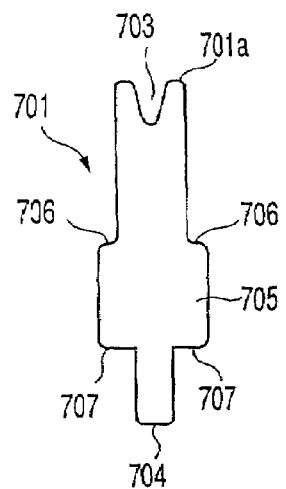
Figure 103C:
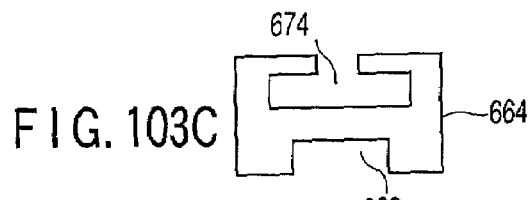
Figure 103E:
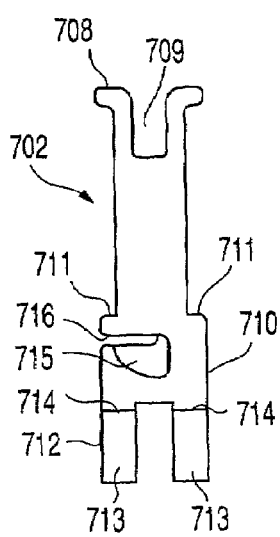
Figures 103F, 103G, 103H:
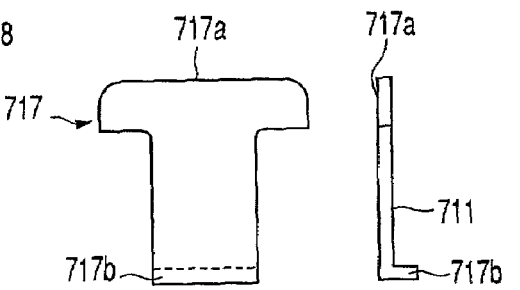
Figures 103I, 103J:
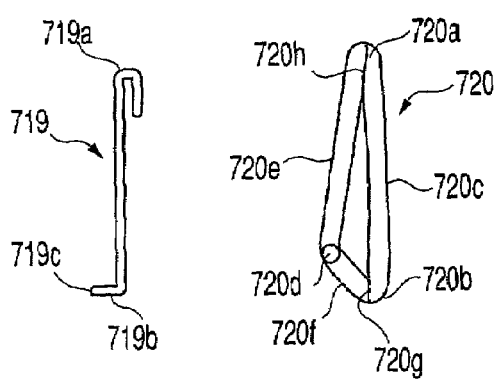
Figure 105A:
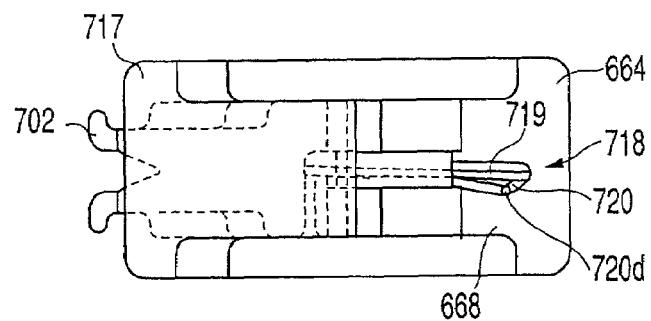
Figure 105B:
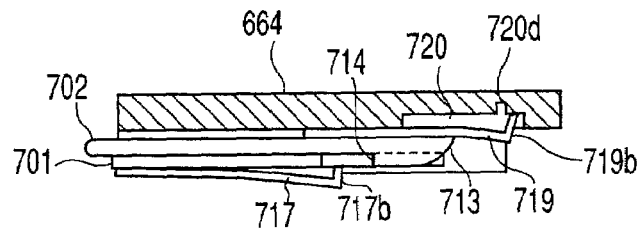
Figure 105C:
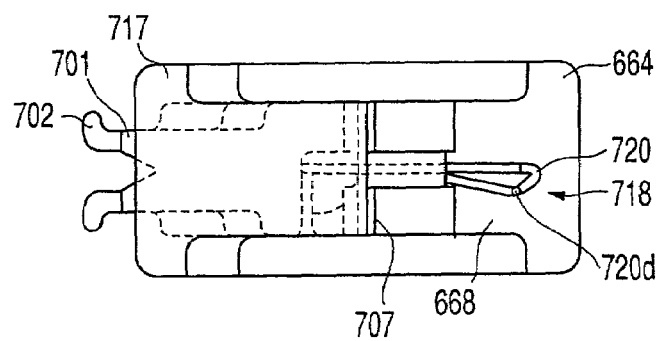
Figure 105D:
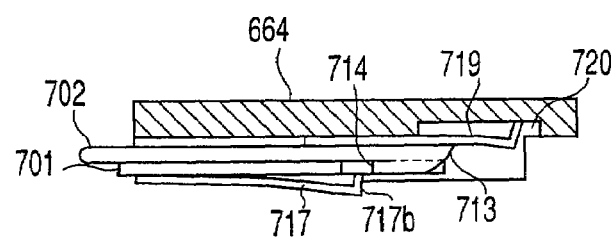
Figure 106A:
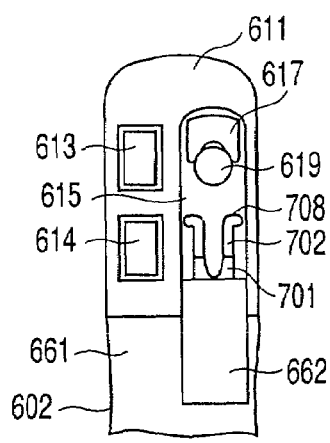
Figure 106B:
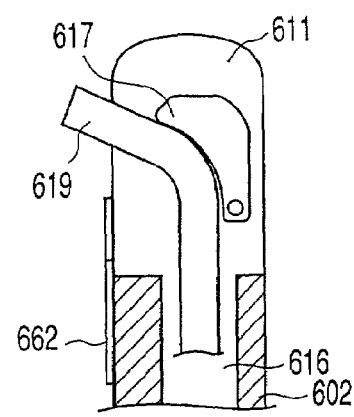
Figure 106C:
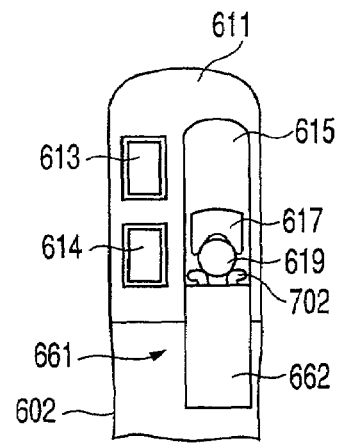
Figure 106D:
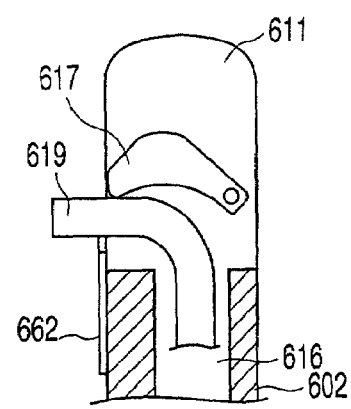
Figure 106E:
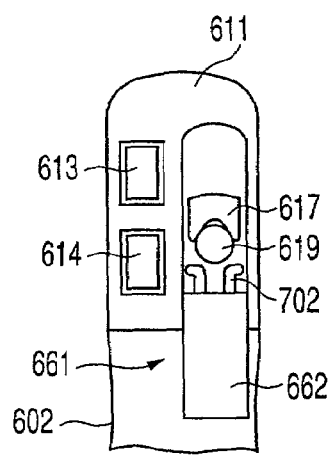
Figure 106F:
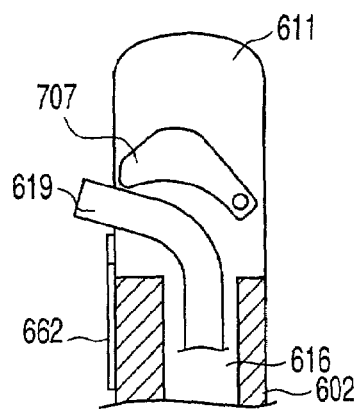
Figure 107A:
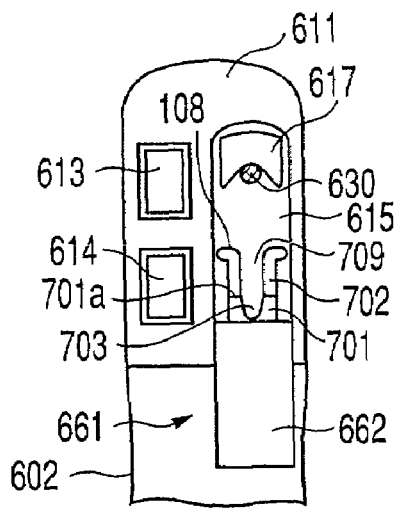
Figure 107B:
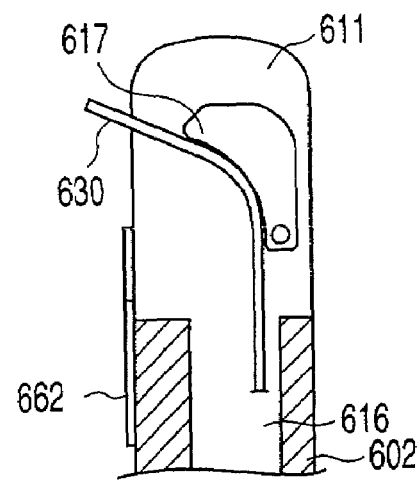
Figure 107C:
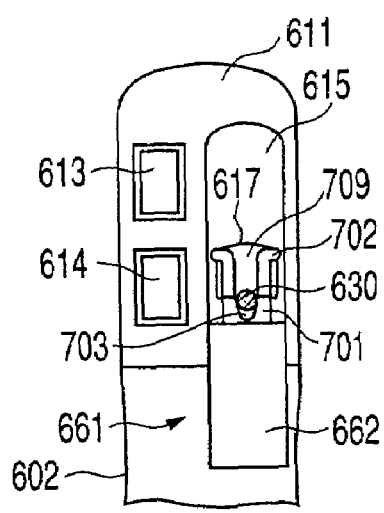
Figure 107D:
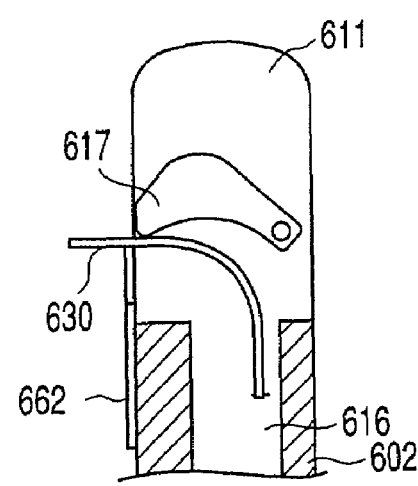
Figure 108A:
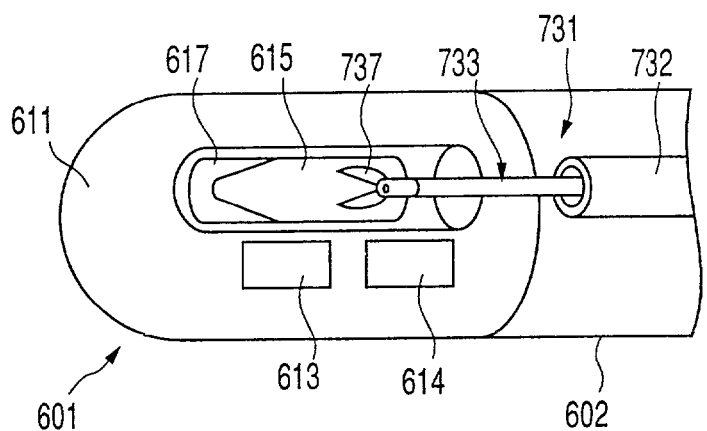
Figure 108B:
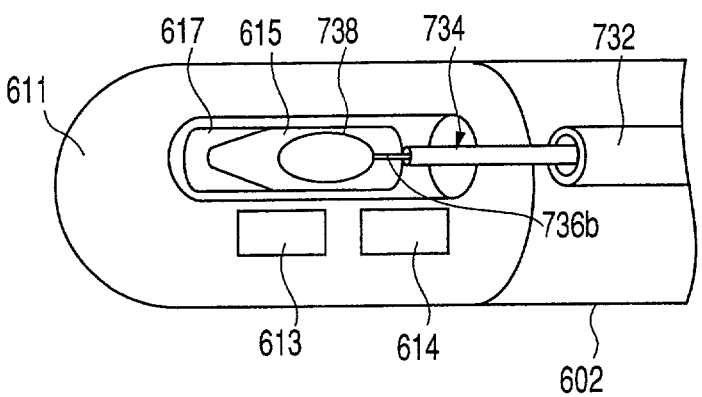
Figure 108C:
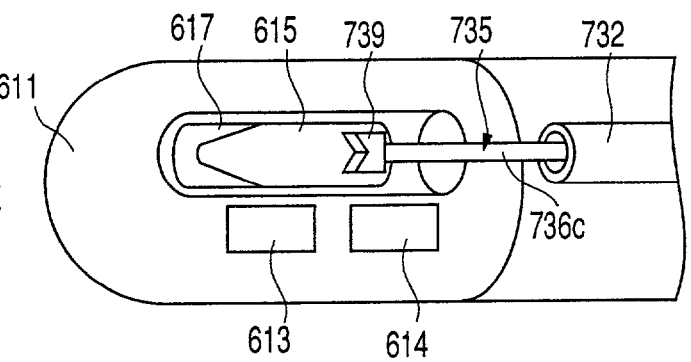
Figure 108D:
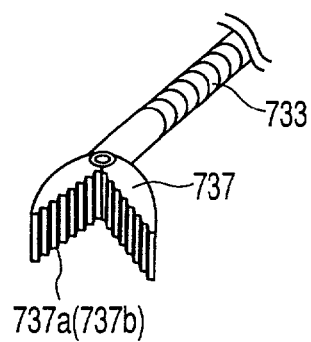
Figure 108E:
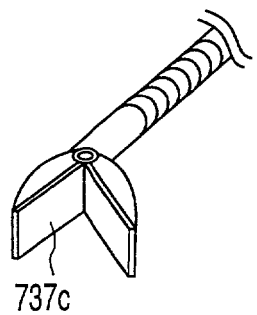
Figure 109:
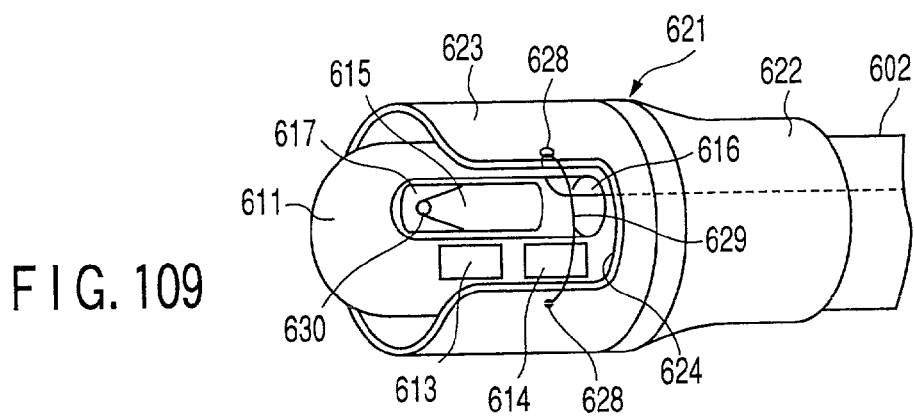
Figure 110A:
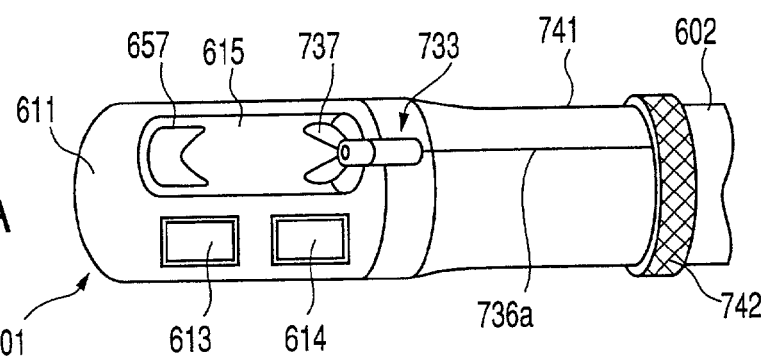
Figures 110B, 110C:
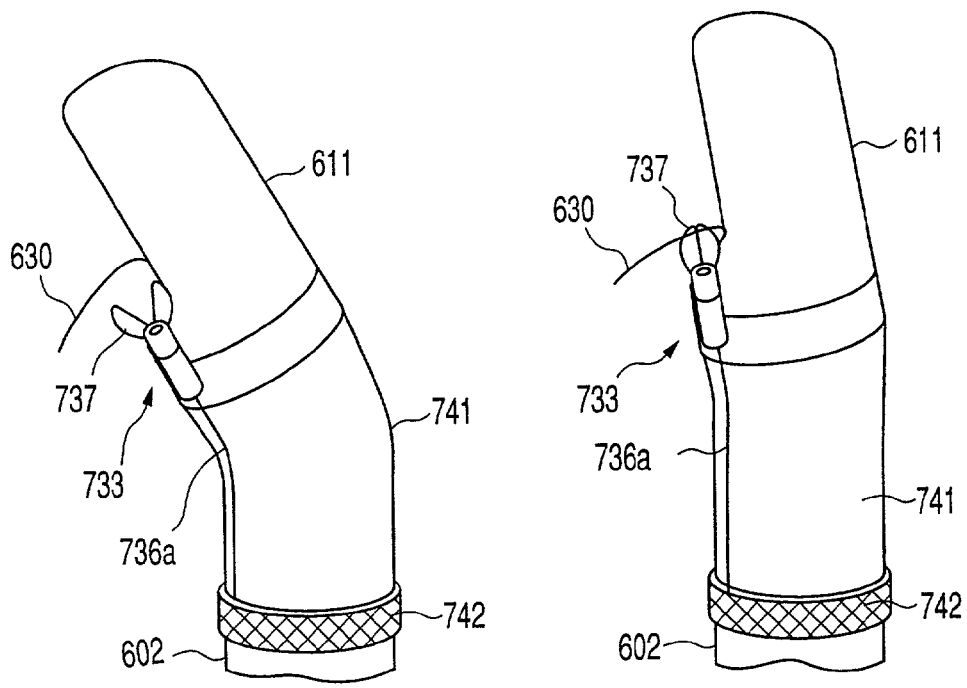
Figure 111A:
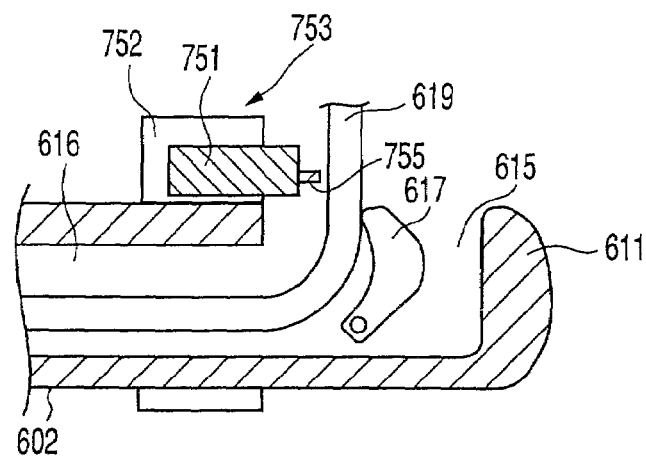
Figure 111B:
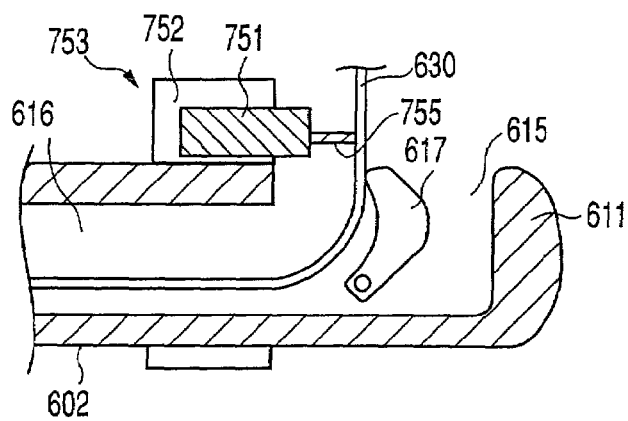
Figure 111C:
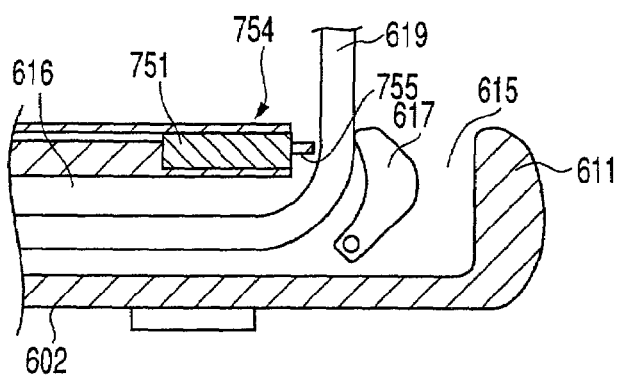
Figure 111D:
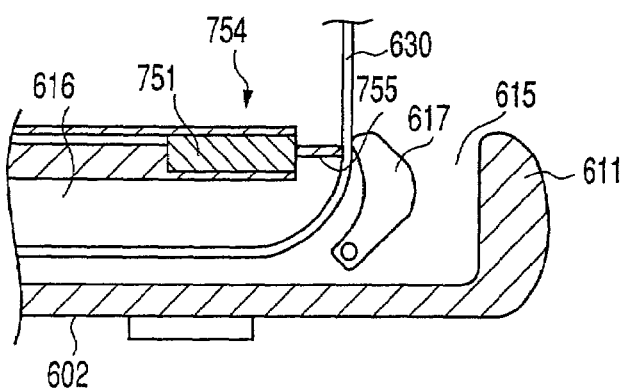
Figure 114A:
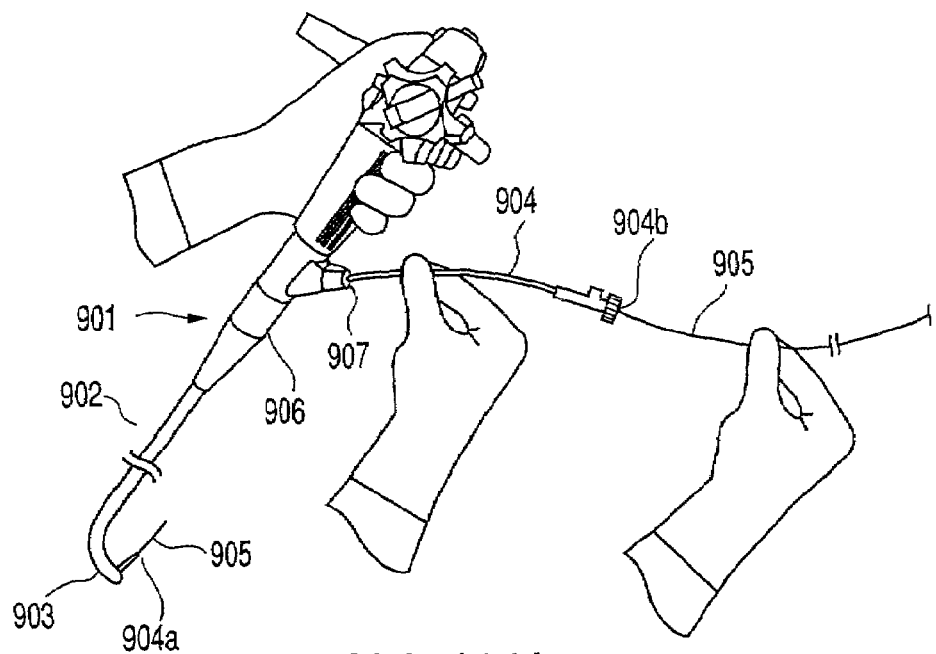
Figure 114B:
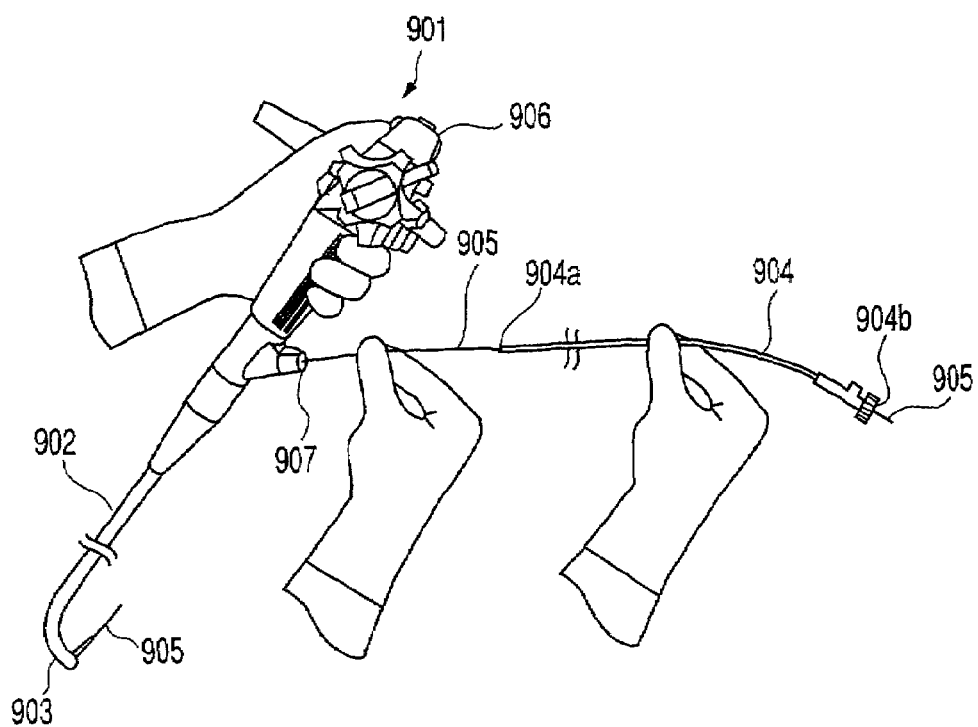

FIG. 82 is a perspective view showing the structure of the guide wire fixing member in the endoscope apparatus according to the 40th embodiment;

FIG. 83A is a perspective view showing the state before a therapeutic instrument elevator base is raised when raising a therapeutic instrument other than a guide wire by using a guide wire fixing member in the endoscope apparatus according to the 40th embodiment;

FIG. 83B is a perspective view showing the state in which the therapeutic instrument elevator base is raised in the endoscope apparatus according to the 40th embodiment;

FIG. 84A is a perspective view showing the state before the therapeutic instrument elevator base is raised when raising the guide wire by using the guide wire fixing member in the endoscope apparatus according to the 40th embodiment;

FIG. 84B is a perspective view showing the state in which the therapeutic instrument elevator base is raised in the endoscope apparatus according to the 40th embodiment;

FIG. 85 is a vertical cross-sectional view of a primary part showing the state in which the guide wire is engaged by using the guide wire fixing member in the endoscope apparatus according to the 40th embodiment;

FIG. 86A is a perspective view of a primary part showing the structure of a guide wire fixing member according to a 41st embodiment of the present invention;

FIG. 86B is a plane view showing an attachment portion of the guide wire fixing member according to the 41st embodiment;

FIG. 87A is a vertical cross-sectional view of a primary part showing an attachment mechanism for the guide wire fixing member in the state before attaching the guide wire fixing member to the end portion of the insertion portion of the endoscope in the endoscope apparatus according to the 41st embodiment;

FIG. 87B is a vertical cross-sectional view of a primary art showing the state in which the guide wire fixing member is attached to the end portion of the insertion portion of the endoscope in the endoscope apparatus according to the 41st embodiment;

FIG. 88A is a perspective view showing the state before a therapeutic instrument elevator base is raised when raising a therapeutic instrument other than a guide wire by using the guide wire fixing member in the endoscope apparatus according to the 41st embodiment;

FIG. 88B is a perspective view showing the state in which the therapeutic instrument elevator base is raised in the endoscope apparatus according to the 41st embodiment;

FIG. 89A is a perspective view showing the state before the therapeutic instrument elevator base is raised when raising the guide wire by using the guide wire fixing member in the endoscope apparatus according to the 41st embodiment;

FIG. 89B is a perspective view showing the state in which the therapeutic instrument elevator base is raised in the endoscope apparatus according to the 41st embodiment;

FIG. 90 is a plane view of a primary part showing the state in which a guide wire fixing member is attached to an end portion of an insertion portion of an endoscope in an endoscope apparatus according to a 42nd embodiment of the present invention;

FIG. 91 is a plane view of a primary part showing an attachment mechanism of the guide wire fixing member in the endoscope apparatus according to the 42nd embodiment;

FIG. 92A is a plane view of a primary part showing an attachment mechanism of the guide wire fixing member in the endoscope apparatus according to the 42nd embodiment;

FIG. 92B is an explanatory view for explaining the state in which the endoscope apparatus according to the 42nd embodiment is inserted into a celom;

FIG. 93A is a plane view of a primary part showing a guide wire fixing member main body having a guide wire identification mechanism portion and a click mechanism in the endoscope apparatus according to the 42nd embodiment;

FIG. 93B is a side view of the guide wire fixing member main body in the endoscope apparatus according to the 42nd embodiment;

FIG. 93C is a plane view showing a back surface of the guide wire fixing mechanism portion in the endoscope apparatus according to the 42nd embodiment;

FIG. 93D is a side view of the guide wire fixing mechanism portion in the endoscope apparatus according to the 42nd embodiment;

FIG. 94A is a plane view of a front surface side of the guide wire fixing member main body in the endoscope apparatus according to the 42nd embodiment;

FIG. 94B is a plane view of a back surface side of a base member in the endoscope apparatus according to the 42nd embodiment;

FIG. 94C is a side view of the base member in the endoscope apparatus according to the 42nd embodiment;

FIG. 95A is a plane view of a guide wire fixture in the endoscope apparatus according to the 42nd embodiment;

FIG. 95B is a plane view of a guide wire identification member in the endoscope apparatus according to the 42nd embodiment;

FIG. 95C is a side view of a guide wire identification member in the endoscope apparatus according to the 42nd embodiment;

FIG. 95D is a side view of a stopper in the endoscope apparatus according to the 42nd embodiment;

FIG. 95E is a plane view of the stopper in the endoscope apparatus according to the 42nd embodiment;

FIG. 96 is a plane view of a top cover arranged on a front surface side of a base member of the guide wire fixing member main body in the endoscope apparatus according to the 42nd embodiment;

FIG. 97A is a side view showing an attachment member of the guide wire fixing member in the endoscope apparatus according to the 42nd embodiment;

FIG. 97B is a plane view showing an attachment member of the guide wire fixing member in the endoscope apparatus according to the 42nd embodiment;

FIG. 98A is a view showing a click pin of the click mechanism of the guide wire fixing member in the endoscope apparatus according to the 42nd embodiment;

FIG. 98B is a view showing a click groove in the endoscope apparatus according to the 42nd embodiment;

FIG. 99A is a plane view showing an initial state of the guide wire fixing member in the endoscope apparatus according to the 42nd embodiment;

FIG. 99B is a side view of the guide wire fixing member in the endoscope apparatus according to the 42nd embodiment;

FIG. 99C is a plane view showing the state in which a stopper releasing portion of a guide wire identification member has pushed open a stopper member in the horizontal direction in the endoscope apparatus according to the 42nd embodiment;

FIG. 99D is a plane view showing the state in which the stopper is released and the guide wire fixture is thrusted down in the endoscope apparatus according to the 42nd embodiment;

FIG. 100A is a plane view showing the state in which the guide sire fixture and the guide wire identification member are held in the thrusted state in the endoscope apparatus according to the 42nd embodiment;

FIG. 100B is a plane view showing the state in which a click pin reaches a second convex portion and the locked state is released;

FIG. 100C is a plane view showing the state in which the guide wire fixture in process of returning to the initial state;

FIG. 101A is a plane view of an end portion of an insertion portion showing the state before the therapeutic instrument elevator base is raised when raising the therapeutic instrument in the endoscope apparatus according to the 42nd embodiment;

FIG. 101B is a vertical cross-sectional view of an end portion of an insertion portion showing the state before the therapeutic instrument elevator base is raised when raising the therapeutic instrument in the endoscope apparatus according to the 42nd embodiment;

FIG. 101C is a plane view of an end portion of an insertion portion showing the state in which the therapeutic instrument elevator base is raised and the stopper is released;

FIG. 101D is a vertical cross-sectional view of the end portion of the insertion portion showing the state before the therapeutic instrument elevator base is raised when raising the therapeutic instrument in the endoscope apparatus according to the 42nd embodiment;

FIG. 101E is a plane view of an end portion of an insertion portion showing the state in which the guide wire fixture and the guide wire identification member are thrusted down according to the 42nd embodiment;

FIG. 101F is a vertical cross-sectional view of the end portion of the insertion portion showing the state in which the guide wire fixture and the guide wire identification member are thrusted down according to the 42nd embodiment;

FIG. 102A is a plane view of the end portion of the insertion portion showing the state before the therapeutic instrument elevator base is raised when raising the guide wire in the endoscope apparatus according to the 42nd embodiment;

FIG. 102B is a vertical cross-sectional view of the end portion of the insertion portion showing the state before the therapeutic instrument elevator base is raised when raising the guide wire in the endoscope apparatus according to the 42nd embodiment;

FIG. 102C is a plane view of the end portion of the insertion portion showing the state in which the guide wire is pressed against and fixed to the therapeutic instrument elevator base and the guide wire fixture in the endoscope apparatus according to the 42nd embodiment;

FIG. 102D is a vertical cross-sectional view of the end portion of the insertion portion showing the state before the therapeutic instrument elevator base is raised when raising the guide wire in the endoscope apparatus according to the 42nd embodiment;

FIG. 103A is a plane view of a front surface side of a base member in a guide wire fixing portion main body according to a 43rd embodiment of the present-invention;

FIG. 103B is a plane view of a back surface side of the base member in the guide wire fixing member main body according to the 43rd embodiment;

FIG. 103C is a side view of the base member of the guide wire fixing member main body according to the 43rd embodiment;

FIG. 103D is a plane view of a guide wire fixture according to the 43rd embodiment;

FIG. 103E is a plane view of a guide wire identification member according to the 43rd embodiment;

FIG. 103F is a side view of the guide wire identification member according to the 43rd embodiment;

FIG. 103G is a plane view of a stopper member according to the 43rd embodiment;

FIG. 103H is a side view of the stopper member according to the 43rd embodiment;

FIG. 103I is a plane view of a click pin of a click mechanism according to the 43rd embodiment;

FIG. 103J is a view showing a click groove of the click mechanism according to the 43rd embodiment;

FIG. 104A is a plane view showing the initial state before a therapeutic instrument elevator base is raised in the operation of a guide wire fixing member main body when raising a therapeutic instrument in the endoscope apparatus according to the 43rd embodiment;

FIG. 104B is a vertical cross-sectional view showing the initial state before the therapeutic instrument elevator base is raised in the operation of the guide wire fixing member main body when raising the therapeutic instrument in the endoscope apparatus according to the 43rd embodiment;

FIG. 104C is a plane view showing the state in which the therapeutic instrument elevator base is raised and a stopper is released in the endoscope apparatus according to the 43rd embodiment;

FIG. 104D is a vertical cross-sectional view in the endoscope apparatus according to the 43rd embodiment;

FIG. 104E is a plane view showing the state in which a guide wire fixture and the guide wire identification member are thrusted down in the endoscope apparatus according to the 43rd embodiment;

FIG. 104F is a vertical cross-sectional view showing the state in which the guide wire fixture and the guide wire identification member are thrusted down in the endoscope apparatus according to the 43rd embodiment;

FIG. 105A is a plane view showing the click releasing state of the guide wire fixture and the guide wire identification member in the endoscope apparatus according to the 43rd embodiment;

FIG. 105B is a vertical cross-sectional view showing the click releasing state of the guide wire fixture and the guide wire identification member in the endoscope apparatus according to the 43rd embodiment;

FIG. 105C is a plane view showing the state in which the guide wire fixture and the guide wire identification member return to initial positions in the endoscope apparatus according to the 43rd embodiment;

FIG. 105D is a vertical cross-sectional view showing the state in which the guide wire fixture and the guide wire identification member return to the initial positions in the endoscope apparatus according to the 43rd embodiment;

FIG. 106A is a plane view of the end portion of the insertion portion showing the state before the therapeutic instrument elevator base is raised in the endoscope apparatus according to the 43rd embodiment;

FIG. 106B is a vertical cross-sectional view of the end portion of the insertion portion showing the state before the therapeutic instrument elevator base is raised in the endoscope apparatus according to the 43rd embodiment;

FIG. 106C is a plane view of the end portion of the insertion portion showing the state in which the therapeutic instrument elevator base is raised and the stopper is released in the endoscope apparatus according to the 43rd embodiment;

FIG. 106D is a vertical cross-sectional view of the end portion of the insertion portion showing the state in which the therapeutic instrument elevator base is raised and the stopper is released in the endoscope apparatus according to the 43rd embodiment;

FIG. 106E is a plane view of the end portion of the insertion portion showing the state in which the guide sire fixture and the guide wire identification member are thrusted down;

FIG. 106F is a vertical cross-sectional view of the end portion of the insertion portion showing the state in which the guide wire fixture and the guide wire identification member are thrusted down;

FIG. 107A is a plane view of the end portion of the insertion portion showing the state before the therapeutic instrument elevator base is raised when the guide wire is raised in the endoscope apparatus according to the 43rd embodiment;

FIG. 107B is a vertical cross-sectional view of the end portion of the insertion portion showing the state before the therapeutic instrument elevator base is raised when the guide wire is raised in the endoscope apparatus according to the 43rd embodiment;

FIG. 107C is a plane view of the end portion of the insertion portion showing the state in which the guide wire is pressed against and fixed to the therapeutic instrument elevator base and the guide wire fixture;

FIG. 107D is a vertical cross-sectional view of the end portion of the insertion portion showing the state before the therapeutic instrument elevator base is raised according to the 43rd embodiment;

FIG. 108A is a perspective view of a primary part showing the state in which a gripping therapeutic instrument is inserted into an external channel according to a 44th embodiment of the present invention;

FIG. 108B is a perspective view of a primary part showing the state in which a snare in the gripping therapeutic instrument is inserted into the external channel according to the 44th embodiment;

FIG. 108C is a perspective view of a primary part showing the state in which a guide wire thrusting plate in the gripping therapeutic instrument is inserted into the external channel according to the 44th embodiment;

FIG. 108D is a perspective view of a primary part showing non-slip zigzag grooves of a contact surface of an arm portion of the gripping therapeutic instrument shown in FIG. 108A with the guide wire;

FIG. 108E is a perspective view of a primary part showing the state in which resin such as rubber is applied to a contact surface of the arm portion of the gripping therapeutic instrument shown in FIG. 108C with the guide wire;

FIG. 109 is a perspective view of a primary part showing the attachment state of a guide wire fixing member in an endoscope apparatus according to a 45th embodiment of the present invention;

FIG. 110A is a perspective view of a primary part showing the state in which a gripping therapeutic instrument is attached to an end portion of an insertion portion in an endoscope according to a 46th embodiment of the present invention;

FIG. 110B is a perspective view of a primary part showing the state in which a bending portion of the endoscope according to the 46th embodiment is curved to relax an operation wire;

FIG. 110C is a perspective view of a primary part showing the state in which a guide wire is raised to a position at which it can be pinched by the gripping therapeutic instrument in the endoscope according to the 46th embodiment;

FIG. 111A is a vertical cross-sectional view of a primary part showing the set-up state of the therapeutic instrument when the guide wire fixing member is detachably attached in the vicinity of the end portion of the insertion portion of the endoscope;

FIG. 111B is a vertical cross-sectional view of a primary part showing the state in which the guide wire is raised in place of the therapeutic instrument shown in FIG. 111A;

FIG. 111C is a vertical cross-sectional view of a primary part showing the set-up state of the therapeutic instrument when the guide wire fixing member is embedded in the vicinity of the end portion of the insertion portion of the endoscope;

FIG. 111D is a vertical cross-sectional view of a primary part showing the state in which the guide wire is raised in place of the therapeutic instrument shown in FIG. 111A;

FIG. 112A is a plane view of a primary part showing the end portion of the insertion portion in an existing endoscope;

FIG. 112B is a side view of FIG. 112A;

FIG. 112C is a plane view of a primary part showing an endoscope which has a guide wire fixing member setting space at the end portion of the insertion portion of the endoscope;

FIG. 112D is a side view of FIG. 112C;

FIG. 112E is a plane view of a primary part showing an endoscope having an attachment member of a guide wire fixing mechanism portion;

FIG. 112F is a side view of FIG. 112E;

FIG. 112G is a plane view of a primary part showing an endoscope in which a guide wire fixing member having a guide wire fixing mechanism portion is undetachably included;

FIG. 112H is a side view of FIG. 112G;

FIG. 113A is a plane view of a primary part showing a modification of a guide wire;

FIG. 113B is a plane view of a primary part showing another modification of the guide wire;

FIG. 113C is a plane view of a primary part showing still another modification of the guide wire;

FIG. 114A is an explanatory drawing for illustrating the operation state for pulling out a catheter from a therapeutic instrument insertion channel of an endoscope when performing endoscopic treatment by using the endoscope by a conventional method; and FIG. 114B is an explanatory drawing for illustrating the operation state for completely pulling out the catheter from the endoscope.

DETAILED DESCRIPTION OF THE INVENTION

Figure 1:
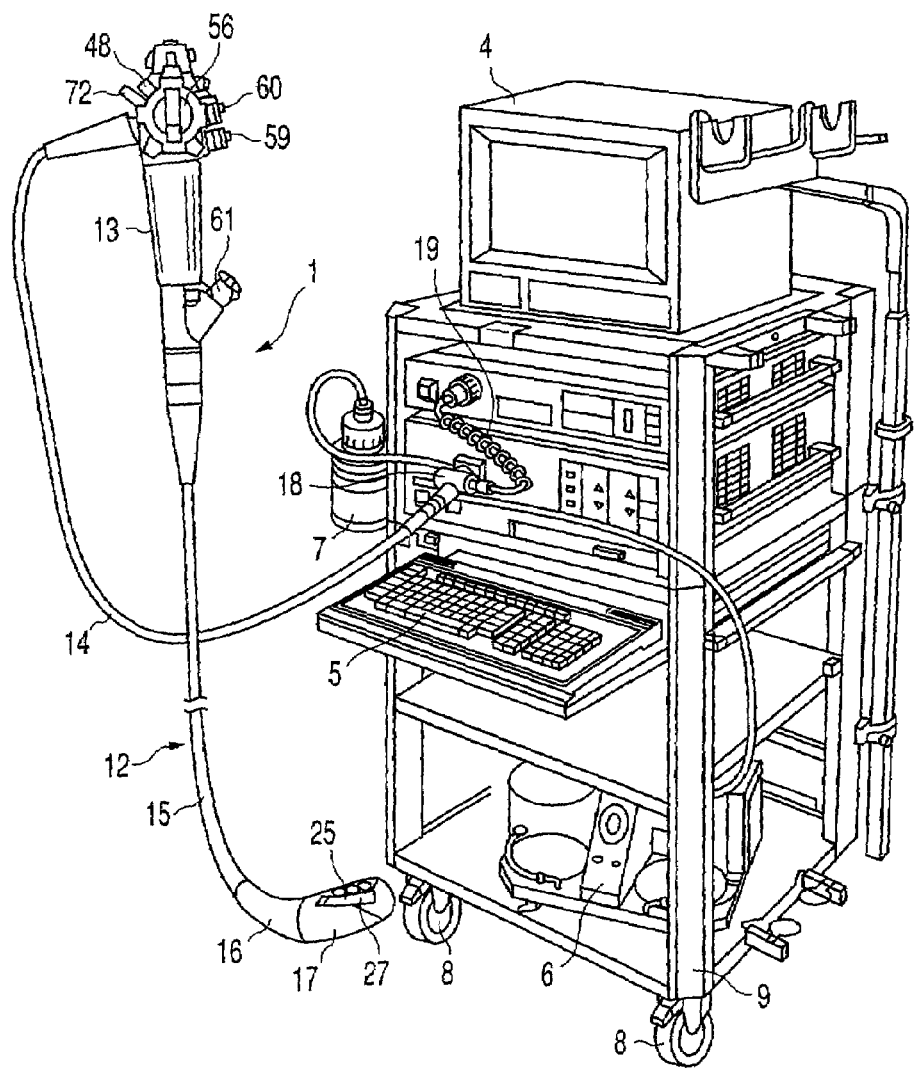
FIG. 1 is a perspective view showing a schematic structure of an entire system of an endoscope apparatus in which an endoscope and various kinds of external devices are incorporated according to a first embodiment of the present invention.

FIGS. 1 to 6B show a first embodiment according to the present invention. FIG. 1 shows a schematic structure of an entire system of an endoscope apparatus in which an endoscope 1 and various kinds of external devices are incorporated according to this embodiment. As the external devices, there are devices such as a light source device 2, an image processing device 3, a monitor 4, an input keyboard 5, a suction pump device 6, a water supply jar 7 and others, and these devices are set in a shelf having carriers 8.

Further, to the endoscope 1 are provided an elongated insertion portion 12 which is inserted into a celoma, an operation portion 13 on a front side which is connected to a base end portion of the insertion portion 12, a universal cord 14 whose base end portion is connected to the operation portion 13. Furthermore, to the insertion portion 12 are provided respective constituent parts including an elongated flexible pipe portion 15 having the flexibility, a bending portion 16 connected to an end of the flexible pipe portion 15, and an end portion 17 arranged at a leading edge position of the insertion portion 12.

Moreover, a connector 18 is provided to an end portion of the universal cord 14 connected to the operation portion 13. A light guide pipe or an electrical contact portion is provided to this connector 18. In addition, this connector 18 is connected to the light source device 2 and the image processing device 3 as the external devices, respectively.

Figure 7A:
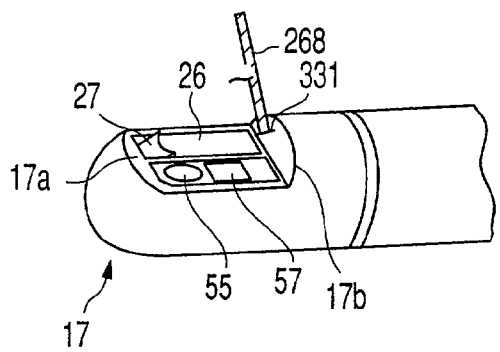
FIG. 7A is a perspective view of a primary part showing a schematic structure of an end portion of an insertion portion in an endoscope according to a second embodiment of the present invention.

Additionally, as shown in FIG. 7A, a concave notch portion 17a obtained by notching one side surface is formed on the outer peripheral surface of the end portion 17 of the endoscope 1. Further, a channel opening portion 26 is arranged on one side portion of this notch portion 17a. Furthermore, an observation optical system object lens (not shown) and an illumination optical system illumination lens (not shown) are provided in alignment next to the channel opening portion 26.

Moreover, an air supply/water supply nozzle (not shown) protrudes on a rear end wall surface 17b of the notch portion 17a of the end portion 17. In addition, a fluid such as water or air is blown from this nozzle to the external surface of the object lens, thereby cleaning the lens surface.

In addition, to the operation portion 13 of the endoscope 1 are provided a curving operation portion 56 for curving the bending portion 16 of the insertion portion 12 in the vertical/horizontal direction, an air supply/water supply button 59, and a suction operation button 60. Also, an insertion opening portion 61 which is connected to the therapeutic instrument insertion channel 23 is provided. Additionally, the nozzle of the end portion 17 is caused to selectively inject the gas and the liquid by the operation of the air supply/water supply button 59. Further, the suction force is selectively caused to act on the channel opening portion 26 of the end portion 17 by the operation of the suction operation button 60 through the therapeutic instrument insertion channel 23, thereby collecting mucin and the like in a celoma.

Figure 3:
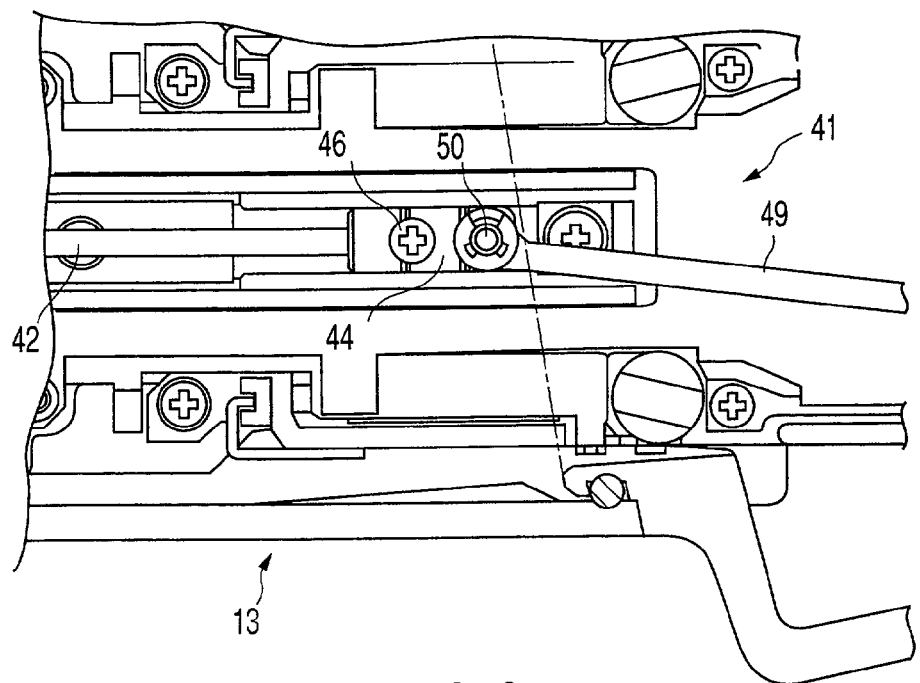
FIG. 3 is a plane view showing a primary part of an elevator base actuation mechanism included in an operation portion in the endoscope according to the first embodiment.
Figure 4:
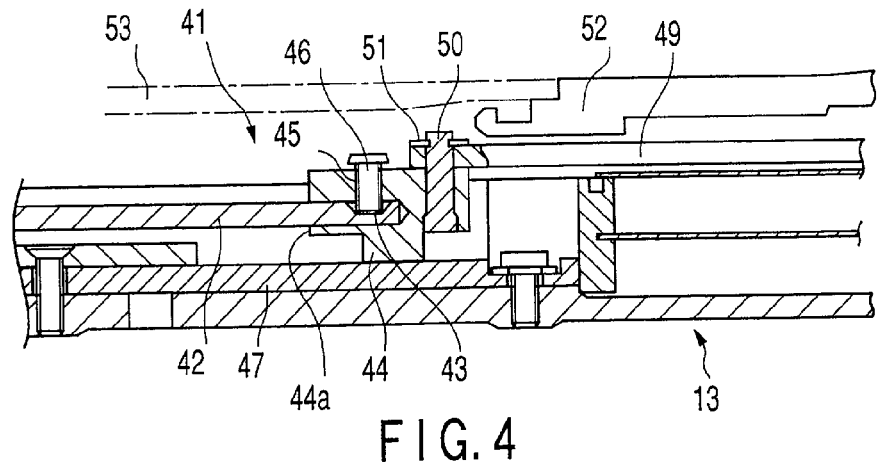
FIG. 4 is a vertical cross-sectional view showing a primary part of the elevator base actuation mechanism included in the operation portion in the endoscope according to the first embodiment.
Figure 5:
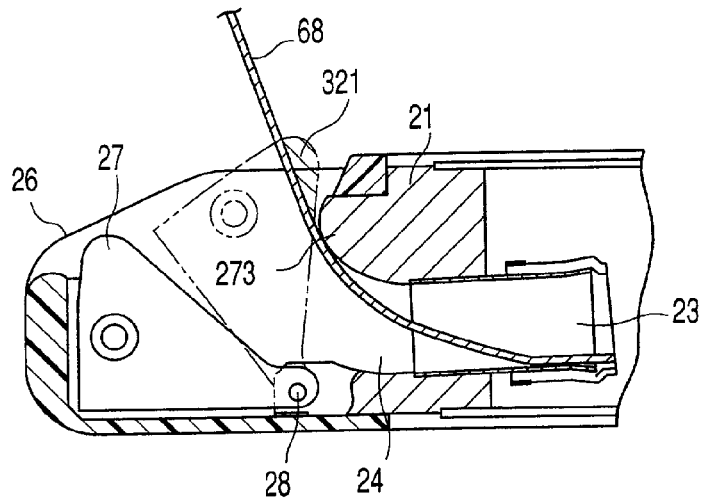
FIG. 5 is a vertical cross-sectional view showing a primary part of the inner structure of the end portion of the insertion portion in the endoscope according to the first embodiment.

Furthermore, as shown in FIGS. 3 and 4, an elevator base actuation mechanism 41 for operating the set-up wire 30 is included in the operation portion 13. A wire fixing member 42 consisting of a hard bar-like material such as a metal is integrally fixed to a base end portion of the set-up wire 30 by solder and the like. An engagement groove 43 made up of a concave portion is formed at a base end portion of the wire fixing member 42 as shown in FIG. 4.

Moreover, a link member 44 constituted by a hard block body such as a metal is fixed to the base end portion of the wire fixing member 42. An insertion hole 44a of the wire fixing member 42 is formed at the link member 44. In addition, the base end portion of the wire fixing member 42 is fitted into the insertion hole 44a of the link member 44. Areas of the base end portion of the wire fixing member 42 to which the engagement groove 43 is formed are all fitted in the insertion hole 44a of the link member 44.

Additionally, a female screw portion 45 to which a fixing screw 46 of the wire fixing member 42 is screwed and inserted is provided to the link member 44. Further, an end portion of the fixing screw 46 screwed to the female screw portion 45 of the link member 44 is engaged in the engagement groove 43 of the wire fixing member 42 in the inserted state. As a result, the wire fixing member 42 is connected to the link member 44 in the fixed state.

Furthermore, a base 47 as a base board of the operation portion 13 is provided inside the operation portion 13. Moreover, the link member 44 is arranged in the longitudinal direction of the base 47 so as to be capable of moving back and forth.

In addition, one end portion of an arm 49 is connected to the link member 44 by a link shaft 50 as a bar-like shaft member so as to be capable of swiveling. An engagement member 51 consisting of a C type or E type snap ring and the like is engaged with an end portion which is on the opposite side to the end portion of the base 47 side in the link shaft 50.

Further, the other end portion of the arm 49 is connected to an elevator operation knob 48 which is provided in contiguity with the curving operation portion 56. Furthermore, a set-up wire 30 is pulled by the operation of the elevator operation knob 48 in the operation portion 13 through the arm 49, the link member 44 and the wire fixing member 42 in sequence, and derricking motion of the therapeutic instrument elevator base 27 is caused around an elevator base swivel supporting point. As a result, a guide catheter and a guide wire 68 which are inserted into the therapeutic instrument insertion channel 23 and led to the outside from the channel opening portion 26 are raised by raising the therapeutic instrument elevator base 27.

Figure 2:
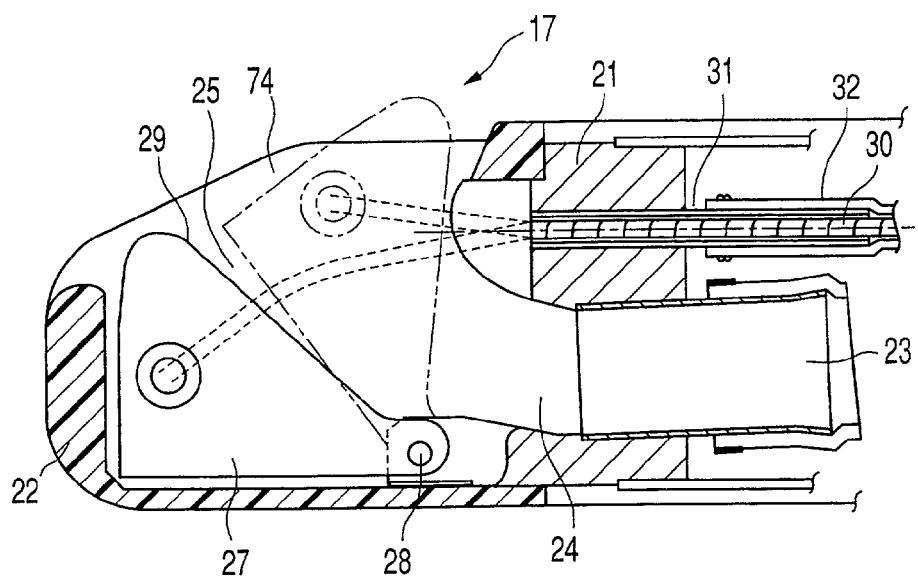
FIG. 2 is a vertical cross-sectional view showing a primary part of an inner structure of an end portion of an insertion portion in the endoscope according to the first embodiment.

The structure of the end portion 17 of the insertion portion 12 will now be described in detail with reference to FIG. 2. An end hard portion 21 as an end portion main body and an end cover 22 which is formed of a non-conductive material such as resin so as to surround the end hard portion 21 are provided to the end portion 17. The end cover 22 is fixed to the end hard portion 21 by an adhesive and the like.

Further, a lead-in guide path 24 for guiding leading of a therapeutic instrument and the like to the end side is formed at the end hard portion 21. This lead-in guide path 24 is formed so as to be connected with the therapeutic instrument insertion channel (insertion hole) 23 as a therapeutic instrument insertion guide path provided in the insertion portion 12 of the endoscope 1.

Furthermore, to the end side of the lead-in guide path 24 is provided an accommodation chamber 25 as a space portion formed by the end hard portion 21 and the end cover 22. Moreover, a channel opening portion 26 constituting the end opening portion of the therapeutic instrument insertion channel 23 is formed by the opening portion of the accommodation chamber 25.

Moreover, a therapeutic instrument elevator base 27 for raising, e.g., a therapeutic instrument led through the channel 23 or a therapeutic instrument such as a guide catheter to a desired position is provided in the accommodation chamber 25. One end of the therapeutic instrument elevator base 27 is pivoted by an elevator base swivel supporting point 28 provided to the end hard portion 21.

The elevator base swivel supporting point 28 is arranged at a lower part of the end opening portion of the lead-in guide path 24. In addition, the therapeutic instrument elevator base 27 is attached in the accommodation chamber 25 with the elevator base swivel supporting point at the center so as to be capable of a derricking motion so that the therapeutic instrument elevator base 27 can swivel from a standby position indicated by solid lines shown in FIG. 2 to a therapeutic instrument set-up position indicated by dotted lines in the same drawing.

In addition, a guide plane 29 for guiding, e.g., a therapeutic instrument or that such as a guide catheter is formed on the therapeutic instrument elevator base 27. This guide plane 29 has a cross-sectional shape which is continuous from the lead-in guide path 24 being formed by a substantially-V-shaped groove.

Additionally, an end portion of a set-up wire 30 is fixed to the therapeutic instrument elevator base 27. This set-up wire 30 is led to the operation portion 13 side through a guide pipe 31 and a guide tube 32 inserted into the insertion portion 12, and connected to a later-described elevator base operation mechanism 41. Further, the therapeutic instrument elevator base 27 is configured to perform the derricking motion with the elevator base swivel supporting point 28 at the center by the towing operation of the set-up wire 30.

Figure 6A:
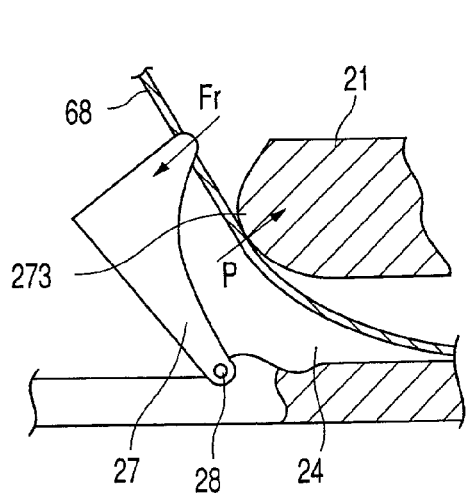
FIG. 6A is a vertical cross-sectional view of a primary part showing the engagement state of a guide wire in the endoscope according to the first embodiment.
Figure 6B:
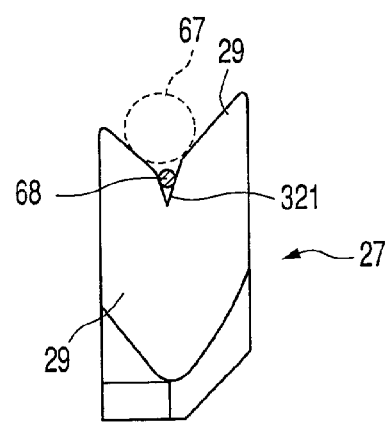
FIG. 6B is a front view of a therapeutic instrument elevator base in the endoscope according to the first embodiment.

Furthermore, as shown in FIG. 6B, a wire engagement groove 321 having a slit-like shape is provided as guide wire fixing means on the bottom of the substantially-V-shaped groove in the guide plane 29 of the therapeutic instrument elevator base. This wire engagement groove 321 has two opposed wall surfaces and a width such that only the outer periphery of the guide wire 68 is brought into contact with the walls. Moreover, the guide wire 68 is releasably engaged with the wire engagement groove in the inserted state.

Incidentally, as the wire engagement groove 321, a grove whose width is narrowed in the tapered shape toward the bottom and which has a substantially-V-shaped cross section is preferable. In addition, it is also good that the relationship between an opening portion slit width (groove width) T1 of the wire engagement groove 321, a wire diameter D1 of the guide wire 68 and an outside diameter D2 of the therapeutic instrument or any other therapeutic instrument such as a catheter is set to "D1<T1<D2".

The effect of this embodiment will now be described. When the endoscope 1 according to this embodiment is used, a guide catheter is inserted into the therapeutic instrument insertion channel 23 from the insertion opening portion 61 of the operation portion 13 of the endoscope 1. Additionally, the guide catheter is caused to protrude from the channel opening portion 26 to the outer side and inserted into a pancreatic/hepatic duct (not shown) in the papillotomy manner. Thereafter, the currently used guide catheter is replaced with a therapeutic instrument which is subsequently used.

In the operation for replacing the therapeutic instrument, the guide wire 68 is first inserted from a mouth ring of the guide catheter on the base end side. Insertion of the end portion of the guide wire 68 into the pancreatic/hepatic duct is confirmed by an observation image (endoscopic image) of the endoscope 1, and the base end side of the guide wire 68 is gripped by hand.

Subsequently, in this state, the operation for pulling out the guide catheter is performed, and an observation image is used to confirm that the guide catheter has been pulled out from the papilla. Thereafter, the catheter is further pulled out toward the front side. Further, with the end of the guide catheter being accommodated in the channel opening portion 26, an elevator operation knob 48 of the therapeutic instrument elevator base 27 is operated. With the operation of the elevator operation knob 48, the set-up wire 30 is operated and towed, and the therapeutic instrument elevator base 27 is caused to swivel around the elevator base swivel supporting point 28 and raised as indicated by the dotted lines shown in FIG. 5.

Furthermore, when raising the therapeutic instrument elevator base 27 as shown in FIG. 6A, the guide wire 68 is led into the wire engagement groove 321 along the substantially-V-shaped groove in the guide plane 29 of the therapeutic instrument elevator base 27 as shown in FIG. 6B. Then, the guide wire 68 is releasably engaged while being inserted in the wire engagement groove 321. At this moment, the guide wire 68 is pressed against an upper surface 273 side of the lead-in guide path 24 of the end hard portion 21 by the therapeutic instrument elevator base 27 as indicated by an arrow P in FIG. 6A. At this moment, since the reaction force indicated by an arrow Fr in FIG. 6A acts from the hard guide wire 68 so as to maintain the linear shape, this reaction force causes the guide wire 68 to be strongly engaged by being pushed into the wire engagement groove 321. As a result, the guide wire 68 is mechanically fixed to the end portion 17 of the insertion portion 12 in this state.

Moreover, after an observation image of the endoscope 1 is used to confirm that the guide wire 68 has been fixed, the guide catheter is completely pulled out from the operation portion 13 side of the endoscope 1 to the outside of the therapeutic instrument insertion channel 23.

Thereafter, a therapeutic instrument which is subsequently used is inserted from the base end side of the guide wire 68. At this moment, with the guide wire 68 being used as a guide, the therapeutic instrument is inserted into the therapeutic instrument insertion channel 23. Then, when the end of the therapeutic instrument is brought into contact with the therapeutic instrument elevator base 27, the therapeutic instrument elevator base 27 is lowered by the operation of the elevator operation knob 48. As a result, when the therapeutic instrument passes the vicinity of the therapeutic instrument elevator base 27, the thrusting force of the therapeutic instrument at this moment pushes out the guide wire 68 from the wire engagement groove 321, thereby releasing fixation of the guide wire 68. In addition, the therapeutic instrument is inserted into a pancreatic/hepatic duct.

The following advantage can be demonstrated in this embodiment. That is, in this embodiment, the guide wire 68 can be readily fixed by the regularly performed operation for raising the therapeutic instrument elevator base 27, namely, operating the elevator operation knob 48 of the operation portion 13 on the front side in the endoscope 1.

Additionally, in this embodiment, since conventional therapeutic instruments can be used as they are, the excellent operability can be maintained without being deteriorated by using the therapeutic instrument that an operator is used to dealing with. Therefore, the therapeutic instrument can be easily replaced in a shorter time without impairing the conventional operation method of the therapeutic instrument or the operation style.

Further, since the guide wire 68 can be fixed at the end portion 17 of the insertion portion 12 of the endoscope 1, the length of the guide wire 68 can be shortened. Therefore, rolling of the guide wire 68 can be facilitated, and a large operation space is no longer necessary. Furthermore, replacement of the therapeutic instrument can be facilitated, and the number of assistants can be decreased, which results in reduction in the operation time.

Moreover, by forming the wire engagement groove 321 into a substantially V shape, the guide wire 68 whose outside diameter subtly differs can be stably and strongly engaged with the wire engagement groove 321. In addition, by providing the wire engagement groove 321 to the therapeutic instrument elevator base 27, the guide wire 68 led to the guide plane 29 is constantly placed in the same wire engagement groove 321. Therefore, at the time of the operation for fixing the guide wire 68, the fixed state of the guide wire 68 is constantly stabled each and every time, and irregularities in the fixing strength caused due to a position of the guide wire 68 can be eliminated.

Additionally, in this embodiment, the relationship between the slit width (groove width) T1 of the wire engagement groove 321, the wire diameter D1 of the guide wire 68 and the outside diameter D2 of the therapeutic instrument or any other counterpart such as the catheter 67 is set to "D1≦T1<D2". Therefore, as indicated by a dotted line in FIG. 6B, the therapeutic instrument which is usually used, for example, the tube-like catheter 67 fitted on the guide wire 68 can be successfully used without being caught in the wire engagement groove 321.

Figure 7B:
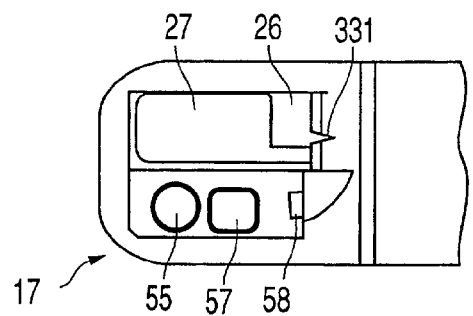
FIG. 7B is a plane view showing the end portion of the insertion portion in the endoscope according to the second embodiment.
Figure 7C:
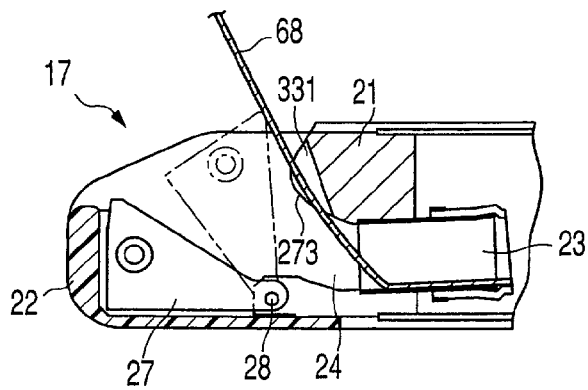
FIG. 7C is a vertical cross-sectional view of a primary part showing the state in which a guide wire in the endoscope is moved to an engagement position according to the second embodiment.

Further, FIGS. 7A to 7C show a second embodiment according to the present invention. In this embodiment, the structure of the end portion 17 of the insertion portion 12 in the endoscope 1 according to the first embodiment is modified as follows.

That is, in this embodiment, a slit-like wire engagement groove 331 corresponding to the wire engagement groove 321 of the therapeutic instrument elevator base 27 for fixing the guide wire 68 in the first embodiment is provided on the upper surface 273 side of the lead-in guide path 24 of the end hard portion 21. The relationship between the opening portion slit width (groove width) T1 of the wire engagement groove 331, the wire diameter D1 of the guide wire 68 and the outside diameter D2 of the therapeutic instrument or any other therapeutic instrument such as the guide catheter is set to "D1≦T1<D2" as in the first embodiment.

The effect of this embodiment will now be described. When the endoscope 1 according to this embodiment is used, as in the first embodiment, after the guide catheter and the guide wire 68 are inserted into the body through the channel 23, the elevator operation knob 48 of the therapeutic instrument elevator base 27 is operated with the guide catheter being pulled into the introduction guide path 24 or the channel 23. With the operation of the elevator operation knob 48, the set-up wire 30 is operated to be towed, and the therapeutic instrument elevator base 27 is caused to swivel around the elevator base swivel supporting point 28 and raised as indicated by dotted lines in FIG. 7C.

Furthermore, when raising the therapeutic instrument elevator base 27, the guide wire 68 is pressed against the upper surface 273 side of the lead-in guide path 24 of the end hard portion 21 by the therapeutic instrument elevator base 27 as shown in FIG. 7C.

At this moment, since the reaction force acts from the hard guide wire 68 so as to maintain the linearity, the guide wire 68 is strongly engaged in the wire engagement groove 331 of the end hard portion 21 by this reaction force. Therefore, as shown in FIG. 7A, the guide wire 68 is mechanically fixed to the end portion 17 of the insertion portion 12 in this state.

Moreover, after confirming that the guide wire 68 has been fixed, the guide catheter is completely pulled out from the operation portion 13 side of the endoscope 1 to the outside of the therapeutic instrument insertion channel 23.

Then, a therapeutic instrument which is subsequently used is inserted from the base end side of the guide wire 68. At this moment, with the guide wire 68 being used as a guide, the therapeutic instrument is inserted into the treatment insertion channel 23. Then, when the end of the therapeutic instrument is brought into contact with the therapeutic instrument elevator base 27, the therapeutic instrument elevator base 27 is lowered by the operation of the elevator operation knob 48. When the therapeutic instrument passes the vicinity of the therapeutic instrument elevator base 27 in this state, the guide wire 68 is pushed out from the wire engagement groove 331 by the thrusting force of the therapeutic instrument at this moment, thereby releasing fixation of the guide wire 68.

The following advantage can be demonstrated in this embodiment. That is, in this embodiment, the guide wire 68 can be readily fixed by only the operation for raising the therapeutic instrument elevator base 27 which is usually carried out on the front operation portion 13 side in the endoscope 1. Thus, the advantage similar to that in the first embodiment can be also obtained in this embodiment.

Moreover, in this embodiment, since the relationship between the opening portion slit width (groove width) T1 of the wire engagement groove 331, the wire diameter D1 of the guide wire 68, and the outside diameter D2 of the therapeutic instrument or any other therapeutic instrument such as the guide catheter is set to "D1≦T1<D2", the regularly used therapeutic instrument can be successfully used without being caught in the wire engagement groove 331.

Figure 7D:
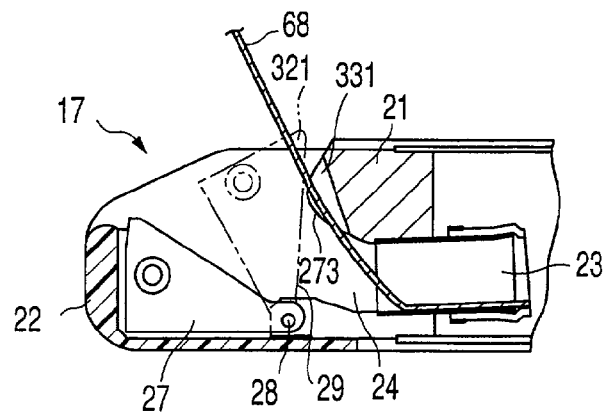
FIG. 7D is a vertical cross-sectional view of a primary part showing a modification of the first and second embodiments.

As a modification of the first and second embodiments, it is possible to provide both the wire engagement grove 331 provided on the upper surface 273 side of the lead-in guide path 24 of the end hard portion 21 described in connection with the second embodiment and the wire engagement groove 321 provided on the guide plane 29 of the therapeutic instrument elevator base 27 described in connection with the first embodiment, as shown in FIG. 7D.

The effect obtained by this modification is that, as in the first and second embodiments, the guide wire 68 enters the respective wire engagement grooves 321 and 331 and is engaged at the two points by raising the therapeutic instrument elevator base 27.

The advantage obtained by this modification lies in that engagement at the two points increases the fixation strength in addition to the advantage similar to that in the above-described first and second embodiments.

Figure 8A:
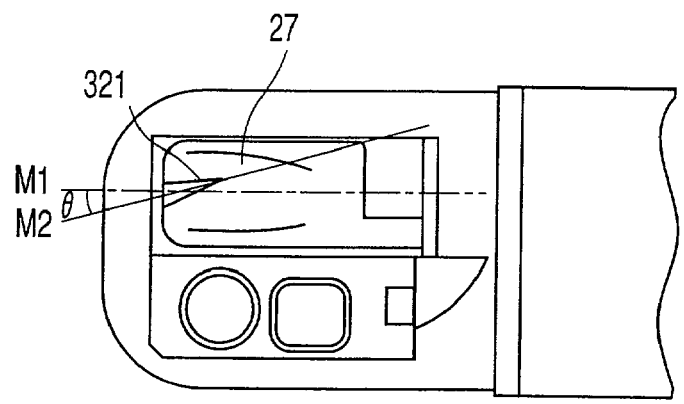
FIG. 8A is a cross-sectional view of a primary part showing a schematic structure of an end portion of an insertion portion in an endoscope according to a third embodiment of the present invention.
Figure 8B:
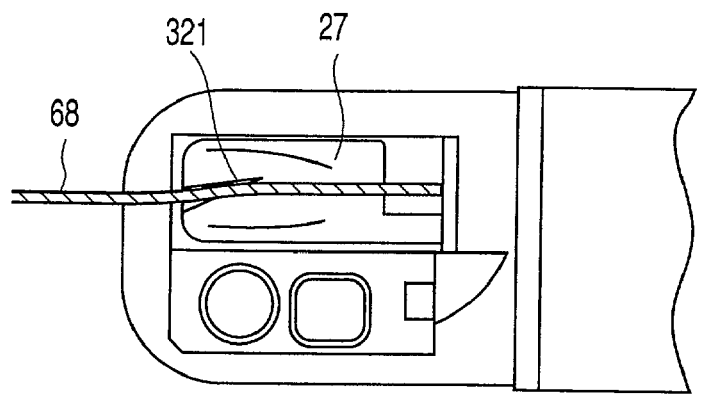
FIG. 8B is a plane view of the end portion of the insertion portion in the endoscope according to the third embodiment.

Moreover, FIGS. 8A and 8B show a third embodiment. In this embodiment, the structure of the end portion 17 of the insertion portion 12 in the endoscope 1 according to the first embodiment is modified as follows.

That is, in this embodiment, as shown in FIGS. 8A and 8B, a slit-like wire engagement groove 321 for releasably engaging the guide wire 68 is provided on the bottom of the substantially-V-shaped groove in the guide plane 29 of the therapeutic instrument elevator base 27. Here, as shown in FIG. 8A, the central axis of the wire engagement groove 321 is determined as M1, and the central axis of the guide plane 29 is determined as M2. In this state, by inclining the part between M1 and M2 by θ, an angle of the wire engagement groove 321 can be inclined by θ.

It is to be noted that with respect to M1 this inclination θ may be given to either the object lens side or the opposite side to the object lens with M1 therebetween.

Figure 8C:
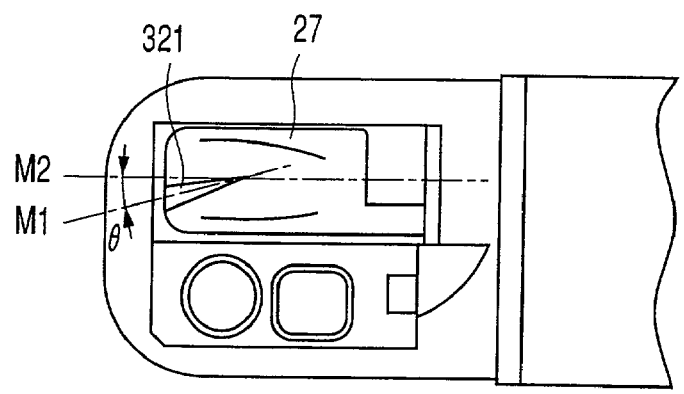
FIG. 8C is a plane view of the end portion of the insertion portion showing the state in which the guide wire in the endoscope is moved to an engagement position according to the third embodiment.

Further, the wire engagement groove 321 does not have to be provided at an intersection between the central axis M1 of the wire engagement groove 321 and the central axis M2 of the guide plane 29. For example, as shown in FIG. 8C, the wire engagement groove 321 may be provided at a position deviating from the center of the guide plane 29 as shown in FIG. 8C.

In this embodiment, when raising the therapeutic instrument elevator base 27, the guide wire 68 is led into the wire engagement groove 321 obliquely provided with respect to the insertion portion axial direction along the guide plane 29 by the therapeutic instrument elevator base 27, and fitted in the wire engagement groove 321 as shown in FIG. 8B, thereby being releasably engaged. The effect obtained thereafter is similar to that of the first embodiment mentioned above.

Figure 9:
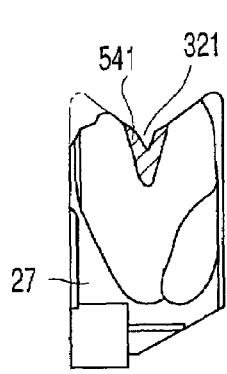
FIG. 9 is a front view showing a therapeutic instrument elevator base according to a fourth embodiment of the present invention.

Furthermore, FIG. 9 shows a fourth embodiment according to the present invention. In this embodiment, the structure of the therapeutic instrument elevator base 27 according to the first embodiment is modified as follows.

That is, in this embodiment, there is formed a surface finished plane 541 having the large friction resistance which has been subjected to surface finishing by which minute irregularities are formed to roughen the inner surface of the wire engagement groove 321 in the therapeutic instrument elevator base 27 according to the first embodiment. This surface finished plane 541 is formed by, for example, surface finishing for causing the chemical reaction such as corrosion on the inner surface of the wire engagement groove 321 or any other finishing for embedding or attaching a member having the large friction resistance, e.g., rubber, silicon or any other elastomer.

The following advantage can be demonstrated in this embodiment. That is, in this embodiment, the advantage similar to that in the first embodiment can be obtained, and the friction resistance between the guide wire 68 and the wire engagement groove 321 is increased by the surface finished plane 541 of the inner surface of the wire engagement groove 321 in the therapeutic instrument elevator base 27, thereby increasing a quantity of fixing power for the guide wire 68.

Figure 10A:
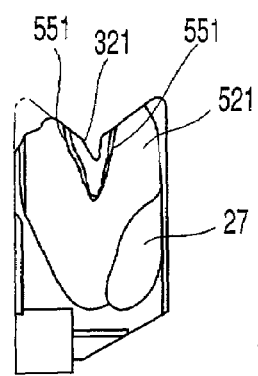
FIG. 10A is a front view of a therapeutic instrument elevator base in an endoscope according to a fifth embodiment of the present invention.
Figure 10B:
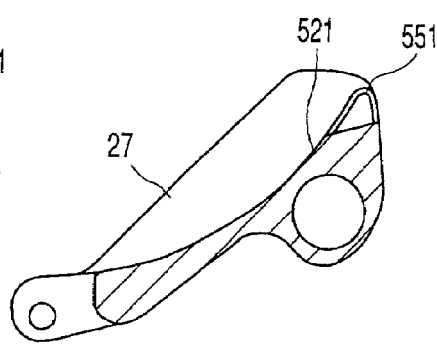
FIG. 10B is a vertical cross-sectional view of the therapeutic instrument elevator base in the endoscope according to the fifth embodiment.

Furthermore, FIGS. 10A and 10B show a fifth embodiment according to the present invention. In this embodiment, the structure of the therapeutic instrument elevator base 27 of the endoscope 1 in the first embodiment is changed as follows.

That is, in the therapeutic instrument elevator base 27 of this embodiment, there is provided a chamfered portion 551 obtained by chamfering the entire edge line between the wire engagement groove 321 and the guide plane 521.

The following advantage can be obtained in this embodiment. That is, the advantage similar to that in the first embodiment can be obtained in this embodiment. In addition to this, when the therapeutic instrument elevator base 27 is raised, the guide wire 68 is guided along the chamfered portion 551 and can thereby readily enter the wire engagement groove 321. Moreover, when inserting the guide wire 68 or any other therapeutic instrument, it is advantageously possible to eliminate damages to the edge portion of the wire engagement groove 321 which are given when the guide wire 68 or any other therapeutic instrument are caught at this edge portion according to the present invention.

Figure 11A:
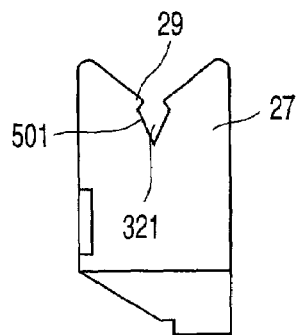
FIG. 11A is a rear view of a therapeutic instrument elevator base in an endoscope according to a sixth embodiment of the present invention.
Figure 11B:
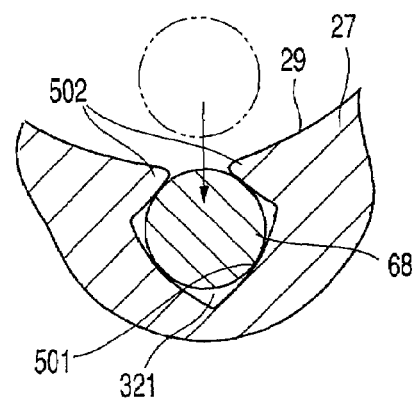
FIG. 11B is an enlarged vertical cross-sectional view showing a wire engagement groove of the therapeutic instrument elevator base in the endoscope according to the sixth embodiment.

In addition, FIGS. 11A and 11B show a sixth embodiment. In this embodiment, the structure of the therapeutic instrument elevator base 27 of the endoscope 1 in the first embodiment is changed as follows.

That is, in this embodiment, engagement protrusions 502 for narrowing the width of the opening end portion of the wire engagement groove 321 are provided at the upper portions of the wall surfaces 501 on the both sides in the wire engagement groove 321 of the therapeutic instrument elevator base 27 A distance between the engagement protrusions 502 on the both sides at the opening end portion of the wire engagement groove 321 is set so as to be a gap which is slightly narrower than the outside diameter dimension of the guide wire 68.

The effect of this embodiment will now be described. In this embodiment, as in the therapeutic instrument elevator base 27 of the endoscope 1 according to the first embodiment, with the guide catheter being pulled into the therapeutic instrument insertion channel 23, the guide wire 68 is led to the wire engagement groove 321 by the guide plane 29 of the therapeutic instrument elevator base 27 by raising the therapeutic instrument elevator base 27.

At this moment, as a swiveling angle of the therapeutic instrument elevator base 27 increases with the swiveling operation of the therapeutic instrument elevator base 27, the guide wire 68 is strongly pushed by the protrusions 502 from the outside, and the guide wire 68 starts to be elastically deformed. Then, with an appropriate angle before the swiveling angle of the therapeutic instrument elevator base 27 reaches a maximum set-up angle, the guide wire 68 gets over the protrusions 502, and the guide wire 68 is fitted in the wire engagement groove 321 as shown in FIG. 11B. As a result, the guide wire 68 is fixed while being in contact with four points, i.e., the wall surfaces 501 on the both sides and the engagement protrusions 502 on the both sides in the wire engagement groove 321 of the therapeutic instrument elevator base 27.

Thereafter, the guide catheter is pulled out at a blast, and any other therapeutic instrument is inserted with the guide wire 68 as a guide. At this moment, when the inserted therapeutic instrument passes along the wire engagement groove 321, the guide wire 68 is pushed out from the wire engagement groove 321 by the thrusting force of the therapeutic instrument, and fixation of the guide wire 68 is released.

The following advantage can be demonstrated in this embodiment. That is, in this embodiment, as in the endoscope 1 of the first embodiment, the guide wire 68 can be easily fixed by only the usually performed operation for raising the therapeutic instrument elevator base 27 by which the elevator operation knob 48 of the front operation portion 13 in the endoscope 1 is operated.

Also, in this embodiment, in addition to the advantage similar to that of the endoscope 1 according to the first embodiment, in the case of fixing the guide wire 68, when the guide wire 68 gets over the engagement protrusions 502 on the both sides of the opening end portion in the wire engagement groove 321 from the outside, the guide wire 68 can be further strongly fixed by sandwiching the guide wire 68 by the wire engagement groove 321 and the engagement protrusions 502 on the both sides.

Additionally, when fixing the guide wire 68, the force of the guide wire 68 to move in the upper surface direction of the therapeutic instrument elevator base 27 can be suppressed by the engagement protrusions 502 on the both sides.

Figure 12A:
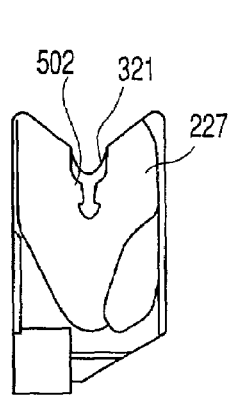
FIG. 12A is a front view showing a first modification of the therapeutic instrument elevator base according to the sixth embodiment.
Figure 12B:
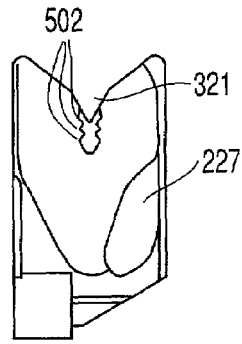
FIG. 12B is a front view showing a second modification of the therapeutic instrument elevator base according to the sixth embodiment.

Further, as in the first modification of the therapeutic instrument elevator base 27 in the sixth embodiment shown in FIG. 12A, the engagement protrusions 502 on the both sides of the opening end portion in the wire engagement groove 321 of the therapeutic instrument elevator base 27 may be provided in the entire area of the wire engagement groove 321 or a part of the wire engagement groove 321 along the insertion portion axial direction. Furthermore, as in the second modification of the therapeutic instrument elevator base 27 in the sixth embodiment shown in FIG. 12B, a plurality of engagement protrusions 502 may be provided on the both sides of the opening end portion in the wire engagement groove 321 of the therapeutic instrument elevator base 27.

Figure 12C:
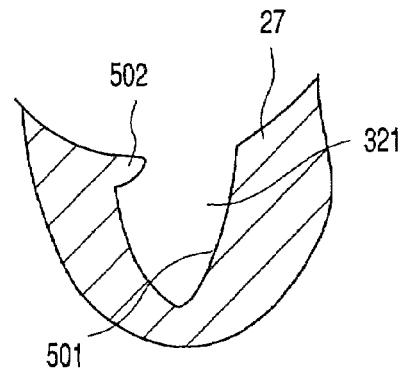
FIG. 12C is a vertical cross-sectional view of a primary part showing a third modification of the therapeutic instrument elevator base according to the sixth embodiment.

Furthermore, as in the third modification of the therapeutic instrument elevator base 27 in the sixth embodiment shown in FIG. 12C, the engagement protrusion 502 may be provided on only one side of the opening end portion in the wire engagement groove 321 of the therapeutic instrument elevator base 27 so as not to extremely lower the fixing capability for the guide wire 68. When the engagement protrusion 502 is provided on only one surface of the opening end portion in the wire engagement groove 321 of the therapeutic instrument elevator base 27 in this manner, since the quantity of the operation force at the time of inserting/removing the guide wire 68 into/from the wire engagement groove 321 is reduced, the fixing operation of the guide wire 68 can become advantageously relatively easy.

Moreover, FIGS. 13 to 15B show a seventh embodiment according to the present invention. In this embodiment, the structure of the therapeutic instrument elevator base 27 of the endoscope 1 according to the first embodiment is modified as follows.

Figure 13:
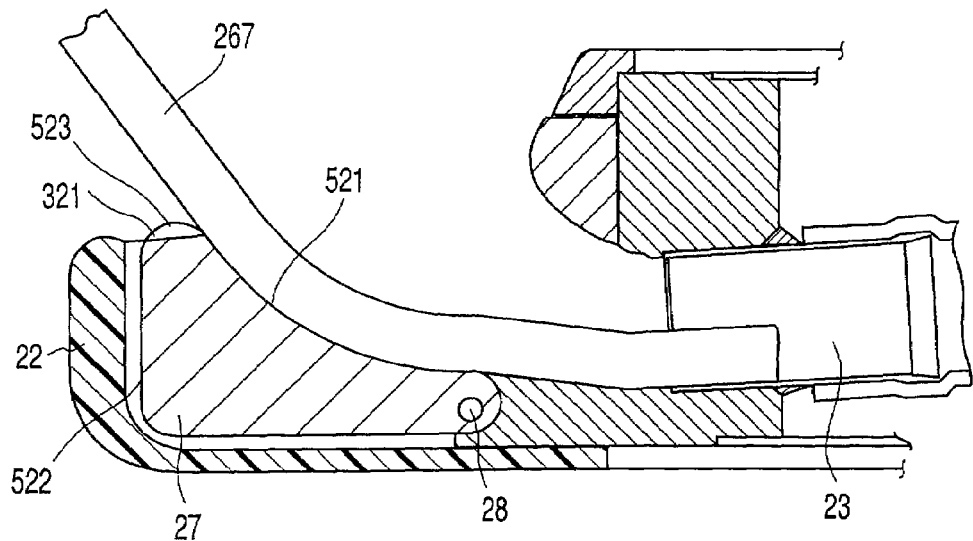
FIG. 13 is a vertical cross-sectional view of a primary part showing the set-down state of the therapeutic instrument elevator base with a guide catheter being inserted in an endoscope according to a seventh embodiment of the present invention.
Figure 14:
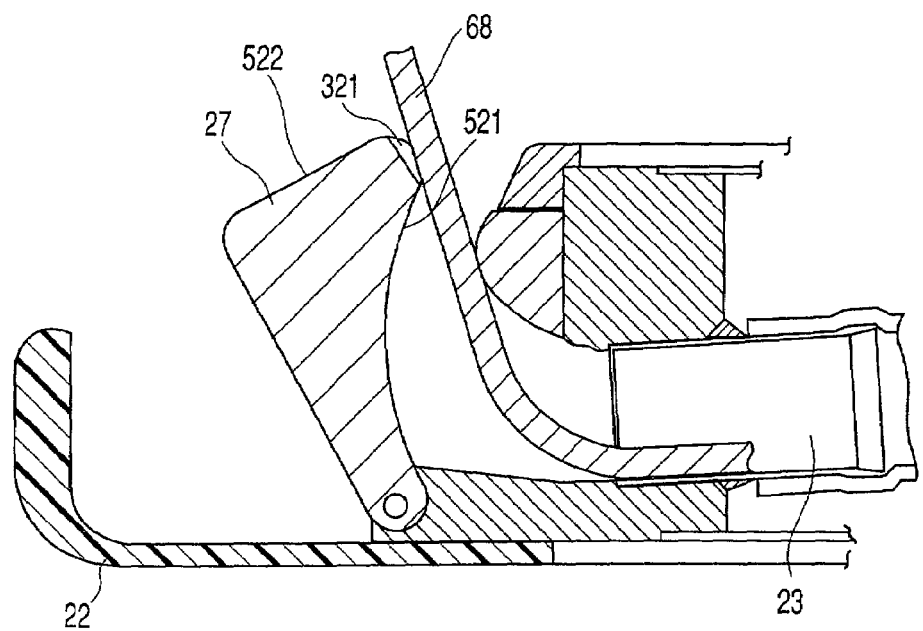
FIG. 14 is a vertical cross-sectional view of a primary part showing the set-up state of the therapeutic instrument elevator base according to the seventh embodiment.

That is, in this embodiment, the wire engagement groove 321 of the therapeutic instrument elevator base 27 is provided at a position at which any other therapeutic instrument doesn't come into contact with the wire engagement groove 321 when the therapeutic instrument moves in/out with the therapeutic instrument elevator base 27 being lowered as shown in FIG. 13. FIG. 13 is a cross-sectional view when the therapeutic instrument elevator base 27 is lowered with the guide catheter 267 being inserted, and FIG. 14 is a cross-sectional view when the therapeutic instrument elevator base 27 is raised. Further, the wire engagement groove 321 of the therapeutic instrument elevator base 27 is constituted by the guide plane 521, an end plane 522 and a connection plane 523 connecting these planes.

Moreover, FIG. 15A is a front view of the therapeutic instrument elevator base 27, and FIG. 15B is a rear view of the therapeutic instrument elevator base 27. In this embodiment, as shown in FIGS. 15A and 15B, the wire engagement groove 321 of the therapeutic instrument elevator base 27 is arranged at a position which cannot seen from the front side. In addition, the wire engagement groove 321 of the therapeutic instrument elevator base 27 is formed so as to be gradually deep from the connection plane 523 toward the end plane 522. As a result, it is set in such a manner that the wire engagement groove 321 is exposed to a traveling position of the guide wire 68 as the therapeutic instrument elevator base 27 is raised.

The effect of this embodiment will now be described. In this embodiment, as in the first embodiment, with the guide catheter 267 being pulled into the therapeutic instrument insertion channel 23, the wire engagement groove 321 appears by raising the therapeutic instrument elevator base 27, and the guide wire 68 is pinched and fixed. Any other process is similar to that in the first embodiment.

The following advantage can be demonstrated in this embodiment. That is, in this embodiment, as in the first embodiment, the guide wire 68 can be easily fixed by only the usually performed operation for raising the therapeutic instrument elevator base 27 by which the elevator operation knob 48 of the front operation portion 13 of the endoscope 1 is operated.

Moreover, in this embodiment, in addition to the advantage similar to that of the endoscope 1 according to the first embodiment, since the wire engagement groove 321 doesn't appear on the guide plane 521 when the therapeutic instrument elevator base 27 is lowered, the therapeutic instrument cannot be damaged, and the therapeutic instrument can smoothly move in/out.

In addition, FIGS. 16 to 18 show an eighth embodiment according to the present invention. In this embodiment, the structure of the therapeutic instrument elevator base 27 of the endoscope 1 in the first embodiment is changed as follows.

That is, although it is desirable to design the wire engagement groove 321 of the therapeutic instrument elevator base 27 to catch the guide wire 68 on the entire surface of the wire engagement groove 321 as shown in FIG. 17 when the guide wire 68 is raised, a certain quantity of displacement is actually generally generated on the contact surface between the wire engagement groove 321 and the guide wire 68 in the relationship of the machining accuracy as shown in FIG. 18. For example, when the guide wire 68 is raised by the therapeutic instrument elevator base 27, it is ideal that the entire bottom portion of the wire engagement groove 321 is in contact with the guide wire 68 as shown in FIG. 17. An angle between an insertion portion axis (central line) O and the bottom portion (contact surface with the guide wire 68) of the wire engagement groove 321 at this moment is determined as $\theta$.

In addition, in the relationship of the machining accuracy of the therapeutic instrument elevator base 27, the displacement may be generated in the contact surface between the wire engagement groove 321 and the guide wire 68. Assuming that an angle between the insertion portion axis O and the bottom portion of the wire engagement groove 321 is $\theta_2$ when this displacement is produced, the relationship of "$\theta<\theta_2$" may be attained. In this case, since the end portion of the guide wire 68 is held down by the end portion of the wire engagement groove 321, a distance L2 between two points, i.e., the guide wire contact point of the therapeutic instrument elevator base 27 holding down the guide wire 68 and the guide wire contact point of the lead-in guide path 24 in the end hard portion 21 is relatively long. Therefore, in this state, there is a problem that the fixing strength for the guide wire 68 is lowered.

In this embodiment, taking a tolerance obtained by finishing the wire engagement groove 321 of the therapeutic instrument elevator base 27 into consideration, when the guide wire 68 is raised by the therapeutic instrument elevator base 27 as shown in FIG. 16, the angle $\theta_1$ between the insertion portion axis O and the wire engagement groove 321 of the therapeutic instrument elevator base 27 is set with respect to the angle $\theta$ between the insertion portion axis O and the wire engagement groove 321 in the ideal stage shown in FIG. 17 so that "$\theta>\theta_1$" can be achieved. As a result, when the guide wire 68 is raised by the therapeutic instrument elevator base 27, the front side of the wire engagement groove 321 of the therapeutic instrument elevator base 27 can be set higher than an ideal position of the end portion of the wire engagement groove 321 on the front side shown in FIG. 17, and the contact point with the guide wire 68 is arranged on the front side of the wire engagement groove 321. Additionally, in this case, since the distance L1 between two points, i.e., the guide wire contact point of the therapeutic instrument elevator base 27 holding down the guide wire 68 and the guide wire contact point of the lead-in guide path 24 in the end hard portion 21 becomes smaller than L2 shown in FIG. 18 (L1<L2), the fixing strength for the guide wire 68 can be increased as compared with the case illustrated in FIG. 18.

Therefore, since a distance between two points, i.e., the wire engagement groove 321 of the therapeutic instrument elevator base 27 and the guide wire contact point of the lead-in guide path 24 in the end hard portion 21 does not become long due to irregularities in the working process when the guide wire 68 is raised by the therapeutic instrument elevator base 27 in this embodiment, the fixing strength for the guide wire 68 is not lowered by irregularities in machining the wire engagement groove 321 of the therapeutic instrument elevator base 27, and there is the advantage that the fixing strength of the guide wire 68 can be stably maintained.

Figure 19:
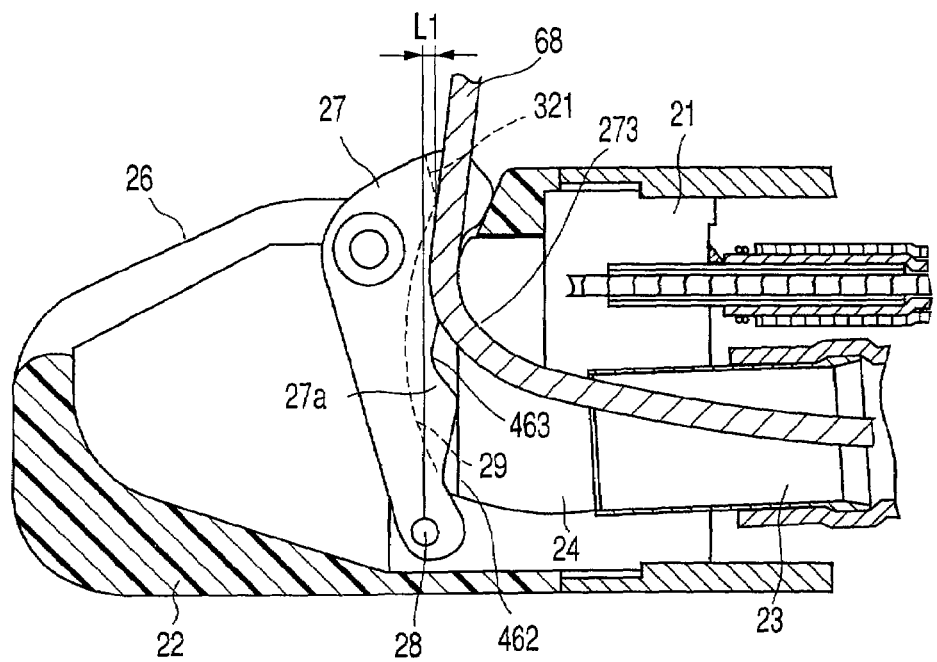
FIG. 19 is a vertical cross-sectional view of a primary part showing a guide wire fixed state according to a ninth embodiment of the present invention.
Figure 20:
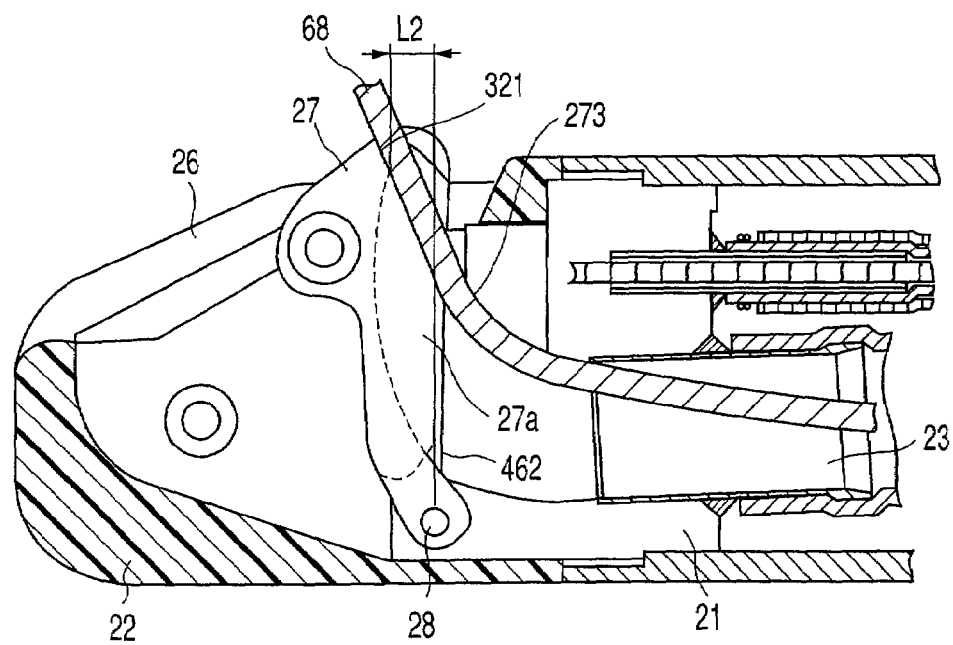
FIG. 20 is a vertical cross-sectional view showing the state when a guide wire is fixed at an end portion of a conventional endoscope.

Further, FIGS. 19 and 20 show a ninth embodiment according to the present invention. In this embodiment, the structure of the therapeutic instrument elevator base 27 according to the first embodiment is changed as follows.

That is, in this embodiment, as shown in FIG. 19, the wire engagement groove 321 for strongly bending the set-up position of the guide wire 68 which is raised by the therapeutic instrument elevator base 27 toward the front side away from the position of the elevator base swivel supporting point 28 when the therapeutic instrument elevator base 27 is raised at the maximum set-up level is provided at the end portion of the therapeutic instrument elevator base 27. This wire engagement groove 321 is arranged at a part in the vicinity of the end of the guide wire 68 of the therapeutic instrument elevator base 27 in the guide plane 29. Further, when the therapeutic instrument elevator base 27 is raised at the maximum set-up level, the wire engagement groove 321 is arranged at a position where it protrudes by an appropriate distance L1 toward the front side away from the position of the elevator base swivel supporting point 28.

It is to be noted that the clearance between the wire engagement groove 321 provided to the therapeutic instrument elevator base 27 and the upper surface 273 of the lead-in guide path 24 when the therapeutic instrument elevator base 27 is raised is assured as in the prior art and maintained so as not to interfere insertion and removal of the guide catheter or any other therapeutic instrument.

Furthermore, a notch portion 463 obtained by scraping off a part opposed to the set-up angle stopper 462 at the end of the end hard portion 2 so as not to come into contact with the set-up angle stopper 462 is formed on a side wall surface 27a on the guide plane side of the therapeutic instrument elevator base 27 in such a manner that the insertion/removal property of the therapeutic instrument is not interfered when the therapeutic instrument elevator base 27 is raised-at the maximum level.

Incidentally, the present invention is not restricted to the above-described structure as long as it is the structure capable of maintaining the positional relationship between the wire engagement groove 321 and the elevator base swivel supporting point 28.

On the contrary, FIG. 20 is a cross-sectional view of the end portion of the endoscope with the conventional guide wire 68 being fixed. As shown in FIG. 20, the position at which the guide wire 68 is fixed in the wire engagement groove 321 when the therapeutic instrument elevator base 27 is raised to the maximum set-up position is arranged on the end side away from the elevator base-swivel supporting point 28 by approximately an appropriate distance L2.

The effect of this embodiment will now be described. In this embodiment, as in the first embodiment, with the guide catheter being pulled into the therapeutic instrument insertion channel 23, the therapeutic instrument elevator base 27 is raised. At this moment, since the therapeutic instrument elevator base 27 is raised beyond the conventional maximum set-up angle position, the guide wire 68 can be further bent. Therefore, the shear force between the wire engagement groove 321 and the upper surface 273 of the lead-in guide path 24 and the reaction force of the guide wire 68 further strongly act, and the guide wire 68 can be hence securely fixed in this state.

After confirming that the guide wire 68 is firmly fixed, the guide catheter is pulled out and another therapeutic instrument is inserted over the guide wire 68. Consequently, at this moment, the therapeutic instrument to be inserted sets down the therapeutic instrument elevator base 27 when passing along the wire engagement groove 321, and the guide wire 68 is pushed out from the wire engagement groove 321 by the thrusting force of this therapeutic instrument, and fixation between the guide wire 68 and the wire engagement groove 321 is released.

The following advantage can be demonstrated in this embodiment. That is, in this embodiment, the advantage similar to the first embodiment can be obtained. In addition to this, there is an advantage that the guide wire 68 can be further firmly fixed.

Incidentally, the above-described guide wire fixing means is not restricted to one having the wire engagement groove 321, and only the therapeutic instrument elevator base 27 may also function as this guide wire fixing means in order to bring in the set-up angle.

Figure 21:
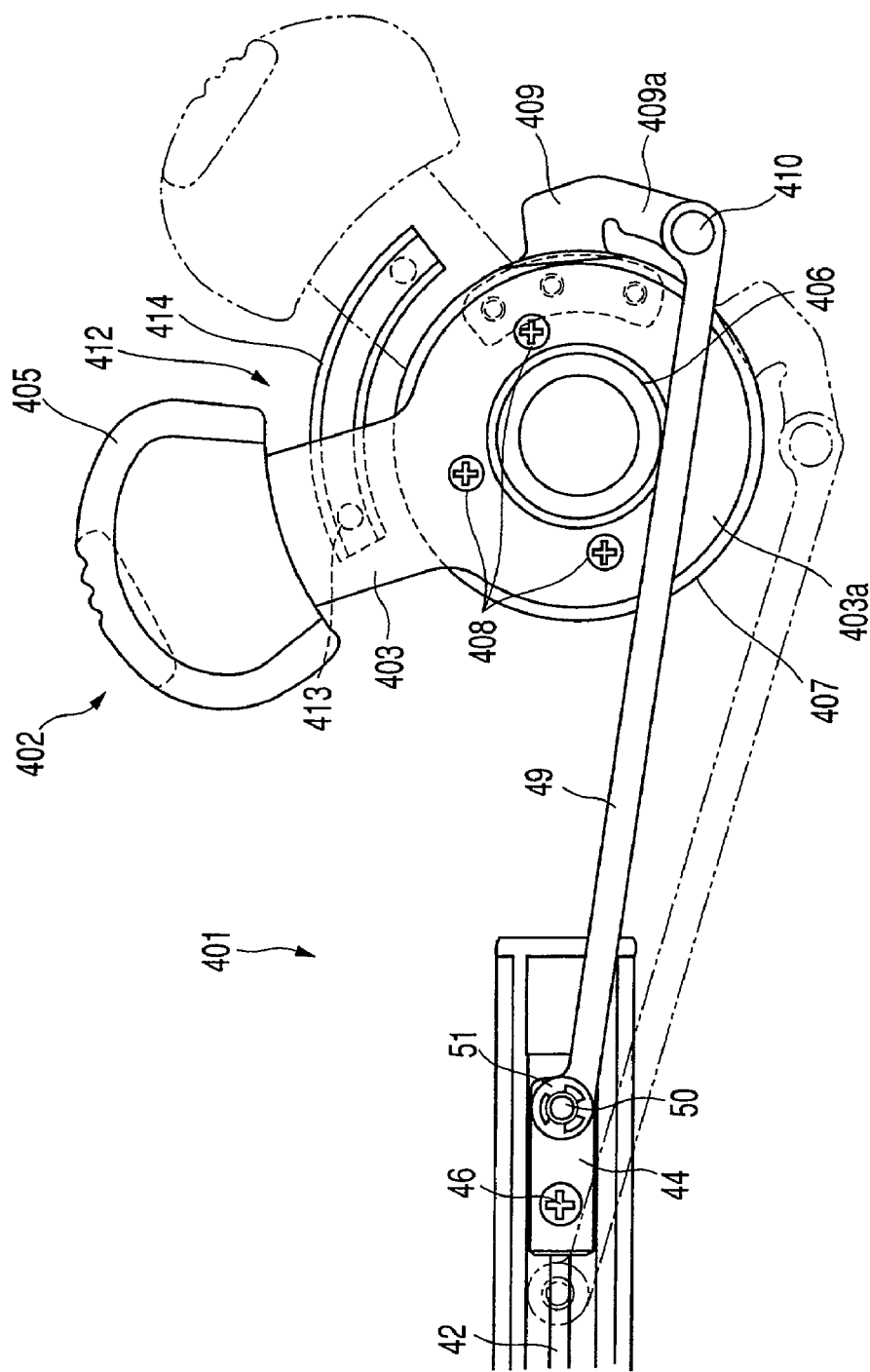
FIG. 21 is a plane view of a primary part of an elevator base actuation mechanism showing an 11th embodiment according to the present invention.

Further, FIG. 21 and FIGS. 22A to 22D show a 10th embodiment according to the present invention. In this embodiment, the elevator base actuation mechanism 401 configured as shown in FIGS. 21 and 22A is provided in place of the elevator base actuation mechanism 41 provided inside the operation portion 13 of the endoscope 1 according to the first embodiment.

A elevator base operation knob 402 is provided at the end edge portion of the operation portion 13 of the endoscope 1. To this elevator base operation knob 402 are provided an operation lever 403 and a finger application portion 405 which is fixed to the outer end portion of the operation lever 403 by the set screw as shown in FIG. 22A.

Furthermore, a fixing cylindrical body 406 for attaching the elevator base operation knob 402 is provided to the operation portion 13 of the endoscope 1 so as to protrude therefrom. A base end portion of the fixing cylindrical body 406 is fixed to a non-illustrated fixing frame provided in an operation portion casing 13a of the operation portion 13.

Moreover, a rotating ring 407 is rotatably fitted in the fixing cylindrical body 406.

It is to be noted that a bearing portion 13b for rotatably supporting the rotating ring 407 is provided to the operation portion casing 13a.

In addition, as shown in FIG. 21, a ring-like connection ring 403a is provided to the inner end portion of the operation lever 403. This connection ring 403a is screwed and fixed to the outer surface of the rotating ring 407 by a plurality of set screws 408. Additionally, the elevator base operation knob 402 has the operation lever 403 being rotatably supported along the central axis of the fixing cylindrical body 406.

Further, a base end portion of a second link member 409 is fixed to the inner surface of the rotating ring 407. A substantially-L-shaped link arm 409a is provided to the second link member 409 so as to protrude therefrom. The other end portion of the arm 49 in the elevator base actuation mechanism 41 according to the first embodiment is connected to the end portion of the link arm 409a through a second link shaft 410 as a bar-like shaft member so as to be capable of swiveling. An engagement member 411 consisting of a C type or E type snap ring is engaged with the end portion on the opposite side to the end portion on the arm 49 side in the second link shaft 410.

Furthermore, by rotating the operation lever 403 with the finger application portion 405 as a supporting point in the swiveling operation of the elevator base operation knob 402 in the operation portion 13, the second link member 409 is operated to swivel through the rotating ring 407, and the link member 44 is driven to move forward/backward along the axial direction of the set-up wire 30 through the arm 49 with the swiveling operation of the second link member 409. As a result, the set-up wire 30 is towed, and the therapeutic instrument elevator base 27 is caused to perform the derricking motion with the elevator base swivel supporting point 28 at the center. Consequently, the therapeutic instrument such as the guide catheter which is inserted into the therapeutic instrument insertion channel 23 and led to the outside from the channel opening portion 26 is raised by raising the therapeutic instrument elevator base 27.

Moreover, a braking mechanism 412 for restraining the swivel operation force of the operation lever 403 of the elevator base operation knob 402 is incorporated in the elevator base actuation mechanism 401 according to this embodiment. As shown in FIG. 22B, to the braking mechanism 412 are provided a deterrent body 413 such as a pin which protrudes in the middle of the operation lever 403 of the elevator base operation knob 402 and a deterrence reinforcement member 414 which is arranged at a position engaged with the deterrent body 413 and shown in FIG. 22C.

In addition, to the deterrence reinforcement member 414 is formed a guide groove 414a to which the deterrent body 413 of the operation lever 403 is inserted and which has a substantially-U-shaped cross section as shown in FIGS. 22C and 22D. This guide groove 414a is extended along the swivel trajectory of the deterrent body 413 in the swiveling operation of the operation lever 403. Additionally, the deterrent body 413 is configured to pass inside the guide groove 414a of the deterrence reinforcement member 414.

Further, a friction resistance member 415 having a large friction resistance is embedded in the guide groove 414a of the deterrence reinforcement member 414 on one end side of the guide groove 414a. This friction resistance member 415 is arranged in an area through which the deterrent body 413 passes in a range L in which swivel of the operation lever 403 should be restrained in the swiveling operation of the operation lever 403 when rotating in that range.

The effect of this embodiment will now be described. In this embodiment, as in the endoscope 1 according to a 29th embodiment, the operation lever 403 of the elevator base operation knob 402 of the operation portion 13 is rotated in the operation for raising the therapeutic instrument elevator base 27. At this moment, when the operation lever 403 is rotated to the deterrence range L, the deterrent body 413 comes into contact with the friction resistance member 415 in the guide groove 414a of the deterrence reinforcement member 414. As a result, the load is applied to the swiveling operation of the operation lever 403, and brake is put on the swiveling operation of the operation lever 403 and this lever is fixed. Therefore, with the therapeutic instrument elevator base 27 being swiveled to the set-up position indicated by dotted lines in FIG. 57A, the therapeutic instrument elevator base 27 can be fixed. Thus, the guide wire 68 led to the outside from the channel opening portion 26 is sandwiched between the end surface of the lead-in guide path 24 of the end hard portion 21 and the therapeutic instrument elevator base 27 and mechanically fixed.

As described above, after confirming that the guide wire 68 has been fixed, the guide catheter is completely pulled out to the outside of the therapeutic instrument insertion channel 23 from the operation portion 13 side of the endoscope 1.

Thereafter, a therapeutic instrument which is subsequently used is inserted from the base end side of the guide wire 68. At this moment, with the guide wire 68 being used as a guide, the therapeutic instrument is inserted into the therapeutic instrument insertion channel 23. Then, when the therapeutic instrument hustles against the therapeutic instrument elevator base 27, the operation lever 403 of the elevator base operation knob 402 is returned to its original position. At this moment, the operation lever 403 exceeds the deterrence range L, and the deterrent body 413 comes off the friction resistance member 415 in the guide groove 414a of the deterrence reinforcement member 414, thereby releasing fixation of the operation lever 403. Consequently, fixation of the guide wire 68 by the therapeutic instrument elevator base 27 is released.

In this embodiment, the following advantage can be demonstrated. That is, in this embodiment, since the braking mechanism 412 for restraining the swivel operation force of the operation lever 403 of the elevator base operation knob 402 is incorporated in the elevator base actuation mechanism 401, the fixed state of the guide wire 68 can be maintained by fixing the therapeutic instrument elevator base 27 with the therapeutic instrument elevator base 27 being swiveled to the set-up position indicated by dotted lines in FIG. 5. Therefore, while the guide wire is fixed, there is no need to grip the operation lever 403, thereby advantageously improving the working property of an operator.

It is to be noted that the braking mechanism 412 according to this embodiment may be incorporated into the operation lever 72 of a later-described guide wire fixing elevator base 267. In this case, with the guide wire fixing elevator base 267 being swiveled to the set-up position shown in FIG. 57C, the fixed state of the guide wire 68 can be maintained by fixing the guide wire fixing elevator base 267. Therefore, while the guide wire 68 is fixed, there is no need to grip the operation lever 72 of the guide wire fixing elevator base 267, thereby advantageously improving the working property of an operator.

Figures 23, 24:
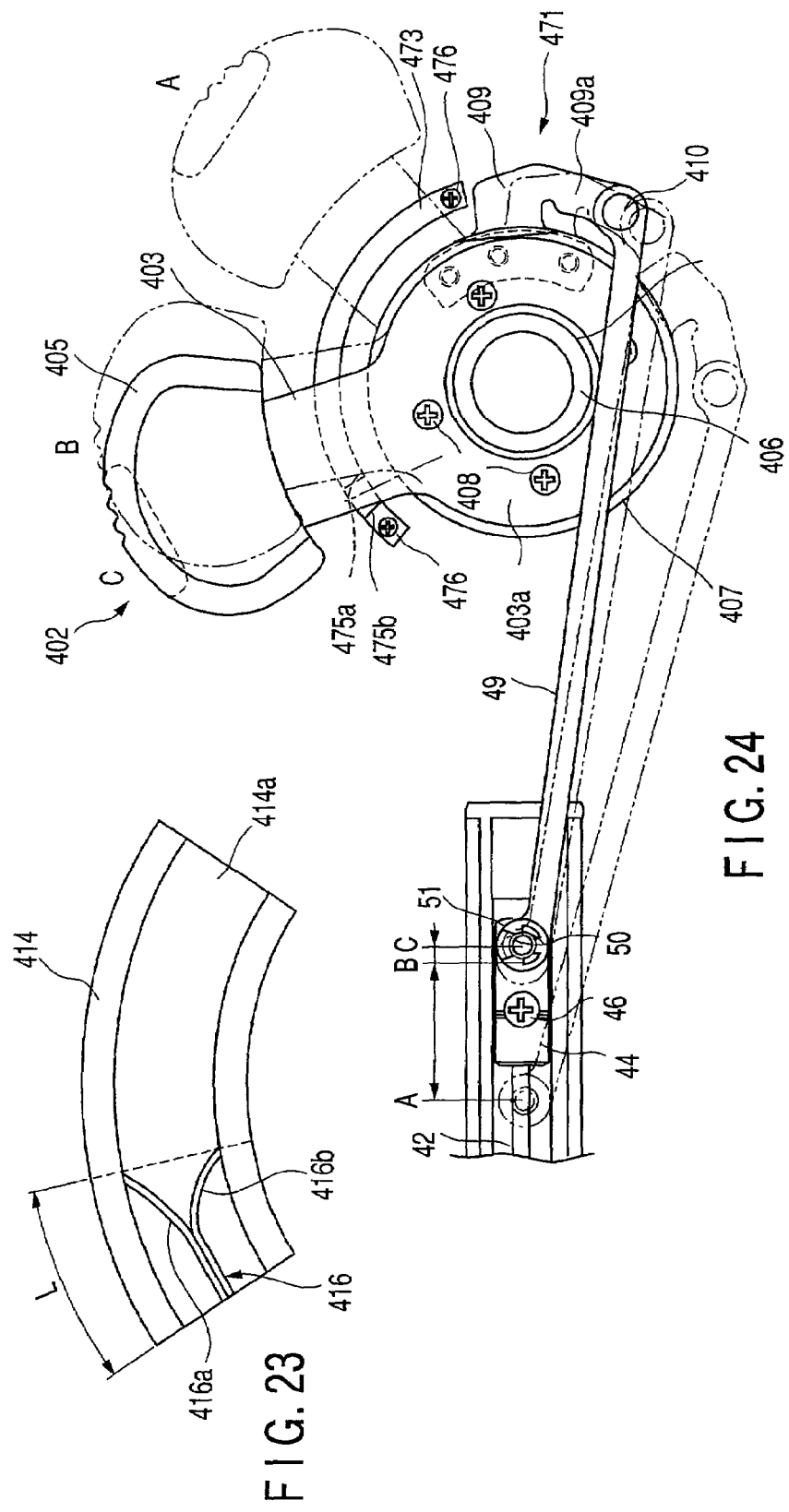
FIG. 23 is a plane view showing a deterrence reinforcement member of a braking mechanism in a first modification of the 11th embodiment.
FIG. 24 is a plane view of a primary part of an elevator base actuation mechanism showing a tenth embodiment according to the present invention.

Further, FIG. 23 shows a first modification of the 10th embodiment. In this modification, an elastic member 416 consisting of, e.g., two flat springs 416a and 416b is arranged in the guide groove 414a of the deterrence reinforcement member 414 of the braking mechanism 412 in place of the friction resistance member 415. This elastic member 416 is formed into such a shape as that the deterrent body 413 is inserted between the two flat springs 416a and 416b and the load is increased as the deterrent body 413 is inserted. Furthermore, the advantage similar to that of the braking mechanism 412 according to an 11th embodiment can be also obtained in the elastic member 416 of this modification.

Figure 51:
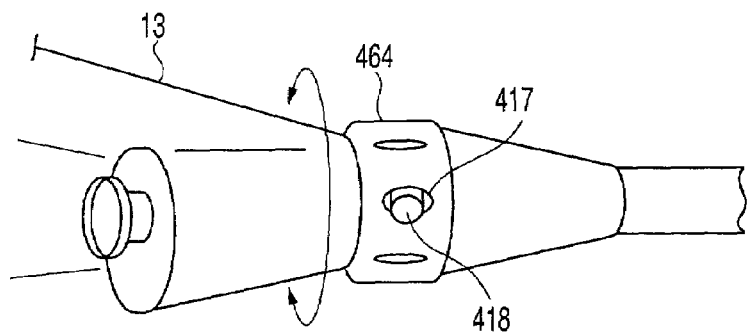
FIG. 51 is a perspective view of a primary part showing a second modification according to the 11th embodiment.

Moreover, FIG. 51 shows a second modification of the 10th embodiment. In this modification, a notch 417 is provided to a tow knob 264 which rotates around the axis along the circumferential direction of the operation portion 13 as in a 33rd embodiment in place of the braking mechanism 412 according to the 10th embodiment. In addition, there is provided a braking mechanism which fixes rotation of the tow knob 264 by releasably engaging a protrusion 418 which protrudes through a non-illustrated elastic member with this notch 417. Additionally, the advantage similar to that of the braking mechanism 412 according to the 11th embodiment can be also obtained in this modification.

Further, FIGS. 24 to 27 show the 11th embodiment according to the present invention. In this embodiment, there is provided elevator operating means 471 having a set-up range selection type structure capable of appropriately and selectively changing the set-up range of the therapeutic instrument elevator base 27 according to the 9th embodiment in a plurality of stages.

That is, to the elevator operating means 471 according to this embodiment is provided an elevator base actuation mechanism 472 having the structure shown in FIGS. 24 and 25A inside the operation portion 13 having the substantially the same structure as the endoscope 1 according to the 10th embodiment.

Figure 26:
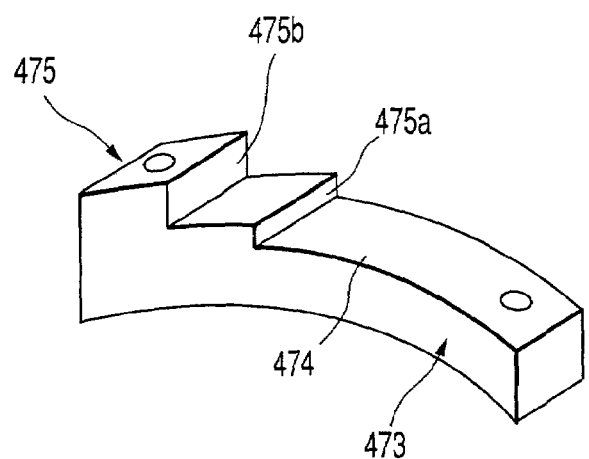
FIG. 26 is a perspective view showing a stopper member of the elevator base actuation mechanism according to the tenth embodiment.
Figure 27:
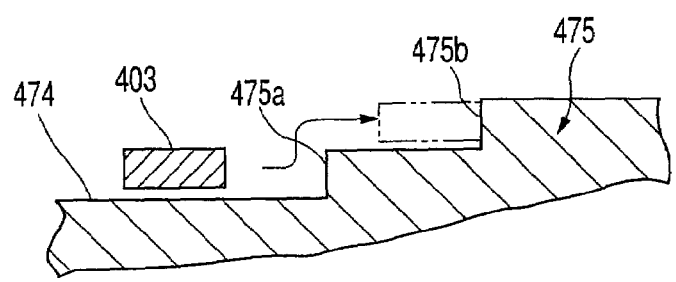
FIG. 27 is an explanatory view for explaining the operation of the elevator base actuation mechanism according to the tenth embodiment.

A segment stopper member 473 with the central axis of the fixing cylindrical body 406 at the center is provided to this elevator base actuation mechanism 472. As shown in FIG. 26, a two-stage protrusion portion 475 which protrudes in the stepped form in the upward direction orthogonal to a flat base plane 474 is formed on one end portion side of the stopper member 473. To this two-stage protrusion portion 475 are provided a low-stage first stopper 475a and a high-stage second stopper 475b. The high-stage second stopper 475b is arranged on the end portion side of the stopper member 473 at the rear of the low-stage first stopper 475a. Additionally, the stopper member 473 is fixed to the casing 13a of the operation portion 13 by a set screw 476.

Further, a height of the first stopper 475a is set in such a manner that elastic deformation of the operation lever 403 is enabled so that the operation lever 403 of the elevator base operation knob 402 can get over the first stopper 475a. Furthermore, the second stopper 475b is set to a height that the operation lever 403 can not get over the second stopper 475b by elastic deformation of the operation lever 403. Moreover, in the swivel operation of the elevator base operation knob 402, the range of the elevator operation of the first stage is restricted at a position B in FIG. 24 where the operation lever 403 of the elevator base operation knob 402 hustles against the fist stopper 475a. At this moment, by swiveling the operation lever 403 in the elevator operation range of the first stage from a position A to the position B in FIG. 24, it is possible to perform the usual elevator operation for the therapeutic instrument for guiding the therapeutic instrument and the like to a desired position as in the prior art.

In addition, by lifting the finger application portion 40S of the elevator base operation knob 402 in a direction indicated by an arrow in FIG. 25B at the position B and provoking elastic deformation of the operation lever 403, the operation lever 403 can get over the fist stopper 475a as shown in FIG. 25B. Further, after the operation lever 403 is caused to get over the first stopper 475a, the elevator operation range of the second stage can be restricted by swiveling the operation lever 403 to a position C shown in FIG. 24 at which the operation lever 403 hustles against the second stopper 475b. Therefore, in this embodiment, the set-up range of the therapeutic instrument elevator base 27 can be changed in two stages by the low-stage first stopper 475a and the high-stage second stopper 475b in the stopper member 473 of the elevator operating means 471. Furthermore, at this position C, the guide wire 68 led from the channel opening portion 26 to the outside is sandwiched and mechanically fixed between the end surface of the lead-in guide path 24 of the end hard portion 21 and the therapeutic instrument elevator base 27.

The effect of this embodiment will now be described. In this embodiment, in the swiveling operation of the elevator base operation knob 402, the elevator operation range of the first stage is restricted at the position B shown in FIG. 24 at which the operation lever 403 of the elevator base operation knob 402 hustles against the low-stage first stopper 475a in the stopper member 473 of the elevator operating means 471. At this moment, by swiveling the operation lever 403 in the elevator operation range of the first stage from the position A to the position B in FIG. 24, it is possible to perform the usual elevator operation for the therapeutic instrument for guiding the therapeutic instrument and the like to a desired position as in the prior art.

Moreover, when fixing the guide wire 68, with the guide catheter being pulled into the therapeutic instrument insertion channel 23 as in the first embodiment, the therapeutic instrument elevator base 27 is raised by performing the swiveling operation of the operation lever 403.

At this moment, at the position B where the operation lever 403 hustles against the first stopper 475a, as indicated by an arrow in FIG. 25B, the operation lever 403 having come into contact with the first stopper 475a is elastically deformed so as to be deflected by pushing up the finger application portion 405 toward the outside. As a result, as indicated by dotted lines in FIG. 27, the operation lever 403 can get over the first stopper 475a.

In addition, after the operation lever 403 is caused to get over the first stopper 475a, the therapeutic instrument elevator base 27 can be further raised by swiveling the operation lever 403 to the position C shown in FIG. 24 at which the operation lever 403 hustles against the second stopper 475b, thereby restricting the elevator operation range of the second stage. Additionally, at the position C, the guide wire 68 led to the outside from the channel opening portion 26 is sandwiched and mechanically securely fixed between the end surface of the lead-in guide path 24 of the end hard portion 21 and the therapeutic instrument elevator base 27.

Therefore, in this embodiment, the low-stage first stopper 475a and the high-stage second stopper 475b are provided to the stopper member 473 of the elevator operating means 471, and the set-up range of the therapeutic instrument elevator base 27 can be changed in two stages by only changing the operation of the regularly used operation lever 403 so as to be switched between the state in which the regularly used operation lever 403 abuts on the first stopper 475a and the state in which the same abuts on the high-stage second stopper 475b. Thus, since there is no need to newly provide a complicated operating means for changing the set-up range of the therapeutic instrument elevator base 27, there can be obtained an advantage that an operator is not confused and the endoscope can be stably operated.

In addition, fine adjustment of the swiveling position of the operation lever 403 does not have to be carried out in the case of raising the therapeutic instrument and the case of fixing the guide wire 68, and the operation lever can be used differently depending on the case of simply raising the therapeutic instrument and the case of fixing the guide wire 68, thereby reducing the burden of an operator during examination.

Additionally, after rotating the operation lever 403 of the elevator base operation knob 402 to the fixing position of the guide wire 68, the operation lever 403 does not hustle against the stopper member 473 of the elevator operating means 471 in the operation for releasing fixation of the guide wire 68 during which the operation lever 403 is swiveled in the direction of the position A from the position C through the position B, thereby readily performing the operation for returning the therapeutic instrument elevator base 27 to the set-down position.

Further, it is good enough that the clearance between the therapeutic instrument elevator base 27 and the wire engagement groove 321 according to the 9th embodiment is assured as in the prior art so as not to prevent insertion/removal of the therapeutic instrument at the position B. Furthermore, the clearance between the therapeutic instrument elevator base 27 and the wire engagement groove 321 can be narrowed when moving from the position B to the position C, thus increasing the fixing strength of the guide wire 68.

It is to be noted that the present invention may adopt the structure in which a number of components can be reduced by integrally molding the stopper member 473 with the operation portion casing 13a of the operation portion 13. Moreover, although the above has described the structure in which the two stoppers, i.e., the low-stage first stopper 475a and the high-stage second stopper 475b are provided in the stopper member 473 in this embodiment, three or more stoppers may be provided according to need.

In addition, although the above has described the structure in which the stopper member 473 is provided to the casing 13a of the operation portion 13 in this embodiment, the present invention is not restricted thereto, and the stopper members may be provided at parts where they come into contact with the operation lever 403, the fixing cylindrical body 406, the second link member 409 and the link member 44, respectively, so as not to deteriorate the set-up operability of the therapeutic instrument elevator base 27.

Figure 28:
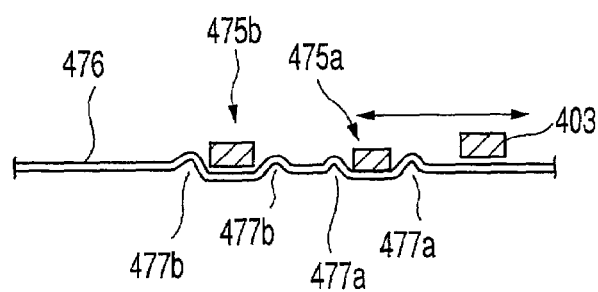
FIG. 28 is a vertical cross-sectional view of a primary part showing a modification of the tenth embodiment.

Additionally, the shape of the stopper member 473 is not restricted to the plate-like member described above, and an elastic member 476 such as a flat spring can substitute as in the modification of the 11th embodiment shown in FIG. 28. In this elastic member 476, a first stopper 475a for restricting the elevator operation range of the first stage is formed by a pair of protrusion portions 477a and 477a which protrude on the trajectory of the operation lever 403, and a second stopper 475b for restricting the elevator operation range of the second stage is formed by a pair of protrusion portions 477b and 477b which protrude at positions away from the first stopper 475a.

Further, FIGS. 29A, 29B and 30 show a 12th embodiment according to the present invention. In this embodiment, when the therapeutic instrument elevator base 27 of the endoscope 1 according to the first embodiment is raised, the therapeutic instrument elevator base 27 is arranged in such a manner that the therapeutic instrument elevator base 27 is partially brought into an observation visual field 482 obtained by an object lens 481 of the object optical system of the endoscope 1 in FIG. 30.

It is to be noted that FIG. 29B shows an observation image 483 obtained by the object lens 481 of the endoscope 1. Furthermore, the object optical system of the endoscope 1 is arranged at a position at which a part of the guide wire 68 fixed by the wire engagement groove 321 of the therapeutic instrument elevator base 27 shown in the observation image 483 is focused.

The effect of this embodiment will now be described. In this embodiment, as in the endoscope 1 according to the first embodiment, with the guide catheter being pulled into the therapeutic instrument insertion channel 23, the therapeutic instrument elevator base 27 and the guide wire 68 fixed to the therapeutic instrument elevator base 27 are brought into the visual field 482 of the object lens 481 of the object optical system by raising the therapeutic instrument elevator base 27. Furthermore, when the therapeutic instrument elevator base 27 is raised at the maximum level, the therapeutic instrument elevator base 27 is arranged at the corner of the observation image 483 obtained by the object lens 481 of the endoscope 1 so as to be capable of being confirmed as shown in FIG. 29B. At this moment, the object lens 481 focuses on the guide wire 68. In this state, the guide catheter is pulled out at a blast, and any other instrument is inserted with the guide wire being used as a guide. When the end of the therapeutic instrument hustles against the therapeutic instrument elevator base 27, the therapeutic instrument elevator base 27 is lowered, and the guide wire 68 is pushed out from the wire engagement groove 321 by the thrusting force from the therapeutic instrument when the therapeutic instrument passes along the wire engagement groove 321, thereby releasing fixation of the guide wire 68.

The following advantage can be obtained in this embodiment. That is, in this embodiment, as in the endoscope 1 according to the first embodiment, the guide wire 68 can be readily fixed by only the usually performed elevator operation of the therapeutic instrument elevator base 27 in which the elevator operation knob 48 of the front operation portion 13 of the endoscope 1 is operated.

Also, in addition to the advantage similar to that of the endoscope 1 according to the first embodiment, by watching the observation image obtained by the object lens 481 of the endoscope 1, it is possible to visually confirm whether the guide wire 68 has been assuredly fixed. Thus, there is an advantage that an erroneous operation such as accidentally pulling out the unfixed guide wire 68 can be prevented from occurring.

Furthermore, since the therapeutic instrument elevator base 27 is brought into the observation visual field 482 obtained by the object lens 481 of the object optical system of the endoscope 1, there is an advantage that the state of the therapeutic instrument elevator base 27 having moved to the fixed position of the guide wire 68 can be visually confirmed.

Incidentally, this embodiment is not necessarily restricted to the endoscope 1 according to the first embodiment, and it can be applied to all which have a mechanism for fixing the guide wire 68 by using the guide wire fixing member.

Moreover, FIG. 31A show a 13th embodiment according to the present invention. In this embodiment, an index 491 consisting of a stripe marking is provided to the guide wire 68 which is fixed by the guide wire fixing means such as the therapeutic instrument elevator base 27 of the endoscope 1 according to the 12th embodiment and brought into the observation visual field 482 obtained by the object lens 481 of the object optical system of the endoscope 1.

Incidentally, display indicative of displacement of a position of the guide wire 68 such as a scale 492 of a first modification shown in FIG. 31B or numerical FIGS. 493 of a second modification shown in FIG. 31C can suffice the index 491.

The following advantage can be obtained in this embodiment. That is, the advantage similar to that of the 12th embodiment can be obtained in this embodiment, and there is an advantage that the displacement of the guide wire 68 can be easily visually confirmed as well as the advantage similar to that of the 12th embodiment.

Figure 32A:
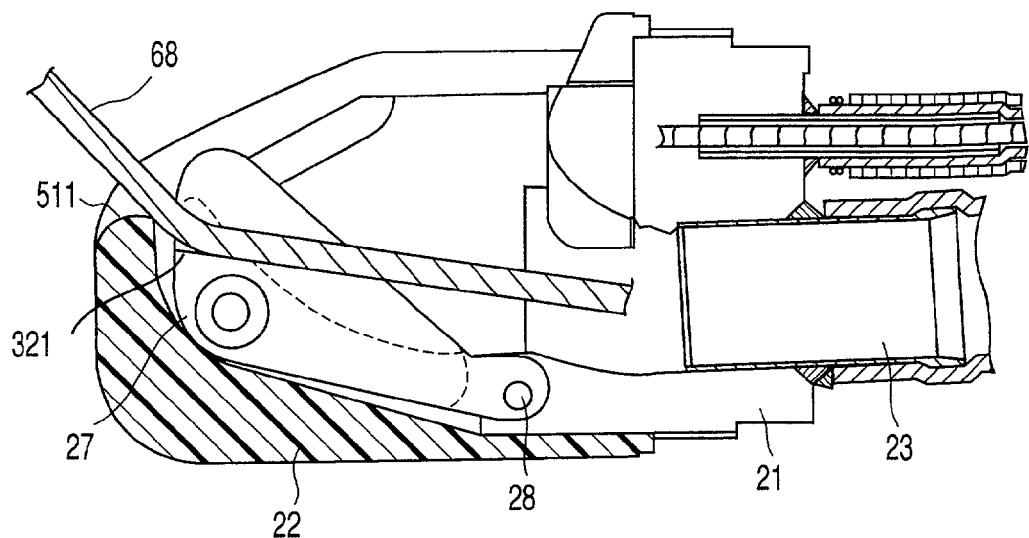
FIG. 32A is a vertical cross-sectional view of a primary part showing the set-down state of a therapeutic instrument elevator base when a guide wire is fixed according to a 14th embodiment of the present invention.

In addition, FIG. 32A shows a 14th embodiment according to the present invention. In this embodiment, the position of the wire engagement groove 321 in the therapeutic instrument elevator base 27 according to the first embodiment is set to be lower than the therapeutic instrument guide plane 511 of the end cover 22 provided at the end portion 17 of the insertion portion 12 of the endoscope 1.

Figure 32B:
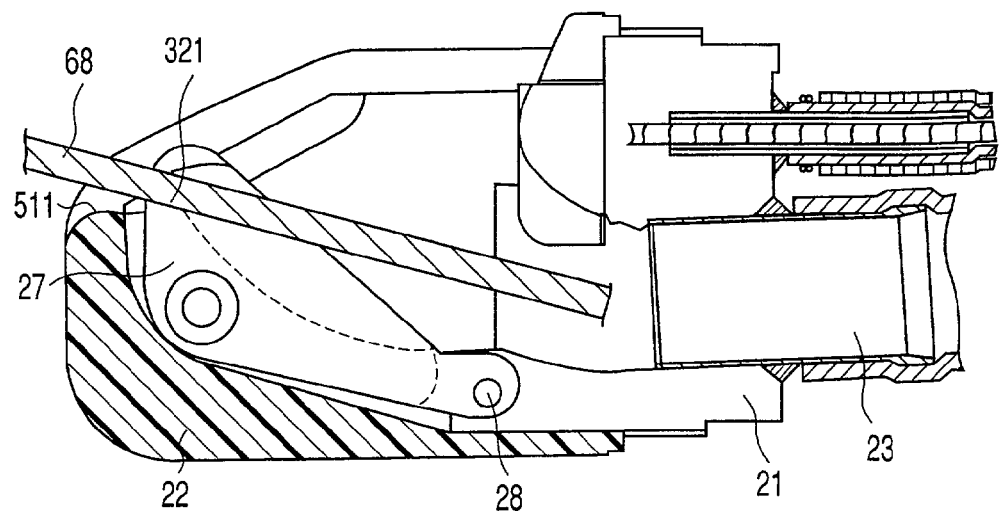
FIG. 32B is a vertical cross-sectional view of a primary part showing the set-down state of a therapeutic instrument elevator base when a conventional guide wire is fixed.

It is to be noted that FIG. 32B shows the set-down state of the conventional treatment elevator base 27 when the guide wire 68 is fixed. As shown in FIG. 32B, in the conventional therapeutic instrument elevator base 27, the position of the wire engagement groove 321 of the therapeutic instrument elevator base 27 is arranged at a position higher than the therapeutic instrument guide plane 511 of the end cover 22 of the insertion portion 12.

The effect of this embodiment will now be described. In the therapeutic instrument elevator base 27 according to this embodiment, as in the therapeutic instrument elevator base 27 of the endoscope 1 according to the first embodiment, after fixing the guide wire 68 and removing the guide catheter, another therapeutic instrument is inserted with the guide wire 68 functioning as a guide. At this moment, in the therapeutic instrument elevator base 27 according to this embodiment, by completely setting down the therapeutic instrument elevator base 27, the guide wire 68 which has been pinched and fixed by the wire engagement groove 321 is pushed up by the therapeutic instrument guide plane 511 of the end cover 22. Therefore, the guide wire 68 is pushed out from the wire engagement groove 321 by this thrusting force and fixation of the guide wire 68 is released.

The following advantage can be demonstrated in this embodiment. That is, in this embodiment, the guide wire 68 is pushed out from the wire engagement groove 321 by only the operation of the therapeutic instrument elevator base 27, and fixation of the guide wire 68 can be released. Therefore, when the inserted therapeutic instrument passes along the wire engagement grove 321, there is the advantage that the working property can be further improved as compared with the method for releasing fixation of the guide wire 68 by the thrusting force of the therapeutic instrument.

Figure 33A:
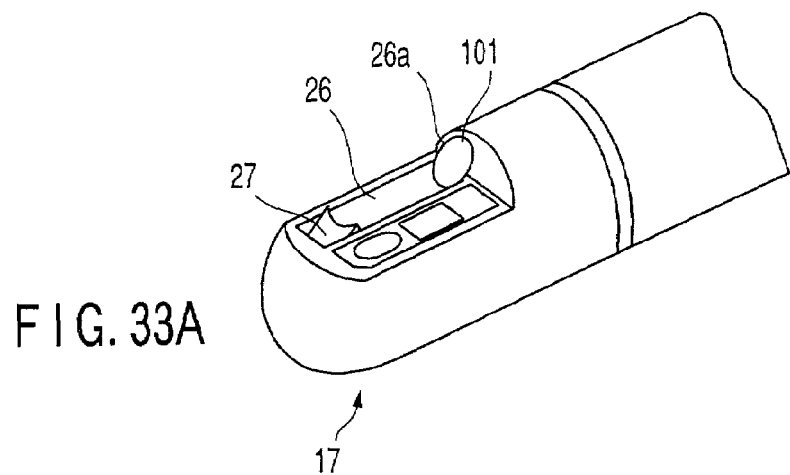
FIG. 33A is a perspective view of a primary part showing a schematic structure of an end portion of an insertion portion in an endoscope according to a 15th embodiment of the present invention.
Figure 33B:
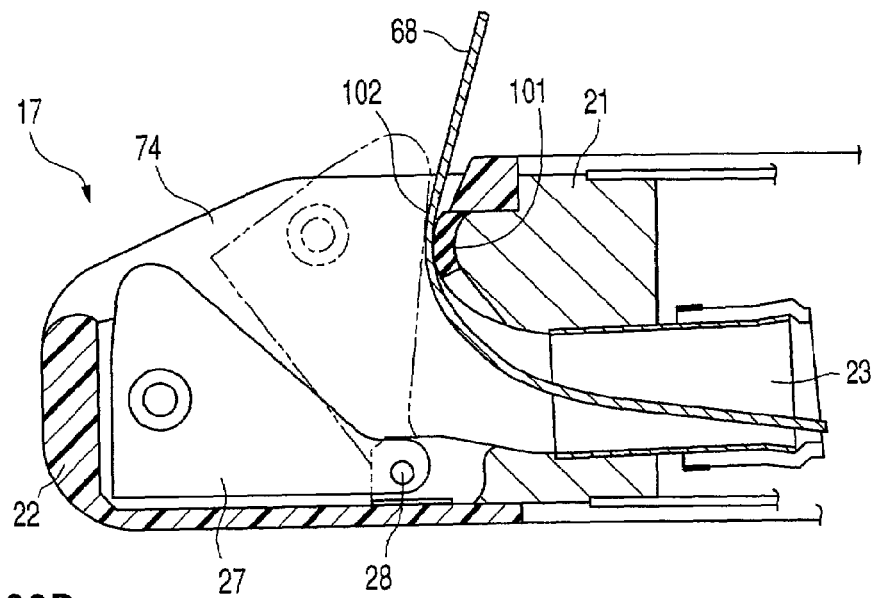
FIG. 33B is a vertical cross-sectional view of a primary part showing the inner structure of an end portion of an insertion section in the endoscope according to the 15th embodiment.

Additionally, FIGS. 33A and 33B show a 15th embodiment according to the present invention. In this embodiment, in place of the wire engagement groove 321 according to the first embodiment, a guide wire fixing mechanism 102 for fixing the guide wire 68 is constituted by embedding an elastic member 101 made of a material having a large friction resistance such as rubber in the front-side wall surface 26a of the channel opening portion 26, raising the therapeutic instrument elevator base 27 and welding the guide wire 68 to the elastic member 101 with pressure by the therapeutic instrument elevator base 27, as shown in FIGS. 33A and 33B.

The effect of this embodiment will now be described. In this embodiment, as in the first embodiment, after inserting the guide wire 68 and the guide catheter into the therapeutic instrument insertion channel 23, the therapeutic instrument elevator base 27 is raised by a set-up wire 30 as towing means by operating the elevator operation knob 48 with the guide catheter being pulled into the lead-in guide path 24 or the channel 23 when the guide wire 68 is fixed. At this moment, as indicated by dotted lines in FIG. 33B, the therapeutic instrument elevator base 27 is raised to a position at which the guide wire 68 is welded to the elastic member 101 with pressure by the therapeutic instrument elevator base 27. When the guide wire 68 is sandwiched between the therapeutic instrument elevator base 27 and the elastic member 101, the guide wire 68 does not slip by the friction resistance of the elastic member 101 but fixed.

In this embodiment, the guide wire 68 can be fixed by raising the therapeutic instrument elevator base 27 by the operation of the elevator operation knob 48 on the front operation portion 13 of the endoscope 1 and sandwiching the guide wire 68 between the therapeutic instrument elevator base 27 and the elastic member 101, thereby obtaining the advantage similar to that of the first embodiment.

Further, in this embodiment in particular, only embedding the elastic member 101 in the front-side wall surface 26a of the channel opening portion 26 can suffice, and an additional component such as an impetus giving mechanism does not have to be newly provided. Therefore, the structure of the end portion 17 of the endoscope 1 is not complicated, which is similar to the prior art.

Figure 34:
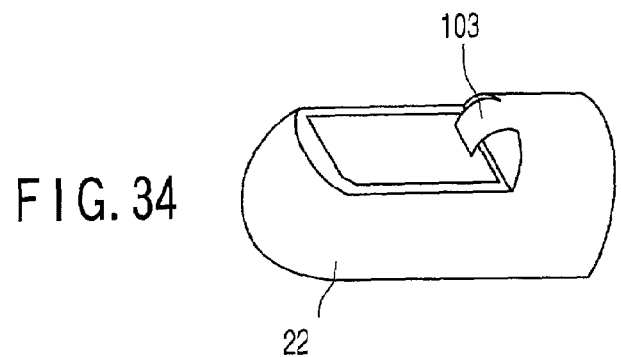
FIG. 34 is a perspective view of a primary part showing a modification of an end cover of the insertion portion in the endoscope according to the 15th embodiment.

Incidentally, in the endoscope 1 which is of a type that the end cover 22 constituted by the elastic member can be attached/detached, as in a modification shown in FIG. 34, the guide wire fixing portion 103 which is extended to the front-side wall surface 26a of the channel opening portion 26 may be provided integrally with the end cover 22 at a part corresponding to the channel opening portion 26 in the end cover 22. In this case, in the endoscope 1 in which the end cover 22 can be attached/detached, the guide wire fixing mechanism 102 can be easily provided to a current scope by replacing the conventional end cover with the end cover 22 according to this embodiment.

Furthermore, the elastic member 101 according to the 15th embodiment may be substituted by a magnet. In this case, as in the first embodiment, after inserting the guide catheter and the metal guide wire 68 into the therapeutic instrument insertion channel 23, the therapeutic instrument elevator base 27 is raised by the elevator operation knob 48 in the operation portion 13 when the guide catheter is drawn into the channel opening portion 26. As a result, the elevator guide wire 68 is attracted to the magnet on the front-side wall surface 26a of the channel opening portion 26 by the magnetic force.

Thereafter, the guide catheter is completely pulled out, and a therapeutic instrument which is subsequently used is inserted from the base end side of the guide wire 68. Then, the therapeutic instrument which is subsequently used is inserted into the therapeutic instrument insertion channel 23 with the guide wire 68 functioning as a guide. At this moment, when the therapeutic instrument passes the position at which the guide wire 68 is fixed by the magnet, the attraction force is weakened, and the guide wire 68 moves away from the magnet. Moreover, the guide wire 68 is inserted into a pancreatic/hepatic duct (not shown). Therefore, the advantage which is the same as the 15th embodiment can be also obtained in this case.

In addition, in the endoscope 1 in which the end cover 22 can be attached/detached, the magnet may be embedded in a part corresponding to the front-side wall surface 26a of the channel opening portion 26 in the end cover 22.

Figures 35A, 35B:
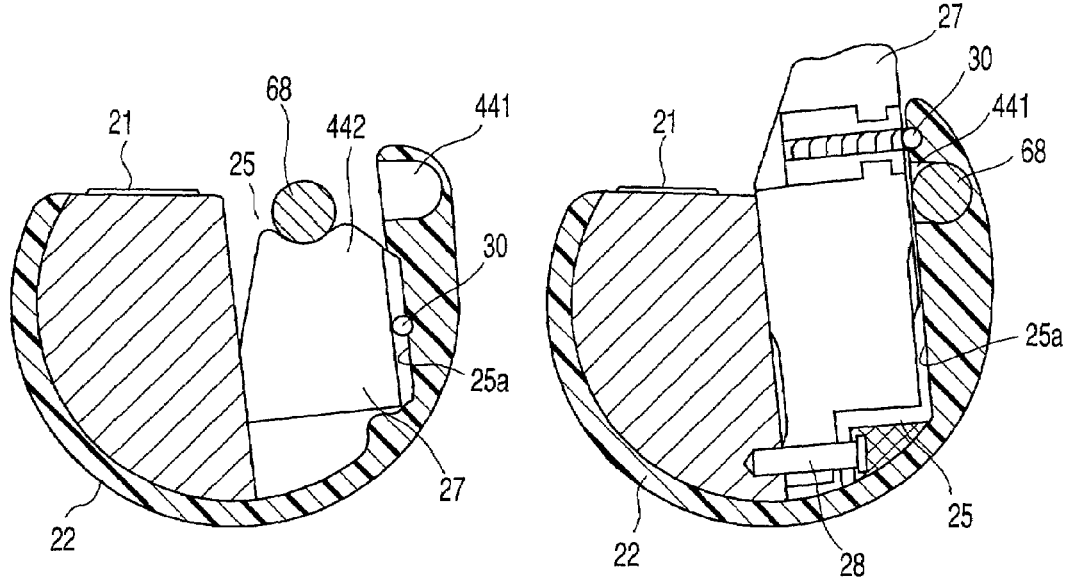
FIG. 35A is a horizontal cross-sectional view showing the set-down state of a therapeutic instrument elevator base seen from an end portion of an endoscope according to a 16th embodiment of the present invention.
FIG. 35B is a horizontal cross-sectional view showing the state in which the therapeutic instrument elevator base is raised in the endoscope according to the 16th embodiment.

Additionally, FIGS. 35A and 35B show a 16th embodiment according to the present invention. In this embodiment, the guide wire engagement groove 441 is provided on an inner wall surface 25a of an accommodation chamber 25 of the therapeutic instrument elevator base 27 in the end cover 22 provided at the end portion 17 of the endoscope 1 according to the first embodiment. The relationship between a groove width M1 of the guide wire engagement groove 441 and a wire diameter D1 of the guide wire 68 is set to, e.g., "M1≦D1". The groove width M1 of the guide wire engagement groove 441 is set to a size that the guide wire 68 fits in the guide wire engagement groove 441 when the guide wire 68 is pushed in a direction of the guide wire engagement groove 441 and the peripheral part of the guide wire engagement groove 441 in the end cover 22 is elastically deformed.

Further, a guide plane 442 which guides the guide wire 68 in a direction of the guide wire engagement groove 441 is formed at the therapeutic instrument elevator base 27. As shown in FIG. 35A, the guide plane 442 is formed by an inclined plane notched on the side surface of the accommodation chamber 25 opposed to the guide wire engagement groove 441 in the state that the therapeutic instrument elevator base 27 is lowered and accommodated in the accommodation chamber 25 (standby position) as shown in FIG. 35A.

Furthermore, in the operation for raising the therapeutic instrument elevator base 27, as the therapeutic instrument elevator base 27 swivels from the standby position to the therapeutic instrument set-up position with the elevator base swivel supporting point 28 at the center, the guide wire 68 is guided to the direction of the guide wire engagement groove 441 by the guide plane 442 of the therapeutic instrument elevator base 27, and the guide wire 68 is partially fitted in the guide wire engagement groove 441. In this state, the side surface of the therapeutic instrument elevator base 27 pushes the guide wire 68 by further raising the therapeutic instrument elevator base 27 as shown in FIG. 35B, and the guide wire 68 is pushed and fixed between the guide wire engagement groove 441 and the side surface of the therapeutic instrument elevator base 27.

The effect of this embodiment will now be described. In this embodiment, as in the first embodiment, the guide wire 68 is guided to the guide wire engagement groove 441 by the guide plane 442 of the therapeutic instrument elevator base 27 when the therapeutic instrument elevator base 27 is raised with the guide catheter being accommodated in the therapeutic instrument insertion channel 23, and the guide wire 68 is partially fitted in the guide wire engagement groove 441.

In this state, the side surface of the therapeutic instrument elevator base 27 pushes the guide sire 68 by further raising the therapeutic instrument elevator base 27, and the guide wire 68 is pushed and fixed between the guide wire engagement groove 441 and the side surface of the therapeutic instrument elevator base 27. At this moment, the movement of the guide wire 68 trying to go out of the guide wire engagement groove 441 can be restricted by maintaining the set-up state of the treatment elevator base 27.

Thereafter, the guide catheter is pulled out from the therapeutic instrument insertion channel 23 at a blast. Another therapeutic instrument is subsequently inserted with the guide wire 68 as a guide. At this moment, when the end of the therapeutic instrument hustles against the therapeutic instrument elevator base 27, the therapeutic instrument elevator base 27 is lowered by the operation of the elevator operation knob 48. Further, when another therapeutic instrument passes along the guide wire engagement groove 441, the guide wire 68 is pushed out from the guide wire engagement groove 441 by the thrusting force from this therapeutic instrument, thereby releasing fixation of the guide wire 68.

The following advantage can be demonstrated in this embodiment. That is, in this embodiment, the advantage similar to that of the endoscope 1 according to the first embodiment can be obtained. In addition to this, further secure fixation is enabled by sandwiching the guide wire 68 inserted into the guide wire engagement groove 441 between the therapeutic instrument elevator base 27 and the guide wire engagement groove 441 and fixing it.

Figures 36A, 36B:
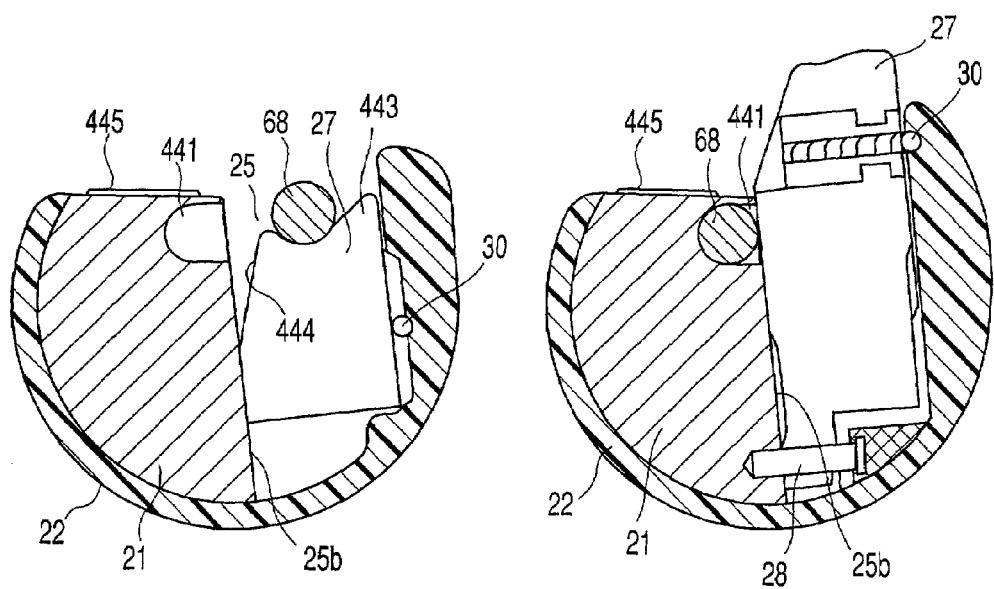
FIG. 36A is a horizontal cross-sectional view showing the set-down state of a therapeutic instrument elevator base seen from an end portion of an endoscope according to a 17th embodiment of the present invention.
FIG. 36B is a horizontal cross-sectional view showing the state in which the therapeutic instrument elevator base is raised in the endoscope according to the 17th embodiment.

Furthermore, FIGS. 36A and 36B show a 17th embodiment according to the present invention. In this embodiment, the guide wire engagement groove 441 according to a 16th embodiment is provided on an inner wall surface 25b on the end hard portion 21 side having an object lens 445 of the object optical system in the accommodation chamber 25 of the therapeutic instrument elevator base 27.

It is to be noted that the groove width of the guide wire engagement groove 441 is similarly set as in the 16th embodiment.

Moreover, a guide wall 443 which restricts a protruding direction of the therapeutic instrument to the end portion on the opposite side to the inner wall surface 25b on the end hard portion 21 side is provided to the end portion of the therapeutic instrument elevator base 27. A guide plane 444 for guiding the guide wire 68 to the direction of the guide wire engagement groove 441 is formed on the side of the guide wall 443.

In this embodiment, the following effect can be demonstrated. That is, in this embodiment, the advantage similar to that of the 16th embodiment can be obtained. In addition to this, since the guide wall 443 for restricting the protruding direction of the therapeutic instrument to the end on the opposite side to the inner wall surface 25b on the end hard portion 21 side is provided to the end portion of the therapeutic instrument elevator base 27, the therapeutic instrument can be caused to protrude toward the object lens 445 side of the end hard portion 21 by the guide wall 443 of the therapeutic instrument elevator base 27 when raising the therapeutic instrument elevator base 27, thereby improving the operability of the therapeutic instrument.

In addition, FIGS. 37A to 37D show an 18th embodiment. In this embodiment, a guide wire fixing mechanism 381 having a different structure substitutes for the wire engagement groove 321 according to the first embodiment.

Figure 37A:
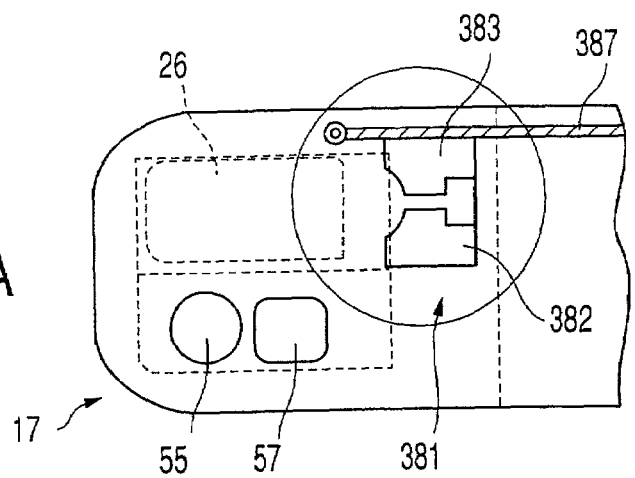
FIG. 37A is a plane view showing an end portion of an insertion portion in an endoscope according to an 18th embodiment of the present invention.

That is, a first impetus giving member 382 and a second impetus giving member 383 for releasably fixing the guide wire 68 when the guide wire 68 is in the pinched state are provided to the guide wire fixing mechanism 381 according to this embodiment. As shown in FIG. 37A, the first impetus giving member 382 is fixed to the front-side end portion of the channel opening portion 26 of the end hard portion 21 provided at the end portion 17 of the insertion portion 12 in the endoscope 1. Additionally, the second impetus giving member 383 is provided next to the first impetus giving member 382 so as to be capable of being connected/disconnected to/from the first impetus giving member 382.

Figure 37B:
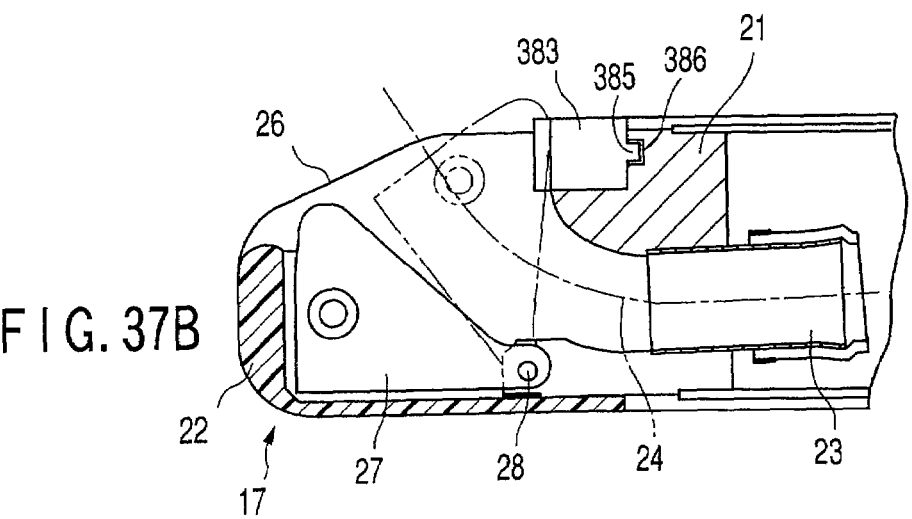
FIG. 37B is a vertical cross-sectional view of a primary part showing the inner structure of the end portion of the insertion portion in the endoscope according to the 18th embodiment.

Further, a therapeutic instrument guide plane 384 of each of the impetus giving members 382 and 383 is formed by whittling away those members in accordance with the therapeutic instrument shape. Furthermore, as shown in FIG. 37B, a guiding protrusion 385 is provided to the second impetus giving member 383 at a position on the opposite side to the therapeutic instrument guide plane 384.

Moreover, a guide groove 386 of the second impetus giving member 383 is provided on a wall surface of the end hard portion 21 on the front side. The guiding protrusion 385 of the second impetus giving member 383 is movably engaged with the guide groove 386. In addition, the second impetus giving member 383 is movably supported substantially vertically with respect to the lead-in guide path 24 along the guide groove 386.

In addition, a tow wire 387 is provided on the side of the second impetus giving member 383 opposed to the first impetus giving member 382. A rotatable roller 388 is connected to the end portion of the tow wire 387.

Additionally, the base end portion of the tow wire 387 is led to the operation portion 13 through a tow wire channel 389 and connected to a non-illustrated link mechanism. Further, as in the first embodiment, the towing operation of the tow wire 387 is enabled by the operation of the operation lever 72 on the front side.

Further, an accommodation chamber 390 is provided to the first impetus giving member 382 and the second impetus giving member 383 on the opposite side to the therapeutic instrument guide plane 384. A coil-like spring member 391 for giving impetus in a direction along which the second impetus giving member 383 is moved away from the first impetus giving member 382 is provided in this accommodation chamber 390. This spring member 391 is arranged substantially vertically with respect to the lead-in guide path 24.

Figures 37C, 37D:
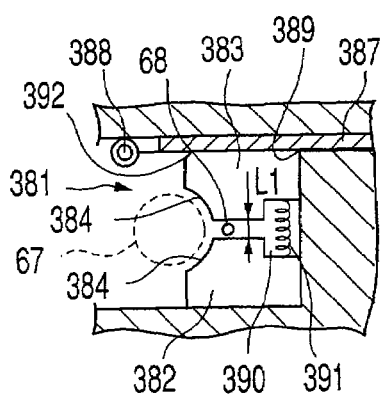
FIG. 37C is a vertical cross-sectional view of a primary part showing the state before fixing a guide wire in the endoscope according to the 18th embodiment.
FIG. 37D is a vertical cross-sectional view of a primary state showing the state in which the guide wire is fixed in the endoscope according to the 18th embodiment.

Furthermore, in this embodiment, as shown in FIG. 37C, in regard to a distance L1 between the first impetus giving member 382 and the second impetus giving member 383 in the usual state, the relationship between a wire diameter D1 of the guide wire 68 and an outside diameter D2 of the therapeutic instrument or any other therapeutic instrument such as the guide catheter is set to "D1<L1<D2".

Moreover, at the time of towing by the operation lever 72, as shown in FIG. 37D, a distance L2 between the first impetus giving member 382 and the second impetus giving member 383 when the second impetus giving member has moved is set to "L2≦D1<D2".

In addition, a chamfered portion 392 obtained by obliquely cutting a corner portion is provided at a part of the second impetus giving member 383 which firstly comes into contact with a roller 388 on the tow wire 387 side.

The effect of this embodiment will now be described. When using the endoscope 1 of this embodiment, as in the 29th embodiment, after inserting the guide catheter and the guide wire 68 into the body through the channel 23, the elevator operation knob 48 of the therapeutic instrument elevator base 27 is operated with the guide catheter being pulled into the lead-in guide path 24 or the channel 23. The set-up wire 30 is towed by the operation of the elevator operation knob 48, and the therapeutic instrument elevator base 27 is swiveled around the elevator base swivel supporting point 28 and raised as indicated by dotted lines in FIG. 37B.

At this moment, when the guide wire 68 is raised by raising the therapeutic instrument elevator base 27, the guide wire 68 is guided between the first impetus giving member 382 and the second impetus giving member 383 and fitted therein as shown in FIG. 37C. In this state, the roller 388 is pulled next to the second impetus giving member 383 through the tow wire 387 by the operation lever 72. As a result, as shown in FIG. 37D, the second impetus giving member 383 is pushed out along the guide groove 386 and comes close to the first impetus giving member 382. Therefore, a width of a space between the first impetus giving member 382 and the second impetus giving member 383 is narrowed, and the guide wire 68 is sandwiched and mechanically fixed.

In addition, after confirming that the guide wire 68 is fixed, the guide catheter is completely pulled outside the therapeutic instrument insertion channel 23 from the operation portion 13 side of the endoscope 1.

Thereafter, a therapeutic instrument which is subsequently used is inserted from the base end portion side of the guide wire 68. At this moment, with the guide wire 68 being used as a guide, the therapeutic instrument is inserted into the therapeutic instrument insertion channel 23. Then, when the therapeutic instrument hustles against the both impetus giving members 382 and 383, the tow wire 387 is loosened by operating the operation lever 72, and the second impetus giving member 383 is pushed back to its original position by the force of the spring member 391. Consequently, fixation of the guide wire 68 is released, and the therapeutic instrument is inserted into a pancreatic/hepatic duct (not shown).

In this embodiment, as in the first embodiment, the guide wire 68 can be easily fixed by the operation of the operation lever 72 of the front-side operation portion 13 of the endoscope 1, and the advantage similar to that of the first embodiment can be obtained.

Figure 38:
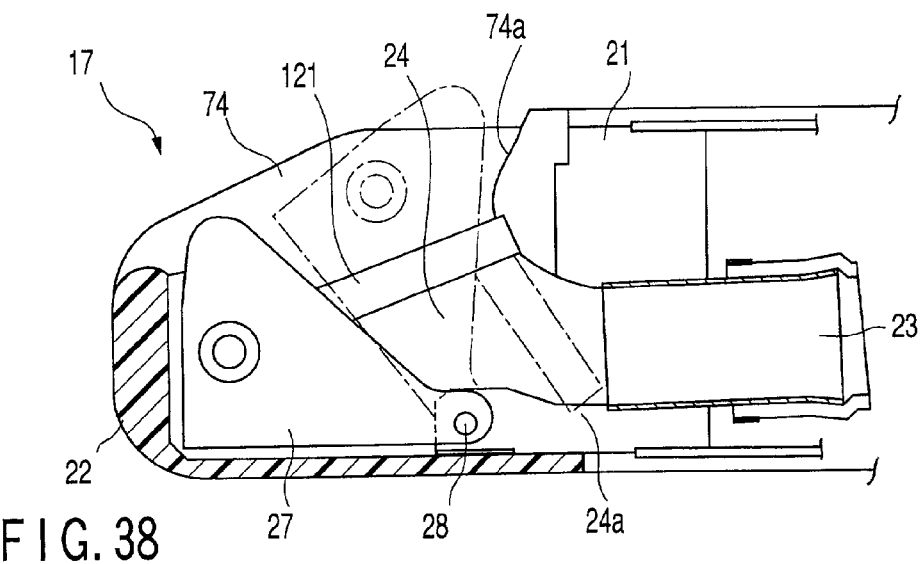
FIG. 38 is a vertical cross-sectional view of a primary part showing an inner structure of an end portion of an insertion portion in an endoscope according to a 19th embodiment of the present invention.
Figure 39:
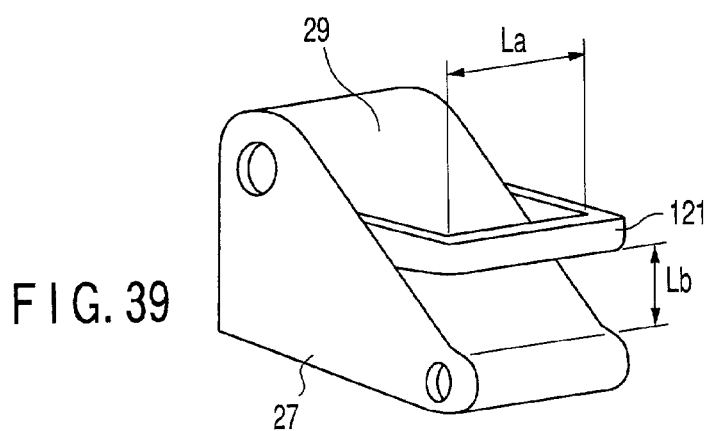
FIG. 39 is a perspective view showing a therapeutic instrument elevator base in the endoscope according to the 19th embodiment.

Additionally, FIGS. 38 and 39 show a 19th embodiment according to the present invention. In this embodiment, a substantially-U-shaped guide wire fixture 121 is provided to the guide plane 29 of the therapeutic instrument elevator base 27 as shown in FIGS. 38 and 39 in place of the wire engagement grove 321 according to the first embodiment.

As illustrated in FIG. 39, dimensions La and Lb of the guide wire fixture 121 are set to the relationship of "La, Lb>d" with respect to the outside diameter dimension d of the therapeutic instrument insertion channel 23.

The effect of this embodiment will now be described. In this embodiment, as in the first embodiment, after inserting the guide wire 68 and the guide catheter into the therapeutic instrument insertion channel 23, the guide catheter is operated to be pulled into the lead-in guide path 24 or the channel 23 when the guide wire 68 is fixed. When the guide catheter enters the channel 23 at the time of removing the guide catheter, the guide wire 68 is sandwiched between the guide wire fixture 121 and the lead-in guide path lower surface 24a of the end hard portion 21 by raising the therapeutic instrument elevator base 27 by performing the elevator operation for the therapeutic instrument elevator base 27, thereby fixing the guide wire 68.

In this embodiment, the therapeutic instrument elevator base 27 is raised by the operation by the elevator operation knob 48 on the front operation portion 13 side of the endoscope 1, and the guide wire 68 can be fixed by sandwiching the guide wire 68 between the guide wire fixture 121 of the therapeutic instrument elevator base 27 and the lead-in guide path lower surface 24a of the end hard portion 21, thereby obtaining the advantage similar to that of the first embodiment.

Further, in this embodiment in particular, insertion of the therapeutic instrument in an usual case can not be avoided by the guide wire fixture 121 of the therapeutic instrument elevator base 27 by securing the opening portion of the guide wire fixture 121 so as to be wider than the therapeutic instrument insertion channel 23, and the guide wire 68 can be fixed by raising the therapeutic instrument elevator base 27.

Figure 40:
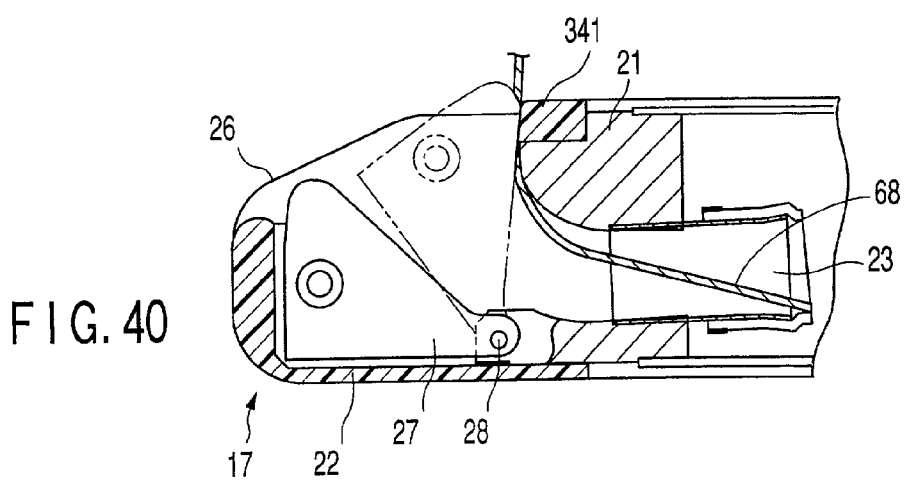
FIG. 40 is a vertical cross-sectional view of a primary part showing the engagement state of a guide wire in an endoscope according to a 20th embodiment of the present invention.

Furthermore, FIG. 40 shows a 20th embodiment according to the present invention. In this embodiment, the structure of the end portion 17 of the insertion portion 12 in the endoscope 1 according to the first embodiment is changed as follows.

That is, an engagement convex portion 341 for fixing the guide wire 68 is provided so as to protrude at a peripheral edge part of the channel opening portion 26 of the end cover 22 in place of the wire engagement groove 331 according to the second embodiment. This engagement convex portion 341 is constituted to be welded to the guide plane 29 of the therapeutic instrument elevator base 27 with pressure as indicated by dotted lines in FIG. 40 when the therapeutic instrument elevator base 27 is raised, and the guide wire 68 is sandwiched between the engagement convex portion 341 and the therapeutic instrument elevator base 27 so that the guide wire 68 is releasably engaged.

The effect of this embodiment will now be described. When using the endoscope 1 according to this embodiment, as in the first embodiment, after inserting the guide catheter and the guide wire 68 into the body through the channel 23, the elevator operation knob 48 of the therapeutic instrument elevator base 27 is operated with the guide catheter being pulled into the introduction guide path 24 or the channel 23. The towing operation of the set-up wire 30 is performed with the manipulation of the elevator operation knob 48, and the therapeutic instrument elevator base 27 is swiveled around the elevator base swivel supporting point 28 and raised as indicated by dotted lines in FIG. 40.

Moreover, the guide plane 29 of the therapeutic instrument elevator base 27 is welded with pressure to the engagement convex portion 341 provided at the peripheral edge part of the channel opening portion 26 of the end cover 22 when the therapeutic instrument elevator base 27 is raised, and the guide wire 68 is sandwiched between the engagement convex portion 341 and the therapeutic instrument elevator base 27 and releasably engaged. In this state, the guide wire 68 is mechanically fixed.

In this embodiment, the following advantage can be demonstrated. That is, the guide wire 68 can be easily fixed by only the elevator operation of the therapeutic instrument elevator base 27 which is usually carried out on the front operation portion 13 side of the endoscope 1 in this embodiment. Therefore, the advantage similar to that of the first embodiment can be also obtained in this embodiment.

Also, in this embodiment, the structure of the end portion 17 of the insertion portion 12 can be simplified since a movable type constituent part does not have to be newly provided at the end portion 17 of the insertion portion 12 of the endoscope 1, in addition to the advantage of the first embodiment.

Additionally, even though the guide wire 68 cannot be pinched because of the set-up angle of the therapeutic instrument elevator base 27 in the conventional elevator base 27, if the endoscope 1 adopts the detachable end cover 22 in this embodiment, the guide wire 68 can be fixed by replacing such a cover with the end cover 22 having a protruding engagement convex portion 341 for fixing the guide wire 68 to the peripheral edge part of the channel opening portion 26 of the end cover 22.

Further, FIGS. 41A and 41B show a 21st embodiment according to the present invention. In this embodiment, guide wire fixing means 351 having a different structure is provided in place of the wire engagement groove 32 according to the first embodiment.

That is, a guide wire fixing member 352 for engaging the guide wire 68 is provided to the guide wire fixing means 351 according to this embodiment at a peripheral edge part of the channel opening portion 26 of the end hard portion 21. As shown in FIG. 41B, two guide wire identification members 353a and 353b made of stainless steel wires which are pendent toward the inner side of the opening portion 26 from the both sides of the channel opening portion 26 of the end hard portion 21 are provided to the guide wire fixing member 352. The base end portions of the guide wire identification members 353a and 353b are embedded in the both side portions of the channel opening portion 26 of the end hard portion 21. Furthermore, at least two guide wire fixing member insertion holes 354a and 354b are provided on the both sides of the side surface of the channel opening portion 26.

Moreover, one of the two guide wire identification members 353a and 353b, namely, the first guide wire identification member 353a is extended from the upper edge side to the inner side of the channel opening portion 26 and bent toward the left side in FIG. 41B. In addition, the other second guide wire identification member 353b is extended from the lower edge side to the inner side of the channel opening portion 26 and bent toward the right side in FIG. 41B. Respective extended parts 353a1 and 353b1 of the two guide wire identification members 353a and 353b are arranged so as to be spaced from and opposed to each other substantially in parallel. Additionally, a space S having an appropriate widthwise dimension L is formed between the respective extended parts 353a1 and 353b1 of these guide wire identification members 353a and 353b. This space S is set so as to be larger than the outside diameter dimension of the guide wire 68, for example.

Further, a guide wire fixture 355 formed by a filate member having no elastic property, e.g., a surgical thread is provided to the guide wire fixing means 351. One end portion of the guide wire fixture 355 is fixed to the first guide wire identification member 353a on the upper side in FIG. 41B. Furthermore, after passing through the guide wire fixing member insertion hole 354a on the upper side (first guide wire identification member 353a side) in FIG. 41B of the channel opening portion 26, the guide wire fixture 355 cuts across the opening portion 26 and passes through the guide wire fixing member insertion hole 354b on the lower side (second guide wire identification member 353b side) in FIG. 41B. Then, the other end portion side of the guide wire fixture 355 is fixed to the second guide wire identification member 353b. As a result, the guide wire fixture 355 is attached so as to be cross-linking between the both side portions on the opening portion 26.

The effect of this embodiment will now be described. When using the endoscope 1 according to this embodiment, as in the first embodiment, the guide catheter and the guide wire 68 are inserted into the body through the channel 23 and set in such a manner that they protrude from the channel opening portion 26 of the end portion 17 in the endoscope 1. In this state, when the therapeutic instrument elevator base 27 is raised by operating the elevator operation knob 48 of the operation portion 13 in the endoscope 1, the guide catheter enters the space between the respective extended parts 353a1 and 353b1 of the guide wire identification members 353a and 353b.

At this moment, a material having a larger diameter than that of the guide wire 68, e.g., the guide catheter enlarges the space between the respective extended parts 353a1 and 353b1 of the guide wire identification members 353a and 353b, and the tensile force of the guide wire fixture 355 hence relaxes. The guide catheter is raised without interfering with the guide wire fixture 355.

Further, when raising the guide wire 68, since the guide wire 68 passes between the respective extended parts 353a1 and 353b1 of the two guide wire identification members 353a and 353b, the tensile force of the guide wire fixture 355 fixed to the guide wire identification members 353a and 353b does not relax. Therefore, in this case, by raising the therapeutic instrument elevator base 27, the guide wire 68 receives the force in the opposite directions by the therapeutic instrument elevator base 27 and the guide wire fixture 355 in the shearing manner, and the guide wire 68 is hence bent into the substantially L shape and fixed.

The following effect can be demonstrated in this embodiment. That is, in this embodiment, since the guide wire fixing member 352 for engaging the guide wire 68 with the peripheral edge part of the channel opening portion 26 of the end hard portion 21 is provided, the guide wire 68 can be readily fixed by only the elevator operation for the therapeutic instrument elevator base 27 which is usually performed by operating the elevator operation knob 48 of the front operation portion 13 of the endoscope 1. Therefore, the advantage similar to that of the first embodiment can be also obtained in this embodiment.

Figure 44:
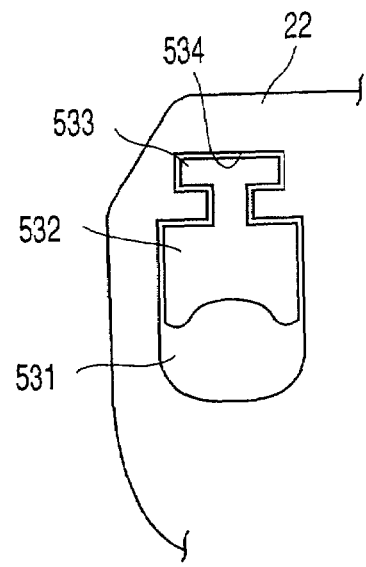
FIG. 44 is a horizontal cross-sectional view of a primary part showing an inner structure of an end portion in an insertion portion in the endoscope according to the 22nd embodiment.

Furthermore, FIGS. 42 to 44 show a 22nd embodiment according to the present invention. In this embodiment, the inner structure of the end portion 17 of the insertion portion 12 in the endoscope 1 according to the first embodiment is changed as follows.

That is, in this embodiment, a guide wire fixing member accommodation chamber 53 is formed at the end hard portion 21 of the end portion 17 of the insertion portion 12 in the endoscope 1. The guide wire fixture 532 formed by an insulating member is accommodated in this accommodation chamber 531 so as to be capable of protruding/retracting from/to the lead-in guide path 24 communicating with the channel opening portion 26. The insulating member of the guide wire fixture 532 is used for preventing sparks caused when the guide wire fixture 532 is accidentally brought into contact with the endoscope end portion 17 when a high frequency flows with a papillotomy knife and the like being inserted in the therapeutic instrument insertion channel 23.

Moreover, as shown in FIG. 44, a substantially-T-shaped guiding protrusion 533 is provided so as to protrude from the upper portion of the guide wire fixture 532. A guide groove 534 having a shape corresponding to the guiding protrusion 533 is formed at the end hard portion 21. This guide groove 534 is conjugated to the guide wire fixing member accommodation chamber 531. In addition, the guiding protrusion 533 of the guide wire fixture 532 is engaged with the guiding groove 534 of the end hard portion 21.

Additionally, a coil-like spring member 535 for giving impetus to the guide wire fixture 532 in the outer direction (direction toward the end of the endoscope 1) of the guide wire fixing member accommodation chamber 531 is provided in this accommodation chamber 531.

Further, the end portion of the tow wire 536 is fixed to the guide wire fixture 532. This tow wire 536 is led to the operation portion 13 through the tow wire channel 537 and connected to a non-illustrated link mechanism. As a result, as in the first embodiment, the towing operation of the guide wire fixture 532 is enabled through the tow wire 536 by the operation of the operation lever 72 on the front side.

The effect of this embodiment will now be described. In this embodiment, when performing the operation for fixing the guide wire 68 to the end portion 17 of the insertion portion 12 in the endoscope 1 at the time of replacing the guide catheter inserted into the body through the guide wire 68 with another therapeutic instrument, as in the first embodiment, the operation for loosening the tow wire 536 is carried out by manipulating the operation lever 72 with the guide catheter being pulled in the therapeutic instrument insertion channel 23. At this moment, the guide wire fixture 532 is pushed out in the direction toward the end of the insertion portion outside the accommodation chamber 531 by the spring force of the spring member 535 and caused to protrude into the lead-in guide path 24 as shown in FIG. 43. Consequently, the guide wire 68 raised by the therapeutic instrument elevator base 27 is sandwiched between the guide wire fixture 532 and the therapeutic instrument elevator base 27 and mechanically fixed.

The following advantage can be demonstrated in this embodiment. That is, in this embodiment, the advantage similar to that of the first embodiment can be obtained. In addition to this, when performing the operation for fixing the guide wire 68 to the end portion 17 of the insertion portion 12 in the endoscope 1, the guide wire 68 can be fixed by the surface contact state between the guide wire fixture 532 and the therapeutic instrument elevator base 27, thereby further securely fixing the guide wire 68 as compared with the prior art.

Figure 45:
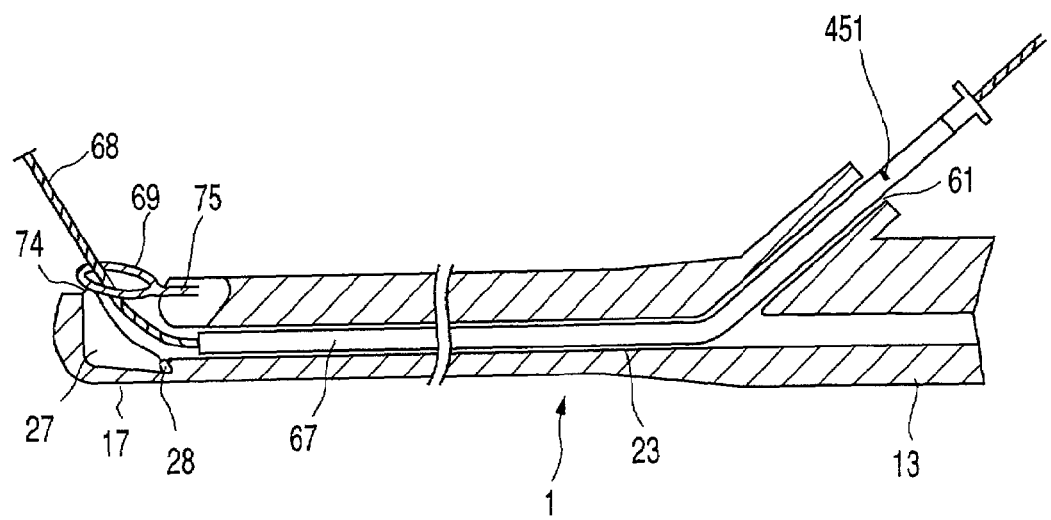
FIG. 45 is a schematic block diagram of an endoscope showing a 23rd embodiment of the present invention.

Further, FIG. 45 shows a 23rd embodiment according to the present invention. In this embodiment, an index 451 indicative of an insertion position of the guide catheter 67 is provided to the base end portion of the guide catheter 67 according to the seventh embodiment. In this embodiment, if the guide catheter 67 or the therapeutic instrument is inserted into the therapeutic instrument insertion channel 23 of the endoscope 1, the index 451 of the guide catheter 67 is arranged at a position corresponding to the insertion opening portion 61 of the operation portion 13 when the guide catheter 67 or the therapeutic instrument is drawn to a position at which the guide wire 68 can be fixed. Furthermore, the index 451 of the guide catheter 67 may be a visual indicator having a color and the like or an indicator with irregularities that can be touched by a hand to feel.

The effect of this embodiment will now be described. In this embodiment, as in the first embodiment, after inserting the guide catheter 67 into the therapeutic instrument insertion channel 23 from the insertion opening portion 61 of the operation portion 13 in the endoscope 1, the guide catheter 67 is caused to protrude toward the outside from the channel opening portion 26 and inserted into a pancreatic/hepatic duct (not shown) in the papillotomy manner.

Then, in the operation for replacing the currently used guide catheter 67 with a therapeutic instrument which is subsequently used, the guide wire 68 is first inserted from the mouth ring of the guide catheter 67 on the base end side. Thereafter, an observation image (endoscopic image) of the endoscope 1 is used to confirm that the end portion of the guide wire has entered the pancreatic/hepatic duct (not shown), and the base end side of the guide wire 68 is gripped by a hand so that the guide wire 68 can not move. Subsequently, in this state, the operation for pulling out the guide catheter 67 is conducted.

At this moment, the endoscopic image is used to confirm that the guide catheter 67 has been drawn out from a papilla (not shown), and the guide wire 67 is further pulled out. Then, with the end of the guide catheter 67 being accommodated in the channel opening portion 26 at the end of the endoscope 1, the index 451 appears on a part of the guide catheter which is exposed from the insertion opening portion 61 of the operation portion 13. Therefore, the position of the end of the guide catheter 67 can be assuredly confirmed when an operator or a worker sees the index 541.

Then, when the state that the end of the guide catheter 67 is accommodated in the channel opening portion 26 at the end of the endoscope 1 is confirmed, the guide wire 68 can be fixed by operating the later-described guide wire fixture 69 and the like.

In this embodiment, the following advantage can be obtained. That is, in this embodiment, the index 451 indicative of an insertion position of the guide catheter 67 is provided at the base end portion of the guide catheter 67. When the guide catheter 67 or the therapeutic instrument is inserted into the therapeutic instrument insertion channel 23 of the endoscope 1, the index 451 is arranged at a position corresponding to the insertion opening portion 61 of the operation portion 13 at the point in time that the guide catheter 67 or the therapeutic instrument is pulled to the position at which the guide wire 68 can be fixed. Therefore, the position of the end of the guide catheter 67 can be assuredly confirmed when an operator or a worker sees this index 451, and there is an advantage that the timing for operating the guide wire fixture 69 can be readily acknowledged.

Further, FIGS. 46A and 46B show a 24th embodiment according to the present invention. A guide wire fixture 69 formed by a wire which is opened in the loop form and has a snare shape is provided to the notch portion 17a of the end portion 17 in the endoscope 1. The end opening portion 71a of the tow wire channel 71 which is inserted into the insertion portion 12 is provided on a rear end wall surface 17b of the notch portion 17a of the end portion 17. The tow wire 75 for towing the guide wire fixture 69 is inserted into the tow wire channel 71. Further, the base end portion of the guide wire fixture 69 is connected to the end portion of the tow wire 75.

Furthermore, the tow wire 75 is led to the operation portion 13 side through the tow wire channel 71. Moreover, the base end portion of the tow wire 75 is connected to the operation lever (operation transmitting means) 72 (see FIG. 1) of the operation portion 13 through the link mechanism having the same structure as the above-described elevator base actuation mechanism 41.

Incidentally, since the link mechanism has the same structure as the above-mentioned elevator base actuation mechanism 41, its explanation is omitted. Moreover, the guide wire fixture 69 is configured to be capable of moving to a protrusion position at which the guide wire fixture is caused to protrude on the upper surface position of the channel opening portion 26 from the end opening portion 71a of the tow wire channel 71 as shown in FIG. 46A and a accommodation position at which the guide wire fixture 69 is accommodated on the end opening portion 71a side of the tow wire channel 71 as shown in FIG. 46B by the operation of the operation lever 72.

In addition, when the guide wire fixture 69 protrudes at the upper surface position of the channel opening portion 26 from the end opening portion 71a of the tow wire channel 71, the guide wire fixture 69 is opened in the state where the wire is opened in the loop form.

Incidentally, when the guide wire fixture 69 is opened, the guide wire fixture 69 is set so as to have dimensions that it can cover the entire channel opening portion 26 as shown in FIG. 46a and be elongated with respect to the axial direction of the insertion portion 12 in the endoscope 1 in the substantially elliptical shape, and it is configured to be opened so that the length of the opening portion which is opened in the loop form in the lengthwise direction can be approximately 20 mm.

Additionally, a protrusion 70 capable of temporarily fixing the guide wire fixture 69 on the end side away from the channel opening portion 26 is provided to the notch portion 17a of the end portion 17 in the endoscope 1. Further, by engaging the guide wire fixture 69 with its end portion being hooked on this protrusion 70, the guide wire fixture 69 can be held at the standby position.

Further, when operating the operation lever 72 in the operation portion 13, the towing operation of the tow wire 75 is effected by the link mechanism having the same structure as the elevator base actuation mechanism 41, and the guide wire fixture 69 is moved to the accommodation position at which the guide wire fixture 69 is accommodated on the end opening portion 71a side of the tow wire channel 71 as shown in FIG. 46B. At this moment, an opening area of the loop-like opening portion formed by the wire of the guide wire fixture 69 is gradually reduced with the movement of the guide wire fixture 69 that the guide wire fixture 69 is pulled to the end opening portion 71a side of the tow wire channel 71. Furthermore, when a large part of the guide wire fixture 69 is accommodated on the end opening portion 71a side of the tow wire channel 71, the guide wire 68 which is inserted into the therapeutic instrument insertion channel 23 and led to the outside from the channel opening portion 26 as shown in FIG. 46B is pressed against the edge part of the channel opening portion 26 on the rear end portion side and fixed.

The effect of this embodiment will now be described. When using the endoscope 1 according to this embodiment, the guide wire fixture 69 is previously moved to the protrusion position at which the guide wire fixture 69 is caused to protrude at the upper surface position of the channel opening portion 26 from the end opening portion 71a of the tow wire channel 71 as shown in FIG. 46A. At this moment, with the loop-shaped opening portion formed by the wire of the guide wire fixture 69 being expanded around the channel opening portion 26, the end portion of the guide wire fixture 69 is hooked on the protrusion 70 of the end portion 17 in the endoscope 1 and engaged, thereby holding the guide wire fixture 69 at the standby position.

In this state, the guide catheter 67 is inserted into the therapeutic insertion channel 23 from the insertion opening portion 61 of the operation portion 13 in the endoscope 1. Then, the guide catheter 67 is caused to protrude to the outer side from the channel opening portion 26 and inserted into a pancreatic/hepatic duct (not shown) in the papillotomy manner.

Thereafter, in the operation for replacing the currently used guide catheter 67 with the therapeutic instrument which is subsequently used, the guide wire 68 is first inserted from the mouth ring of the guide catheter 67 on the base end side thereof. Then, an observation image (endoscopic image) of the endoscope 1 is used to confirm that the end portion of the guide wire 68 has been inserted into the pancreatic/hepatic duct (not shown), and the base end side of the guide wire 68 is gripped by a hand so that the guide wire 68 can not move. Subsequently, in this state, the operation for pulling out the guide catheter 67 is performed.

At this moment, after confirming in an endoscopic image that the guide catheter 67 has been pulled out from a papilla (not shown), the guide catheter 67 is further pulled out. Then, with the end of the guide catheter 67 being accommodated in the channel opening portion 26 at the end of the endoscope 1, the end opening portion 71a of the tow wire channel 71 is narrowed down as shown in FIG. 46B by towing the guide wire fixture 73 by the operation lever 72, and the guide wire 68 led from the channel opening portion 26 to the outer side is pressed against the edge part of the channel opening portion 26 on the rear edge portion side and mechanically fixed.

Moreover, after confirming that the guide wire 68 has been fixed, the guide catheter 67 is completely pulled to the outside of the therapeutic instrument insertion channel 23 from the operation portion 13 side of the endoscope 1.

Then, a therapeutic instrument which is subsequently used is inserted from the base end side of the guide wire 68. At this moment, with the guide wire 68 being used as a guide, the therapeutic instrument is inserted into the therapeutic instrument insertion channel 23. Then, when the therapeutic instrument hustles against the guide wire fixture 69, fixation of the guide wire 68 by the guide wire fixture 69 is released by operating the operation lever 72, and the therapeutic instrument is inserted into the pancreatic/hepatic duct (not shown). Thereafter, the therapeutic instrument can be replaced by the same method for a necessary number of times.

The following advantage can be demonstrated in this embodiment. That is, the guide wire 68 can be readily fixed by the guide wire fixture 69 by the operation of the operation lever 72 on the front operation portion 13 side of the endoscope 1 in this embodiment.

In addition, since the guide wire fixture 69 according to this embodiment is formed by a snare-shaped wire which is opened in the loop form, secure fixation is enabled by snaring the snare-shaped wire of the guide wire fixture 69 when operating the operation lever 72.

Additionally, in an usual case, accommodating the guide wire fixture 69 in the end opening portion 71a of the tow wire channel 71 can prevent the guide wire fixture 69 from entering the observation visual field of the endoscope 1. Thus, this causes no problems.

Further, in this embodiment, the protrusion 70 is provided on the end side away from the channel opening portion 26 of the end portion 17 in the endoscope 1, and the guide wire fixture 69 can be temporarily fixed to this protrusion. Therefore, as shown in FIG. 46A, the wire of the guide wire fixture 69 can be stably opened in the loop form at the protrusion position where the guide wire fixture 69 is caused to protrude at the upper surface position of the channel opening portion 26 from the end opening portion 71a of the tow wire channel 71.

Incidentally, although this embodiment has illustrated the structure for effecting the towing operation of the tow wire 75 by the operation lever 72 of the operation portion 13 through the link mechanism as an example of the operation of the guide wire fixture 69, the present invention is not restricted thereto. Any other means may be used if the guide wire fixture 69 can be led in the axial direction of the insertion portion 12 of the endoscope 1. For example, an operator manually tows a part of the tow wire 75 of the guide wire fixture 69 protruding from the operation portion 13 to the outer side.

Furthermore, FIGS. 47A and 47B show a 25th embodiment according to the present invention. In this embodiment, the structure is changed so that a guide wire fixture 73 having a hook-like guide wire engagement portion 73a is provided as shown in FIGS. 47A and 47B in place of the snare-shaped wire which is opened in the loop form as in the guide wire fixture 69 according to the 24th embodiment.

The end portion of the tow wire 75 according to the 24th embodiment is fixed to the base end portion of the guide wire fixture 73. Moreover, a guide wire engagement portion 73a is formed at the end portion of the guide wire fixture 73.

The effect of this embodiment will now be described. In an usual case when using the endoscope 1 according to this embodiment, the guide wire fixture 73 is towed to the front side by the operation lever 72 and accommodated in the end opening portion 71a of the tow wire channel 71.

In addition, when fixing the guide wire 68, the operation lever 72 is used to cause the guide wire fixture 73 to protrude from the end opening portion 71a of the tow wire channel 71 as shown in FIG. 47A. Then, the guide wire engagement portion 73a of the guide wire fixture 73 is hooked on the guide wire 68. Subsequently, in this state, the operation lever 72 is used to tow the guide wire fixture 73 toward the front side. As a result, as shown in FIG. 47B, the guide wire 68 led to the outer side from the channel opening portion 26 is pressed against the edge part of the channel opening portion 26 on the rear end portion side and mechanically fixed by the guide wire engagement portion 73a of the guide wire fixture 73.

In this embodiment, the following advantage can be demonstrated. That is, as in the 24th embodiment, the guide wire 68 can be also easily fixed using the guide wire fixture 73 by the manipulation by the operation lever 72 on the front operation portion 13 side of the endoscope 1 in this embodiment, and the advantage similar to that of the 24th embodiment can be obtained.

Further, in this embodiment in particular, since the guide wire fixture 73 including the guide wire engagement portion 73a having a hook shape is provided, it is not necessary to set the state in which the loop-like opening portion formed by the wire of the guide wire fixture 69 is opened as in the 24th embodiment when inserting the guide catheter 67 into the therapeutic instrument insertion channel 23 from the insertion opening portion 61 of the operation portion 13 of the endoscope 1. Therefore, the guide wire 68 can be readily fixed by the manipulation of the operation lever 72 on the front side only when fixing the guide wire 68, and hence the operability of the endoscope 1 can be further improved.

Figure 49:
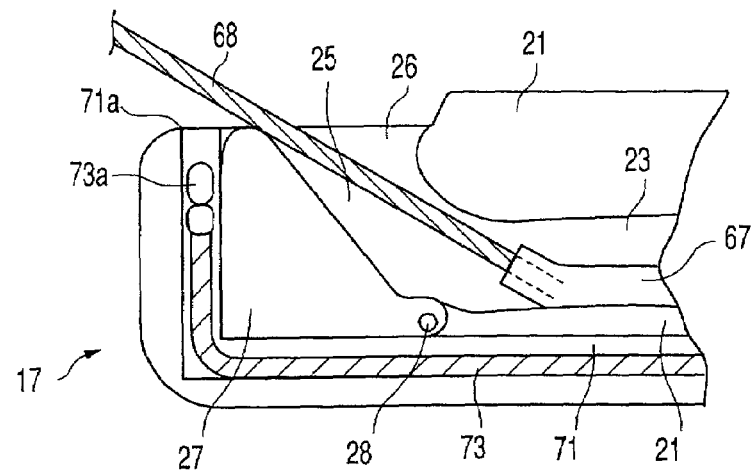
FIG. 49 is a vertical cross-sectional view of a primary part showing the state in which a guide wire fixture is held at a standby position in the endoscope according to the 26th embodiment.
Figure 50:
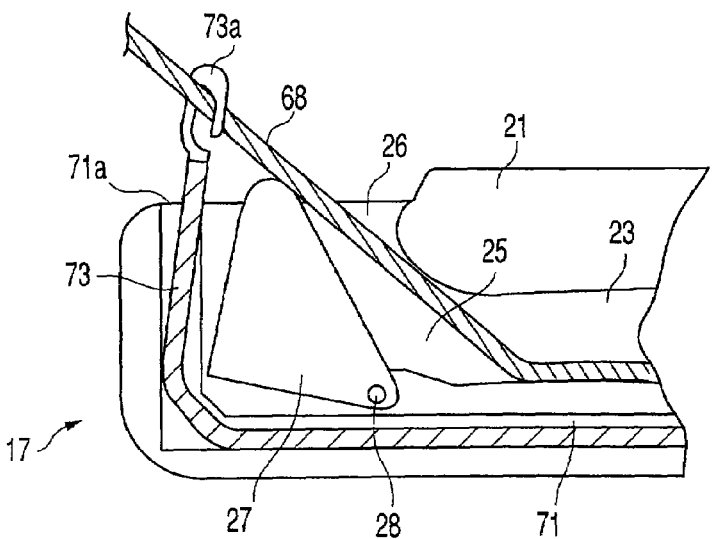
FIG. 50 is a vertical cross-sectional view of a primary part showing the fixed state of the guide wire by the guide wire fixture in the endoscope according to the 26th embodiment.

Furthermore, FIGS. 48 to 50 show a 26th embodiment according to the present invention. In this embodiment, the structure of the end portion 17 of the endoscope 1 according to the 25th embodiment is changed as follows.

That is, in this embodiment, as shown in FIG. 48, the end opening portion 71a of the tow wire channel 71 is provided on the end portion side away from the channel opening portion 26 in the notch portion 17a of the end portion 17 in the endoscope 1, and the guide wire fixture 73 according to the 25th embodiment is caused to protrude from the end opening portion 71a on the end portion side away from the channel opening portion 26.

Moreover, to the end hard portion 21 is formed the tow wire channel 71 which is bent into the substantially L shape along the lower surface side and the left end portion (end portion) in the accommodation chamber 25 of the therapeutic instrument elevator base 27 in FIG. 49 and FIG. 50. In addition, the end opening portion 71a of the tow wire channel 71 is arranged on the notched surface of the notch portion 17a of the end portion 17.

Additionally, the guide wire fixture 73 having a hook shape according to the 25th embodiment is inserted into the tow wire channel 71. The base end portion of the guide wire fixture 73 is led to the operation portion 13 side as in the 24th embodiment and connected to the operation lever 72 through the link mechanism. Since this link mechanism has the same structure as the above-described elevator base actuation mechanism 41, its explanation is omitted.

The effect of this embodiment will now be described. In the endoscope 1 according to this embodiment, the guide wire fixture 73 having a hook shape protrudes from the end opening portion 71a on the end portion side away from the channel opening portion 26 in the notch portion 17a of the end portion 17 in the endoscope 1 at the time of manipulation of the operation lever 72.

Further, with the guide wire engagement portion 73a of the guide wire fixture 73 being hitched to the guide wire 68, by towing the guide wire fixture 73 to the front side by the operation lever 72, the guide wire 68 led to the outer side from the channel opening portion 26 can be pressed against the edge portion side of the end opening portion 71a on the end portion side away from the channel opening portion 26 and mechanically fixed by the guide wire engagement portion 73a of the guide wire fixture 73 as shown in FIG. 50.

Furthermore, in this embodiment, as shown in FIG. 50, with the guide wire 68 being hooked by the guide wire engagement portion 73a of the guide wire fixture 73, by raising the therapeutic instrument elevator base 27, the tension from the guide wire fixture 73 and the thrusting force from the therapeutic instrument elevator base 27 act on the guide wire 68 in the opposed directions in the shearing manner. Therefore, upon receiving the force in the opposed directions, the guide wire 68 is bent in to the substantially L shape, and the guide wire 68 can be hence firmly fixed to the end portion 17 of the endoscope 1.

In this embodiment, as in the first and 25th embodiments, the guide wire 68 can be easily fixed using the guide wire fixture 73 by the manipulation of the operation lever 72 on the front operation portion 13 side of the endoscope 1, and the advantage similar to that of the 24th embodiment can be obtained.

Moreover, in this embodiment in particular, since the end opening portion 71a of the tow wire channel 71 is provided on the end portion side away from the channel opening portion 26 in the notch portion 17a of the end portion 17 of the endoscope 1, the tension from the guide wire fixture 73 and the thrusting force from the therapeutic instrument elevator base 27 can act on the guide wire 68 in the opposed directions in the shearing manner by raising the therapeutic instrument elevator base with the guide wire 68 being hooked by the guide wire engagement portion 73a of the guide wire fixture 73. Therefore, upon receiving the force in the opposed directions, the guide wire 68 can be bent in to the substantially L shape and firmly fixed in this state. Accordingly, there is the advantage that the guide wire 68 can be further securely fixed to the end portion 17 of the endoscope 1 as compared with the case where the guide wire fixture 73 having a hook shape is caused to protrude from the front side of the channel opening portion 26 as in the 25th embodiment.

Figure 52:
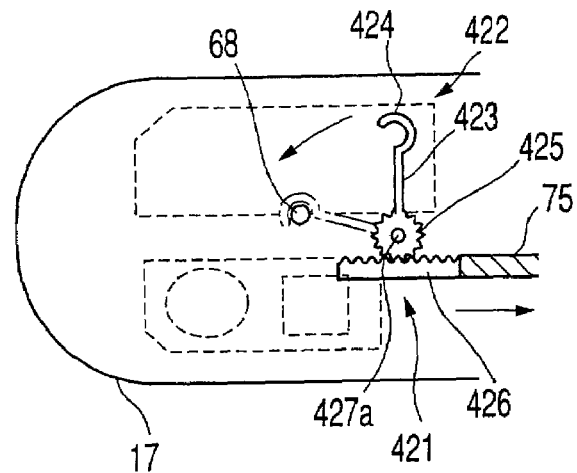
FIG. 52 is a schematic block diagram of a primary part showing a 27th embodiment of the present invention.

In addition, FIG. 52 and FIGS. 54A to 54B show a 27th embodiment according to the present invention. In this embodiment, a guide wire engagement member 422 having a hook shape which is driven to rotate by a rotary operation mechanism 421 formed by rack and pinion gears is provided in place of the guide wire engagement portion 73a having a hook shape in the guide wire fixture 73 which is driven to move forward and backward along the towing direction of the two wire 75 as in the 25th embodiment.

As shown in FIG. 54A, a guide wire engagement portion 424 having a hook shape is provided at the end portion of an elongated arm portion 423 in the guide wire engagement member 422. Further, a pinion gear 425 is provided to the base end portion of the arm portion 423.

Furthermore, as shown in FIG. 54B, a rack gear 426 is fixed to the end portion of the tow wire 75 according to the 25th embodiment. The rack gear 426 of the tow wire 75 is meshed with the pinion gear 425 of the guide wire engagement member 422 as shown in FIG. 52. Moreover, the rotary operation mechanism 421 consisting of rack and pinion gears is formed by the pinion gear 425 and the rack gear 426 of the guide wire engagement member 422.

Figure 53:
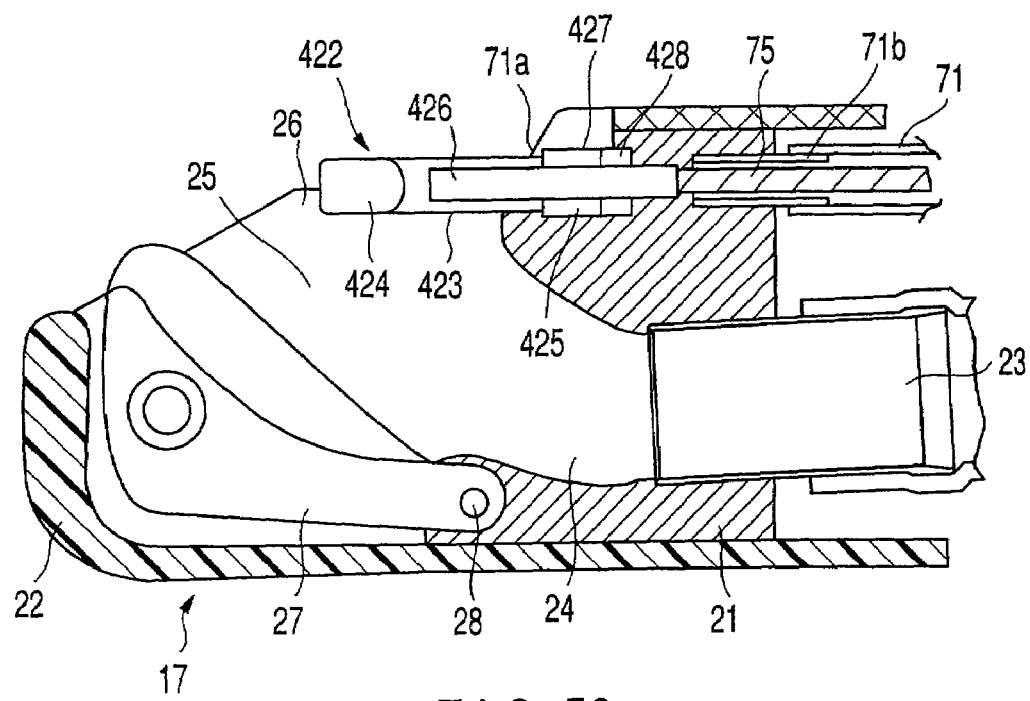
FIG. 53 is a vertical cross-sectional view showing an inner structure of an end portion in the endoscope according to the 27th embodiment.

In addition, as shown in FIG. 53, an engagement member accommodation chamber 428 for accommodating the guide wire engagement member 422 is formed at the end opening portion 71a of the tow wire channel 71 in the end hard portion 21 of the endoscope 1.

It is to be noted that the end portion of the tow channel 71 is connected to a connection pipe 71b fitted in to a channel hole formed to the end hard portion 21. Further, a bearing portion 427 which rotatably supports the pinion gear 425 of the guide wire engagement member 422 is provided to the engagement member accommodation chamber 428. Furthermore, the pinion gear 425 of the guide wire engagement member 422 is rotatably supported by a support shaft 427a (shown in FIG. 52) of the bearing portion 427.

The fixing position of the pinion gear 425 of the guide wire engagement member 422 is arranged on the side end of the engagement member accommodation chamber 428 in such a manner that the guide wire 68 which protrudes from the channel opening portion 26 of the end portion 17 of the endoscope 1 can be grabbed by the guide wire engagement portion 424 having a hook shape.

The effect of this embodiment will now be described. In this embodiment, the guide wire engagement member 422 is usually held at the standby position that the guide wire engagement portion 424 having a hook shape is moved to the rear end portion of the channel opening portion 26 as indicted by solid lines in FIG. 52. Moreover, by pulling the tow wire 75 to the front side by the manipulation of the operation lever 72 of the operation portion 13, the guide wire engagement member 422 is driven to rotate by the rotary operation mechanism 421 consisting of the rack and the pinion. At this moment, when the guide wire engagement portion 424 having a hook shape cuts across the channel opening portion 26, the guide wire 68 is grabbed by the guide wire engagement portion 424 having a hook shape, and the guide wire 68 is led to the direction of the side wall of the end hard portion 21. In this state, when the guide wire engagement member 422 further rotates, the guide wire 68 is held between the side wall of the end hard portion 21 and the guide wire engagement portion 424, thereby fixing the guide wire 68.

In addition, when releasing fixation of the guide wire 68, the guide wire engagement member 422 rotates in the opposite direction by returning the operation lever 72 of the operation portion 13 to its original position, and the guide wire engagement portion 424 having a hook shape returns to the standby position that the guide wire engagement portion 424 having a hook shape is moved to the rear end position of the channel opening portion 26 as indicated by solid lines in FIG. 52. As a result, the guide wire 68 comes off the guide wire engagement portion 424 having a hook shape, and fixation of the guide wire 68 is released.

The following advantage can be demonstrated in this embodiment. That is, in this embodiment, as in the 25th embodiment, the guide wire 68 can be readily fixed by the guide wire engagement member 422 by the manipulation of the operation lever 72 on the front operation portion 13 side of the endoscope 1, and the guide wire 68 does not have to be gripped on the operation portion 13 side of the endoscope 1 as in the prior art. Therefore, the operation for replacing the therapeutic instrument is facilitated, and the operation time required for replacing the therapeutic instrument can be hence shortened.

In addition, since the guide wire engagement member 422 including the guide wire engagement portion 424 having a hook shape is provided in this embodiment, the guide wire 68 can be easily fixed by the manipulation of the operation lever 72 on the front side only when fixing the guide wire 68. Therefore, the operability of the endoscope 1 can be further enhanced.

Additionally, in this embodiment in particular, since the elongated arm portion 423 of the guide wire engagement member 422 is not deeply pulled inside the end hard portion 21, the depth of the engagement member accommodation chamber 428 is reduced. Thus, a brush/cleaning fluid can easily spread inside the engagement member accommodation chamber 428 at the time of cleaning the endoscope 1, and the operability during cleaning/sterilization can be improved.

Further, in case of guiding the guide wire 68 in the direction of the side wall of the end hard portion 21 by the guide wire engagement portion 424 having a hook shape, when the guide wire 68 enters the visual field, it can be advantageously readily confirmed that the guide wire 68 is fixed.

It is to be noted that, as in a modification of the 27th embodiment illustrated in FIG. 55, the arm portion 423 of the guide wire engagement member 422 and the guide wire engagement portion 424 having a hook shape at the end portion of the arm portion 423 may be formed by separate members and a friction reinforcement member 429 having the large friction resistance may be used for only the guide wire engagement portion 424 having a hook shape.

Furthermore, FIGS. 56A and 56B show a 28th embodiment according to the present invention. In this embodiment, the guide wire engagement member 422 according to the 27th embodiment is changed as follows.

That is, in the guide wire engagement member 431 according to this embodiment, as shown in FIG. 56B, a ring-like shaft fixing portion 432 is provided to the base end portion of the arm portion 423 which is similar to that of the guide wire engagement member 422 according to the 27th embodiment. One end portion of the support shaft 433 is fixed to the shaft fixing portion 432. A pinion gear 434 is fixed to the other end portion of the support shaft 433. Moreover, an O ring 435 for sealing is fitted on the outer peripheral surface of the support shaft 433 between the shaft fixing portion 432 and the pinion gear 434 of the guide wire engagement member 431.

In addition, as shown in FIG. 56A, a gear portion accommodation chamber 436 is additionally provided below the engagement member accommodation chamber 428 in the end hard portion 21 of the endoscope 1. Additionally, the shaft fixing portion 432 of the guide wire engagement member 431 is accommodated in the engagement member accommodation chamber 428 and the pinion gear 434 is housed in the gear portion accommodation chamber 436, respectively, in the end hard portion 21. Further, a sliding plane 637 coming in to contact with the O ring 435 is formed in the communication path between the engagement member accommodation chamber 428 and the gear portion accommodation chamber 436. Furthermore, this O ring 435 assures the water-tightness between the engagement member accommodation chamber 428 and the gear portion accommodation chamber 436.

Moreover, the end portion of the channel hole of the tow wire channel 71 which is formed at the end hard portion 21 is caused to communicate with the gear portion accommodation chamber 436. In addition, the rack gear 426 at the end portion of the tow wire 75 is meshed with the pinion gear 434 in the gear portion accommodation chamber 436.

Additionally, the guide wire engagement member 431 according to this embodiment is driven to rotate by the operation similar to that of the 27th embodiment through the meshed portion between the rack gear 426 at the end portion of the tow wire 75 and the pinion gear 434 in the gear accommodation chamber 436.

The following advantage can be demonstrated in this embodiment. That is, in this embodiment, as in the 27th embodiment, the guide wire 68 can be readily fixed using the guide wire engagement member 431 by the manipulation of the operation lever 72 on the front operation portion 13 side of the endoscope 1, and the guide wire 68 does not have to be gripped on the operation portion 13 side of the endoscope 1 as in the prior art. Therefore, since the operation for replacing the therapeutic instrument is facilitated, there is the advantage that the operation time required for replacing the therapeutic instrument can be shortened.

Further, in this embodiment, the gear portion accommodation chamber 436 is additionally provided below the engagement member accommodation chamber 428 in the end hard portion 21 of the endoscope 1, and the O ring 435 is used to assure the water-tightness between the engagement member accommodation chamber 428 and the gear portion accommodation chamber 436. Therefore, dirt, etc does not enter the gear portion accommodation chamber 436 configured to have a complicated shape and the tow wire channel 71. Thus, in addition to the advantage of the 27th embodiment, there is the advantage that the cleaning/sterilization property can be further improved.

Figure 57A:
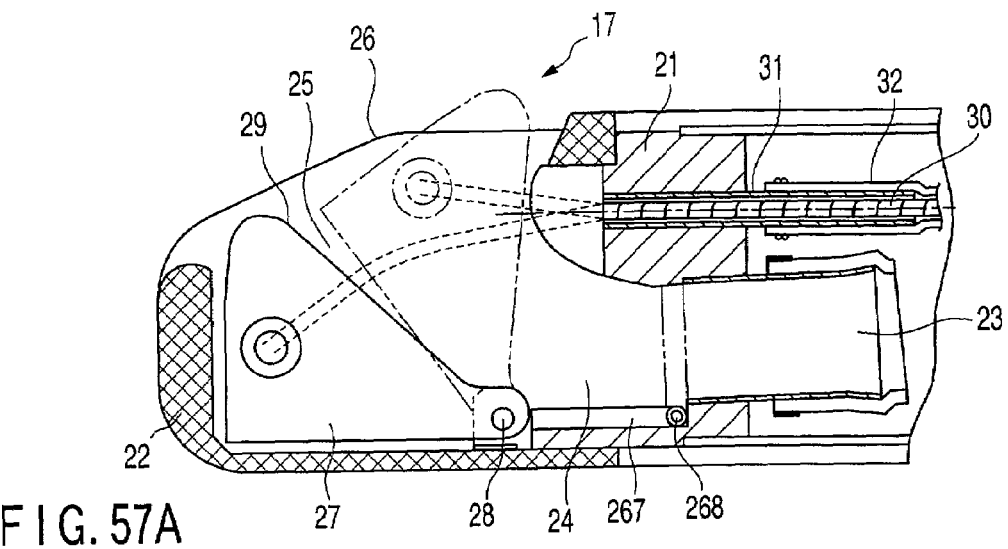
FIG. 57A is a vertical cross-sectional view of a primary part showing an inner structure of an end portion of an insertion portion in an endoscope according to a 29th embodiment of the present invention.
Figure 57B:
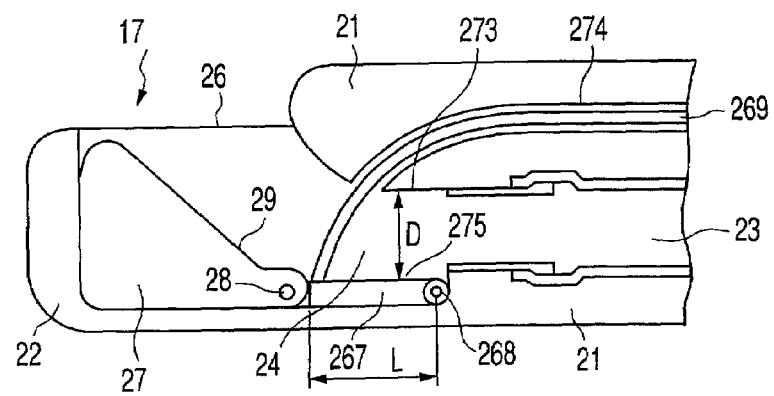
FIG. 57B is a vertical cross-sectional view of a primary part showing the state in which a guide wire fixing elevator base of an elevator base actuation mechanism is held at a standby position in the endoscope according to the 29th embodiment.
Figure 57C:
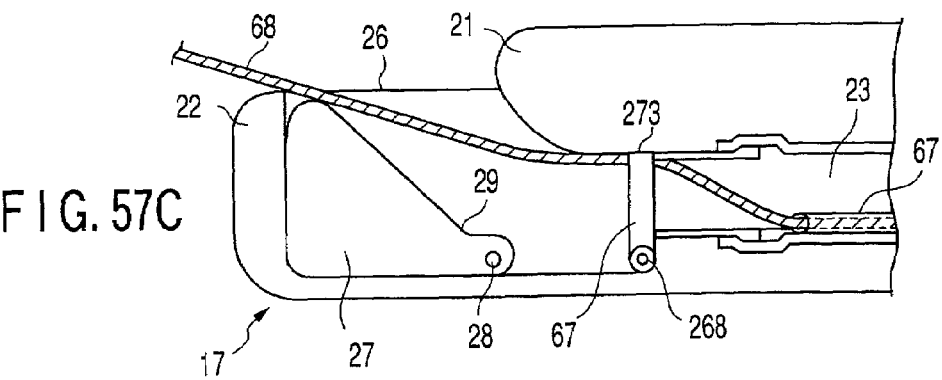
FIG. 57C is a vertical cross-sectional view of a primary part showing the state in which the guide wire fixing elevator base of the elevator base actuation mechanism is moved to an engagement position of the guide wire in the endoscope according to the 29th embodiment.

Furthermore, FIGS. 57A, 57B and 57C show a 29th embodiment according to the present invention. In this embodiment, the end portion 17 of the endoscope 1 according to the first embodiment is changed as follows.

The structure of the end portion 17 of the endoscope 1 will now be described with reference to FIG. 57A. A guide wire fixing elevator base 26 is provided on the lower surface of the lead-in guide path 24 in the end hard portion 21 at the end portion 17 of the endoscope 1. One end portion of the guide wire fixing elevator base 267 is pivoted with respect to the end hard portion 21 by the elevator base swivel supporting point 268. This elevator base swivel supporting point 268 is arranged at a lower part of the end opening portion of the lead-in guide path 24. Moreover, the guide wire fixing elevator base 267 is attached so as to be capable of a derricking motion in such a manner that it swivels around the elevator base swivel supporting point 268 from the standby position indicated by solid lines in FIG. 57A to the set-up position indicated by dotted lines in the same drawing in the introduction guide path 24.

Moreover, the end portion of the tow wire 269 is fixed to the other end portion of the guide wire fixing elevator base 267 as shown in FIG. 57B. The tow wire 269 is led to the operation portion 13 through the tow wire channel 274.

In addition, a non-illustrated link mechanism for operating the tow wire 269 of the guide wire fixing elevator base 267 is included in the operation portion 13. Since this link mechanism has the same structure as the elevator base actuation mechanism 41, the explanation thereof is omitted. Additionally, the tow wire 269 is operated to be towed by manipulation of the operation lever 72 in the operation portion 13 through the arm 49, the link member 44 and the wire mixing member 42, which have the link mechanism similar to the elevator base actuation mechanism 41, in sequence as in the therapeutic instrument elevator base 27, and the derricking motion of the guide wire fixing elevator base 267 is performed around the elevator base swivel supporting point 268. As a result, as shown in FIG. 57C, the guide wire 68 which is inserted in to the therapeutic instrument insertion channel 23 and led to the outer side from the channel opening portion 26 is fixed by raising the guide wire fixing elevator base 267.

It is to be noted that means for actuating the guide wire fixing elevator base is not restricted to this embodiment as long as it can tow the guide wire fixing elevator base 267.

Further, on the guide plane 275 of the guide wire fixing elevator base 267, steps are reduced as much as possible so that the channel 23 and the guide plane 29 of the therapeutic instrument elevator base 27 can be smoothly connected when the guide wire fixing elevator base 267 is lowered.

It is to be noted that, assuming that the length of the guide wire fixing elevator base 267 is L and the diameter of the lead-in guide path 24 is D as shown in FIG. 57B, the dimensional relationship of the guide wire fixing elevator base 267 is set to "$D \leq L$".

The effect of this embodiment will now be described. When using the endoscope 1 according to this embodiment, the guide wire fixing elevator base 267 is held at the standby position shown in FIG. 57B in advance.

In this state, the guide catheter 67 is inserted in to the therapeutic instrument insertion channel 23 from the insertion opening portion 61 of the operation portion 13 in the endoscope 1. Then, the guide catheter 67 is caused to protrude to the outer side from the channel opening portion 26 and inserted in to a pancreatic/hepatic duct (not shown) in the papillotomy manner. At this moment, since the guide plane 275 of the guide wire fixing elevator base 267, the channel 23 and the therapeutic instrument elevator base 27 are smoothly connected to each other, the guide catheter 67 can be inserted without being caught.

Thereafter, when replacing the currently used guide catheter 67 with a therapeutic instrument which is subsequently used, the guide wire 68 is first inserted from the mouth ring on the base end side of the guide catheter 67. Then, an observation image (endoscopic image) of the endoscope 1 is used to confirm that the end portion of the guide wire 68 has entered the pancreatic/hepatic duct (not shown), and the base end side of the guide wire 68 is gripped by a hand in such a manner that the guide wire 68 can not move. Subsequently, the operation for pulling out the guide catheter 67 is conducted in this state.

At this moment, after an endoscopic image is used to confirm that the guide catheter 67 has been pulled from a papilla (not shown), the guide catheter 67 is further pulled out. Then, with the end of the guide catheter 67 being housed in the therapeutic instrument insertion channel 23, the guide wire fixing elevator base 267 is swiveled to the set-up position indicated by solid lines in FIG. 57A by towing the two wire 269 using the operation lever 72. Consequently, as shown in FIG. 57C, the guide wire 68 led to the outer side from the channel opening portion 26 is sandwiched between the upper surface 273 of the lead-in guide path 24 of the end hard portion 21 and the guide wire fixing elevator base 267 and mechanically fixed.

Furthermore, after confirming that the guide-wire 68 is fixed, the guide catheter 67 is completely pulled to the outside of the therapeutic instrument insertion channel 23 from the operation portion 13 side of the endoscope 1.

Then, a therapeutic instrument which is subsequently used is inserted from the base end portion side of the guide wire 68. At this moment, with the guide wire 68 being used as a guide, the therapeutic instrument is inserted in to the therapeutic instrument insertion channel 23. Moreover, when the therapeutic instrument hustles against the guide wire fixing elevator base 267, fixation by the guide wire fixing elevator base 267 is released by manipulating the operation lever 72, and the therapeutic instrument is inserted in to the pancreatic/hepatic duct (not shown).

The following advantage can be demonstrated in this embodiment. That is, in this embodiment, the guide wire 68 can be easily fixed by operating the guide wire fixing elevator base 267 by using the operation lever 72 on the front operation portion 13 side of the endoscope 1. In addition, in case of fixing the guide wire 68, secure fixation is enabled by holding the operation lever 72 at the operation position.

Additionally, in an usual case, by setting down the guide wire fixing elevator base 267 to the standby position shown in FIG. 57B, the therapeutic instrument can be inserted without any problem since the introduction guide path 24 of the end hard portion 21 is opened.

Further, since conventional therapeutic instruments can be used as they are in this embodiment, the excellent operability can be maintained by using an operator's favorite therapeutic instrument. Therefore, the therapeutic instrument can be replaced in a shorter time without deteriorating the conventional method for operating the therapeutic instrument or the operation sense.

Furthermore, since the guide wire 68 can be fixed by the guide wire fixing elevator base 267 at the end portion 17 of the insertion portion 12, the length of the guide wire 68 can be shortened. Accordingly, there is the advantage that rolling and handling of the guide wire 68 can be facilitated and a large working space is no longer necessary. Moreover, replacement of the therapeutic instrument can be facilitated and the number of assistants can be reduced, which advantageously leads to a decrease in the time of operation.

Figure 59A:
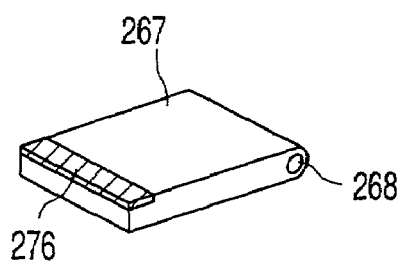
FIG. 59A is a perspective view showing a modification of the guide wire fixing elevator base in the endoscope according to the 29th embodiment.

In addition, in order to increase the fixation strength by the friction resistance on the guide wire contact surface of the guide wire fixing elevator base 267 in the endoscope 1 according to the 29th embodiment, an elastic member 276 may be provided to the guide wire fixing elevator base 267 as in the first modification shown in FIG. 59A or a protrusion 277 may be provided on the guide wire contact surface of the guide wire fixing elevator base 267 as in the second modification shown in FIG. 59 as long as insertion of the therapeutic instrument is not interfered.

Figure 58A:
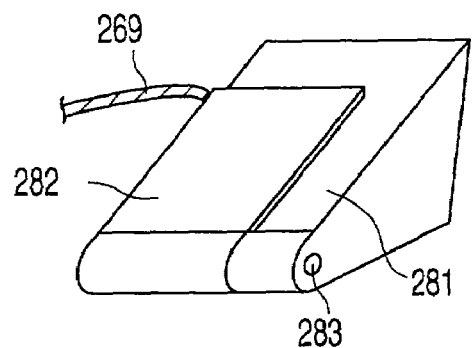
FIG. 58A is a perspective view showing a guide wire fixing elevator base of a therapeutic instrument elevator base according to a 30th embodiment of the present invention.
Figure 58B:
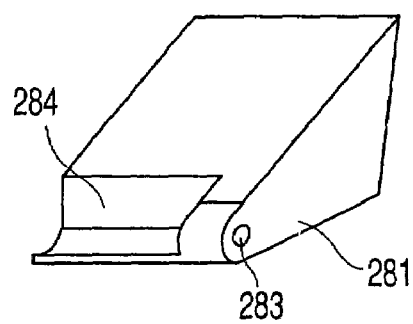
FIG. 58B is a perspective view showing a reception portion of the therapeutic instrument elevator base according to the 30th embodiment.
Figure 58C:
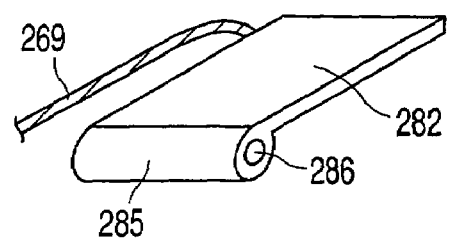
FIG. 58C is a perspective view showing a guide wire fixing elevator base according to the 30th embodiment.

Additionally, FIGS. 58A to 58C show 30th embodiment according to the present invention. In this embodiment, the structure of the therapeutic instrument elevator base 27 and the guide wire fixing elevator base 267 in the endoscope 1 according to the 29th embodiment is changed as follows.

That is, in this embodiment, as shown in FIG. 58A, a platy guide wire fixing elevator base 282 is provided so as to be superimposed on the therapeutic instrument elevator base 281. As shown in FIG. 58B, in the therapeutic instrument elevator base 281, an attachment concave portion 284 of the guide wire fixing elevator base 282 is provided to a swiveling portion in the vicinity of the elevator base swivel supporting point 283.

Further, as shown in FIG. 58C, a bearing portion 285 is formed on one end side portion side of the guide wire fixing elevator base 282. This bearing portion 285 is inserted in to the concave portion 284 of the therapeutic instrument elevator base 281 so as to be capable of swiveling. Furthermore, the swivel supporting point 286 of the guide wire fixing elevator base 282 is provided coaxially with the swivel supporting point 283 of the therapeutic instrument elevator base 281.

It is to be noted that the swivel supporting point 286 of the guide wire fixing elevator base 282 and the swivel supporting point 283 of the therapeutic instrument elevator base 281 may have different axes.

Moreover, the end portion of the tow wire 269 according to the 29th embodiment is fixed to the side surface of the guide wire fixing elevator base 282. The tow wire 269 is led to the operation portion 13 through the tow wire channel 274 and connected to a non-illustrated link mechanism. In addition, the towing operation of the guide wire fixing elevator base 282 is enabled through the tow wire 269 by manipulating the operation lever 72 on the front side as in the 29th embodiment.

Figure 59B:
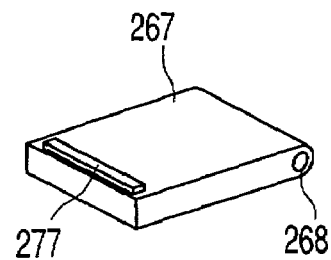
FIG. 59B is a perspective view showing a second modification of the guide wire fixing elevator base.

It is to be noted that an elastic member 276 shown in FIG. 59A or a protrusion 277 shown in FIG. 59B may be provided on the top face of the guide wire fixing elevator base 282 as in the 29th embodiment.

Additionally, in this embodiment, by towing the tow wire 269 by the operation lever 72, the guide wire fixing elevator base 282 is swiveled to the set-up position. Consequently, the guide wire 68 which is led to the outer side from the channel opening portion 26 is sandwiched between the upper surface 273 of the lead-in guide path 24 of the end hard portion 21 and the guide wire fixing elevator base 282 and mechanically fixed.

The following advantage can be demonstrated in this embodiment. That is, the guide wire 68 can be also releasably fixed at the end portion 17 of the insertion portion 12 in the endoscope 1 by using the guide wire fixing elevator base 282 when the tow wire 269 is towed by the operation lever 72, thereby obtaining the advantage similar to that of the 29th embodiment. Further, in this embodiment in particular, since a platy guide wire fixing elevator base 282 is provided so as to be superimposed on the therapeutic instrument elevator base 281, a space for installing the guide wire fixing elevator base 282 does not have to be solely provided, thereby further saving the space.

Furthermore, FIG. 60A and FIGS. 60B to 62 show a 31st embodiment according to the present invention. In this embodiment, the structure of the 29th embodiment is changed so that the guide wire fixing elevator base 267 is incorporated in the therapeutic instrument elevator base 27.

Figure 61A:
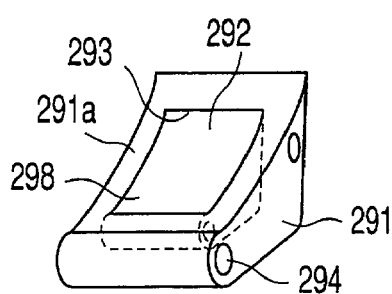
FIG. 61A is a perspective view showing the guide wire fixing elevator base on a therapeutic instrument elevator base in the endoscope according to the 31st embodiment.
Figure 61B:
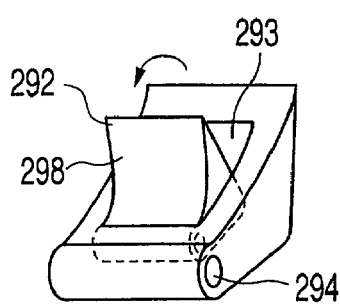
FIG. 61B is a perspective view showing the operation state of the guide wire fixing elevator base of the elevator base actuation mechanism in the endoscope according to the 31st embodiment.

That is, as shown in FIGS. 61A and 61B, an opening portion 293 for accommodating incorporated components is provided on the guide plane 291a of the therapeutic instrument elevator base 291 according to this embodiment. In this opening portion 293 are housed a guide wire fixing elevator base 292 and an elevator base moving member 295 according to this embodiment.

The elevator base swivel supporting point 294 of the guide wire fixing elevator base 292 is coaxially pivoted together with the swivel supporting point 294 of the therapeutic instrument elevator base 291.

It is to be noted that the elevator base swivel supporting point 294 of the guide wire fixing elevator base 292 may have an axis different from that of the swivel supporting point 294 of the therapeutic instrument elevator base 291.

Moreover, the elevator base moving member 295 is provided at a position on the end side of the endoscope 1 away from the guide wire fixing elevator base 292. The end portion of the tow wire 269 according to the 29th embodiment is fixed to the elevator base moving member 295. The tow wire 269 is led to the operation portion 13 through the tow wire channel 274 and connected to a non-illustrated link mechanism. In addition, as in the 29th embodiment, the towing operation of the tow wire 269 can be effected by manipulating the operation lever 72 on the front side.

Figure 60A:
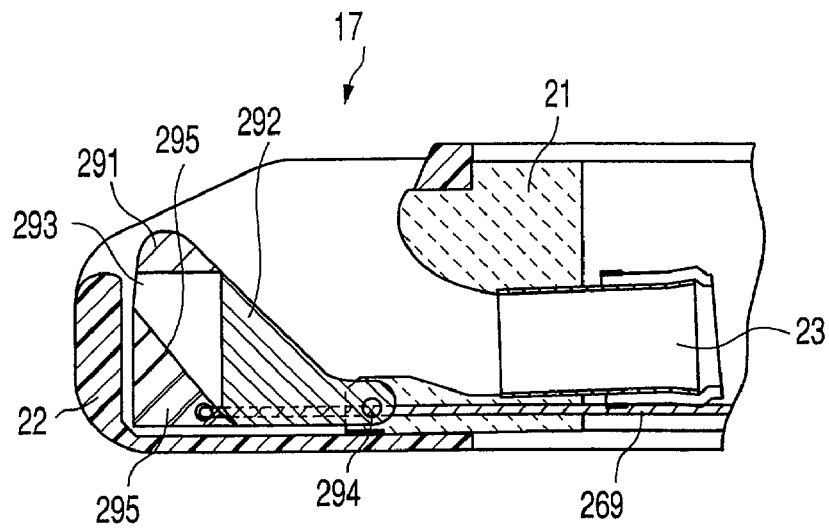
FIG. 60A is a vertical cross-sectional view of a primary part showing the state in which a guide wire fixing elevator base of an elevator base actuation mechanism is held at a standby position according to a 31st embodiment of the present invention.

It is to be noted that the elevator base moving member 295 is usually held at the standby position arranged ahead away from the guide wire fixing elevator base 292 as shown in FIG. 60A. In this state, the guide wire fixing elevator base 292 is held at the standby position where the guide wire fixing elevator base 292 is lowered.

Figure 60B:
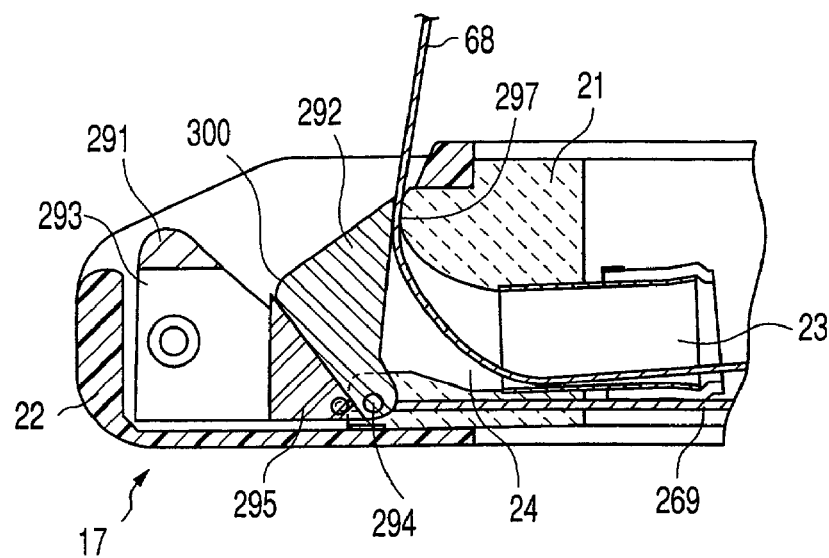
FIG. 60B is a vertical cross-sectional view of a primary part showing the state in which the guide wire fixing elevator base of the elevator base actuation mechanism is moved to an engagement position of a guide wire.

Additionally, when towing the elevator base moving member 295, as shown in FIG. 60B, the elevator base moving member 295 is configured to move to the front side and pushes the guide wire fixing elevator base 292. As a result, the guide wire fixing elevator base 292 swivels around the elevator base swivel supporting point 294 and swivels to the set-up position shown in FIG. 60B. At this moment, the guide wire fixing elevator base 292 is set to a height corresponding to the upper surface 297 of the lead-in guide path 24 of the end hard portion 21.

It is to be noted that the guide planes 291a and 298 are smoothly connected to each other without making irregularities when the therapeutic instrument elevator base 291 and the guide wire fixing elevator base 292 are lowered.

Further, an R bending portion 300 is formed by cutting the edge of the back surface portion of the guide wire fixing elevator base 292 so that the elevator base moving member 295 can easily move to the back surface side of the guide wire fixing elevator base 292. Furthermore, in order to reduce the friction resistance of the guide plane 298 of the guide wire fixing elevator base 292, a material of the elevator base moving member 295 may be changed from metal to plastic.

Moreover, in this embodiment, as shown in FIG. 62, the relationship between a set-up angle $\theta 1$ of the therapeutic instrument elevator base 291 and an elevator base $\theta 2$ of the guide wire fixing elevator base 292 is set to "$\theta 1 < \theta 2$".

The effect of this embodiment will now be described. When using the endoscope 1 according to this embodiment, as in the 29th embodiment, with the guide catheter 67 being pulled in the lead-in guide path 24 or the channel 23, the operation for raising the guide wire fixing elevator base 292 is performed. In such a case, in this embodiment, by towing the elevator base moving member 295 by using the operation lever 72, the elevator base moving member 295 moves below the guide wire fixing elevator base 292 and sets up the guide wire fixing elevator base 292. Then, the guide wire 68 is sandwiched between the guide wire fixing elevator base 292 and the upper surface 297 of the lead-in guide path 24 of the end hard portion 21, and the guide wire 68 is fixed.

In this embodiment, since the guide wire fixing elevator base 292 and the elevator base moving member 295 are accommodated in the opening portion 293 of the therapeutic instrument elevator base 291, the advantage similar to that of the 30th embodiment can be obtained. In addition to the advantage of the 30th embodiment, the guide wire 68 can be fixed by the guide wire fixing elevator base 292 which is dimensionally smaller than the therapeutic instrument elevator base 291 since the relationship between the set-up angle $\theta 1$ of the therapeutic instrument elevator base 291 and the set-up angle $\theta 2$ of the guide wire fixing elevator base 292 is set to "$\theta 1 < \theta 2$" in this embodiment in particular.

Further, as in the modification of the guide wire fixing elevator base 292 in the endoscope 1 according to the 31st embodiment shown in FIG. 63, a roller 299 may be provided on the back surface of the guide wire fixing elevator base 292 or the guide plane 298 of the elevator base moving member 295 so that the friction resistance between the back surface of the guide wire fixing elevator base 292 and the guide plane 298 of the elevator base moving member 295 can be reduced.

Furthermore, FIGS. 64 and 65 show a 32nd embodiment according to the present invention. In this embodiment, a guide wire fixing elevator base 301 having a different structure is provided in place of the guide wire fixing elevator base 267 in the endoscope 1 according to the 29th embodiment.

That is, as shown in FIG. 64, at the end portion 17 of the insertion portion 12 in the endoscope 1 according to this embodiment, the guide wire fixing elevator base 301 is provided on the rear end wall surface 17b of the notch portion 17a. This guide wire fixing elevator base 301 is arranged at a part opposed to the therapeutic instrument elevator base 27 in the channel opening portion 26.

Moreover, one end portion of the guide wire fixing elevator base 301 is pivoted to the end hard portion 21 of the end portion 17 so as to be capable of swiveling through a swivel supporting point 302. In addition, the end portion of the tow wire 303 is fixed on the other end side of the guide wire fixing elevator base 301. The base end portion of the tow wire 303 is led to the operation portion 13 and connected to a non-illustrated link mechanism. Additionally, the operation for towing the guide wire fixing elevator base 301 is enabled by manipulation of the operation lever 72 on the front side through the tow wire 303 as in the 29th embodiment.

It is to be noted that the elastic member 276 shown in FIG. 59A or the protrusion 277 shown in FIG. 59B may be provided on a top face 301a of the guide wire fixing elevator base 301 as in the 29th embodiment.

The effect of this embodiment will now be described. In an usual case, when the guide wire fixing elevator base 301 is pushed out by the operation lever 72, the guide wire fixing elevator base 301 can swivel with the guide wire fixing elevator base swivel supporting point 302 as a base point as indicated by a dotted line in FIG. 65, and insertion of the therapeutic instrument can be performed without any problem in an usual case.

Further, in this embodiment, the guide wire fixing elevator base 301 is swiveled in a direction along which it comes in to contact with the therapeutic instrument elevator base 27 side as indicated by solid lines in FIG. 65 by towing the two wire 303 by using the operation lever 72. As a result, the guide wire 68 led from the channel opening portion 26 to the outer side is sandwiched between the guide wire fixing elevator base 301 and the therapeutic instrument elevator base 27 and mechanically fixed, and the guide wire 68 can be fixed as in the 29th embodiment.

Since the guide wire 68 can be likewise fixed by the guide wire fixing elevator base 301 in this embodiment as in the 29th embodiment, the advantage similar to the 29th embodiment can be also obtained in this embodiment.

Furthermore, FIGS. 66A to 66D show a 33rd embodiment according to the present invention. In this embodiment, an operation mechanism for the guide wire fixing elevator base 267, which has a different structure, is provided in place of the operation lever 72 for the guide wire fixing elevator base 267 in the operation portion 13 of the endoscope 1 according to the 29th embodiment.

Figure 66A:
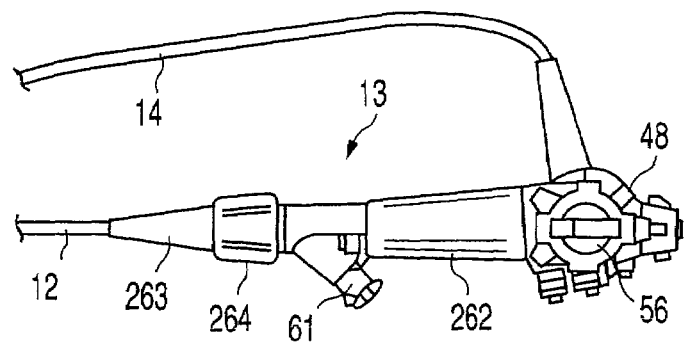
FIG. 66A is a plane view showing an operation portion of an endoscope according to a 33rd embodiment of the present invention.

That is, as shown in FIG. 66A, to the operation portion 13 of the endoscope 1 according to this embodiment is provided a tow knob 264 for operation which is formed in to a substantially cylindrical shape between a grip 262 for holding the operation portion 13 and a bend prevention portion 263 below the insertion portion 61. This tow knob 264 is rotatably fitted to the base 47 as a base board of the operation portion 13 as shown in FIG. 66C. Moreover, a rotary shaft 01 of the tow knob 264 is coaxial with the central axis 02 of the insertion portion 12.

Incidentally, the rotary shaft of the elevator operation knob 48 of the therapeutic instrument elevator base 27 is coaxial with the curved operation portion 56, and hence it exists orthogonally with respect to the central shaft 02 of the insertion portion 12. Moreover, the rotary shaft 01 of the tow knob 264 exists at a position orthogonal to the rotary shaft of the elevator operation knob 48.

In addition, as shown in FIG. 66C, a cylindrical cam member 265 is embedded in the two knob 264. As shown in FIG. 66D, a cam groove 265a is obliquely provided to this cam member 26S. A moving pin 266 is engaged with the cam groove 265a of the cam member 265 so as to be capable of moving along the cam groove 265a.

Additionally, the base end portion of the tow wire 269 inserted in to the tow wire channel 274 is fixed to the moving pin 266. When the moving pin 266 moves along the cam groove 265a of the cam member 265 with the rotating operation of the tow know 264, the two wire 269 moves forward/backward along the direction of the central axis O2 of the insertion portion 12 through the moving pin 266.

The effect of this embodiment will now be described. When using the endoscope 1 according to this embodiment, if the guide wire fixing elevator base 267 is towed, the tow knob 264 is rotated. At this moment, since the cam member 265 also rotates integrally with the tow knob 264, the moving pin 266 moves in the cam groove 265a with rotation of the cam member 265, and the guide wire fixing elevator base 267 is operated to be towed by towing the tow wire 269.

The following advantage can be demonstrated in this embodiment. That is, in this embodiment, the guide wire 68 can be easily fixed at the end portion 17 of the insertion portion 12 of the endoscope 1 by the operation of the tow knob 264 on the front operation portion 13 side of the endoscope 1 as in the 29th embodiment, and the advantage similar to that of the 29th embodiment can be obtained.

Additionally, in this embodiment in particular, since the rotary shaft 01 of the tow knob 264 of the guide wire fixing elevator base 267 exists at a position orthogonal to the rotary shaft of the elevator operation knob 48 of the therapeutic instrument elevator base 27, the operation direction of the elevator operation knob 48 of the therapeutic instrument elevator base 27 is different from the operation direction of the tow knob 264 of the guide wire fixing elevator base 267. Therefore, it is possible to prevent occurrence of an erroneous operation that the elevator operation knob 48 of the therapeutic instrument elevator base 27 and the tow knob 267 of the guide wire fixing elevator base 267 are mixed up and actuated.

Further, since the insertion opening of the guide wire 68 and the tow knob 264 of the guide wire fixing elevator base 267 can get close to each other by providing the tow knob 264 of the guide wire fixing elevator base 267 to a position in the vicinity to the insertion opening portion 61, the operability can be further improved.

Figure 67A:
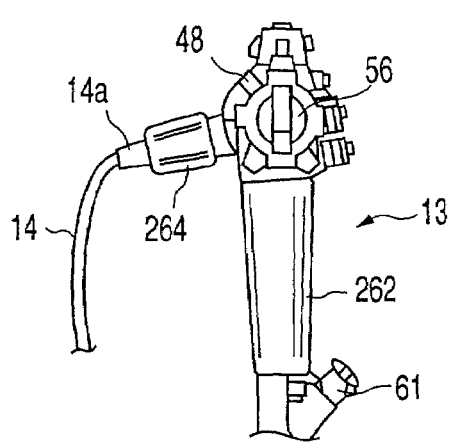
FIG. 67A is a plane view showing a first modification of an operation portion in the endoscope according to the 33rd embodiment.

It is to be noted that the tow knob 264 is not restricted to a position between the bend prevention portion 263 below the insertion opening portion 61 and the grip 262. For example, as in the first modification of the operation portion 13 of the endoscope 1 according to the 33rd embodiment shown in FIG. 67A it may be provided to the connector-side bend prevention portion 14a arranged at a connection portion with the universal cord 14, the connector 18 or the grip 262.

Figure 67B:
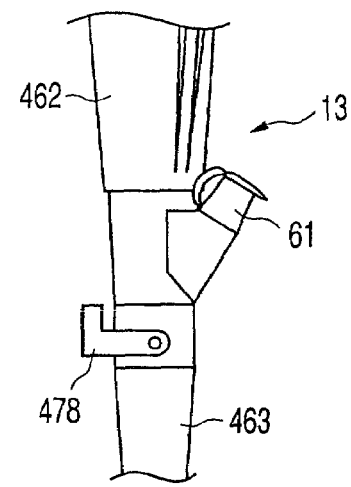
FIG. 67B is a plane view showing a second modification of the operation portion in the endoscope according to the 33rd embodiment.

Furthermore, the operating means of the guide wire fixing elevator base 267 is not restricted to a knob type, and it may be a lever type using the operation lever 278 as in the second modification of the operation portion 13 in the endoscope 1 shown in FIG. 67B. At this moment, although the link mechanism described in the 29th embodiment is the basis as the operation force transmission mechanism of the operation lever 278, the present invention is not restricted there to if the towing operation is possible.

Figure 66B:
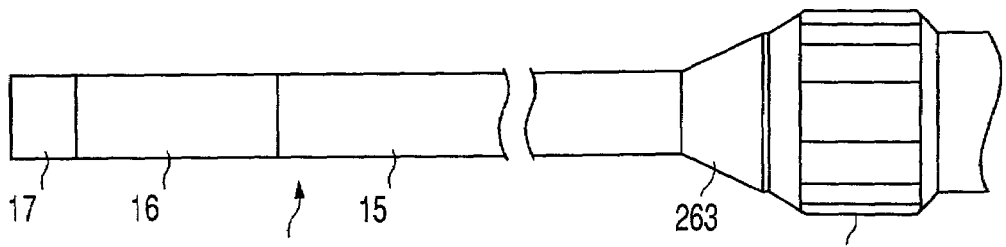
FIG. 66B is a plane view showing an insertion portion of the endoscope according to the 33rd embodiment.
Figure 66C:
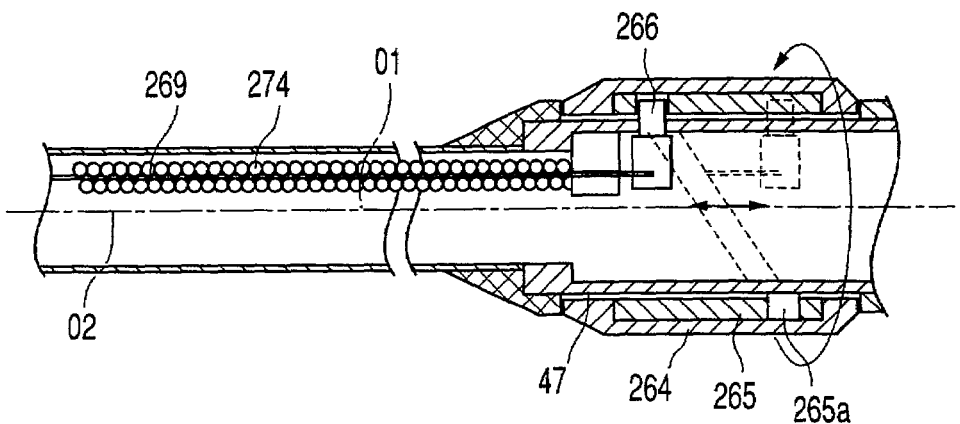
FIG. 66C is a vertical cross-sectional view of a primary part showing an inner structure of the insertion portion of the endoscope according to the 33rd embodiment.
Figure 66D:
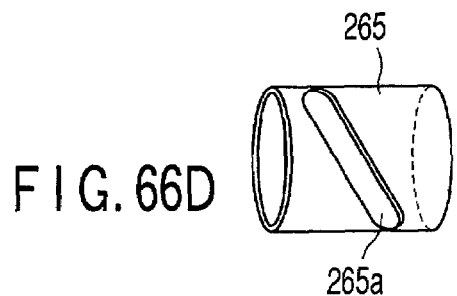
FIG. 66D is a perspective view showing a cam member in the endoscope according to the 33rd embodiment.

Moreover, FIGS. 66A and 66B show a 34th embodiment according to the present invention. In this embodiment, a guide wire fixing mechanism 361 having a different structure is provided in place of the guide wire fixing elevator base 267 according to the 29th embodiment.

That is, a substantially block-like guide wire fixture 362 is provided to the guide wire fixing mechanism 361 according to the present embodiment. In the end hard portion 21 at the end portion 17 of the insertion portion 12 in the endoscope 1, an accommodation chamber 363 of the guide wire fixture 362 is provided on the upper surface of the lead-in guide path 24 communicating with the channel opening portion 26. A coil-like spring member 364 for giving impetus in the direction along which the guide wire fixture 362 is pulled to the outside of the accommodation chamber 363 in the substantially vertical direction is provided in this accommodation chamber 363.

In addition, an end portion of the tow wire 365 is fixed to the guide wire fixture 362. The tow wire 365 is led to the operation portion 13 through the tow wire channel 366 and connected to a non-illustrated link mechanism. As a result, the towing operation of the guide wire fixture 362 is enabled through the tow wire 365 by the operation of the operation lever 72 on the front side as in the 29th embodiment.

It is to be noted that an elastic member 276 shown in FIG. 59A and a protrusion 277 shown in FIG. 59B may be provided on the contact surface with the guide wire 68 in the guide wire fixture 362 as in the 29th embodiment.

Figure 68A:
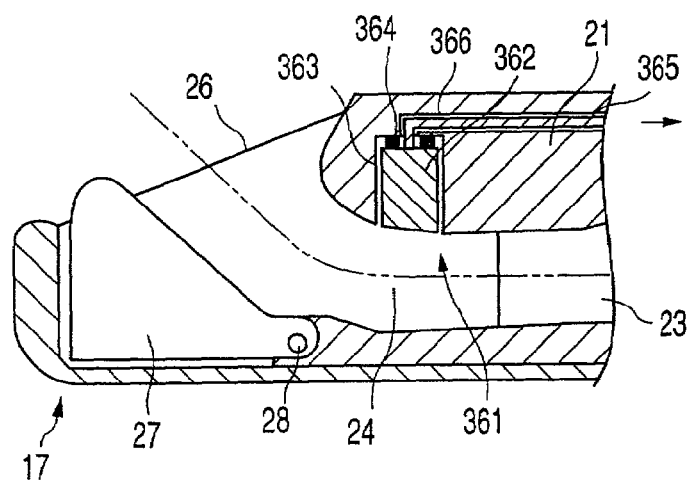
FIG. 68A is a vertical cross-sectional view of a primary part showing an inner structure of an end portion of an insertion portion in an endoscope according to a 34th embodiment of the present invention.

The effect of this embodiment will now be described. When using the endoscope 1 according to this embodiment, the tow wire 365 is pulled by the operation lever 72 in the initial state in advance, and the guide wire fixture 362 is drawn in to the accommodation chamber 363 as shown in FIG. 68A.

Figure 68B:
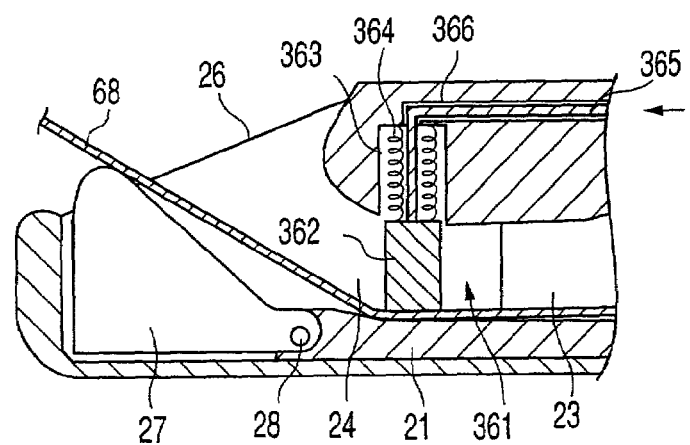
FIG. 68B is a vertical cross-section of a primary part showing the operation state of a guide wire fixture in the endoscope according to the 34th embodiment.

Then, as in the 29th embodiment, after the guide catheter 67 and the guide wire 68 are inserted in to the body through the channel 23, the operation for loosening the tow wire 365 is carried out by the manipulation of the operation lever 72 with the guide catheter 67 being pulled in to the channel 23. At this moment, the guide wire fixture 362 is substantially vertically pulled to the outside of the accommodation chamber 363 by the elastic force of the spring member 364 and caused to protrude in to the lead-in guide path 24 as shown in FIG. 68B. As a result, the guide wire 68 is sandwiched between the end hard portion 21 and the guide wire fixture 362 and mechanically fixed.

Additionally, after confirming that the guide wire 68 is fixed, the guide catheter 67 is completely pulled to the outside of the therapeutic instrument insertion channel 23 from the operation portion 13 side of the endoscope 1.

Thereafter, a therapeutic instrument which is subsequently used is inserted from the base end portion side of the guide wire 68. At this moment, with the guide wire 68 being used as a guide, the therapeutic instrument is inserted in to used to the therapeutic instrument insertion channel 23. Then, when the therapeutic instrument hustles against the guide wire fixture 362, the operation lever 72 is operated to release fixation by the guide wire fixture 362 in order to further insert the therapeutic instrument in to a pancreatic/hepatic duct (not shown).

The following advantage can be demonstrated in this embodiment. That is, in this embodiment, the guide wire 68 can be readily fixed by the manipulation of the operation lever 72 of the front operation portion 13 in the endoscope 1, and the lead-in guide path 24 is opened by accommodating the guide wire fixture 362 in the accommodation chamber 363 in a usual case. Therefore, the therapeutic instrument can be inserted without incident.

Further, since conventional therapeutic instruments can be used in this embodiment, the excellent operability can be maintained by use of an operator's favorite therapeutic instrument. Furthermore, since the guide wire 68 can be fixed at the end portion 17 of the insertion portion 12 in the endoscope 1, the length of the guide wire 68 can be shortened as compared with a prior art, thereby improving the operability.

Figure 69A:
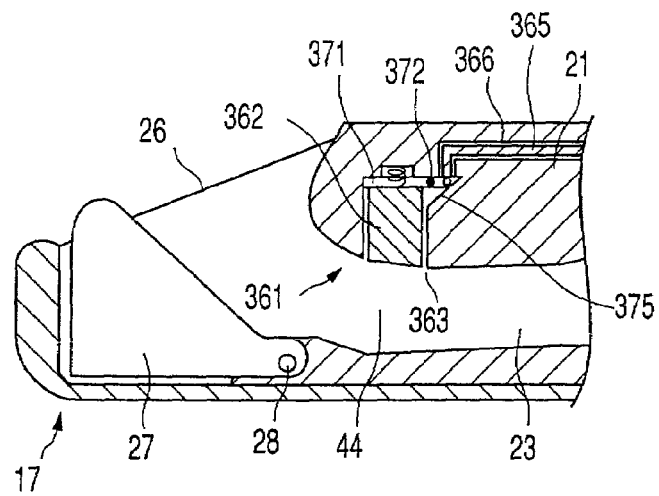
FIG. 69A is a vertical cross-sectional view of a primary part showing an inner structure of an end portion of an insertion portion in an endoscope according to a 35th embodiment of the present invention.
Figure 69B:
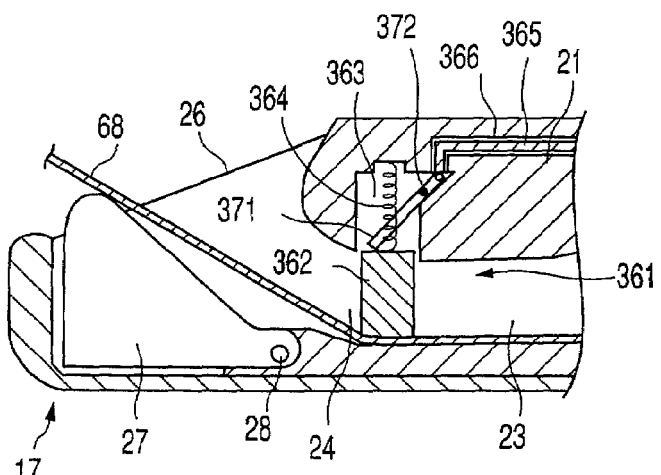
FIG. 69B is a vertical cross-sectional view of a primary part showing the operation state of a guide wire fixture in the endoscope according to the 35th embodiment.
Figure 69C:
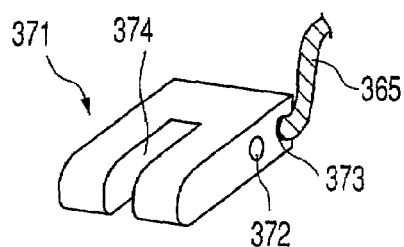
FIG. 69C is a perspective view showing a torque transmission member in the endoscope according to the 35th embodiment.

Moreover, FIGS. 69A to 69C show a 35th embodiment according to the present invention. In this embodiment, the structure is changed so that a torque transmission member 371 is provided between the guide wire fixture 362 according to the 34th embodiment and the tow wire 365. This torque transmission member 371 is provided at the upper portion in the accommodation chamber 363 of the end hard portion 21 provided at the end portion 17.

In addition, as shown in FIG. 69C, a rotary shaft 372 is provided in the vicinity of the center of the torque transmission member 371. Further, an end portion of the tow wire 365 is fixed to one end portion of the torque transmission member 371.

Furthermore, a slit-like opening portion 374 in to which the spring member 364 is inserted is provided on the opposite side to the fixing end 373 of the tow wire 365 in the torque transmission member 371.

Moreover, a recess portion 375 for preventing interference with the torque transmission member 371 during rotation of the torque transmission member 371 is formed at the end hard portion 21 by scraping away the lower part of the rotary shaft 372.

The effect of this embodiment will now be described. When using the endoscope 1 of this embodiment, the torque transmission member 371 is previously arranged so as to be substantially parallel to the lead-in guide path 24 in the initial state as shown in FIG. 69A. As a result, since the spring member 364 has a natural length, the guide wire fixture 362 is accommodated in the accommodation chamber 363.

In addition, as in the 29th embodiment, after the guide catheter 67 and the guide wire 68 are inserted in to the body through the channel 23, the operation for towing the tow wire 365 is performed by the manipulation of the operation lever 72 with the guide catheter 67 being pulled in to the channel 23. At this moment, one end of the torque transmission member 371 is pulled by the tow wire 365 and moves upwards and, at the same time, the other end moves downward.

Consequently, the guide wire fixture 362 is substantially vertically pulled to the outside of the accommodation chamber 363 and caused to protrude to the inside of the lead-in guide path 24 as shown in FIG. 69B. As a result, the guide wire 68 is sandwiched between the end hard portion 21 and the guide wire fixture 362 and mechanically fixed.

Additionally, when releasing fixation of the guide wire 68, the torque transmission member 371 returns to its original position by returning the operation lever 72 to its original position, and the guide wire fixture 362 also returns to the accommodation chamber 36 by the resilience of the spring member 364, thereby releasing fixation of the guide wire 68.

In this embodiment, the following advantage can be demonstrated. That is, in this embodiment, the guide wire 68 can be readily fixed by the manipulation of the operation lever 72 of the front operation portion 13 of the endoscope 1 as in the 34th embodiment, and the lead-in guide path 24 is opened by accommodating the guide wire fixture 362 in the accommodation chamber 363 in an usual case. Thus, the therapeutic instrument can be inserted without incidence.

Also, in this embodiment, in addition to the advantage similar to that of the 34th embodiment, since the towing state by the operation lever 72 can be maintained at the time of fixing the guide wire 68, the strong force can be applied to the guide wire fixture 362 through the torque transmission member 371.

Figure 70A:
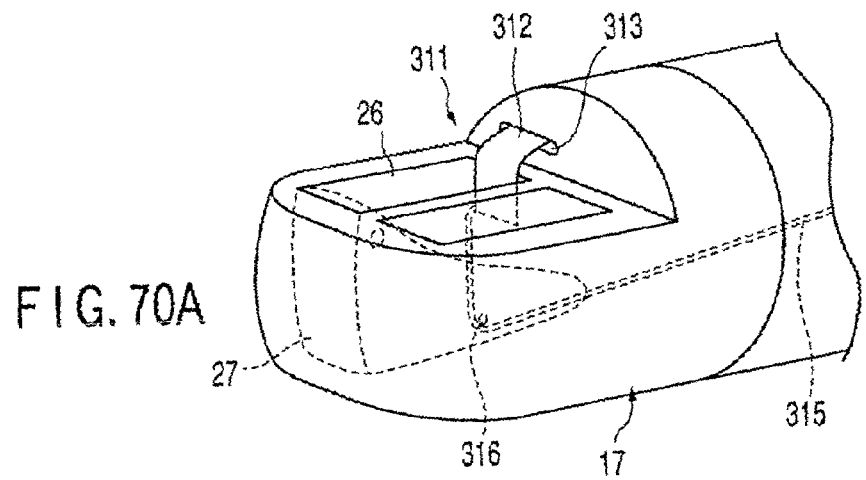
FIG. 70A is a perspective view of a primary part showing a schematic structure of an end portion of an insertion portion in an endoscope according to a 36th embodiment of the present invention.
Figure 70B:
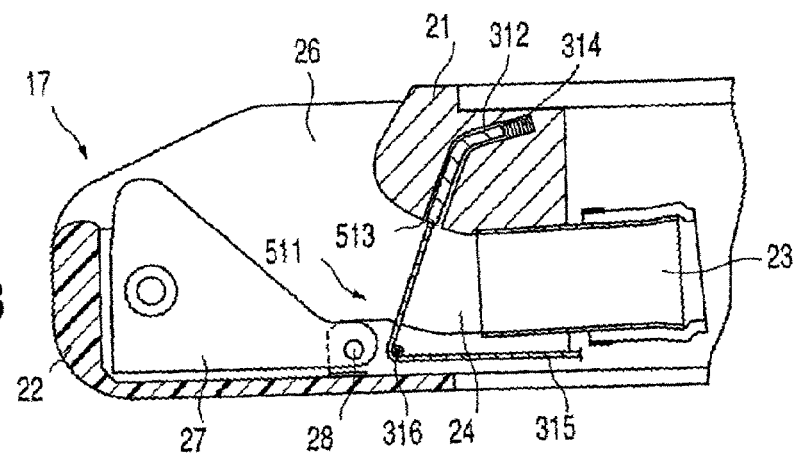
FIG. 70B is a vertical cross-sectional view of a primary part showing an inner structure of the end portion of the insertion portion in the endoscope according to the 36th embodiment.
Figure 70C:
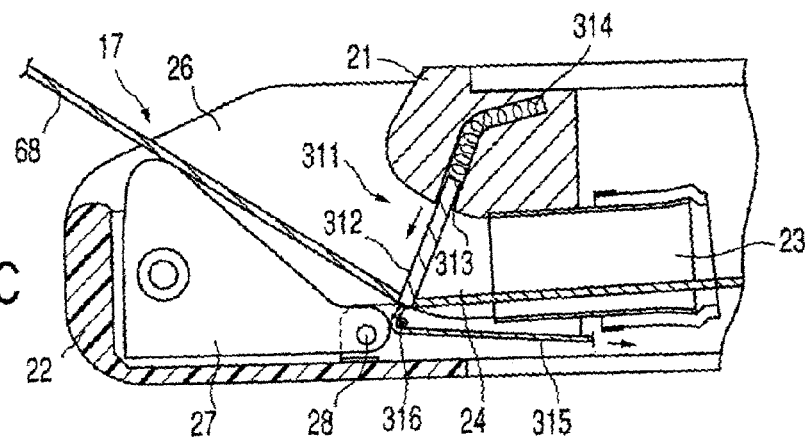
FIG. 70C is a vertical cross-sectional view of a primary part showing a state in which a guide wire fixing elevator base is moved to an engagement position of a guide wire in the endoscope according to the 36th embodiment.

Further, FIGS. 70A to 70C show a 36th embodiment according to the present invention. In this embodiment, the guide wire fixing mechanism 311 having a different structure is provided in place of the guide wire fixing elevator base 267 according to the 29th embodiment.

That is, as shown in FIG. 70A, a platy guide wire fixing member 312 which can be elastically deformed is provided to the guide wire fixing mechanism 311 according to this embodiment. In the end hard portion 21 at the end portion 17 of the insertion portion 12 in the endoscope 1, an accommodation chamber 313 of the guide wire fixing member 312 is provided on the upper surface of the lead-in guide path 24 communicating with the channel opening portion 26. A coil-like spring member 314 for giving impetus in the direction along which the guide wire fixing member 312 is pulled in to the accommodation chamber 313 is provided in this accommodation chamber 313.

The end portion of the tow wire 315 is fixed to the guide wire fixing member 312.

Furthermore, a guide roller 316 which is rotatable below the accommodation chamber 313 on the lower surface of the lead-in guide path 24 is provide to the end hard portion 21. Moreover, the tow wire 315 running out toward the lower part of the accommodation chamber 313 is led to the operation portion 13 side in the state that it is bent toward the operation portion 13 side by the guide roller 316, and connected to the non-illustrated link mechanism. As a result, as in the 29th embodiment, the towing operation of the guide wire fixing member 312 is enabled through the tow wire 315 by the manipulation of the operation lever 72 on the front side.

Incidentally, although the above-described link mechanism is the basis as the towing mechanism for the guide wire fixing member 312, the present invention is not restricted there to as long as the guide wire fixing member 312 can be towed.

The effect of this embodiment will now be described. When using the endoscope 1 according to this embodiment, as in the 29th embodiment, after the guide catheter 67 and the guide wire 68 are inserted in to the body through the channel 23, the operation for towing the guide wire fixing member 312 is carried out through the tow wire 315 by the manipulation of the operation lever 72 with the guide catheter 67 being pulled in to the lead-in guide path 24 or the channel 23. At this moment, the guide wire fixing member 312 is pulled out from the accommodation chamber 313, and the lower end portion of the guide wire fixing member 312 is brought in to contact with the lower surface of the lead-in guide path 24 of the end hard portion 12 as shown in FIG. 70C. As a result, the guide wire 68 is fixed by sandwiching the guide wire 68 between the lower surface of the lead-in guide path 24 of the end hard portion 21 and the guide wire fixing member 312.

In addition, when the operation lever 72 is returned to its original position, the guide wire fixing member 312 is returned to the state that it is pulled in to the accommodation chamber 313 by the resilience of the spring member 314. Consequently, the lower end portion of the guide wire fixing member 312 moves away from the guide wire 68, and fixation of the guide wire 68 is hence released.

In this embodiment, the guide wire fixing member 312 is subjected to the towing operation through the tow wire 315 by the manipulation of the operation lever 72, and the guide wire 68 can be releasably fixed at the end portion 17 of the insertion portion 12 of the endoscope 1 by the guide wire fixing member 312, thereby obtaining the advantage similar to the 29th embodiment. In addition to the advantage of the 29th embodiment, there is an advantage that the guide wire fixing member 312 does not interfere with a case when the guide wire fixing member 312 is accommodated in the accommodation chamber 313 of the end portion 17 in case of releasing fixation of the guide wire 68 in this embodiment in particular.

Figure 71:
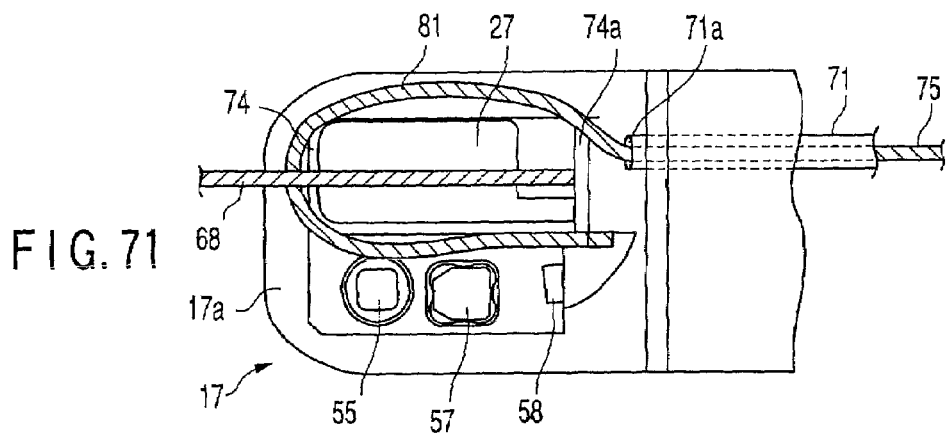
FIG. 71 is a plane view of a primary part showing a state in which a guide wire fixing portion is held at a standby position in an endoscope according to a 37th embodiment of the present invention.
Figure 72:
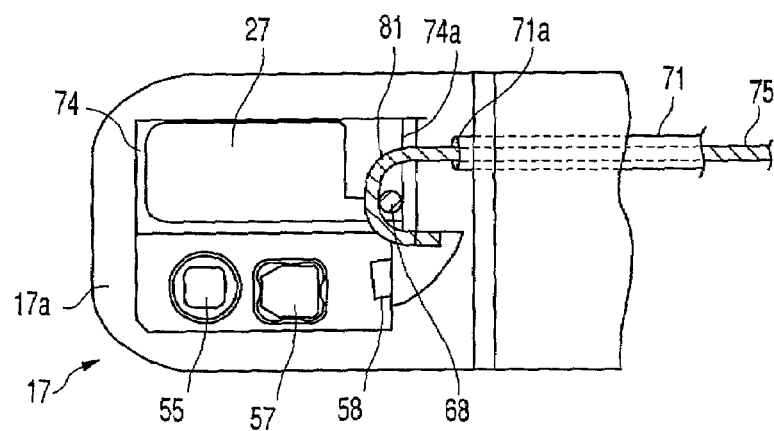
FIG. 72 is a plane view of a primary part showing a fixed state of a guide wire in the endoscope according to the 37th embodiment.

Additionally, FIGS. 71 and 72 show a 37th embodiment according to the present invention. In this embodiment, the structure of the end portion 17 of the endoscope 1 according to the 24th embodiment is changed as follows.

That is, in this embodiment, a wire-type guide wire fixture 81 which is curved in to a substantially U shape is provided at the end portion of the tow wire 75 according to the 24th embodiment as shown in FIG. 71, and the end portion of the guide wire fixture 81 is fixed on the side surface of the channel opening portion 26 in the notch portion 17a at the end portion 17 in the endoscope 1. A method for fixing the guide wire fixture 81 to the end portion 17 is adhesion, soldering, screwing and others.

The effect of this embodiment will now be described. When using the endoscope 1 according to this embodiment, the guide wire fixture 81 is previously set in the extended state so as to surround the channel opening portion 26 as shown in FIG. 71.

Then, as in the 24th embodiment, after the guide wire 68 and the guide catheter 67 are inserted in to the therapeutic instrument insertion channel 23, the guide catheter 67 is pulled to the inside of the channel 23 and only the guide wire 68 is caused to protrude to the outside of the channel opening portion 26 in case of fixing the guide wire 68. In this state, the operation for pulling the guide wire fixture 81 to the front side is carried out by the manipulation of the operation lever 72 on the front side. As a result, as shown in FIG. 72, the guide wire 68 is sandwiched between the front side wall surface 26a of the channel opening portion 26 and the guide wire fixture 81 as shown in FIG. 72, and the guide wire 68 is fixed.

In this embodiment, the guide wire 68 can be easily fixed by the guide wire fixture 81 at the end portion of the tow wire 75 by manipulating the operation lever 72 on the front operation portion 13 side in the endoscope 1 as in the 24th embodiment, thereby obtaining the advantage similar to that of the 24th embodiment.

Also, in this embodiment in particular, besides the advantage of the 24th embodiment, the guide wire fixture 81 is formed by only fixing the end portion of the tow wire 75 as the operating means on the side surface of the channel opening portion 26 in the notch portion 17a of the end portion 17 in the endoscope 1, which is inexpensive.

Figure 73:
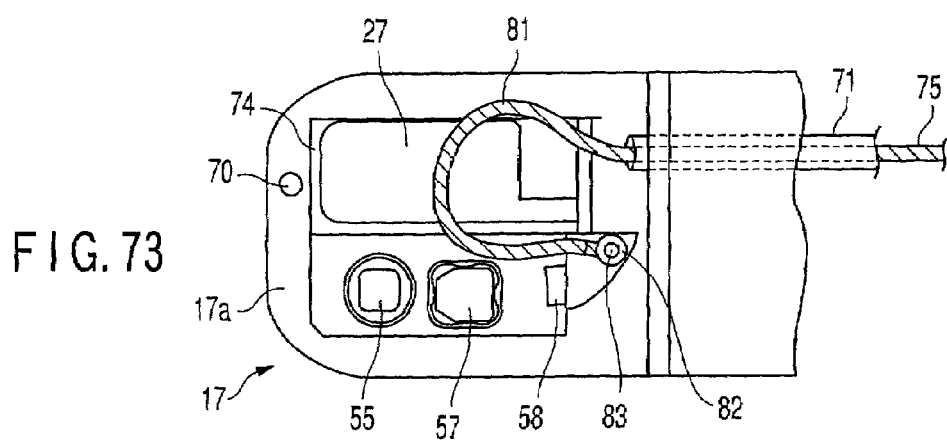
FIG. 73 is a plane view showing a modification of a fixed state of an end portion of the guide wire fixing portion in the endoscope according to the 37th embodiment.

Further, FIG. 73 shows a modification of the tow wire 75 which is in the fixed state at the end portion of the guide wire fixture 81 in the endoscope 1 according to the 37th embodiment.

In this modification, as shown in FIG. 73, a plate material 82 is fixed to the end portion of the guide wire fixture 81 by solder and the like, and the plate material 82 is connected to the end portion 17 of the endoscope 1 by a pin 83 and the like so as to be capable of swiveling.

Furthermore, as in the 24th embodiment, a protrusion 70 by which the guide wire fixture 81 can be temporarily fixed in the extended state may be provided to the notch portion 17a of the end portion 17 in the endoscope 1 on the end side away from the channel opening portion 26.

Thus, in this modification, the plate material 82 is fixed to the guide wire fixture 81, and the plate material 82 is connected to the end portion 17 of the endoscope 1 by the pin 83 and the like so as to be capable of swiveling. Therefore, there is an advantage that the load acting on the guide wire fixture 81 can be reduced when operating the guide wire fixture 81.

Figure 74A:
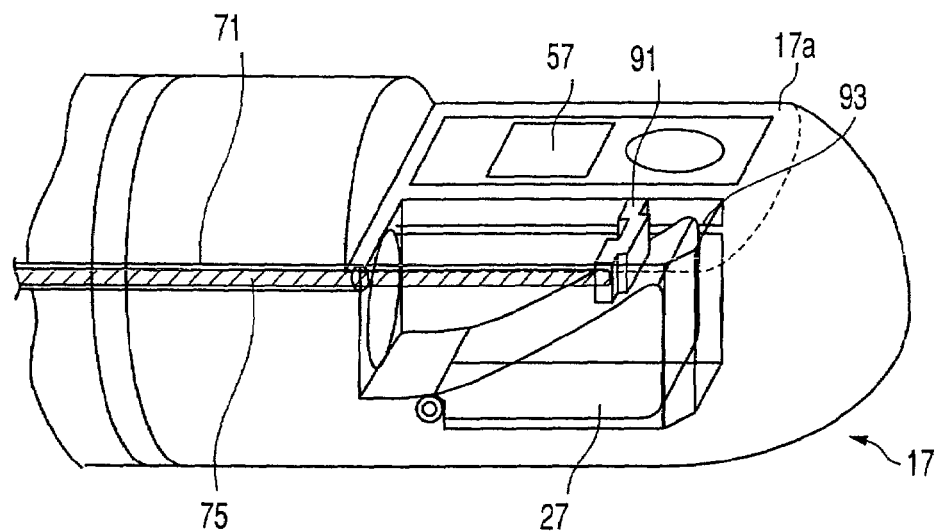
Figure 74B:
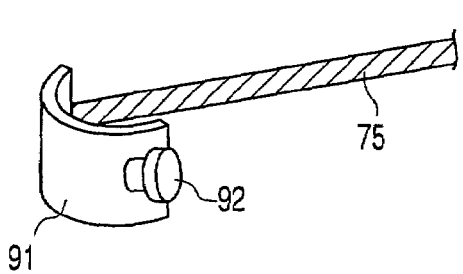
Figure 74C:
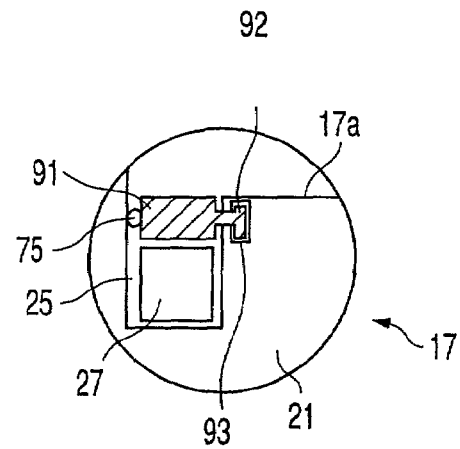

Moreover, FIGS. 74A to 74C show a 38th embodiment according to the present invention. In this embodiment, the structure of the end portion 17 of the endoscope 1 according to the 24th embodiment is changed as follows.

That is, in this embodiment, as shown in FIGS. 74A and 74B, a guide wire fixture 91 which is a member different from the tow wire 75 is connected to the end portion of the tow wire 75 according to the 24th embodiment.

The guide wire fixing plane of this guide wire fixture 91 may have a circular shape, a planar shape or a irregular shape according to the wire diameter of the guide wire 68. In addition, the end portion of the tow wire 75 is fixed to one end portion of the guide wire fixture 91. Additionally, a guiding protrusion 92 is provide to the other end portion of the guide wire fixture 91 so as to protrude therefrom.

Further, as shown in FIG. 74C, a guide groove 93 for guiding movement of the guide wire fixture 91 extends on the side surface portion of the accommodation chamber 25 of the end hard portion 21 along the axial direction of the insertion portion 12 of the endoscope 1. The guiding protrusion 92 of the guide wire fixture 91 is engaged with the guide groove 93. Furthermore, in the state that the guiding protrusion 92 slides along the guide groove 93 with the operation of the tow wire 75, the guide wire fixture 91 is moved along the axial direction of the insertion portion 12 of the endoscope 1.

Moreover, a range of movement of the guide wire fixture 91 by the operation of the tow wire 75 is set from the front side wall surface 26a of the channel opening portion 26 to the end side away from the therapeutic instrument elevator base 27.

The effect of this embodiment will now be described. In this embodiment, before inserting the guide catheter 67, the guide wire fixture 91 is set in the state that it is thrusted to the end side of the end portion 17 of the endoscope 1 in advance.

Then, as in the 24th embodiment, after the guide wire 68 ad the guide catheter 67 are inserted in to the therapeutic instrument insertion channel 23, the guide catheter 67 is pulled to the inside of the channel 23 and only the guide wire 68 is caused to protrude to the outside of the channel opening portion 26 in case of fixing the guide wire 68. In this state, the operation for pulling the guide wire fixture 91 to the front side is carried out through the tow wire 75 by the manipulation of the operation lever 72 on the front side. As a result, the guide wire 68 is sandwiched between the front side wall surface 26*a* of the channel opening portion 26 and the guide wire fixture 91, and the guide wire 68 is fixed.

In this embodiment, the guide wire 68 can be likewise easily fixed by the guide wire fixture 91 at the end portion of the tow wire 75 by manipulating the operation lever 72 on the front operation portion 13 side in the endoscope 1 as in the 24th embodiment, and the advantage similar to that of the 24th embodiment can be obtained.

Also, in this embodiment in particular, the guide groove 93 is provided on the side surface portion of the accommodation chamber 25 of the end hard portion 21, and the guiding protrusion 92 of the guide wire fixture 91 is engaged with the guide groove 93. Therefore, the guide wire fixture 91 does not move out from the channel opening portion 26, thereby enabling the stable operation for fixing the guide wire 68.

Figure 75:
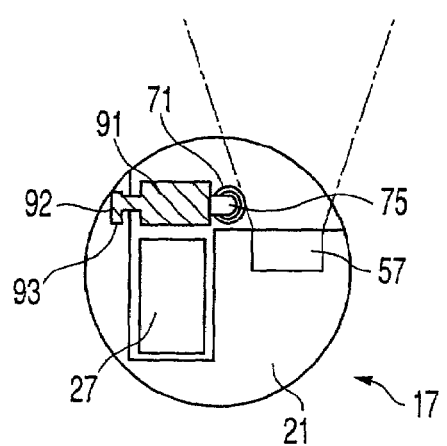

Further, as in the modification of the endoscope 1 in the 38th embodiment shown in FIG. 75, the tow wire 75 of the guide wire fixture 91 may be provided on the upper surface portion of the end hard portion 21 as long as the tow wire 75 does not enter the observation visual field extending from the object lens 57.

Furthermore, FIGS. 76 to 80 show a 39th embodiment. In this embodiment, the inner structure of the end portion 17 of the insertion portion 12 in the endoscope 1 according to the 24th embodiment is changed as follows.

Figure 78:
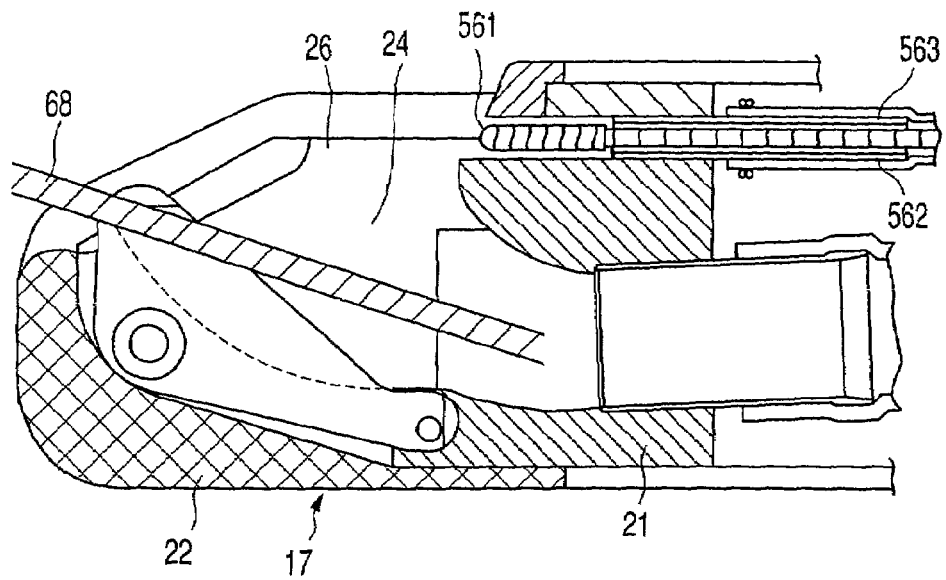

That is, in this embodiment, as shown in FIG. 78, a second opening portion 561 is formed at the upper surface portion of the channel opening 26 in the end hard portion 21. The base end portion of the second opening portion 561 is connected to the end portion of the guide wire fixture insertion channel 563 through a connection pipe 562 fixed to the channel hole of the end hard portion 21. The base end portion of the guide wire fixture insertion channel 563 is connected to a second insertion mouth ring portion 564 provided to the operation portion 13 of the endoscope 1 as shown in FIG. 76.

Figure 76:
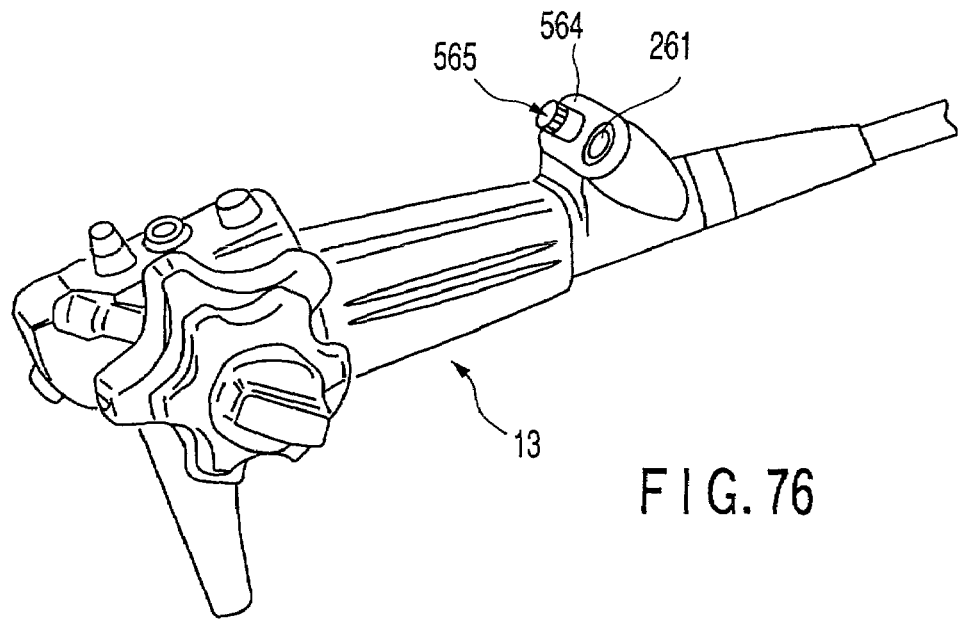

It is to be noted that the opening position of the guide wire fixation insertion channel 563 on the front side is not restricted to the position of the second insertion mouth ring portion 564 of the operation portion 13 shown in FIG. 76, and it may be set anywhere as long as that position can facilitate the fixing operation.

Moreover, the guide wire fixture 565 which performs the operation for fixing the guide wire 68 is configured to be removably inserted in to the guide wire fixture insertion channel 563. The guide wire fixture 565 is constituted by assembling three components, i.e., a snare unit 566, an elastic member 567 such as a coil spring, and an exterior unit 568 shown in FIG. 80.

In the snare unit 566, an end member 570 on the front side is connected to the base end portion of the elongated tow wire 569. The end member 570 is formed by a two-stage columnar member to which a columnar gripping portion 571 having a large diameter and a second columnar portion 572 having a small diameter are connected.

In addition, an engagement protrusion 573 is provided to the second columnar portion 572 of the end member 570, and an elastic member stopper 574 is provide to the step portion, respectively.

Additionally, an index 575 by which a rotation position can be confirmed is provided to one side portion of the gripping portion 571 of the end member 570.

Further, a loop-shaped snare 576 is provided to the end portion of the tow wire 569.

It is to be noted that the end portion of the tow wire 569 is not restricted to the snare 576 and it may have a hook shape which can hook and catch the guide wire 68.

Furthermore, a soft tube 578 for guiding the tow wire 569 of the snare unit 566 is provided to the exterior unit 568. A fixing member 579 which is releasably engaged with the end member 570 of the snare unit 566 is provided to the base end portion of the soft tube 578.

To the fixing member 579 are provided a mouth ring pressure member 580 which can be attached to the second insertion mouth ring portion 564, and a cylindrical member 581 which protrudes on the upper surface of the mouth ring pressure member 580. Moreover, an L-shaped engagement groove 582 is formed at the cylindrical member 581. An engagement protrusion 573 of the snare unit 566 can be engaged with the engagement groove 582.

In addition, a second s topper 583 is provided to the lower portion of the cylindrical member 581.

Additionally, the guide wire fixture 565 is integrally assembled by inserting the snare unit 566 in to the cylindrical member 581 of the exterior unit 568 through the elastic member 567 such as a coil spring. At this moment, the elastic member 567 is arranged between the elastic member s topper 574 of the snare unit 566 and the second s topper 583 of the exterior unit 568 and set in the state that the engagement protrusion 573 of the snare unit 566 is inserted in the engagement groove 582 of the cylindrical member 581.

It is to be noted that the guide wire fixture 565 according to this embodiment may be substituted by a snare or a gripping therapeutic instrument which is usually used as a therapeutic instrument.

The effect of this embodiment will now be described. Usually, as shown in FIG. 79B, the impetus in the direction along which the engagement protrusion 573 of the snare unit 566 hustles against the end portion of the engagement groove 582 on the opening end side (start end portion 582*a*) acts on the guide wire fixture 565 according to this embodiment by the elastic force of the elastic member 567, and the position of the snare unit 566 is restricted in this state. In such a state, the gripping portion 571 of the snare unit 566 is caused to protrude to the outer side of the cylindrical member 581 of the exterior unit 568 and held in this state, and the snare 576 is held in the closed state.

Further, when opening the snare 576, the gripping portion 571 of the snare unit 566 is operated to be pushed to the inner side of the cylindrical member 581 of the exterior unit 568 against the elastic force of the elastic member 567. With this operation, the engagement protrusion 573 of the snare unit 566 slides in the axial direction along the engagement groove 582 and moves to the position at which it is brought in to contact with the end portion of the engagement groove 582 on the mouth ring pressure member 580 side. In this state, the snare 576 protrudes from the soft tube 578 as shown in FIG. 79A, and the snare 576 is opened.

Figure 79A:
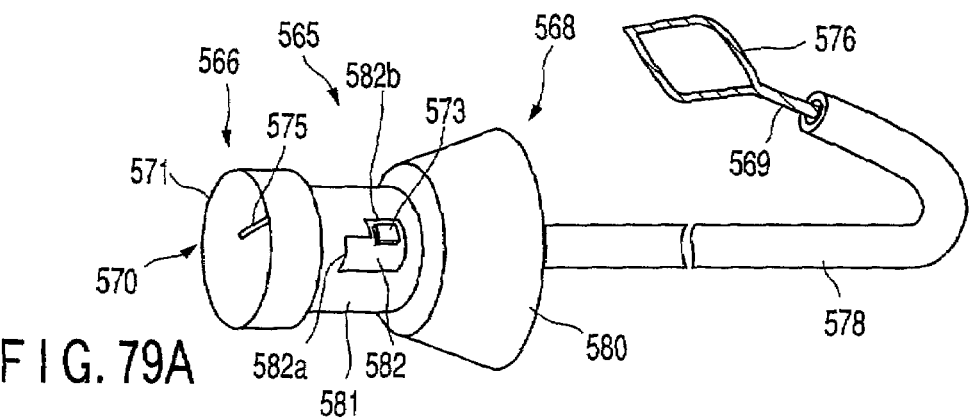
Figure 79B:
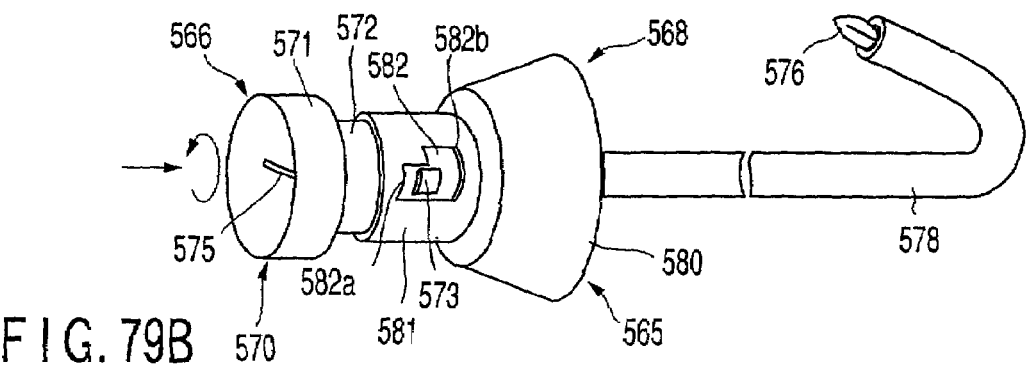
Figure 80:
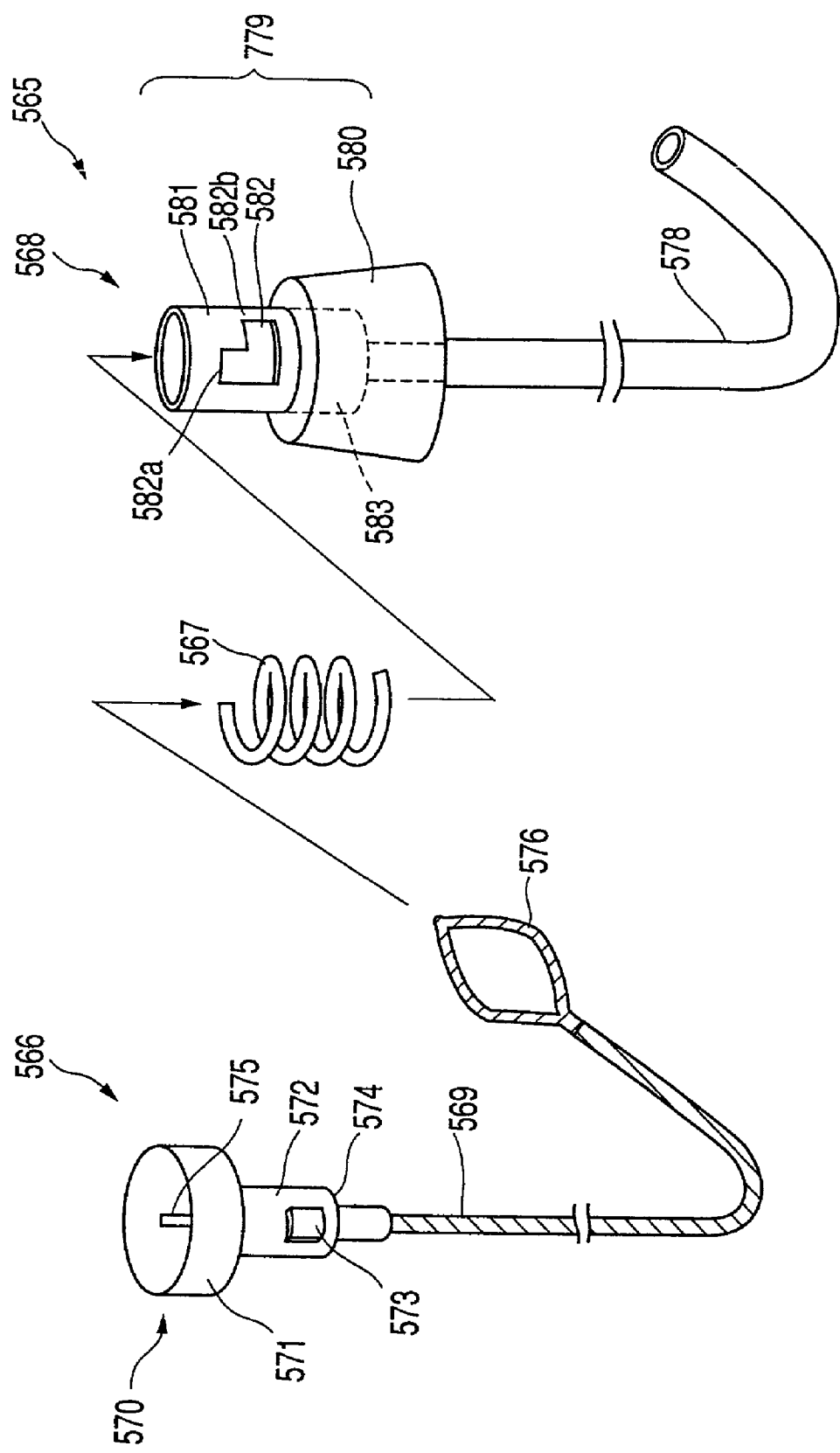

Subsequently, the gripping portion 571 is swiveled in the counterclockwise direction at this position, and the engagement protrusion 573 is brought in to contact with the engagement end portion 582b at the dead end of the engagement groove 582 as shown in FIG. 79A. As a result, the engagement protrusion 573 can be engaged, and the snare 576 can be held in the opened state.

Furthermore, when closing the snare 576, the engagement protrusion 573 comes off the engagement end portion 582b at the dead end of the engagement groove 582 by rotating the gripping portion 571 in the clockwise direction, and the snare unit 566 returns to its original position shown in FIG. 79B by the elastic force of the elastic member 567.

Figure 77A:
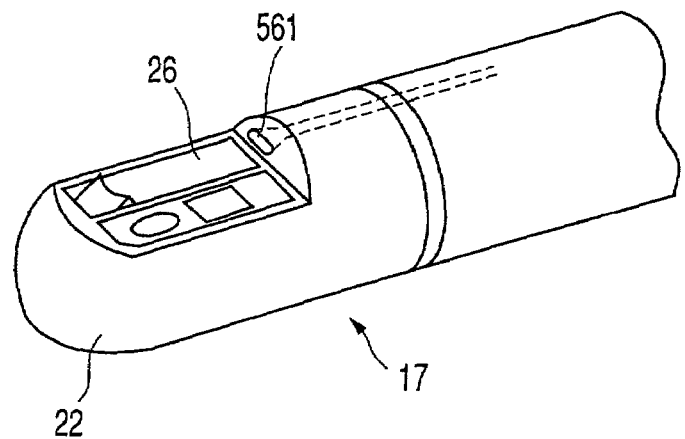
Figure 77B:
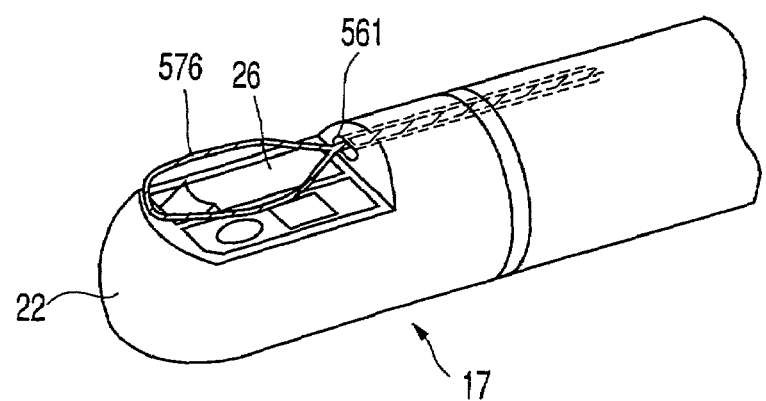

Description will now be given as to the method for fixing the guide wire 68 to the end portion 17 of the insertion portion 12 by using the guide wire fixture 566 according to this embodiment. The endoscope 1 is first inserted in to the body. Then, when a papilla is captured by the end portion 17 of the insertion portion 12, the guide wire fixture 565 is inserted from the second insertion mouth ring portion 564 with the snare 576 being closed. Thereafter, when the end of the guide wire fixture 565 protrudes from the second opening portion 561, the snare 576 is caused to protrude as shown in FIG. 77B by pushing the gripping portion 571. The subsequent operation is similar to that of the guide wire fixture 69 according to the 24th embodiment.

The following advantage can be demonstrated in this embodiment. That is, the advantage similar to that of the 24th embodiment can be obtained in this embodiment. In addition to this, since the guide wire fixture 565 can be easily removed from the endoscope 1, the end portion 17, the inside of the guide wire fixture insertion channel 563 and the guide wire fixture 565 can be readily cleaned/sterilized.

Moreover, there is an advantage that the inner structure of the end portion 17 of the insertion portion 12 in the endoscope 1 can be simplified.

In addition, the existing snare, the therapeutic instrument for gripping and others can substitute the guide wire fixture 565. Also, when the guide wire fixture 565 is not used, the guide wire fixture insertion channel 563 can be used as the treatment channel or the front water supply duct.

A 40th embodiment according to the present invention will now be described with reference to FIGS. 81 to 85. FIG. 81 shows a schematic structure in an end portion 603 of an insertion portion 602 of an endoscope 601 in an endoscope apparatus according to this embodiment. In the endoscope apparatus according to this embodiment, there is used a side viewing type endoscope 601 for observing a direction substantially orthogonal to the axial direction of the insertion portion 602.

To the side viewing type endoscope 601 is formed a substantially planar side viewing reference plane 612 which is formed by notching the outer peripheral surface of the end portion 603 of the insertion portion 602. An illumination window 613 of an illumination optical system and an observation window 614 of an observation optical system are aligned on the side viewing reference plane 612 in the front-and-back direction. Additionally, a channel opening portion 615 is provided next the alignment portion of the illumination window 613 and the observation window 614 on the side viewing reference plane 612. This channel opening portion 615 constitutes the end opening portion of the therapeutic instrument insertion channel 616 provided in the insertion portion 602 of the endoscope 601.

Further, a therapeutic instrument elevator base 617 is provided to the channel opening portion 615. As shown in FIG. 85, one end portion of the therapeutic instrument elevator base 617 is connected to a main body 611a of the end portion 603 through a swiveling shaft 618 so as to be capable of swiveling without restraint.

Furthermore, one end portion of a non-illustrated flexible operation wire is fixed to the other end portion of the therapeutic instrument elevator base 617. The other end portion of the operation wire is extended to an operation portion 606 side. Moreover, the operation wire is towed in cooperation with manipulation of a non-illustrated therapeutic instrument elevator base operation lever provided to the operation portion 606, and the operation of this operation wire drives the therapeutic instrument elevator base 617 to swivel around the swiveling shat 618. At this moment, the therapeutic instrument elevator base 617 is caused to swivel from a standby position (set-down position) indicated by dotted lines in FIG. 85 to a maximum swivel position (set-up position) indicated by solid lines in FIG. 85, and each of the elevator operation and the set-down operation in a therapeutic instrument 619, for example, an contrasting tube shown in FIGS. 83A and 83B, which is extended from the channel opening portion 615 to the outside is carried out in the visual field of the observation window 614 by the swiveling operation of the therapeutic instrument elevator base 617.

Moreover, as the therapeutic instrument 619 inserted in to the therapeutic instrument insertion channel 616 of the endoscope 601 according to this embodiment, a therapeutic instrument such as an existing contrasting tube provided with a guide wire lumen in to which a later-described guide wire 630 can be inserted can be used as it is.

Incidentally, the therapeutic instrument 619 which has a structure for reducing the frictional force with respect to the guide wire 630 or has the smoothed inner surface of the guide wire lumen by applying coating to the guide wire lumen is further preferable in this embodiment.

In addition, a substantially-V-shaped receiving groove portion 20 is formed on the opposite surface to the therapeutic instrument 619 in the therapeutic instrument elevator base 617. Additionally, when raising the therapeutic instrument 619, the therapeutic instrument 619 is brought in to contact with the therapeutic instrument elevator base 617 with the therapeutic instrument 619 being inserted in the receiving groove portion 20 to be positioned, and the therapeutic instrument 619 is guided in the vertical direction.

Further, in the side viewing type endoscope 601 according to this embodiment, a guide wire fixing member 621 as guide wire fixing means is attached in the vicinity of the end portion 603 of the insertion portion 602. To the guide wire fixing member 621 are provided a substantially cylindrical soft attachment portion 622 which is formed of a material such as chloroethene and a substantially cylindrical cap portion 623 connected to the end side of the attachment portion 622.

Furthermore, a material of the attachment portion 622 does not have to be necessarily chloroethene, and it may be polyethylene, polystyrene or polyurethane as long as it is a soft resin. Moreover, with the cap portion 623 being arranged around the end portion 603 of the insertion portion 602, the attachment portion 622 is attached in the vicinity of the end portion 603 of the insertion portion 602 in the endoscope 601. As a result, the guide wire fixing member 621 is detachably attached on the channel opening portion 615 or the insertion portion 602 on the base end side away from the channel opening portion 615 in the vicinity of the end portion 603 of the insertion portion 602 in the endoscope 601.

In addition, the cap portion 623 is made of polycarbonate resin having the transparency. As to a color tone of the cap portion 623, one having the high transparency is preferable, but it does not have to be necessarily transparent.

Incidentally, in regard to a composition of a material of the cap portion 623, polycarbonate resin is most preferable, but acrylic resin, polyethylene resin, polypropylene resin, polystyrene resin and others can be also used.

Further, on the end side of the cap portion 623 is formed a therapeutic instrument insertion opening window 624 at a position corresponding to the illumination window 613, the observation window 614 and the channel opening portion 615 on the side viewing reference plane of the end portion 603. The therapeutic instrument insertion opening window 624 of the cap portion 623 is opened on the reference plane 612 side of the insertion portion 602 of the endoscope 601. The opening window 624 is formed in to a substantially rectangular shape in such a manner that a width thereof is approximately ¼ of the circumference of the cap portion 623 whilst a length thereof is approximately 10 mm. As a result, the visual field of the observation window 614 of the endoscope 601 or the forward/backward movement of the therapeutic instrument 619 such as a contrasting tube extended to the outer side from the channel opening portion 615 can not be obstructed, and later-described guide wire identification members 627a and 627b can be easily actuated. Also, a later-described guide wire fixture insertion hole 628 can be arranged at an effective position.

Furthermore, a guide wire identification mechanism portion 625 and a guide wire fixing mechanism 626 are provided to the therapeutic instrument insertion opening window 624 of the cap portion 623. To the guide wire identification mechanism portion 625 are provided guide wire identification members 627a and 627b which consist of two stainless steel wires projecting to the inner side of the opening window 624 from the both sides of the opening window 624.

Moreover, one of the two guide wire identification members 627a and 627b, i.e., the first guide wire identification member 627a is extended from the left side of the therapeutic instrument insertion opening window 624 to the inner side along the upper edge portion of the cap portion 623 and curved downward in FIG. 82. In addition the other second guide wire identification member 627b is extended from the right side of the therapeutic instrument insertion opening window 624 to the inner side along the upper edge portion of the cap portion 623 and curved downward in FIG. 82. Respective lower extended portions 627a1 and 627b1 of the two guide wire identification members 627a and 627b are spaced from each other and oppositely arranged substantially in parallel along the direction of the center line of the guide wire fixing member 621. A space S having an appropriate width dimension L is formed between the respective lower extended portions 627a1 and 627b1 of the guide wire identification members 627a and 627b. This space S is set so as to be larger than, e.g., the outside diameter dimension of the guide wire 630.

Additionally, guide wire fixture insertion holes 628 are respectively formed to the both side portions of the therapeutic instrument insertion opening window 624 in the cap portion 623. These guide wire fixture insertion holes 628 are arranged at a substantially central position of the therapeutic instrument insertion opening window 624 along the direction of the center line of the guide wire fixing member 621.

Further, to the guide wire fixing mechanism portion 626 is provided a guide wire fixture 629 formed of a filate member having no elastic property, e.g., a surgical suture having an outside diameter dimension of approximately 0.2 mm. One end portion of the guide wire fixture 629 is fixed to the first guide wire identification member 627a on the left side in FIG. 82. Furthermore, the guide wire fixture 629 passes through the guide wire fixture insertion hole 628 of the therapeutic instrument insertion opening window 624 on the left side (first guide wire identification member 627a side) in FIG. 82, then cuts across the opening window 624, and passes through the guide wire fixture insertion hole 628 on the right side (second guide wire identification member 627b side) in FIG. 82 so that the other end portion side of the guide wire fixture 629 is fixed to the second guide wire identification member 627b. As a result, the guide wire fixture 629 is attached so as to be spanned between the both side portions on the opening window 624.

Incidentally, although the surgical suture having an outside diameter dimension of approximately 0.2 mm is used as the guide wire fixture 629 in this embodiment, any other thread made of a resin such as nylon may be used as long as it is a pliable filate member which has no elastic property but the high tensile strength.

Moreover, the guide wire identification members 627a and 627b are not restricted to stainless steel wires, and a copper wire, any other metallic wire made of, e.g., superelastic alloy manufactured by NiTi or a resin wire may be used as long as it is an elastic member.

Consequently, when the therapeutic instrument 619 is being drawn from the channel opening portion 615 on the end portion 603 side of the insertion portion 602 in the endoscope 601, the guide wire fixing mechanism portion 626 does not obstruct the operation of the therapeutic instrument 619. Also, when only the guide wire 630 is being drawn from the channel opening portion 615, the guide wire 630 is welded with pressure to and engaged with the guide wire fixture 629 between the both side portions on the opening window 624 of the guide wire fixing member 621 by the thrusting force from the therapeutic instrument elevator base 617.

When the therapeutic instrument 619 is being pulled to the operation portion front side by the guide wire fixing mechanism portion 626 after being inserted in to the therapeutic instrument insertion channel 616, a protruding length of the therapeutic instrument 619 which is required for the operation is assured from the channel opening portion 615 as the operation portion front side opening of the therapeutic instrument insertion channel 616.

In addition, when the guide wire 630 is inserted in to the guide wire lumen of the therapeutic instrument 619, a necessary protruding length of the guide wire 630 is provided from the end of the therapeutic instrument 619 in accordance with a target portion, and a protruding length of the same which is required for the operation is assured from the rear end of the therapeutic instrument 619.

The protruding length from the end of the therapeutic instrument 619 is approximately not more than 40 cm, and an protrusion amount of approximately 10 cm from the mouth ring 604a provided on the base end side of the therapeutic instrument 619 can obtain the most excellent operability and is ideal.

The effect of this embodiment will now be described. When using the endoscope apparatus according to this embodiment, if the therapeutic instrument 619 such as a contrasting tube is inserted in to the therapeutic instrument insertion channel 616 on the operation portion 606 side of the endoscope 601 and used, the end portion of the therapeutic instrument 619 is caused to protrude from the channel opening portion 615 of the end portion 603 of the insertion portion 602 in the endoscope 601. At this moment, if the therapeutic instrument elevator base 617 is held at a standby position (set-down position) indicated by dotted lines in FIG. 85, the end portion of the therapeutic instrument 619 is moved away from the guide wire identification members 627*a* and 627*b* of the guide wire identification mechanism portion 625 and held at a freely movable position as shown in FIG. 83A.

In this state, by manipulating a non-illustrated therapeutic instrument elevator base operation lever of the operation portion 606 of the endoscope 601, the therapeutic instrument elevator base 617 at the end portion 603 of the insertion portion 602 is operated to be raised. Then, the end portion of the therapeutic instrument 619 is pushed out in the direction along which it is inserted in to the therapeutic instrument insertion opening window 624 of the cap portion 623 by the therapeutic instrument elevator base 617 with this operation.

At this moment, the therapeutic instrument 619 is inserted between the respective lower extended portions 627*a*1 and 627*b*1 of the two guide wire identification members 627*a* and 627*b* projecting from the both sides of the therapeutic instrument insertion opening window 624 of the cap portion 623. Therefore, the space between the respective lower extended portions 627*a*1 and 627*b*1 of the two guide wire identification members 627*a* and 627*b* is extended by the therapeutic instrument 619, and the gap between the respective lower extended portions 627*a*1 and 627*b*1 is widened. Consequently, when the respective guide wire identification members 627*a* and 627*b* move close to the guide wire fixture insertion holes 628 on the both sides of the therapeutic instrument insertion opening window 624, the tensile force of the guide wire fixtures 629 respectively fixed to the respective guide wire identification members 627*a* and 627*b* is relaxed. As a result of relaxing the tensile force of the guide wire fixture 629 in this manner, when the end portion of the therapeutic instrument 619 is pushed out in the direction along which it is inserted in to the therapeutic instrument insertion opening window 624 of the cap portion 623 by the therapeutic instrument elevator base 617, the therapeutic instrument 619 is not engaged by the guide wire fixture 629, and the operation for raising the therapeutic instrument 619 is carried out as usual.

Additionally, if the therapeutic instrument elevator base 617 is held at the standby position (set-down position) indicated by dotted lines in FIG. 85 when the end portion of the guide wire 630 is led out from the channel opening portion 615 of the endoscope 601, the guide wire 630 moves away from the guide wire fixture 629 as shown in FIG. 84A and is held at a freely movable engagement releasing position.

When the therapeutic instrument elevator base 617 is swiveled to a maximum swiveling position (set-up position) indicated by solid lines in FIG. 85 in this state, the guide wire 630 is pushed out in the direction along which it is inserted between the guide wire identification members 627*a* and 627*b* of the guide wire identification mechanism portion 625 by the therapeutic instrument elevator base 617 as shown in FIG. 84B. At this moment, since the space S between the respective lower extended portions 627*a*1 and 27*b*1 of the guide wire identification members 627*a* and 627*b* is larger than, e.g., the outside diameter dimension of the guide wire 630, the space S between the two lower extended portions 627*a*1 and 627*b*1 is not widened by the guide wire 630 inserted between the respective lower extended portions 627*a*1 and 627*b*1 of the guide wire identification members 627*a* and 627*b*, and the tensile force of the guide wire fixture 629 spanned between the both side portions over the opening window 624 of the guide wire fixing member 621 is not relaxed.

In this case, with the operation by which the therapeutic instrument elevator base 617 of the end portion 603 of the insertion portion 602 is raised by manipulation of the non-illustrated therapeutic instrument elevator base operation lever, the guide wire 630 is welded with pressure to the guide wire fixture 629 between the both side portions over the opening window 624 in the guide wire fixing member 621 by the thrusting force from the therapeutic instrument elevator base 617. At this moment, since the guide wire 630 receives the force in the opposite directions between the therapeutic instrument elevator base 617 and the guide wire fixture 629 alternately in the shearing manner, the guide wire 630 is releasably engaged.

Further, when using the endoscope apparatus according to this embodiment, after the therapeutic instrument 619 such as a contrasting tube is inserted in to a pancreatic/hepatic duct (not shown) in the papillotomy manner, the operation for replacing the therapeutic instrument 619 is carried out as follows. The guide wire 630 is first inserted from the mouth ring 4*b* provided on the base end side of the therapeutic instrument 619 and led to the pancreatic/hepatic duct (not shown).

Insertion of the guide wire 630 in to the pancreatic/hepatic duct (not shown) is confirmed, and the therapeutic instrument 619 is pulled out while gripping the base end side of the guide wire 630 by a hand so as to avoid movement of the guide wire 630. At this moment, after confirming that the end portion of the therapeutic instrument 619 has been pulled out of a papilla (not shown) by an endoscopic image, the therapeutic instrument 619 is further pulled out.

Subsequently, when the end of the therapeutic instrument 619 is accommodated in the channel opening portion 615 on the end portion 603 side of the insertion portion 602, the guide wire 630 is similarly raised along the therapeutic instrument elevator base 617 by raising the therapeutic instrument base 617, and the guide wire 630 is mechanically fixed in the vicinity of the end portion 603 of the insertion portion 602 of the endoscope 601 by the guide wire fixing mechanism portion 626.

Furthermore, after confirming that the guide wire 630 is fixed, the therapeutic instrument 619 is completely pulled out from the operation portion 606 side of the endoscope 601. Thereafter, a therapeutic instrument 619 which is subsequently used is inserted from the base end side of the guide wire 630 and caused to hustle against the therapeutic instrument elevator base 617. Then, the therapeutic instrument elevator base 617 is lowered, and only the therapeutic instrument 619 is inserted in to the pancreatic/hepatic duct (not shown) with the guide wire 630 being used as a guide while gripping the base end portion of the guide wire 630.

Therefore, an operator does not have to keep gripping the guide wire 630 when replacing the therapeutic instrument 619. Moreover, the therapeutic instrument can be thereafter replaced for a necessary number of times by the similar method.

The following advantage can be demonstrated in this embodiment. That is, in this embodiment, the therapeutic instrument 619 other than the guide wire 630 can be raised or moved forward/backward by operating the therapeutic instrument elevator base 617 as in the prior art, and only the guide wire 630 is sandwiched between the therapeutic instrument elevator base 617 and the guide wire fixture 629 by the operation of the therapeutic instrument elevator base 617 and fixed in the engaged state. Therefore, in the operation for replacing the therapeutic instrument 619, it is no longer necessary to grip the guide wire 630 on the operation portion 606 side of the endoscope 601 as in the prior art by engaging only the guide wire 630 between the therapeutic instrument elevator base 617 and the guide wire fixture 629 by the operation of the therapeutic instrument elevator base 617. Accordingly, since there is an advantage that the operation for replacing the therapeutic instrument 619 can be facilitated, the operation time required for replacing the therapeutic instrument 619 can be shortened.

In addition, when inserting the guide wire 630 in to the therapeutic instrument 619, for example, 4 m of the guide wire 630 must be inserted in the prior art, but insertion of, e.g., approximately 2.5 m of the guide wire 630 can suffice in the present invention. Thus, the entire length of the guide wire is approximately 4 m in the prior art, and more than a half of the guide wire 630 is projecting from the endoscope 601 even when it is being inserted in the endoscope 601. Therefore, the possibility that the guide wire 630 may be brought in to contact with an unclean area such as a floor during handling is high, and caution is needed. In the present invention, however, a length of the part of the guide wire 630 which is projecting from the endoscope 601 is short, and the possibility that the guide wire 630 may be brought in to contact with the unclean area is low, thereby facilitating handling.

Further, when only the therapeutic instrument 619 is removed with the guide wire 630 remaining at a papilla, the two operations, i.e., the therapeutic instrument 619 is pulled out whilst the guide wire 630 is pushed in by an amount according to a removed amount of the therapeutic instrument 619, must be carried out at the same time in the prior art. In the present invention, however, the guide wire 630 does not have to be gripped on the operation portion 606 side, and one operation, namely, directly pulling out only the therapeutic instrument 619 can suffice. Thus, it is possible to reduce the time required for replacing the therapeutic instrument and a number of assistants and simplify the technique.

Furthermore, FIGS. 86A, 86B to 89A and 89B show a 41st embodiment according to the present invention. In this embodiment, a guide wire fixing member 641 which is different from the guide wire fixing member 621 according to the 40th embodiment and has a structure shown in FIGS. 86A and 86B is attached to the end portion 603 of the insertion portion 602 in the endoscope 601 according to the 40th embodiment.

That is, to the guide wire fixing member 641 according to this embodiment are provided a substantially-funnel-like attachment portion 642 and a substantially cylindrical cap portion 643 connected to the end side of the attachment portion 642.

Moreover, as shown in FIG. 87A, to the attachment portion 642 is provided a tapered attachment portion main body 644 which has a substantially cylindrical shape and whose outside diameter dimension becomes large in such a manner that its wall thickness gradually increases toward the base end portion side (lower side in FIG. 87A) of the insertion portion 602 of the endoscope 601. A plurality of, for example, four slits 645 are formed to a cylindrical wall portion of the attachment portion main body 644 in this embodiment as shown in FIG. 86B. These slits 645 are opened on the base end portion side of the attachment portion main body 644. In addition, four elastically deformable tongue pieces 646 are formed by parts between the respective slits 645.

Additionally, to the outer side of the guide wire fixing member 641 is provided a fixing ring 647 which releasably fixes the attachment portion 642 of the guide wire fixing member 641 to the end portion 603 of the insertion portion 602 in the endoscope 601. The inside diameter dimension of the fixing ring 647 is set in such a manner that it is larger than a minimum outside diameter portion 646 at which the outside diameter dimension of the tongue piece 646 of the attachment portion main body 644 is minimum in the guide wire fixing member 641 and it is smaller than a maximum outside diameter portion 646b at which the outside diameter dimension of the tongue piece 646 of the attachment portion main body 644 is maximum in the guide wire fixing member 641.

Further, as shown in FIG. 87A, in the state that the fixing ring 647 is held at the engagement releasing position at which the fixing ring 647 is not engaged with the tongue pieces 646 of the attachment portion main body 644, the guide wire fixing member 641 is held so as to be movable with respect to the insertion portion 602 of the endoscope 601.

Furthermore, when the fixing ring 647 is moved in the direction of the engagement position at which the fixing ring 647 is engaged with the tongue pieces 646 of the attachment portion main body 644, the tongue pieces 646 of the attachment portion main body 644 is inwardly pushed by the fixing ring 647 so that the inner end portion side of each of the four tongue pieces 646 is inwardly elastically deformed.

Incidentally, in this embodiment, taking the dimensions of the end portion 603 of the insertion portion 602 in the endoscope 601 in to consideration, the inside diameter dimension of the attachment portion 642 of the guide wire fixing member 641 is set to, e.g., 14 mm, the length of the same is set to 10 mm, and the tapered plane of the tongue piece 646 of the attachment portion main body 646 is set to a taper angle of 5°. Moreover, the four slits 645 of the attachment portion main body 644 are equally arranged on the circumference of the attachment portion 642 at intervals of substantially 90°.

In addition, the length of each slit 645 is parallel to the axial direction of the endoscope 601 from the base end side of the attachment portion 642 to the end side and set to approximately 9 mm. Additionally, as to a number of the slits 645 of the attachment portion main body 644, two to six is preferable when moldability or facilitation of attachment to the endoscope 601 is taken in to consideration.

Further, the inside diameter dimension of the fixing ring 647 movably attached to the attachment portion 642 is set to 16 mm, the outside diameter dimension of the same is set to 18 mm and the width of the same is set to approximately 2 mm, for example.

Incidentally, the fixing ring 647 is not restricted to the above-described dimensions, and any dimensions can be adopted as long as the fixing ring 647 has a function for fastening the slits 645 of the attachment portion 642. Therefore, as to the shape of the fixing ring 647, a belt-like member or a filate member may be used.

Furthermore, as to the materials of the attachment portion 642 and the fixing ring 647, it is preferable that these members are integrally manufactured by polycarbonate which is the same as the material of the cap portion 643 in terms of the cost. However, any other hard resin such as acrylic, crude rubber, synthetic rubber, soft resin such as silicon or urethane, or a metal such as stainless steel may be also used. They do not have to be transparent in particular as long as they have the elasticity to some measure and the smooth inner surface so that the end portion 603 of the insertion portion 602 of the endoscope 601 can not be damaged.

Moreover, as in the guide wire fixing member 621 according to the 40th embodiment, as shown in FIG. 86A, an opening window 648 is formed on the end side of the cap portion 643 of the guide wire fixing member 641. With the end portion 603 side of the insertion portion 602 of the endoscope 601 being opened, the opening window 648 is formed at a part corresponding to the illumination window 613, the observation window 614 and the channel opening portion 615 in the side viewing reference plane 612 of the end portion 603 of the endoscope 601.

In addition, a guide wire identification mechanism portion 649 and a guide wire fixing mechanism portion 650 are provided to the opening window 648 of the cap portion 643. To the guide wire identification mechanism portion 649 is provided a guide wire identification member 651 consisting of one stainless steel wire which is projecting with respect to the opening window 648 from one side end portion of the opening window 648 (opposite side to the observation window 614 in the endoscope 601) toward the inner side of the opening window 648. In FIG. 86A, this guide wire identification member 651 is extended from the right side of the opening window 648 to the inner side along the upper edge portion of the cap portion 643 and curves downward.

Additionally, guide wire fixing member insertion holes 652 are respectively formed to the cap portion 643 on the both side portions of the opening window 648. These guide wire fixing member insertion holes 652 are arranged at substantially central positions of the opening window 648 along the central line direction of the guide wire fixing member 641.

Further, to the guide wire fixing mechanism portion 650 is provided a guide wire fixture formed by a dilate member which is made up of, e.g., a surgical suture and as no elastic property. One end portion of the guide wire fixture 653 cuts across the opening window 648, and passes through the guide wire fixing member insertion hole 652 on the right side of the opening window 648 in FIG. 86A. Also, the other end portion side of the guide wire fixture 653 is fixed to the guide wire identification member 651. As a result, the guide wire fixture 653 is attached so as to be spanned between the both side portions on the opening window 648.

The effect of this embodiment will now be described. In the first instance, the following operation is carried out when the guide wire fixing member 641 is attached to the insertion portion 602 of the endoscope 601 of the endoscope apparatus according to this embodiment. As shown in FIG. 87A, in the engagement releasing state that the fixing ring 647 has been moved to the end portion side of the guide wire fixing member 641, the end portion 603 of the insertion portion 602 in the endoscope 601 is first inserted into the attachment portion 642 of the guide wire fixing member 641 from the slit 645 side of the guide wire fixing member 641.

Moreover, after inserting the end portion 603 of the insertion portion 602 in the endoscope 601 into the attachment portion 642, with the opening window 648 on the cap portion 643 being matched with the position of the channel opening portion 615 of the endoscope 601, the fixing ring 647 is again moved to the base end portion side of the guide wire fixing member 641. At this moment, with the operation for moving the fixing ring 647 to the base end portion side, the tongue piece 646 between the respective slits 645 of the attachment portion 642 is thrusted to the inner side in the radial direction as shown in FIG. 87B. Therefore, at this moment, the inner end portion side of each of the four tongue pieces 646 which are elastically deformed inwardly is engaged so as to be strongly welded to the outer peripheral surface of the insertion portion 602 of the endoscope 601 with pressure, and the guide wire fixing member 641 is immovably fixed to the insertion portion 602 of the endoscope 601.

In addition, when using the endoscope apparatus according to this embodiment, if the therapeutic instrument 619 such as a contrasting tube is inserted into the therapeutic instrument insertion channel 616 on the operation portion 606 side of the endoscope 601 and used, the end portion of the therapeutic instrument 619 is caused to protrude from the channel opening portion 615 of the end portion 603 of the insertion portion 602 in the endoscope 601. At this moment, in cases where the therapeutic instrument elevator base 617 is held at the standby position (set-down position) indicated by dotted lines in FIG. 85, the end portion of the therapeutic instrument 619 moves away from the guide wire identification member 651 of the guide wire identification mechanism portion 649 and is held at a position enabling free movement as shown in FIG. 88A.

In this state, by manipulating a non-illustrated therapeutic instrument elevator base operation lever of the operation portion 606 of the endoscope 601, the therapeutic instrument elevator base 617 of the end portion 603 of the insertion portion 602 is operated to be raised. Then, with this operation, the end portion of the therapeutic instrument 619 is thrusted by the therapeutic instrument elevator base 617 in the direction along which it is inserted into the opening window 648 of the cap portion 643.

A lower extended portion 651a of the guide wire identification member 651 in the opening window 648 of the cap portion 643 is thrusted in the transverse direction by the moving operation of the therapeutic instrument 619 at this moment. Additionally, the tensile force of the guide wire fixture 653 fixed to the guide wire identification member 651 is relaxed by the moving operation of the guide wire identification member 651. When the tensile force of the guide wire fixture 653 is relaxed in this manner, the therapeutic instrument 619 does not interfere with the guide wire fixture 653 even though the end portion of the therapeutic instrument 619 is thrusted by the therapeutic instrument elevator base 617 in the direction along which it is inserted into the opening window 648 of the cap portion 643, and the operation for raising the therapeutic instrument 619 is carried out as usual.

Further, with the end portion of the guide wire 630 being led out from the channel opening portion 615 of the endoscope 601, when the non-illustrated therapeutic instrument elevator base operation lever of the operation portion 606 of the endoscope 601 is operated and the therapeutic instrument elevator base 617 at the end portion 603 of the insertion portion 602 is operated to be raised, the guide wire 630 is thrusted by the therapeutic instrument elevator base 617 in the direction along which it is inserted into the opening window 648 as shown in FIG. 89B. At this moment, the lower extended portion 651a of the guide wire identification member 651 is not thrusted by the guide wire 630 in the transverse direction, and the tensile force of the guide wire fixture 653 spanned between the both side portions over the opening window 648 of the guide wire fixing member 641 is not relaxed. Thus, in this case, with the operation for raising the therapeutic instrument elevator base 617 at the end portion 603 of the insertion portion 602 by manipulating the non-illustrated therapeutic instrument elevator base operation lever, the guide wire 630 is welded with pressure to the guide wire fixture 653 between the both side portions over the opening window 648 of the guide wire fixing member 641 by the thrusting force from the therapeutic instrument elevator base 617. At this moment, since the guide wire 630 receives the force in the opposed directions alternately in the shearing manner between the therapeutic instrument elevator base 617 and the guide wire fixture 653, it is releasably engaged.

As a result, the guide wire fixing mechanism portion 650 does not prevent the operation of the therapeutic instrument 619 when the therapeutic instrument 619 is projecting from the channel opening portion 615 on the end portion 603 side of the insertion portion 602. Also, when only the guide wire 630 is projecting from the channel opening portion 615, the guide wire 630 is welded with pressure to and engaged with the guide wire fixture 653 between the both side portions over the opening window 648 of the guide wire fixing member 641 by the thrusting force from the therapeutic instrument elevator base 617.

The following advantage can be demonstrated in this embodiment. That is, in this embodiment, the therapeutic instrument 619 other than the guide wire 630 can be operated to be raised or moved forward/backward by the operation of the therapeutic instrument elevator base 617 as in the prior art, and only the guide wire 630 is sandwiched and engaged between the therapeutic instrument elevator base 617 and the guide wire fixture 653 by the operation of the therapeutic instrument elevator base 617. Therefore, in the operation for replacing the therapeutic instrument 619, it is no longer necessary to grip the guide wire 630 on the operation portion 606 side of the endoscope 601 as in the prior art by engaging only the guide wire 630 between the therapeutic instrument elevator base 617 and the guide wire fixture 653 by the operation of the therapeutic instrument elevator base 617. Accordingly, in this embodiment, the operation for replacing the therapeutic instrument 619 can be facilitated as in the 40th embodiment, thereby shortening the operation time required for the operation for replacing the therapeutic instrument 619.

Also, in addition to the advantage similar to that of the 40th embodiment, the tensile force of the guide wire fixture 653 can be adjusted by one guide wire identification member 651 in this embodiment in particular. Thus, of the two guide wire identification members 627a and 627b used in the 40th embodiment, the guide wire identification member 627a on the observation window 614 side of the endoscope 601 can be omitted. Therefore, there is an advantage that the visual field of the observation window 614 of the endoscope 601 can be assured.

Furthermore, since the principle of the fixing portion for fixing the guide wire fixing member 641 to the end portion 603 of the insertion portion 602 in the endoscope 601 is based on the mechanical engaging/releasing operation of the fixing ring 647 which does not utilize the resilience of rubber, it is advantageously possible to cope with a plurality of kinds of endoscopes 601 having different thicknesses at the attachment portion 642 in the guide wire fixing member 641 in one size.

Moreover, since a rubber component of the insertion portion 602 in the endoscope 601 is not scraped when the guide wire fixing member 641 is attached, there is an advantage that the insertion portion 602 in the endoscope 601 is hard to be damaged and the operation for attaching the guide wire fixing member 641 can be further facilitated.

In addition, FIGS. 90 through 102A to 102D show a 42nd embodiment according to the present invention. In this embodiment, a guide wire fixing member 661 having a structure shown in FIG. 91 which is different from the guide wire fixing member 621 according to the 40th embodiment is attached to the end portion 603 of the insertion portion 602 of the side viewing type endoscope 601 in the endoscope apparatus according to the 40th embodiment.

That is, to the guide wire fixing member 661 according to this embodiment are provided a guide wire fixing member main body 662 and an attachment member 663 for attaching the guide wire fixing member main body 662 to the endoscope 601 side.

The guide wire fixing member main body 662 will be first described. To the guide wire fixing member main body 662 are provided a base member 664 shown in FIGS. 94A to 94C, a guide wire fixture 665 shown in FIG. 95A, a guide wire identification member 666 shown in FIGS. 95B and 95C, and a top cover 667 shown in FIG. 96. Additionally, the guide wire fixture 665 and the guide wire identification member 666 are supported so as to protrude/retreat with respect to the base member 664.

Further, a guide groove 668 for guiding the protruding/retreating operation of the guide wire fixture 665 and the guide wire identification member 666 is provided on the front surface side of the base member 664. Furthermore, as shown in FIGS. 99A and 99B, a movement restriction portion 669 for restricting movement of the guide wire fixture 665 and the guide wire identification member 666 at a protruding position that the guide wire fixture 665 and the guide wire identification member 666 are caused to protrude to the outer side of the base member 664 along the guide groove 668 is provided to the base member 664 on the end portion side of the guide groove 668.

Moreover, a click groove 672 for guiding a click pin 671 of a later-described click mechanism 670 which temporarily fixes the guide wire identification member 666 is provided on the base end portion side of the guide groove 668 of the base member 664. In addition, on the end portion side of the base member 664, stopper insertion holes 673 which pierce from the back surface side to the front surface side are respectively formed on the both sides of the guide groove 668 at a part in the vicinity of the movement restriction portion 669 of the guide groove 668.

It is to be noted that an engagement groove 674 for engagement with the attachment member 663 and a stopper fixing groove 76 for fixing a later-described stopper member 675 are provided on the back surface side of the base member 664 as shown in FIG. 94B.

In addition, the guide wire fixture 665 is a substantially tabular member having a longitudinal dimension of approximately 10 mm, a transverse dimension of approximately 4 mm and a thickness of approximately 0.2 mm, and a material thereof is stainless steel.

Incidentally, the guide wire fixture 665 has an enough board thickness, and its material is not restricted to stainless steel as long as it can maintain the rigidity. Any other metal material such as aluminium or hard resin such as acrylic, polycarbonate or ABS resin may be used.

As shown in FIG. 95A, a concave impingement portion 677 which engages with the guide wire identification member 666 is formed at the guide wire fixture 665 at the center of the base end portion. Further, a guide wire fixing portion 678 for receiving the guide wire 630 is formed at the end portion on the end side of the guide wire fixture 665.

Incidentally, it is more preferable to attach an elastic member such as rubber to the guide wire fixing portion 678 in order to increase the friction between the guide wire fixing portion 678 and the guide wire 630 and prevent the guide wire 630 from being damaged.

Furthermore, shoulder portions 679 which hustle against the movement restriction portion 669 of the base member 664 of the guide wire fixing member main body 662 and slit-like stopper impingement portions 680 for receiving the stopper member 675 are respectively formed in the middle of the guide wire fixture 665 on the both sides.

Moreover, as shown in FIGS. 95B and 95C, the guide wire identification member 666 is a substantially tabular member which has a longitudinal dimension of approximately 10 mm, a transverse dimension of approximately 4 mm and a thickness of approximately 0.4 mm, and a material thereof is stainless steel.

Incidentally, the guide wire identification member 666 is not restricted to stainless steel if it has an enough board thickness and can maintain the rigidity. Any other metal material such as aluminium or hard resin such as acrylic, polycarbonate or ABS resin may be used.

A therapeutic instrument receiving portion 681 is formed at the end portion of the guide wire identification member 666. A guide wire insertion groove 682 which is opened on the end side and has a width of approximately 1 mm is formed at the central position of the therapeutic instrument receiving portion 681. In addition, the therapeutic instrument receiving portion 681 is configured to receive the therapeutic instrument 619 other than the guide wire 630.

It is to be noted that fluorine coating and the like may be applied to the therapeutic instrument receiving portion 681 in order to reduce the friction with respect to the therapeutic instrument 619 and an end of the therapeutic instrument 681 may be R-chamfered.

Additionally, a thrusting portion 683 which is bent in the substantially L shape as shown in FIG. 95C is formed at the base end portion of the guide wire identification member 666. Further, a large width portion 684 having a large lateral width is formed in the middle of the guide wire identification portion 666 at a substantially central part thereof. Furthermore, shoulder portions 85 which hustle against the movement restriction portion 669 of the base member 664 in the guide wire fixing member main body 662 are formed on the both sides of the large width portion 684 on the end portion side, and smoothly curved stopper releasing portions 686 are formed on the both sides of the same on the base end portion side, respectively.

Moreover, a concave portion 687 having a depth of approximately 0.2 mm is formed at the large width portion 684 of the guide wire identification member 666. A slit 688 through which a click pin 671 is inserted is formed in the concave portion 687.

In addition, as shown in FIG. 93B, the guide wire identification member 666 is arranged on the guide groove 668 on the front surface side of the base member 664 of the guide wire fixing member main body 662, and the guide wire fixture 665 is arranged on the guide wire identification member 666. Therefore, the guide wire identification member 666 is arranged in such a manner that it is sandwiched between the base member 664 of the guide wire fixing member main body 662 and the guide wire fixture 665.

The end side of the guide wire fixture 665 is caused to protrude from the base member 664 of the guide wire fixing member main body 662 so as to be capable of moving forward/backward. Additionally, the end side of the guide wire fixture 665 reaches the channel opening portion 615 on the end portion 603 side of the insertion portion 602 in the endoscope 601.

It is to be noted that the end side of the guide wire identification member 666 is attached in such a manner that it is caused to protrude on the end side away from the guide wire fixture 665 so as to be capable of moving forward/backward.

Further, when the guide wire identification member 666 moves in the direction along which it protrudes from the guide groove 668 of the base member 664 to the outer side, the thrusting portion 683 of the guide wire identification member 666 is engaged with the impingement portion 677 of the guide wire fixture 665 in the hooked manner.

Furthermore, a stopper member 675 for causing the guide wire identification member 666 to interlock with the guide wire fixture 665 is fixed to the stopper fixing groove 76 provided on the back surface side of the base member 664 of the guide wire fixing member main body 662. As shown in FIGS. 95D and 95E, the stopper member 675 is two thin wire rods each having a wire diameter of approximately 0.2 mm, and superelastic alloy manufactured by NiTi is desirable for a material thereof. However, any other metal, e.g., stainless steel or hard resin such as acrylic or polycarbonate may be used as long as it is a wire rod having the elasticity.

Moreover, a linear portion 675*a* having a substantially rectilinear shape is formed at the part of the thin wire rod of the stopper member 675 which is arranged on the back surface side of the base member 664 of the guide wire fixing member main body 662. In addition, one end portion side of the stopper member 675 is extended to the front surface side of the base member 664 through the stopper insertion hole 673 opened on the end side of the base member 664 of the guide wire fixing member main body 662. In addition, a bent portion 675*b* which is bent in the substantially L shape is formed at the extended portion on the front surface side of the base member 664. Additionally, the end part of the bent portion 675*b* of the stopper member 675 is bent in the direction away from the base member 664 of the guide wire fixing member main body 662 so that the end part can reach the guide wire fixture 665 across the guide wire identification member 666.

Additionally, the bent portion 675*b* of the stopper member 675 is brought into contact with the stopper releasing portion 686 of the guide wire identification member 666, and the guide wire identification member 666 is configured to use the stopper releasing portion 686 to extend the space between the bent portions 675*b* in the horizontal direction.

Further, as shown in FIGS. 93A and 93B, a top cover 667 is provided on the front surface side of the guide wire fixing member main body 662. A spring fixing pin 89 is provided so as to protrude on the end side of the top cover 667, and a window portion 90 from which the thrusting portion 683 of the guide wire identification member 666 protrudes is formed on the base end portion side of the top cover 667.

Furthermore, a spring member 691 as a torsion bar for giving impetus to the guide wire identification member 666 in the direction along which the guide wire identification member 666 is pushed to the end portion side of the base member 664 is provided to the top cover 667. One end portion of the spring member 691 is fixed to the spring fixing pin 89, and the other end portion of the same is engaged with the thrusting portion 683 of the guide wire identification member 666.

Incidentally, it is desirable that the wire diameter of the wire strand of the spring member 691 is, e.g., approximately 0.2 mm and the material thereof is superelastic alloy manufactured by NiTi.

Moreover, the click mechanism 670 for temporarily fixing the guide wire identification member 666 is provided to the guide wire fixing member main body 662 according to this embodiment. To the click mechanism 670 are provided a click pin 671 shown in FIG. 98A and a click groove 672 set to the base member 664 of the guide wire fixing member main body 662.

Although the material of the click pin 671 is stainless steel, the elasticity is not necessarily required if the material is strong to some extent, and hard resin may be used.

Incidentally, although a circular shape may be used as the cross-sectional shape of the click pin 671, a rectangular shape and the like by which the click pin 671 is hard to be inclined with respect to the click groove 672 is desirable.

In addition, a U-shaped bent portion 671a which is bent in the substantially U shape is formed at one end portion of the click pin 671. Additionally, an L-shaped bent portion 671b which is bent in the substantially L shape is formed at the other end portion of the click pin 671. Further, the U-shaped bent portion 671a of the click pin 671 is rotatably attached to the slit 688 of the guide wire identification member 666. Furthermore, the L-shaped bent portion 671b of the click pin 671 is movably inserted into the click groove 672 of the base member 664.

It is to be noted that an edge portion 671c which is smoothly rounded so that it can smoothly move in the click groove 672 for guiding the pin is formed at the pin end portion of the click pin 671 on the L-shaped bent portion 671b side.

Moreover, the shape of the click groove 672 of the base member 664 is set as shown in FIG. 98B. That is, the click groove 672 is formed into a distorted ring shape connecting an end side convex portion 672b which is arranged on the end side of the base member 664 and provided with one linear portion 672a extending in the substantially axial direction, two rear end side convex portions 672c and 672d arranged on the rear end side of the base member 664 side by side, and a concave portion 672e arranged between the two rear end side convex portions 672c and 672d. In addition, when the guide wire fixture 665 protrudes from the guide groove 668 of the base member 664 of the guide wire fixing member main body 662, the click pin 671 is arranged on the end side convex portion 672b side. When the guide wire fixture 665 is embedded in the guide groove 668 of the base member 664 of the guide wire fixing member main body 662, the click pin 671 is arranged on the side of the two rear end side convex portions 672c and 672d.

Additionally, the inner wall of the click groove 672 is smooth along the entire length. Taking the allowance of the click pin 671 into consideration, approximately 0.25 mm is desirable for the groove width of the click groove 672, and the depth of the same is set so as to vary in a range of approximately 0.4 mm to 0.2 mm as follows. That is, the depth of the linear portion 672a of the click groove 672 on the end side is set to approximately 0.4 mm. A left groove 672f and a right groove 672g obtained by bifurcation are connected to the end portion of the linear portion 672a. The depth of the left groove 672f does not vary at the bifurcated portion, and it is set to approximately 0.4 mm.

Further, the depth of the right groove 672g discontinuously varies at a discontinuous point 672h and is set to approximately 0.2 mm.

Furthermore, after being bifurcated, the depth of the left groove 672f becomes shallow to 0.2 mm and reaches the rear end side convex portion 672c on the left side.

The depth of the rear end side convex portion 672c on the left side becomes deep to approximately 0.4 mm at the discontinuous point 672i.

Moreover, the depth of the click groove 672 becomes discontinuously shallow to 0.2 mm from the rear end side convex portion 672c on the left side and reaches the concave portion 672e. The depth of the concave portion 672e discontinuously varies at the discontinuous point 672j and is set to 0.4 mm. Then, the depth of the click groove 672 becomes discontinuously shallow to 0.2 mm and reaches the rear end side convex portion 672d on the right side. The depth of the rear end side convex portion 672d on the right side becomes discontinuously varies at the discontinuous point 672k and is set to 0.4 mm.

In addition, the click groove 672 extends from the rear end side convex portion 672d on the right side to the end side and becomes the right groove 672g. Also, the depth of the click groove 672 becomes continuously shallow to 0.2 mm and runs together with a bifurcation at the dead end portion of the linear portion 672a.

Additionally, as shown in FIGS. 92A, 97A and 97B, a substantially-C-shaped belt-like attachment portion 693 having a discontinuous notch portion 692 at a part of the ring is provided to the attachment member 663. The belt shape of the belt-like attachment portion 693 is a zonal member having a width of approximately 10 mm and a thickness of approximately 0.5 mm.

Further, a mucous protection portion 694 for preventing the guide wire fixing member 661 from being caught by the mucous is provided to the belt-like attachment portion 693 so as to protrude therefrom. This mucous protection portion 694 is arranged on the opposite side to the observation window 614 of the endoscope 601.

Furthermore, a positioning convex portion 95 which is fitted in the channel opening portion 615 of the end portion 603 when attached to the endoscope 601 is provided to the attachment member 663 so as to protrude therefrom. Moreover, as shown in FIG. 92A, substantially-L-shaped engagement convex portions 696 which are fitted in the engagement groove 674 provided on the back surface side of the base member 664 of the guide wire fixing member main body 662 are provided on the both ends of the discontinuous notch portion 692 in the belt-like attachment portion 693 so as to protrude therefrom.

Incidentally, although polycarbonate is desirable as a material of the attachment member 663, any other resin such as rubber or metal such as stainless steel can suffice if it has the strength and its surface is smoothed so as not to damage the endoscope 601.

The effect of this embodiment will now be described. Description will first be given as to the operation for attaching the guide wire fixing member 661 according to this embodiment to the end portion 603 of the insertion portion 602 of the endoscope 601. In the operation for attaching the guide wire fixing member 661, the convex portion 95 used for positioning the attachment member 663 is fitted in the channel opening portion 615 of the endoscope 601. Subsequently, the discontinuous notch portion 692 of the belt-like attachment portion 693 of the attachment member 663 being butted, the engagement convex portion 696 of the attachment member 663 is fitted in the engagement groove 674 of the guide wire fixing member main body 662. At this moment, as shown in FIG. 91, the guide wire fixing member 661 is slid from the end side of the belt-like attachment portion 693, and the guide wire fixing member 661 is fixed to the end portion 603 of the insertion portion 602 in the endoscope 601.

In addition, in the case of inserting the end portion 603 of the endoscope 601 having the guide wire fixing member 661 being attached thereto into a celoma, as shown in FIG. 92B, the mucous 697 is not caught by the guide wire fixing member main body 662 since the mucous protection portion 694 of the guide wire fixing member 661 thrusts away the mucous 697 in the celoma.

Additionally, when the therapeutic instrument 619 such as a tube other than the guide wire 630 is inserted into the therapeutic instrument insertion channel 616 on the operation portion 606 side of the endoscope 601 and is used with the end portion 603 of the endoscope 601 being inserted into a celoma, the end portion of the therapeutic instrument 619 is caused to protrude from the channel opening portion 615 of the end portion 603 of the insertion portion 602 in the endoscope 601. In the initial state, the therapeutic instrument elevator base 617 is held at the standby position (set-down position) shown in FIGS. 101A and 101B, and the guide wire fixing member main body 662 is held in the state depicted in FIGS. 99A and 99B.

At this moment, impetus is given to the guide wire identification member 666 of the guide wire fixing member 661 in the direction along which it is pushed to the end portion side of the base member 664 by the spring force of the spring member 691, and the thrusting portion 683 of the guide wire identification member 666 is held in the state that it hustles against the impingement portion 677 of the guide wire fixture 665. Then, the click pin 671 is held in the state it is being inserted in the linear portion 672a on the end side of the click groove 672.

Further, in case of raising the therapeutic instrument 619 from the initial state, the following operation is conducted. The therapeutic instrument elevator base 617 of the end portion 603 of the insertion portion 602 is first swiveled in the elevator operation direction by manipulating the non-illustrated therapeutic instrument elevator base operation lever of the operation portion 606 of the endoscope 601. Then, the end portion of the therapeutic instrument 619 is thrusted in the direction for raising the therapeutic instrument which is orthogonal to the axial direction of the insertion portion 602 by the therapeutic instrument elevator base 617 with the swivel operation of the therapeutic instrument elevator base 617.

At this moment, the end portion of the therapeutic instrument 619 which is thrusted by the therapeutic instrument elevator base 617 is brought into contact with the therapeutic instrument receiving portion 681 of the guide wire identification member 666 in the middle of the swivel operation of the therapeutic instrument elevator base 617. Thus, the guide wire identification member 666 is thrusted down to the base end side of the endoscope 601 by the subsequent swivel operation of the therapeutic instrument elevator base 617.

Furthermore, with the operation by which the guide wire identification member 666 is thrusted down to the base end side of the endoscope 601, the stopper member 675 is outthrusted from side to side along the stopper releasing portion 686 of the guide wire identification member 666. At this moment, when the stopper member 675 moves to the dead end position along the stopper releasing portion 686 of the guide wire identification member 666, the stopper member 675 comes off the stopper impingement portion 680 of the guide wire fixture 665 as shown in FIG. 99C. Therefore, since the stopper of the guide wire fixture 665 is released in this state, the guide wire fixture 665 is also thrusted down to the base end side of the endoscope 601 together with the guide wire identification member 666.

Then, when the end portion of the therapeutic instrument 619 is thrusted in the therapeutic instrument set-up direction orthogonal to the axial direction of the insertion portion 602 by the therapeutic instrument elevator base 617 as shown in FIGS. 101C and 101D, the guide wire identification member 666 is pushed to the maximum thrust position in the guide groove 668 of the base member 664 as illustrated in FIG. 99D. At this moment, the click pin 671 moves along the left groove 672f of the click groove 672 in cooperation with the guide wire identification member 666 and reaches the rear end side convex portion 672c on the left side.

Thereafter, by carrying out the operation for returning the therapeutic instrument elevator base 617 in the direction toward the standby position (set-down position) shown in FIG. 101A, the guide wire identification member 666 is pushed back in the direction of the end of the insertion portion 602 by the spring force of the spring member 691 as depicted in FIGS. 101E and 101F. At the same time, as shown in FIG. 100A, the click pin 671 connected to the guide wire identification member 666 moves to the position of the concave portion 672e along the click groove 672, and the guide wire fixture 665 and the guide wire identification member 666 are held in the thrusted state.

At this moment, since the click pin 671 has passed the discontinuous point 672i at the rear end side convex portion 672 on the left side, it does not rotate in the opposite direction.

It is to be noted that the similar reverse rotation prevention effect is provided at all the discontinuous points in the click groove 672.

In this state, the guide wire fixture 665 and the guide wire identification member 666 do not interfere with the therapeutic instrument 619, and the guide wire fixture 665 and the guide wire identification member 666 do not obstruct in the visual filed of the observation window 614 of the endoscope 601.

Moreover, when the therapeutic instrument 619 is again raised, the guide wire fixture 665 and the guide wire identification member 666 are again thrusted down to the maximum thrust position in the guide groove 668 of the base member 664 as shown in FIGS. 101C and 101D. At this moment, as illustrated in FIG. 101B, the click pin 671 reaches the rear end side convex portion 672d on the right side along the click groove 672 and the locked state is released.

Thereafter, when the operation for returning the therapeutic instrument elevator base 617 in the direction toward the standby position (set-down position) shown in FIG. 101A is performed, the guide wire identification member 666 is pushed back in the direction toward the end of the insertion portion 602 by the spring force of the spring member 691. At the same time, with the movement of the guide wire identification member 666 at this moment, the thrusting portion 683 of the guide wire identification member 666 is caused to hustle against the impingement portion 677 of the guide wire fixture 665 as depicted in FIG. 100C. As a result, the guide wire fixture 665 is also thrusted to the end side of the endoscope 601 together with the guide wire identification member 666, thereby returning to the initial state shown in FIGS. 99A and 99B.

In addition, as illustrated in FIGS. 102A and 102B, with the end portion of the guide wire 630 being led out from the channel opening portion 615 of the endoscope 601 (initial state), when the therapeutic instrument elevator base 617 is raised, the following operation is carried out.

That is, when the therapeutic instrument elevator base 617 at the end portion 603 of the insertion portion 602 from the initial state is caused to swivel, the guide wire 630 is inserted into the guide wire insertion groove 682 provided to the therapeutic instrument receiving portion 681 at the end of the guide wire identification member 666 by the therapeutic instrument elevator base 617 with the swivel operation of the therapeutic instrument elevator base 617 at this moment. Thus, the guide wire identification member 666 is not thrusted down by the guide wire 630 in this case.

Additionally, as shown in FIGS. 102C and 102D, the guide wire 630 inserted into the guide wire insertion groove 682 of the therapeutic instrument receiving portion 681 by swiveling of the therapeutic instrument elevator base 617 directly hustles against the guide wire fixing portion 678 of the guide wire fixture 665.

At this moment, since the guide wire fixture 665 is restricted by the stopper member 675 at the stopper impingement portion 680 as shown in FIG. 99A, it is not thrusted down, and the guide wire 630 is pressed between the therapeutic instrument elevator base 617 and the guide wire fixture 665 and fixed in the engaged state.

Incidentally, when releasing engagement of the guide wire 630, it is good enough to effect the operation for returning the therapeutic instrument elevator base 617 in the direction toward the standby position (set-down position) shown in FIGS. 102A and 102B.

The following advantage can be demonstrated in this embodiment. That is, in this embodiment, the therapeutic instrument 619 other than the guide wire 630 can be operated to be raised or moved forward/backward by manipulation of the therapeutic instrument elevator base 617 as in the prior art, and only the guide wire 630 is sandwiched between the therapeutic instrument elevator base 617 and the guide wire fixture 665 and fixed in the engaged manner by manipulation of the therapeutic instrument elevator base 617. Therefore, in case of the operation for replacing the therapeutic instrument 619, the necessity to grip the guide wire 630 on the operation portion 606 side of the endoscope 601 as in the prior art can be eliminated by engaging only the guide wire 630 between the therapeutic instrument elevator base 617 and the guide wire fixture 665 by manipulating the therapeutic instrument elevator base 617. Accordingly, since there is as advantage that the operation for replacing the therapeutic instrument 619 is facilitated also in this embodiment as in the 40th embodiment, the operation time required for replacing the therapeutic instrument 619 can be reduced.

Also, in addition to the advantage similar to that of the 40th embodiment, this embodiment has an advantage that actuation of the guide wire identification member 666 is secure and the visual field of the observation window 614 of the endoscope 601 can be further widely assured.

Further, FIGS. 103A to 103J and FIGS. 107A to 107D show a 43rd embodiment according to the present invention. In this embodiment, the structure of the guide wire fixing member main body 662 in the guide wire fixing member 661 according to the 42nd embodiment is changed as follows.

Incidentally, parts other than the above have the structure equal to that of the 42nd embodiment, and like reference numerals denote parts similar to those of the 42nd embodiment, thereby omitting their explanation.

That is, to the guide wire fixing member main body 662 according to this embodiment are provided a guide wire fixture 701 show in FIG. 103D and a guide wire identification member 702 depicted in FIGS. 103E and 103F which have the structures different from those of the guide wire fixture 665 and the guide wire identification member 666 according to the 42nd embodiment.

A substantially-V-shaped guide wire engagement groove 703 whose width is smaller than the outside diameter dimension of the guide wire 630 is formed at the end portion of the guide wire fixture 701 according to this embodiment. Furthermore, a stopper impingement portion 704 for receiving a later-described stopper member is provided at a central part of the guide wire fixture 701 on the base end portion side.

Moreover, a large width portion 705 having a large transverse width is formed in the middle of the guide wire fixture 701. In addition, shoulder portions 106 which hustle against the movement restriction portion 669 of the base member 664 are formed on the both sides of the large width portion 705 on the end portion side, and guide wire identification member impingement portions 707 are formed on the both sides of the large width portion 705 on the base end portion side.

Additionally, the guide wire identification member 702 according to this embodiment is configured as shown in FIGS. 103E and 103F. A therapeutic instrument receiving portion 708 is formed at the end portion of the guide wire identification member 702. A guide wire insertion groove 709 which is opened on the end side is formed at a central part of the therapeutic instrument receiving portion 708. Further, the therapeutic instrument receiving portion 708 is configured to receive the therapeutic instrument 619 other than the guide wire 630.

Further, a large width portion 710 having a large transverse width is formed on the base end portion side of the guide wire identification member 702. Furthermore, shoulder portions 711 which hustle against the movement restriction portion 669 of the base member 664 in the guide wire fixing member main body 662 are formed on the both sides of the large width portion 710 on the end portion side.

Moreover, a bifurcated edge portion 712 which is bifurcated as shown in FIG. 103E is formed at the base end portion side of the large width portion 710. As shown in FIG. 103F, to the bifurcated edge portion 712 are formed stopper releasing portions 713 each of which has a board thickness smoothly changing into a wall thickness from the base end portion side to the end portion side. In addition, a thrusting portion 744 for the guide wire fixture 701 is formed at a step portion at the end of each stopper releasing portion 713. Additionally, when the guide wire identification member 702 protrudes, a guide wire identification member impingement portion 707 of the guide wire fixture 701 is configured to receive the thrusting portion 714 for the guide wire identification member 702.

It is to be noted that at the large width portion 710 of the guide wire identification member 702 are formed a concave portion 715 and a slit 716 which are similar to the concave portion 687 and the slit 688 of the guide wire identification member 666 according to the 42nd embodiment.

Further, FIGS. 103A to 103C show the base member 664 of the guide wire fixing member main body 662 according to this embodiment. To the end portion of the base member 664 on the front surface side is attached a substantially-T-shaped stopper member 717 which has a top cover function for covering the guide wire fixture 701 and causes the guide wire identification member 702 and the guide wire fixture 701 to interlock with each other as shown in FIG. 103G.

This stopper member 717 is a platy member having a board thickness of approximately 0.2 mm, and superelastic alloy manufactured by NiTi is desirable as a material thereof. However, a member having the elasticity such as stainless steel can suffice.

A fixing portion 717a which is fixed on the end portion on the front surface side of the base member 664 of the guide wire fixing member main body 662 is provided on the end side of the stopper member 717. Furthermore, as shown in FIG. 103H, a bent portion 717b which is bent at substantially 90 degrees is provided to the base end portion of the stopper member 717. The bent portion 717b is in contact with the stopper impingement portion 704 of the guide wire fixture 701.

Moreover, a click mechanism 718 having a structure different from that of the click mechanism 670 according to the 42nd embodiment is provided on the base end portion side of the guide groove 668 of the base member 664. To the click mechanism 718 are provided a click pin 719 shown in FIG. 103I which has the same structure as the click pin 671 according to the 42nd embodiment and a click groove 720 shown in FIG. 103J which is arranged on the base end portion side of the guide groove 668 in the base member 664 of the guide wire fixing member main body 662.

In addition, a U-shaped bent portion 719a which is bent in the substantially U shape is formed at one end portion of the click pin 719. Additionally, an L-shaped bent portion 719b which is bent in the L shape at substantially right angles is formed at the other end portion of the click pin 719. Further, the U-shaped bent portion 719a of the click pin 719 is rotatably attached to the slit 716 of the guide wire identification member 702. Furthermore, the L-shaped bent portion 719b of the click pin 719 is movably inserted into the click groove 720 of the base member 664.

An edge portion 719c which is smoothly rounded so as to smoothly move in the click groove 720 for guiding the pin is formed at the pin end portion of the click pin 719 on the L-shaped bent portion 719b side.

Moreover, the shape of the click groove 720 of the base member 664 is set as shown in FIG. 103J. That is, the click groove 720 is formed into a substantially triangular distorted ring shape including a groove end portion 720a arranged on the end side of the base member 664, a groove rear end portion 720b arranged on the rear end side of the base member 664, a linear groove portion 720c connecting the groove end portion 720c and the groove rear end portion 720b to each other, a hole portion 720d arranged on the side of the linear groove portion 720c, a linear groove portion 720e connecting the hole portion 720d and the groove end portion 720a to each other, and a linear groove portion 720f connecting the hole portion 720d and the groove rear end portion 720b to each other. In addition, when the guide wire fixture 701 protrudes from the guide groove 668 of the base member 664 of the guide wire fixing member main body 662, the click pin 719 is arranged on the groove end portion 720a side. Also, when the guide wire fixture 701 is embedded in the guide groove 668 of the base member 664 of the guide wire fixing member main body 662, the click pin 719 is arranged on the groove rear end portion 720b side.

Description will now be given as to the detailed structure of the shape of the click groove 720 of the base member 664. That is, the depth of the linear groove portion 720e connecting the groove end portion 720a and the hole portion 720d of the click groove 720 is set to approximately 0.4 mm. The depth of the hole portion 720d is set to approximately 0.6 mm. Further, the distance between the hole portion 720d and the groove rear end portion 720b is set to approximately 0.5 mm. Furthermore, the depth becomes continuously shallow between the hole portion 720d and the groove rear end portion 720b and is set to 0.2 mm. The click groove 720 discontinuously has the depth of 0.4 mm at the discontinuous point 720g of the groove rear end portion 720b. Then, this groove extends from the groove rear end portion 720b to the end side along the liner groove portion 720c and its depth becomes continuously shallow to 0.2 mm. Also, it runs together with the groove end portion 720a on the end side through the discontinuous point 720h.

The effect of the guide wire fixing member main body 662 according to this embodiment will now be described. FIGS. 106A to 106F show the operation state when the therapeutic instrument 619 other than the guide wire 630 is raised by using the guide wire fixing member 661, and FIGS. 107A to 107D show the operation state when the guide wire 630 is raised by using the guide wire fixing member 661.

Description will be first given as to the case where the therapeutic instrument 619 other than the guide wire 630 is raised. When the therapeutic instrument 619 such as a contrasting tube other than the guide wire 630 is inserted into the therapeutic instrument insertion channel 616 on the operation portion 606 side of the endoscope 601 and used with the end portion 603 of the endoscope 601 being inserted into a celoma, the end portion of the therapeutic instrument 619 is caused to protrude from the channel opening portion 615 at the end portion 603 of the insertion portion 602 in the endoscope 601. In the initial state, the therapeutic instrument elevator base 617 is held at the standby position (set-down position) shown in FIGS. 106A and 106B, and the guide wire fixing member 661 is held in the state depicted in FIGS. 104A and 104B.

At this moment, impetus is given to the guide wire identification member 702 of the guide wire fixing member 661 in the direction for thrusting to the end portion side of the base member 664 by the spring force of the spring member 691, and the thrusting portion 714 of the guide wire identification member 702 is held in such a manner that it is caused to hustle against the guide wire identification member impingement portion 707 of the guide wire fixture 701. Moreover, the click pin 719 is held being inserted in the groove end portion 720a on the end side of the click groove 720.

In addition, in case of raising the therapeutic instrument 619 from the initial state, the following operation is conducted. The therapeutic instrument elevator base 617 at the end portion 603 of the insertion portion 602 is first swiveled in the elevator operation direction by manipulating the non-illustrated therapeutic instrument elevator operation lever of the operation portion 606 in the endoscope 601. Then, with the swivel operation of the therapeutic instrument elevator base 617, the end portion of the therapeutic instrument 619 is thrusted in the direction for raising the therapeutic instrument which is orthogonal to the axial direction of the insertion portion 602 by the therapeutic instrument elevator base 617.

At this moment, the end portion of the therapeutic instrument 619 thrusted by the therapeutic instrument elevator base 617 is brought into contact with the therapeutic instrument receiving portion 708 of the guide wire identification member 702 in the middle of the swivel operation of the therapeutic instrument elevator base 617. Thus, the guide wire identification member 702 is thrusted down to the base end side of the endoscope 601 by the subsequent swivel operation of the therapeutic instrument elevator base 617.

Additionally, with the operation for thrusting down the guide wire identification member 702 to the base end side of the endoscope 601, the bent portion 717b of the stopper member 717 is pushed up in a direction along which it moves away from the stopper impingement portion 704 of the guide wire fixture 701 by the stopper releasing portion 713 of the guide wire identification member 702. At this moment, when the stopper member 717 moves to the dead end position along the stopper releasing portion 713 of the guide wire identification member 702, the stopper member 717 comes off the stopper impingement portion 704 of the guide wire fixture 701 as shown in FIG. 104D. Therefore, since the stopper of the guide wire fixture 701 is released in this state, the guide wire fixture 701 is also thrusted down to the base end side of the endoscope 601 together with the guide wire identification member 702. At this moment, the click pin 719 moves along the linear groove portion 720e of the click groove 720 on the left side in FIG. 103J in cooperation with the guide wire identification member 702.

Then, when the end portion of the therapeutic instrument 619 is thrusted in the direction for raising the therapeutic instrument which is orthogonal to the axial direction of the insertion portion 602 by the therapeutic instrument elevator base 617 as shown in FIGS. 106C and 106D, the guide wire identification member 702 is pushed into the guide groove 668 of the base member 664 to the thrust position shown in FIGS. 104E and 104F. At this moment, the click pin 719 reaches the hole portion 720d. The click pin 719 is caught by the hole portion 720d and fixed in the engaged state. Therefore, the guide wire fixture 701 and the guide wire identification member 702 are held in the thrusted state as shown in FIGS. 104E and 104F.

When the therapeutic instrument elevator base 617 is lowered a little from this state, the guide wire fixture 701 and the guide wire identification member 702 do not interfere with the therapeutic instrument 619, and the guide wire fixture 701 and the guide wire identification member 702 do not obstruct in the visual field of the observation window 614 of the endoscope 601.

Further, when the therapeutic instrument 619 is again set-up, the guide wire fixture 701 and the guide wire identification member 702 are thrusted down to the maximum thrust position in the guide groove 668 as shown in FIGS. 105A and 105B. At this moment, the click pin 719 moves out of the hole portion 720d of the click groove 720 and reaches the groove rear end portion 720b along the linear groove portion 720f, thereby releasing the locked state.

Thereafter, when the operation for returning the therapeutic instrument elevator base 617 to the direction of the standby position (set-down position) shown in FIGS. 106A and 106B is carried out, the guide wire identification member 702 is pushed back to the direction of the end of the insertion portion 602 by the spring force of the spring member 691. At the same time, with the moving operation of the guide wire identification member 702 at this moment, the thrusting portion 714 of the guide wire identification member 702 is caused to hustle against the impingement portion 707 of the guide wire fixture 701 as shown in FIGS. 105C and 105D. As a result, the guide wire fixture 701 is also pushed to the end side of the endoscope 601 together with the guide wire identification member 702 and returns to the initial state shown in FIGS. 104A and 104B.

Furthermore, as shown in FIGS. 107A and 107B, when the therapeutic instrument elevator base 617 is raised with the end portion of the guide wire 630 being led out from the channel opening portion 615 of the endoscope 601 (initial state), the following operation is performed.

That is, when the therapeutic instrument elevator base 617 of the end portion 603 of the insertion portion 602 is operated to swivel from the initial state mentioned above, the guide wire 630 is inserted in the guide wire insertion groove 709 of the therapeutic instrument receiving portion 708 provided at the end of the guide wire identification member 702 by the therapeutic instrument elevator base 617 with the swiveling operation of the therapeutic instrument elevator base 617 at this moment. Therefore, in this case, the guide wire identification member 702 is not thrusted down by the guide wire 630.

Moreover, the guide wire 630 existing in the guide wire insertion groove 709 of the therapeutic instrument receiving portion 708 reaches the position of the end portion 701a of the guide wire fixture 701 by swiveling of the therapeutic instrument elevator base 617. At this moment, since the guide wire identification member 702 is not thrusted down, the guide wire fixture 701 is restricted with the stopper member 717 being engaged with the stopper impingement portion 704 and hence it is not thrusted down.

In addition, when the therapeutic instrument elevator base 617 is operated to be raised, the guide wire 630 is pressed against the guide wire engagement groove 703 of the end portion 701a of the guide wire fixture 701 by the therapeutic instrument elevator base 617 and fixed in such a manner that it is held by and engaged with the guide wire engagement groove 703 as shown in FIGS. 107C and 107D.

Incidentally, when releasing engagement of the guide wire 630, the therapeutic instrument 619 is inserted with the guide wire 630 being used as a guide and caused to protrude from the channel opening portion 615 at the end portion 603 of the insertion portion 602 in the endoscope 601. As a result, the therapeutic instrument 619 pushes out the guide wire 630 in the direction along which the guide wire 630 comes off the guide wire engagement groove 703, thereby releasing engagement.

The following advantage can be obtained in this embodiment. That is, in this embodiment, the therapeutic instrument 619 other than the guide wire 630 can be operated to be raised or moved forward/backward by manipulation of the therapeutic instrument elevator base 617 as in the prior art, and only the guide wire 630 is pressed against the guide wire engagement groove 703 at the end portion 701a of the guide wire fixture 701 by the therapeutic instrument elevator base 617 and fixed so as to be held by and engaged with the guide wire engagement groove 703. Therefore, in case of the operation for replacing the therapeutic instrument 619, the necessity of gripping the guide wire 630 on the operation portion 606 side of the endoscope 601 as in the prior art can be eliminated by engaging only the guide wire 630 with the guide wire engagement groove 703 at the end portion 701a of the guide wire fixture 701 by manipulating the therapeutic instrument elevator base 617. Accordingly, since the operation for replacing the therapeutic instrument 619 can be facilitated also in this embodiment as in the 40th embodiment, the operation time required for replacing the therapeutic instrument 619 can be reduced.

Also, in addition to the advantage similar to that of the 40th embodiment, this embodiment has an advantage that a number of constituent components of the guide wire fixing member main body 662 can be reduced and the operation for assembling the guide wire fixing member main body 662 can be facilitated.

In addition, FIGS. 108A to 108E show a 44th embodiment according to the present invention. In this embodiment, a guide wire fixing member 731 having a structure different from that of the guide wire fixing member 621 according to the 40th embodiment is provided to the end portion 603 of the insertion portion 602 of the side viewing type endoscope 601 in the endoscope apparatus according to the 40th embodiment.

That is, in this embodiment, an external channel 732 is provided along the side surface of the insertion portion 602 in the endoscope 601 over the substantially entire length of the insertion portion 602. The end portion of the external channel 732 is arranged at a part in the vicinity of the channel opening portion 615 provided at the end portion 603 of the insertion portion 602. Additionally, the base end portion of the external channel 732 is arranged at a part in the vicinity of the operation portion 606 (see FIGS. 114A and 114B) in the endoscope 601.

Further, the guide wire fixing member 731 according to this embodiment is inserted into the external channel 732 so as to be capable of moving forward/backward therein without restraint. FIG. 108A shows an example in which a gripping therapeutic instrument 733 is used as the guide wire fixing member 731. Furthermore, FIG. 108B shows an example in which a snare 734 is used as the guide wire fixing member 731, and FIG. 108C shows an example in which a guide wire thruster 735 is used as a guide wire fixing member 731.

Moreover, although a porous PTFE is desirable as a material of the external channel 732, the material is not restricted to porous PTFE as long as it has a nearly equal hardness and buckling resistant property. If the material of the external channel 732 is hard, the external channel 732 may buckle or the stiffness of the insertion portion 602 may increase depending on the insertion shape of the endoscope 601, thereby reducing the insertion ability.

On the contrary, if the material of the external channel 732 is soft, the amount of force needed for advance or retreat of the guide wire fixing member 731 is increased. Therefore, the hardness of the external channel 732 can be set to the appropriate state by forming the external channel 732 by using porous PTFE.

As to the dimensions of the inside and outside diameters of the external channel 732, the small outside diameter is preferable when taking into consideration the insertion ability into a celoma. On the other hand, however, when the outside diameter dimension of the guide wire fixing member 731 to be inserted into the external channel 732 is taken into account, a diameter of at least approximately 3 mm is necessary, and it is desirable to set the inside diameter to approximately 3 mm and the outside diameter to approximately 4 mm, for example.

Incidentally, an arm portion 737 which is a gripping portion and can be opened/closed is provided on the gripping therapeutic instrument 733 of the guide wire fixing member 731 at the end portion of the operation wire 736. In addition, the arm portion 737 is configured to hold the guide wire 630 therein. Additionally, as shown in FIG. 108D, zigzag grooves 737a or irregular grooves 737b to prevent slipping which are substantially orthogonal to the axial direction of the guide wire 630 are formed on the contact plane in the arm portion 737 with respect to the guide wire 630. The grooves on the contact plane in the arm portion 737 with respect to the guide wire 630 may be formed in the staggered manner so that the opposed grooves can be fitted to each other.

Further, as shown in FIG. 108E, the contact plane with which the guide wire 630 is brought into contact may be covered with resin such as rubber 737c.

It is to be noted that a loop-like snare wire 738 is provided for the snare 734 shown in FIG. 108B at the end portion of the operation wire 736b. The snare wire 738 is configured to grip the guide wire 630 therein. Furthermore, a tabular thrusting plate 739 is provided to the guide wire thruster 735 shown in FIG. 108C at the end portion of the operation wire 736b. Moreover, it is configured that the guide wire 630 is gripped between the thrusting plate 739 and the therapeutic instrument elevator base 617.

The effect of this embodiment will now be described. At first, in case of raising the therapeutic instrument 619 other than the guide wire 630, the gripping therapeutic instrument 733 as the guide wire fixing member 731 is accommodated in the external channel 732 so as not to affect the operation of the therapeutic instrument 619.

In addition, when raising the guide wire 630, the gripping therapeutic instrument 733 is caused to protrude from the external channel 732, the operation portion (not shown) of the gripping therapeutic instrument 733 provided on the operation portion 606 side of the endoscope 601 is operated while confirming using an endoscopic image, and the guide wire 630 is gripped.

Additionally, the non-slip grooves which are substantially orthogonal to the guide wire 630 are formed on the contact plane in the arm portion 737 of the gripping therapeutic instrument 733 with respect to the guide wire 630. When the opposed grooves are staggered so that they can be fitted to each other, the guide wire 630 is engaged so as to receive the force in the shearing manner along the grooves of the arm portion 737.

Further, when the guide wire fixing member 731 is the snare 734, the snare wire 738 at the end of the snare 734 is caused to protrude from the external channel 732 and opened, and the guide wire 630 is inserted into the snare wire 738. In this state, the operation portion (not shown) of the snare provided on the operation portion 606 side of the endoscope 601 is manipulated, and the loop of the snare wire 736 is decreased, thereby engaging the guide wire 630.

Furthermore, when the guide wire fixing member 731 is the guide wire thruster 735, the guide wire 630 is raised, and the guide wire thruster 735 is pushed in from the operation portion 606 side of the endoscope 601, and the guide wire 630 is sandwiched between the therapeutic instrument elevator base 617 and the guide wire thruster 735, thereby engaging the guide wire 630.

The following advantage can be demonstrated in this embodiment. That is, in addition to the advantage similar to that of the 40th embodiment, the guide wire fixing member 731 according to this embodiment can be used to fix and release the guide wire 630 by the will of an operator, and the existing gripping therapeutic instruments can be used, thereby readily making preparations.

Moreover, when there are grooves on the plane with which the guide wire 630 is brought into contact, the force for fixing the guide wire 630 can be increased. In addition, when the plane with which the guide wire 630 is brought into contact is covered with resin such as rubber, the force for fixing the guide wire 630 can be increased and the guide wire 630 can be prevented from being damaged.

Additionally, in cases where the guide wire fixing member 731 is the snare 734, by inserting the guide wire 630 into the loop of the snare wire 738 in the first operation, the operation for assuring the guide wire 630 can be facilitated when fixing the guide wire 630 in the second and subsequent operations.

Further, if the guide wire fixing member 731 is the guide wire thruster 735, since only the operation wire 736c for operating the guide wire thruster 735 can be inserted into the external channel 732, the inside and outside diameters of the external channel 732 can be reduced, and the insertion ability with respect to a celoma can be hence improved.

Furthermore, FIG. 109 shows a 45th embodiment according to the present invention. In this embodiment, the structure of the guide wire fixing member 621 according to the 40th embodiment is changed as follows.

Incidentally, any other parts have the same structure as the 40th embodiment, and like reference numerals denote parts similar to those in the 40th embodiment, thereby omitting their explanation.

That is, in the guide wire fixing member 621 according to this embodiment, one end portion of the guide wire fixture 629 is fixed to the guide wire fixture insertion hole 628 arranged on one side of the therapeutic instrument insertion opening window 624 of the cap portion 623. The guide wire fixture 629 cuts across the therapeutic instrument insertion opening window 624 and passes through the other guide wire fixture insertion hole 628 of the therapeutic instrument insertion opening window 624. Then, the guide wire fixture 629 is extended to the operation portion 606 side of the endoscope 601 through the therapeutic instrument insertion channel 616 provided inside the insertion portion 602 of the endoscope 601. Moreover, the extended end portion of the guide wire fixture 629 is configured to be connected to the operation portion (not shown) of the guide wire fixture 629 provided on the operation portion 606 side of the endoscope 601.

The effect of this embodiment will now be described. In this embodiment, when the therapeutic instrument 619 other than the guide wire 630 is raised, the guide wire fixture 629 is loosened on the operation portion 606 side of the endoscope 601 so as not to prevent set-up of the therapeutic instrument 619.

In addition, when the guide wire 630 is raised, the guide wire fixture 629 is pulled from the operation portion 606 side of the endoscope 601, and the tensile force is generated to the guide wire fixture 629 cutting across the therapeutic instrument insertion opening window 624 of the cap portion 623. In this state, the guide wire 630 is raised by the therapeutic instrument elevator base 617, and the guide wire 630 is sandwiched and engaged between the therapeutic instrument elevator base 617 and the guide wire fixture 629 cutting across the therapeutic instrument insertion opening window 624.

The following advantage can be demonstrated in this embodiment. That is, in addition to the advantage similar to that of the 40th embodiment, in this embodiment, the guide wire 630 can be fixed and released by the will of an operator and there is no external channel 732 according to the 44th embodiment, thereby improving the insertion ability to a celoma.

Additionally, FIGS. 110A to 110C show a 46th embodiment according to the present invention. In this embodiment, the structure of the guide wire fixing member 731 according to the 44th embodiment is changed as follows.

That is, in this embodiment, the gripping therapeutic instrument 733 is attached to the end portion 603 of the insertion portion 602 in the endoscope 601. Further, a bending portion 741 is connected to the rear end portion of the end portion 603 of the insertion portion 602. A wire fixing ring 742 is fixed to the bending portion 741 on the base end side. Furthermore, the base end portion of the operation wire 736a of the gripping therapeutic instrument 733 is fixed to the wire fixing ring 742.

The effect of this embodiment will now be described. In this embodiment, as shown in FIG. 110B, when the guide wire 630 is raised, the bending portion 741 of the endoscope 601 is once curved, and the operation wire 736a is loosened. In this state, an endoscopic image is used to confirm that the guide wire 630 has been raised so that it can be held by the arm portion 737 of the gripping therapeutic instrument 733.

Then, curve of the bending portion 741 in the endoscope 601 is released. As a result, as shown in FIG. 110C, the operation wire 736a becomes tensed, the arm portion 737 of the gripping therapeutic instrument 733 is closed, and the guide wire 630 is engaged with the arm portion 737 so as to be held therein.

The following advantage can be demonstrated in this embodiment. That is, in addition to the advantage of the 44th embodiment, in this embodiment, the external channel 732 does not have to be attached and it does not take troubles to insert the operation wire into the therapeutic instrument insertion channel 616 as in the 45th embodiment.

It is to be noted that the present invention is not restricted to the foregoing embodiments. For example, a shown in FIGS. 111A and 111B, the guide wire fixing member 753 consisting of the guide wire fixing mechanism portion 751 and the attachment member 752 may be attached to the end portion 603 of the insertion portion 602 in the endoscope 601 having the therapeutic instrument elevator base 617. Moreover, as shown in FIGS. 111C and 111D, the guide wire fixing member 754 consisting of only the guide wire fixing mechanism portion 751 included in the end portion 603 of the insertion portion 602 in the endoscope 601 may be provided. The guide wire fixture 755 is included in the guide wire fixing mechanism portion 751.

Meanwhile, FIGS. 111A and 111C show the state in which the therapeutic instrument elevator base 617 is raised with the end portion of the therapeutic instrument 619 other than the guide wire 630 being led out from the channel opening portion 615 of the endoscope 601, and FIGS. 111B and 111D show the state in which the therapeutic instrument elevator base 617 is raised with the end portion of the guide wire 630 being led out from the channel opening portion 615 of the endoscope 601, respectively.

In addition, the endoscope 601 used in the present invention may be an existing endoscope 761 as shown in FIGS. 112A and 112B. Additionally, as illustrated in FIGS. 112C and 112D, it may be an endoscope 763 having a guide wire fixing member installation space 762 in which the guide wire fixing mechanism portion 751 is previously incorporated to the end portion 603 of the insertion portion 602 of the endoscope 601.

Further, as depicted in FIGS. 112E and 112F, it may be an endoscope 765 having the attachment member 764 of the guide wire fixing mechanism portion 751. Furthermore, as shown in FIGS. 112G and 112H, it may be an endoscope 767 in which the guide wire fixing member 766 having the guide wire fixing mechanism portion 751 being undetachably included.

Moreover, although the guide wire must have the length which is twofold of that of the therapeutic instrument when inserting/removing the therapeutic instrument running on the guide wire in the prior art, the length of the guide wire 630a in this embodiment may be not more than twofold of that of the therapeutic instrument since the guide wire 630a can be fixed in the vicinity of the end of the endoscope. In addition, in the endoscope 601 used in the present invention, it is good enough that the guide wire 630a has a length that it protrudes by an amount not more than 40 cm from the channel opening portion 615 of the endoscope 601 toward the inside of the body and protrudes approximately 10 cm from the mouth ring 4a (see FIGS. 114A and 114B) provided on the base end side of the therapeutic instrument 619.

That is, although the existing guide wire 5 (see FIGS. 114A and 114B) having a length of approximately 400 cm can be used, the guide wire 630A having an entire length of not more than 250 cm can be used in this embodiment as shown in FIG. 113A.

Additionally, although 1 mm or a shorter length is desirable as the outside diameter dimension of the guide wire 630A, it does not have to be restricted in particular.

Further, as shown in FIG. 113B, it is possible to use the extendable guide wire 630b provided with connection portions 630b and 630b by which the extension guide wire 630a can be connected to the base end portion side of the guide wire 630B according to needs. Alternatively, as illustrated in FIG. 113C, the guide wire 630C having a circular portion 630d which is curved in the circular form at the end thereof can suffice.

Furthermore, as the therapeutic instrument 619, existing therapeutic instruments can be used as they are. A therapeutic instrument having a coated guide wire lumen in order to reduce the frictional force with respect to the guide wire 630 or another therapeutic instrument having the inner surface being smoothed is more preferable in this embodiment.

Moreover, when the therapeutic instrument 619 is projecting from the channel opening portion 615 on the end portion 603 side of the insertion portion 602, the guide wire fixing mechanism portion 751 does not obstruct the operation of the therapeutic instrument 619. When only the guide wire 630 is projecting, the guide wire fixing mechanism portion 751 can fix the guide wire 630.

For example, as illustrated in connection with the 44th and 45th embodiments, the guide wire fixing mechanism portion may be operated in the vicinity of the operation portion 606 of the endoscope 601 by using operation wires 736b and 736c and others arranged in the therapeutic instrument insertion channel 616 or the external channel 732 provided beside the endoscope insertion portion 602 so as to be capable of moving forward/backward, or it may be automatically operated by the guide wire identification mechanism portion as illustrated in the 40th and 43rd embodiment.

In addition, the present invention is not restricted to the foregoing embodiments, and various modifications can be of course carried out without departing from the scope of the present invention.

According to the present invention, when the end portion of the guide wire inserted into the therapeutic instrument insertion channel is led out from the end opening portion of the therapeutic instrument insertion channel, the guide wire is releasably engaged by the guide wire fixing means in the vicinity of the end portion of the insertion portion. Therefore, at the time of replacing the therapeutic instrument, the guide wire does not have to be gripped on the endoscope operation portion side. Accordingly, the therapeutic instrument can be readily replaced in a shorter time and one operator can perform replacement without impairing the conventional operation method of the therapeutic instrument or the sense of operation.

The present invention is effective in the technical field of using a combination of therapeutic instruments and the endoscope such that the operation for replacing the therapeutic instrument is carried out by using the guide wire, the field for manufacturing and using the endoscope, and the technical field of a treatment method for curing by using this endoscope system.

What is claimed is:

1. An endoscope in which a therapeutic instrument insertion channel is provided in an insertion portion inserted into a celoma and an end opening portion of said therapeutic instrument insertion channel is provided in the vicinity of an end of said insertion portion,
   wherein a guide wire for guiding an insertion operation of a therapeutic instrument is inserted into said therapeutic instrument insertion channel; and
   said insertion portion has a guide wire fixing means for releasably engaging said guide wire when said therapeutic instrument running on said guide wire is inserted/removed with an end portion of said guide wire being led out from said end opening portion of said therapeutic instrument insertion channel;
   wherein said guide wire fixing means includes a therapeutic instrument elevator base provided in the vicinity of said end opening portion of said therapeutic instrument insertion channel and a constituent member provided at a opposed position when said therapeutic instrument elevator base is raised and a slit capable of engaging only said guide wire by raising said guide wire by manipulating said therapeutic instrument elevator base is provided at a top portion of a guide plane of said therapeutic instrument elevator base.

2. The endoscope according to claim 1, wherein said slit is provided on a top face of an opening portion of said therapeutic instrument insertion channel of a distal end hard portion.

3. The endoscope according to claim 1, further comprising a wire contact plane provided on a top portion of said opening portion of said therapeutic instrument insertion channel, wherein when said elevator base is swiveled and raised and said guide wire is held/fixed between said slit and said wire contact plane, a contact portion between said wire contact plane and said guide wire on the leading end side is positioned on the base end side away from a swiveling shaft of said elevator base.

4. The endoscope according to claim 1, wherein a protrusion portion through which the outside diameter of said guide wire which has been elastically deformed passes when said elevator base is swiveled and raised is provided to an opening portion of said slit, and a space in which the outside diameter of said guide wire is held in cooperation with said protrusion portion is formed inside said slit.

5. The endoscope according to claim 4, wherein said protrusion portion is provided on the both sides of said opening portion of said slit.

6. The endoscope according to claim 4, wherein said protrusion portion is provided in an axial direction of an insertion portion of said opening portion of said slit over the entire length.

7. The endoscope according to claim 1, wherein a slit having two opposed wall surfaces is provided on the top portion of said guide plane of said therapeutic instrument elevator base, and only said guide wire is fixed when said wall surfaces are brought into contact with only the outer periphery of said guide wire.

8. The endoscope according to claim 1, wherein a width of said opening portion of said slit is larger than an outside diameter of said guide wire and smaller than an outside diameter of said therapeutic instrument externally attached to said guide wire.

9. The endoscope according to claim 1, wherein a central axis of said slit with respect to an axial direction of said insertion portion is inclined relative to a central axis of said guide plane.

10. The endoscope according to claim 1, wherein an intermediate stopper for stopping the operation of said operation member halfway at a position in a predetermined operation range from start of raising said therapeutic instrument elevator base is provided, and further comprising operating means for releasing said intermediate stopper to enable the operation in the full operation range of said therapeutic instrument elevator base.

11. The endoscope according to claim 10, wherein a plurality of said intermediate stoppers are provided.

12. The endoscope according to claim 10, wherein said operating means includes a protrusion portion provided to said operation member and an elastic member engaging with a protrusion portion.

13. The endoscope according to claim 1, wherein, when said elevator base is swiveled to be lowered, a height of a wall surface of an accommodation chamber of said therapeutic instrument elevator base opposed to said slit is higher than a bottom surface of said slit.

14. The endoscope according to claim 1, wherein said guide wire fixing means has guide wire fixing portions which are at least two movable members arranged substantially in parallel to each other and can move in the direction along which said portions move close to each other and the direction along which said portions move away from each other.

15. The endoscope according to claim 14, wherein said two guide wire fixing portions sandwich and fix said guide wire therebetween when said guide wire fixing portions move close to each other.

16. An endoscope in which a therapeutic instrument insertion channel is provided in an insertion portion inserted into a celoma and an end opening portion of said therapeutic instrument insertion channel is provided in the vicinity of an end of said insertion portion,
   wherein a guide wire for guiding an insertion operation of a therapeutic instrument is inserted into said therapeutic instrument insertion channel; and
   said insertion portion has a guide wire fixing means for releasably engaging said guide wire when said therapeutic instrument running on said guide wire is inserted/removed with an end portion of said guide wire being led out from said end opening portion of said therapeutic instrument insertion channel;
   wherein said guide wire fixing means includes a therapeutic instrument elevator base provided in the vicinity of said end opening portion of said therapeutic instrument insertion channel and a constituent member provided at a opposed position when said therapeutic instrument elevator base is raised;
   wherein a wire contact plane provided at the upper portion of an opening portion of said therapeutic instrument insertion channel is included, a contact portion of said therapeutic instrument elevator base and said guide wire on the leading end side is positioned on the base end side away from a swiveling axis of said elevator base when said elevator base is swiveled and raised and said guide wire is held/fixed between said elevator base and said wire contact plane.

17. An endoscope in which a therapeutic instrument insertion channel is provided in an insertion portion inserted into a celoma and an end opening portion of said therapeutic instrument insertion channel is provided in the vicinity of an end of said insertion portion,
   wherein a guide wire for guiding an insertion operation of a therapeutic instrument is inserted into said therapeutic instrument insertion channel; and
   said insertion portion has a guide wire fixing means for releasably engaging said guide wire when said therapeutic instrument running on said guide wire is inserted/removed with an end portion of said guide wire being led out from said end opening portion of said therapeutic instrument insertion channel;
   wherein said guide wire fixing means includes a therapeutic instrument elevator base provided in the vicinity of said end opening portion of said therapeutic instrument insertion channel and a constituent member provided at a opposed position when said therapeutic instrument elevator base is raised;
   wherein an intermediate stopper for stopping the operation of said operation member halfway at a position in a predetermined operation range from start of raising said therapeutic instrument elevator base is provided, and said endoscope further comprises operating means for releasing said intermediate stopper to enable the operation in the full operation range of said therapeutic instrument elevator base.

18. The endoscope according to claim 17, wherein a plurality of said intermediate stoppers are provided.

19. The endoscope according to claim 17, wherein said operating means includes a protrusion portion provided to an operating member and an elastic member engaging with said protrusion portion.

20. An endoscope in which a therapeutic instrument insertion channel is provided in an insertion portion inserted into a celoma and an end opening portion of said therapeutic instrument insertion channel is provided in the vicinity of an end of said insertion portion,
   wherein a guide wire for guiding an insertion operation of a therapeutic instrument is inserted into said therapeutic instrument insertion channel; and
   said insertion portion has a guide wire fixing means for releasably engaging said guide wire when said therapeutic instrument running on said guide wire is inserted/removed with an end portion of said guide wire being led out from said end opening portion of said therapeutic instrument insertion channel;
   wherein said guide wire fixing means includes a therapeutic instrument elevator base provided in the vicinity of said end opening portion of said therapeutic instrument insertion channel and a constituent member provided at a opposed position when said therapeutic instrument elevator base is raised;
   wherein an operation portion is connected to a front side end portion of the insertion portion inserted into a celoma, the end opening portion of the therapeutic instrument insertion channel provided in said insertion portion is arranged at a distal end portion of said insertion portion, the elevator base for swiveling around a swiveling shaft provided at a lower portion of said endoscope on the distal end side to raised/lowered said therapeutic instrument, an operation lever capable of operating said elevator base, and a towing member having one end fixed to said elevator base and the other end fixed to a rotator integrally swiveling coaxially with said operation lever are provided; and
   wherein a swivel deterrent body which is provided oppositely to said rotator and suppresses swiveling of said rotator and a deterrence reinforcement mechanism for increasing the deterrence by the deterrent body when said rotator rotates by the predetermined amount are provided between said rotator and said deterrent body.

21. An endoscope in which a therapeutic instrument insertion channel is provided in an insertion portion inserted into a celoma and an end opening portion of said therapeutic instrument insertion channel is provided in the vicinity of an end of said insertion portion,
   wherein a guide wire for guiding an insertion operation of a therapeutic instrument is inserted into said therapeutic instrument insertion channel; and
   said insertion portion has a guide wire fixing means for releasably engaging said guide wire when said therapeutic instrument running on said guide wire is inserted/removed with an end portion of said guide wire being led out from said end opening portion of said therapeutic instrument insertion channel;
   wherein said guide wire fixing means includes a therapeutic instrument elevator base provided in the vicinity of said end opening portion of said therapeutic instrument insertion channel and a constituent member provided at a opposed position when said therapeutic instrument elevator base is raised;

wherein said constituent member is formed by a high friction resistance portion.

22. The endoscope according to claim 21, wherein said friction resistance portion is formed by embedding, rubber or an elastic member.

23. The endoscope according to claim 21, wherein said friction resistance portion is formed by embedding a magnet.

24. The endoscope according to claim 21, wherein a detachable distal end cover in said endoscope is formed by an elastic member, and said friction resistance portion is formed by extending said elastic member to a position at which said distal end cover is opposed to said therapeutic instrument elevator base.

25. An endoscope in which a therapeutic instrument insertion channel is provided in an insertion portion inserted into a celoma and an end opening portion of said therapeutic instrument insertion channel is provided in the vicinity of an end of said insertion portion, wherein a guide wire for guiding an insertion operation of a therapeutic instrument is inserted into said therapeutic instrument insertion channel; and said insertion portion has a guide wire fixing means for releasably engaging said guide wire when said therapeutic instrument running on said guide wire is inserted/removed with an end portion of said guide wire being led out from said end opening portion of said therapeutic instrument insertion channel;

wherein said guide wire fixing means includes a therapeutic instrument elevator base provided in the vicinity of said end opening portion of said therapeutic instrument insertion channel and a constituent member provided at a opposed position when said therapeutic instrument elevator base is raised;

wherein a guide wire engagement groove in which said guide wire is fitted in is provided on a side wall of an accommodation chamber of said therapeutic instrument elevator base.

26. The endoscope according to claim 25, wherein a width of said guide wire engagement groove is such that said guide wire can be elastically deformed and held in said guide wire engagement groove by pressing said guide wire between a side surface of said therapeutic instrument elevator base and said guide wire engagement groove.

27. The endoscope according to claim 25, wherein a guide wall for leading said guide wire to said guide wire engagement groove when said therapeutic instrument elevator base is raised is provided on a guide plane of said therapeutic instrument elevator base.

28. The endoscope according to claim 25, wherein said guide wire engagement groove is provided at a position where said guide wire is fixed so as to be inclined in the direction along which an object optical system is arranged.

29. An endoscope in which a therapeutic instrument insertion channel is provided in an insertion portion inserted into a celoma and an end opening portion of said therapeutic instrument insertion channel is provided in the vicinity of an end of said insertion portion, wherein a guide wire for guiding an insertion operation of a therapeutic instrument is inserted into said therapeutic instrument insertion channel; and said insertion portion has a guide wire fixing means for releasably engaging said guide wire when said therapeutic instrument running on said guide wire is inserted/removed with an end portion of said guide wire being led out from said end opening portion of said therapeutic instrument insertion channel;

wherein said guide wire fixing means includes a therapeutic instrument elevator base provided in the vicinity of said end opening portion of said therapeutic instrument insertion channel and a constituent member provided at a opposed position when said therapeutic instrument elevator base is raised;

the endoscope further comprising:

a first impetus giving member fixed on a proximal operation portion side of said therapeutic instrument channel opening portion at the distal end of said endoscope;

a second impetus giving member which is arranged beside said first impetus giving member and can move substantially vertically to an axis of said insertion portion of said endoscope;

a roller for thrusting said second impetus giving member to said first impetus giving member side;

guide wire fixing means constituted by an elastic member arranged between said first impetus giving member and said second impetus giving member; and operating means for towing said roller.

30. An endoscope in which a therapeutic instrument insertion channel is provided in an insertion portion inserted into a celoma and an end opening portion of said therapeutic instrument insertion channel is provided in the vicinity of an end of said insertion portion, wherein a guide wire for guiding an insertion operation of a therapeutic instrument is inserted into said therapeutic instrument insertion channel; and said insertion portion has a guide wire fixing means for releasably engaging said guide wire when said therapeutic instrument running on said guide wire is inserted/removed with an end portion of said guide wire being led out from said end opening portion of said therapeutic instrument insertion channel;

wherein said guide wire fixing means is constituted detachably with respect to said insertion portion.

31. The endoscope according to claim 30, wherein said guide wire fixing means is constituted detachably with respect to the distal end of said insertion portion.

32. The endoscope according to claim 30, further comprising an attachment mechanism for attaching said guide wire fixing means to said insertion portion.

33. The endoscope according to claim 32, wherein said attachment mechanism consists of soft resin such as chloroethene or rubber.

34. The endoscope according to claim 32, wherein said attachment mechanism has a positioning member consisting of a convex portion which is fitted in said opening of said therapeutic instrument insertion channel.

35. The endoscope according to claim 32, wherein said attachment mechanism has a length extending from at least the distal end of said insertion portion to said guide wire fixing means for covering a protrusion portion provided to said guide wire fixing means, and has a mucous protection portion from which corners are eliminated as a whole.

36. The endoscope according to claim 32, wherein said attachment mechanism includes: an attachment portion formed into a substantially cylindrical shape; a wall thickness varying portion formed so as to be wall-thick toward one end in the axial direction in said attachment portion; at least one slit which is provided to said wall thickness varying portion and has an opening on said one end side; and a ring member capable of moving on at least an outer peripheral portion of said wall thickness varying portion in the axial direction in said attachment portion, said wall thickness varying portion being fitted to the distal end of said insertion portion in said endoscope.

37. The endoscope according to claim 30, further comprising a guide wire fixing member insertion channel having at the end thereof a first opening portion which is opened at the distal end of said therapeutic instrument insertion channel and a second opening portion which is opened in the vicinity of said first opening portion, wherein said guide wire fixing means for holding/fixing said guide wire extended from said first opening portion is extended from said second opening portion in order to guide said therapeutic instrument to said therapeutic target part.

38. The endoscope according to claim 37, wherein a distal end portion of said guide wire fixing means has a snare shape.

39. The endoscope according to claim 37, wherein a distal end portion of said guide wire fixing means has a hook shape consisting of a soft member.

40. An endoscope in which a therapeutic instrument insertion channel is provided in an insertion portion inserted into a celoma and an end opening portion of said therapeutic instrument insertion channel is provided in the vicinity of an end of said insertion portion, wherein a guide wire for guiding an insertion operation of a therapeutic instrument is inserted into said therapeutic instrument insertion channel; and said insertion portion has a guide wire fixing means for releasably engaging said guide wire when said therapeutic instrument running on said guide wire is inserted/removed with an end portion of said guide wire being led out from said end opening portion of said therapeutic instrument insertion channel;

wherein said guide wire fixing means is arranged so as to cut across an opening of said therapeutic instrument insertion channel in the vicinity of said opening, attached in the longitudinal direction of said insertion portion so as to be capable of moving in the direction along which it moves close to said therapeutic instrument elevator base provided at said distal end portion of said endoscope and the direction along which it moves away from the same, and has on its plane opposed to said therapeutic instrument elevator base a guide wire fixing portion having a part with which said guide wire is brought into contact.

41. An endoscope in which a therapeutic instrument insertion channel is provided in an insertion portion inserted into a celoma and an end opening portion of said therapeutic instrument insertion channel is provided in the vicinity of an end of said insertion portion, wherein a guide wire for guiding an insertion operation of a therapeutic instrument is inserted into said therapeutic instrument insertion channel; and said insertion portion has a guide wire fixing means for releasably engaging said guide wire when said therapeutic instrument running on said guide wire is inserted/removed with an end portion of said guide wire being led out from said end opening portion of said therapeutic instrument insertion channel;

wherein said guide wire fixing means consists of at least one loop-like member, and a loop diameter of said loop-like member can be enlarged and decreased.

42. An endoscope in which a therapeutic instrument insertion channel is provided in an insertion portion inserted into a celoma and an end opening portion of said therapeutic instrument insertion channel is provided in the vicinity of an end of said insertion portion, wherein a guide wire for guiding an insertion operation of a therapeutic instrument is inserted into said therapeutic instrument insertion channel; and said insertion portion has a guide wire fixing means for releasably engaging said guide wire when said therapeutic instrument running on said guide wire is inserted/removed with an end portion of said guide wire being led out from said end opening portion of said therapeutic instrument insertion channel;

wherein said guide wire fixing means has a groove whose width is smaller than the outside diameter of said guide wire in some measure on its plane opposed to said therapeutic instrument elevator base arranged at the distal end of said insertion portion.

43. An endoscope in which a therapeutic instrument insertion channel is provided in an insertion portion inserted into a celoma and an end opening portion of said therapeutic instrument insertion channel is provided in the vicinity of an end of said insertion portion, wherein a guide wire for guiding an insertion operation of a therapeutic instrument is inserted into said therapeutic instrument insertion channel; and said insertion portion has a guide wire fixing means for releasably engaging said guide wire when said therapeutic instrument running on said guide wire is inserted/removed with an end portion of said guide wire being led out from said end opening portion of said therapeutic instrument insertion channel;

wherein said guide wire fixing means has a guide wire fixing portion having irregularities formed thereto on its plane with which said guide wire is brought into contact.

44. The endoscope according to claim 43, wherein said guide wire fixing portion consists of a pair of guide wire fixing members sandwiching said guide wire therebetween.

45. The endoscope according to claim 44, wherein, in said irregularities, convex portions in one guide wire fixing member are fitted in concave portions in the other guide wire fixing member.

46. The endoscope according to claim 43, wherein said irregularities consist of steps which are substantially orthogonal to said guide wire.

47. An endoscope in which a therapeutic instrument insertion channel is provided in an insertion portion inserted into a celoma and an end opening portion of said therapeutic instrument insertion channel is provided in the vicinity of an end of said insertion portion, wherein a guide wire for guiding an insertion operation of a therapeutic instrument is inserted into said therapeutic instrument insertion channel; and said insertion portion has a guide wire fixing means for releasably engaging said guide wire when said therapeutic instrument running on said guide wire is inserted/removed with an end portion of said guide wire being led out from said end opening portion of said therapeutic instrument insertion channel;

wherein a material which consists of an elastic member such as rubber and has the large friction resistance is arranged on a plane of said guide wire fixing means with which said guide wire is brought into contact.

48. An endoscope in which a therapeutic instrument insertion channel is provided in an insertion portion inserted into a celoma and an end opening portion of said therapeutic instrument insertion channel is provided in the vicinity of an end of said insertion portion,
- wherein a guide wire for guiding an insertion operation of a therapeutic instrument is inserted into said therapeutic instrument insertion channel; and
- said insertion portion has a guide wire fixing means for releasably engaging said guide wire when said therapeutic instrument running on said guide wire is inserted/removed with an end portion of said guide wire being led out from said end opening portion of said therapeutic instrument insertion channel;
- wherein said guide wire fixing means is arranged in a transparent substantially-cylindrical member having a therapeutic instrument insertion opening portion through which said therapeutic instrument projecting from the opening of said therapeutic instrument insertion channel can pass.

49. An endoscope in which a therapeutic instrument insertion channel is provided in an insertion portion inserted into a celoma and an end opening portion of said therapeutic instrument insertion channel is provided in the vicinity of an end of said insertion portion,
- wherein a guide wire for guiding an insertion operation of a therapeutic instrument is inserted into said therapeutic instrument insertion channel; and
- said insertion portion has a guide wire fixing means for releasably engaging said guide wire when said therapeutic instrument running on said guide wire is inserted/removed with an end portion of said guide wire being led out from said end opening portion of said therapeutic instrument insertion channel;
- wherein said guide wire fixing means has a guide wire identification mechanism for identifying said guide wire and said therapeutic instrument other than said guide wire.

50. The endoscope according to claim 49, wherein said guide wire identification mechanism has a protrusion portion having at least a part which protrudes on the opening of said therapeutic instrument insertion channel so as to be capable of moving forward and backward.

51. The endoscope according to claim 50, wherein said guide wire identification mechanism has a protrusion portion which protrudes on the opening of said therapeutic instrument insertion channel from the base end side in the longitudinal direction of said insertion portion so as to be capable of moving forward and backward, and said protrusion portion has a gap whose width is larger than the diameter of said guide wire on a side opposed to said guide wire.

52. The endoscope according to claim 49, further comprising a guide wire fixing member or a guide wire identification member which can move with respect to said guide wire fixing means and to which impetus is given at a first position where said guide wire is fixed by an elastic member or a second position where said therapeutic instrument other than said guide wire can be inserted.

53. The endoscope according to claim 52, wherein said guide wire fixing means has a click mechanism which can engage at least one of said guide wire fixing member or said guide wire identification member at said first position or said second position.

54. The endoscope according to claim 53, wherein said click mechanism consists of a click pin and a click groove for guiding said click pin.

55. The endoscope according to claim 54, wherein said click groove has a step for preventing reverse rotation of said click pin.

56. The endoscope according to claim 55, wherein said click pin is rotatably attached to a moving member consisting of at least either said guide wire fixing member or said guide wire identification member, and there are provided a hole in which said click pin is fitted when said moving member reaches the vicinity of the opposite side to that where impetus is given and a step for preventing reverse rotation at a turnback point in said click groove in such a manner that an outward route and an inward route of said click pin are different from each other when said moving member reciprocates between said first position and said second position.

57. The endoscope according to claim 54, wherein said click pin is rotatably attached to a moving member consisting of at least either said guide wire fixing member and said guide wire identification member, said endoscope includes one convex portion provided on the side where impetus is given to said guide wire fixing portion, a first convex portion and a second convex portion provided on the opposite side to the side where impetus is given and a concave portion provided between said two convex portions, and steps for preventing reverse rotation are provided at all turnback points in such a manner that an outward route and an inward route of said click pin are different from each other when said guide wire fixing portion reciprocates between said first position and said second position.

58. The endoscope according to claim 49, wherein said guide wire fixing means interlocks with said guide wire identification mechanism.

59. The endoscope according to claim 58, wherein said guide wire fixing means has a part which is caught by said guide wire identification mechanism portion.

60. An endoscope comprising:
- an insertion portion inserted into a celoma;
- an operation portion connected to a proximal end portion of said insertion portion; and
- a therapeutic instrument elevator base which is arranged at the distal end portion of said insertion portion and can be operated by said operation portion,
- wherein a slit which can engage only a guide wire by raising said guide wire by operating said therapeutic instrument elevator base is provided at a top portion on a guide plane of said therapeutic instrument elevator base.

61. The endoscope according to claim 60, wherein a slit having two opposed wall surfaces is provided on the top portion of said guide plane of said therapeutic instrument elevator base, and only said guide wire is fixed when said wall surfaces are brought into contact with only the outer periphery of said guide wire.

62. The endoscope according to claim 60, wherein a width of an opening portion of said slit is larger than the outside diameter of said guide wire and smaller than the outside diameter of a therapeutic instrument externally attached to said guide wire.

63. The endoscope according to claim 60, wherein said slit is provided on the top face of a therapeutic instrument insertion channel opening portion of an end hard portion in said endoscope.

64. The endoscope according to claim 60, wherein a wire contact plane is provided on the top portion of the opening portion of said therapeutic instrument insertion channel provided at the distal end of said endoscope a contact portion of said slit and said guide wire on the leading end side is positioned on the base end side away from a swiveling shaft of said elevator base when said elevator base is swiveled and raised and said guide wire is held/fixed between said slit and said wire contact plane.

65. The endoscope according to claim 60, further comprising an object optical system at the distal end portion of said endoscope wherein said object optical system is set in such a manner that a part of said therapeutic instrument elevator base exists in an observation visual field when said guide wire is fixed and a part of said guide wire which is fixed and enters said observation visual field is focused.

66. The endoscope according to claim 60, wherein a protrusion portion through which the outside diameter of said guide wire passes after being elastically deformed when said elevator base is swiveled and raised is provided at the opening portion of said slit, and a space in which the outside diameter of said guide wire is held in cooperation with said protrusion portion is formed inside said slit.

67. The endoscope according to claim 66, wherein said protrusion portion is provided on both sides of the opening portion of said slit.

68. The endoscope according to claim 66, wherein said protrusion portion is provided in the axial direction of said insertion portion of said opening portion of said slit over the entire length.

69. The endoscope according to claim 60, wherein an intermediate stopper for stopping the operation of said operation member of said therapeutic instrument elevator base halfway at a position in a predetermined operation range from start of raising said therapeutic instrument elevator base is provided, and said endoscope further includes operating means which can release said intermediate stopper and enables operation in the full operation range of said operation member.

70. The endoscope according to claim 69, wherein a plurality of said intermediate stopper are provided.

71. The endoscope according to claim 69, wherein said operating means consists of a protrusion portion provided to said operation member and an elastic member engaging with said protrusion portion.

72. The endoscope according to claim 60, wherein, when said elevator base is swiveled and lowered, a height of a wall surface of an accommodation chamber of said therapeutic instrument elevator base opposed to said slit is higher than a bottom surface of said slit.

73. The endoscope according to claim 60, wherein said therapeutic instrument elevator base has a guide plane which is opposed to the opening portion of said therapeutic instrument insertion channel and guides said therapeutic instrument, another plane facing the distal end of said endoscope and a connection plane for smoothly connecting said guide plane with another plane, and said slit is provided on said connection plane or from said connection plane to another plane.

74. The endoscope according to claim 60, wherein a central axis relative to an axial direction of the insertion portion of said slit is inclined with respect to a central axis of said guide plane.

75. An endoscope system comprising:
an endoscope in which a therapeutic instrument insertion channel is provided in an insertion portion inserted into a celoma, an opening portion at the distal end of said therapeutic instrument insertion channel is provided in the vicinity of the distal end of said insertion portion and a therapeutic instrument insertion opening as an opening portion of said therapeutic instrument insertion channel is provided on the proximal side of an operation portion;
a guide wire which can pass through said therapeutic instrument insertion channel; and
a therapeutic instrument which has a pipe through which said guide wire can pass and which can be inserted into said therapeutic instrument insertion channel,
wherein said therapeutic instrument has a protrusion length from said distal end opening portion which is required for treatment and a protrusion length from said therapeutic instrument insertion opening which is required for operation on the proximal side with said therapeutic instrument being inserted into said therapeutic instrument insertion channel, guide wire fixing means for releasably engaging said guide wire when inserting/removing said therapeutic instrument running on said guide wire with the distal end portion of said guide wire inserted through said therapeutic instrument insertion channel being led out from said distal end opening portion is provided in the vicinity of the distal end portion of said insertion portion, and said guide wire has a length projecting from the proximal end portion of said therapeutic instrument with the end portion of said therapeutic instrument being drawn to the front side of said operation portion from said engagement position and engaged by said guide wire fixing means;
wherein a slit which can engage only said guide wire by raising said guide wire by operating a therapeutic instrument elevator base provided in the vicinity of the end opening portion of said therapeutic instrument insertion channel is provided on a top portion on a guide plane of said therapeutic instrument elevator base.

76. The endoscope system according to claim 75, further comprising a protrusion portion provided on an upper portion of the opening portion of said therapeutic instrument insertion channel, wherein a contact portion of said protrusion portion and said guide wire on the leading end side is positioned on the base end side away from a swiveling shaft of said elevator base when said elevator base is swiveled and raised and said guide wire is held/fixed between said slit and said protrusion portion.

77. The endoscope system according to claim 75, wherein an intermediate stopper for stopping the operation of said operation member halfway at a position in a predetermined operation range from start of raising said therapeutic instrument elevator base is provided, and said endoscope system further includes operating means which releases said intermediate stopper and can operate in the full operation range of said operation member.

78. The endoscope system according to claim 77, wherein said operating means consists of a protrusion portion provided to said operation member and an elastic member which engages with said protrusion portion.

79. The endoscope system according to claim 75, wherein said slit has two opposed wall surfaces and said wall surfaces are set so as to engage only the outer peripheral surface of said guide wire.

80. The endoscope system according to claim 75, wherein a width of said slit is set larger than the outside diameter of said guide wire and smaller than the outside diameter of a therapeutic instrument externally attached to said guide wire.

81. The endoscope system according to claim 75, wherein a central axis of said slit relative to the direction of a central axis of said insertion portion is inclined with respect to a central axis of said guide plane.

82. An endoscope system comprising:
an endoscope in which a therapeutic instrument insertion channel is provided in an insertion portion inserted into a celoma, an opening portion at the distal end of said therapeutic instrument insertion channel is provided in the vicinity of the distal end of said insertion portion and a therapeutic instrument insertion opening as an opening portion of said therapeutic instrument insertion channel is provided on the proximal side of an operation portion;
a guide wire which can pass through said therapeutic instrument insertion channel; and
a therapeutic instrument which has a pipe through which said guide wire can pass and which can be inserted into said therapeutic instrument insertion channel,
wherein said therapeutic instrument has a protrusion length from said distal end opening portion which is required for treatment and a protrusion length from said therapeutic instrument insertion opening which is required for operation on the proximal side with said therapeutic instrument being inserted into said therapeutic instrument insertion channel, guide wire fixing means for releasably engaging said guide wire when inserting/removing said therapeutic instrument running on said guide wire with the distal end portion of said guide wire inserted through said therapeutic instrument insertion channel being led out from said distal end opening portion is provided in the vicinity of the distal end portion of said insertion portion, and said guide wire has a length projecting from the proximal end portion of said therapeutic instrument with the end portion of said therapeutic instrument being drawn to the front side of said operation portion from said engagement position and engaged by said guide wire fixing means;
wherein an entire length of said guide wire is set to be not more than twofold of an entire length of said therapeutic instrument.

83. An endoscope system comprising:
an endoscope in which a therapeutic instrument insertion channel is provided in an insertion portion inserted into a celoma, an opening portion at the distal end of said therapeutic instrument insertion channel is provided in the vicinity of the distal end of said insertion portion and a therapeutic instrument insertion opening as an opening portion of said therapeutic instrument insertion channel is provided on the proximal side of an operation portion;
a guide wire which can pass through said therapeutic instrument insertion channel; and
a therapeutic instrument which has a pipe through which said guide wire can pass and which can be inserted into said therapeutic instrument insertion channel,
wherein said therapeutic instrument has a protrusion length from said distal end opening portion which is required for treatment and a protrusion length from said therapeutic instrument insertion opening which is required for operation on the proximal side with said therapeutic instrument being inserted into said therapeutic instrument insertion channel, guide wire fixing means for releasably engaging said guide wire when inserting/removing said therapeutic instrument running on said guide wire with the distal end portion of said guide wire inserted through said therapeutic instrument insertion channel being led out from said distal end opening portion is provided in the vicinity of the distal end portion of said insertion portion, and said guide wire has a length projecting from the proximal end portion of said therapeutic instrument with the end portion of said therapeutic instrument being drawn to the front side of said operation portion from said engagement position and engaged by said guide wire fixing means;
wherein the entire length of said guide wire is set in such a manner that said guide wire can protrude from the opening portion of said therapeutic instrument insertion channel and protrude from the front end portion of said therapeutic instrument with the distal end portion of said therapeutic instrument being pulled to said operation side on the proximal side from said engagement position and said guide wire being fixed to said guide wire fixing means.

84. An endoscope system comprising:
an endoscope in which a therapeutic instrument insertion channel is provided in an insertion portion inserted into a celoma, an opening portion at the distal end of said therapeutic instrument insertion channel is provided in the vicinity of the distal end of said insertion portion and a therapeutic instrument insertion opening as an opening portion of said therapeutic instrument insertion channel is provided on the proximal side of an operation portion;
a guide wire which can pass through said therapeutic instrument insertion channel; and
a therapeutic instrument which has a pipe through which said guide wire can pass and which can be inserted into said therapeutic instrument insertion channel,
wherein said therapeutic instrument has a protrusion length from said distal end opening portion which is required for treatment and a protrusion length from said therapeutic instrument insertion opening which is required for operation on the proximal side with said therapeutic instrument being inserted into said therapeutic instrument insertion channel, guide wire fixing means for releasably engaging said guide wire when inserting/removing said therapeutic instrument running on said guide wire with the distal end portion of said guide wire inserted through said therapeutic instrument insertion channel being led out from said distal end opening portion is provided in the vicinity of the distal end portion of said insertion portion, and said guide wire has a length projecting from the proximal end portion of said therapeutic instrument with the end portion of said therapeutic instrument being drawn to the front side of said operation portion from said engagement position and engaged by said guide wire fixing means;
wherein a protrusion length of said therapeutic instrument from said therapeutic instrument insertion opening is set to 30 to 60 cm in the state where the end portion of said therapeutic instrument is pulled to said operation portion side on the front side from said engagement position and said guide wire is engaged by said guide wire fixing means, and a length of said guide wire protruding from the proximal side of said therapeutic instrument in the same state is set to not more than 20 cm.

85. An endoscope comprising:
an elongated insertion portion;
a therapeutic instrument insertion channel provided in the insertion portion;
a therapeutic instrument elevator base for controlling directions of leading portions of a therapeutic instrument and a guide wire inserted in the therapeutic insertion channel, the leading portions of the therapeutic instrument and the guide wire being out from an opening of the therapeutic insertion channel at a distal end of the insertion portion; and a guide wire fixing mechanism that restricts relative movement of the guide wire with respect to the insertion portion in a longitudinal direction of the insertion portion, at a portion close to the opening of the therapeutic insertion channel.

86. The endoscope according to claim 85, which is applied to surgery on a pancreatic/hepatic duct.

87. The endoscope according to claim 85, wherein the guide wire fixing mechanism includes a portion by which the guide wire is to be releasably held.

88. The endoscope according to claim 87, wherein the guide wire fixing mechanism includes a slit which is formed in a guide surface of the therapeutic instrument elevator base in an axial direction of the insertion portion in such a manner as to enable the guide wire to be held by the slit.

89. The endoscope according to claim 88, wherein the guide wire fixing mechanism restricts the movement of the guide wire by holding the guide wire with the slit.

90. The endoscope according to claim 89, wherein the slit is provided with a V-shaped cross section.

91. The endoscope according to claim 89, wherein the slit has a center line provided at a position different from a center of the guide surface of the therapeutic instrument elevator base which is determined with respect to the axial direction of the insertion portion.

92. The endoscope according to claim 89, wherein the slit has a center line provided at a position deviating from a center of the guide surface of the therapeutic instrument elevator base which is determined with respect to the axial direction of the insertion point.

93. The endoscope according to claim 89, wherein an inner surface of the slit has a higher frictional resistance than other portion of the guide surface of the therapeutic instrument elevator base.

94. The endoscope according to claim 89, wherein the slit is formed such that an end portion of the slit, which is proximal to the opening of the therapeutic instrument channel, contacts the guide wire, with the movement of the guide wire restricted.

95. The endoscope according to claim 89, wherein the slit has a size which is smaller than an outside diameter of the therapeutic instrument, and is greater than an outside diameter of the guide wire.

96. The endoscope according to claim 85, wherein the guide wire fixing mechanism includes an elastic member which is located on a portion of a distal end structural member located in the distal end of the insertion portion, which contacts the guide wire, when the movement of the guide wire is restricted.

97. The endoscope according to claim 85, wherein an optical system is arranged at a position at which a part of the guide wire is shown in an observation image, when the relative movement of the guide wire is restricted.

98. The endoscope according to claim 97, wherein at least a part of the guide wire fixing mechanism is provided at the therapeutic instrument elevator base, and the movement of the guide wire is restricted by the guide wire fixing mechanism when the therapeutic instrument elevator base is raised.

99. An endoscope comprising:
an elongated insertion portion;
a therapeutic instrument insertion channel provided in the insertion portion,
a therapeutic instrument elevator base for controlling directions of leading portions of a therapeutic instrument and a guide wire inserted in the therapeutic insertion channel, the leading portions of the therapeutic instrument and the guide wire being out from an opening of the therapeutic insertion channel at a distal end of the insertion portion;
a guide wire fixing mechanism that restricts relative movement of the guide wire with respect to the insertion portion in a longitudinal direction of the insertion portion, at a portion close to the opening of the therapeutic insertion channel; and
a brake mechanism for maintaining the movement of the guide wire restricted.

100. The endoscope according to claim 99, wherein at least a part of the guide wire fixing mechanism is provided at the therapeutic instrument elevator base, the movement of the guide wire is restricted by the guide wire fixing mechanism when the therapeutic instrument elevator base is raised, and the brake mechanism keeps the movement of the guide wire restricted by maintaining a position of an elevator base operation member for operating the therapeutic instrument elevator base.

101. The endoscope according to claim 100, wherein an object optical system is arranged at a position at which a part of the guide wire is shown in an observation image, when the relative movement of the guide wire is restricted.

102. An endoscope comprising:
an elongated insertion portion;
a therapeutic instrument insertion channel provided in the insertion portion,
a therapeutic instrument elevator base for controlling directions of leading portions of a therapeutic instrument and a guide wire inserted in the therapeutic insertion channel, the leading portions of the therapeutic instrument and the guide wire being out from an opening of the therapeutic insertion channel at a distal end of the insertion portion; and
a guide wire fixing mechanism that restricts relative movement of the guide wire with respect to the insertion portion in a longitudinal direction of the insertion portion, at a portion close to the opening of the therapeutic insertion channel, at least a portion of the guide wiring fixing mechanism being provided at the therapeutic instrument elevator base,
wherein the therapeutic instrument elevator base has a first range in which the directions of the leading portions of the therapeutic instrument and the guide wire are controlled, and a second range in which the relative movement of the guide wire is restricted.

103. The endoscope according to claim 102, wherein an object optical system is arranged at a position at which a part of the guide wire is shown in an observation image, when the relative movement of the guide wire is restricted.

104. The endoscope according to claim 103, wherein said guide wire fixing means is arranged in the vicinity of said therapeutic instrument elevator base provided at a distal end of said insertion portion.

105. The endoscope according to claim 104, further comprising operation transmitting means includes an operation lever provided to said operation portion and an operation wire having one end connected to said operation lever and the other end connected to said guide wire fixing means.

106. The endoscope according to claim 105, wherein a rotating shaft of said operation lever is provided at a position different from the rotating shaft of elevator base raised lever.

107. The endoscope according to claim 106, wherein said rotating shaft of said operating lever is provided at a position which is substantially orthogonal to said rotating shaft of said therapeutic instrument elevator base raised lever.

108. The endoscope according to claim 106, wherein said rotating shaft of said therapeutic instrument elevator base raised lever is provided on an axis which is substantially orthogonal to a central axis of said insertion portion, and said rotating shaft of said operation lever is provided on an axis which is substantially parallel to said central axis of said insertion portion.

109. The endoscope according to claim 106, wherein a therapeutic instrument insertion opening for leading said therapeutic instrument to said therapeutic instrument insertion channel is provided to a grip for holding said operation portion, and said operation lever is provided at an end portion of said grip on said insertion portion side.

110. The endoscope according to claim 106, wherein said therapeutic instrument set-up lever is provided on the front side away from said grip and said operation lever is provided on said insertion portion side away from said grip.

111. The endoscope according to claim 104, wherein said guide wire fixing means has a snare shape.

112. The endoscope according to claim 111, wherein a fixing member which can temporarily fix said guide wire fixing means is provided to said endoscope in the vicinity of said opening portion side of said therapeutic instrument insertion channel.

113. The endoscope according to claim 104, wherein said guide wire fixing means has a hook-like shape.

114. The endoscope according to claim 113, further comprising:
 a fixing portion for fixing said guide wire;
 a guide wire fixing member consisting of an arm portion provided on the base end side of said fixing portion and a support shaft for swiveling and supporting said arm portion so as to be orthogonal to said arm portion;
 a swivel mechanism for swiveling said support shaft of said guide wire fixing member; and
 a tow wire which is inserted into said insertion portion of said endoscope in order to remotely operate said swivel mechanism,
 wherein said fixing member is brought into contact with an outside diameter portion of said guide wire and held and fixed between said outside diameter portion and a main body portion of said insertion portion at the end thereof by swiveling said arm portion.

115. The endoscope according to claim 114, wherein at least said support shaft and said swivel mechanism are water-tightly arranged inside said distal end hard portion of said endoscope.

116. The endoscope according to claim 104, wherein a guide wire fixing elevator base capable of moving to an engagement position where said guide wire which is inserted into said therapeutic instrument insertion channel and guides said therapeutic instrument is releasably engaged and an engagement releasing position where engagement of said guide wire is released is provided at said end portion of said insertion portion as said guide wire fixing means.

117. The endoscope according to claim 116, wherein operating means for operating engagement or release of said guide wire by said guide wire fixing elevator base is provided to said operation portion of said endoscope.

118. The endoscope according to claim 116, wherein said guide wire is held and fixed by a wall surface portion of a therapeutic instrument insertion path arranged at the distal end of said endoscope and said guide wire fixing elevator base.

119. The endoscope according to claim 116, wherein said guide wire fixing elevator base is provided on said therapeutic instrument elevator base for raising said therapeutic instrument in the direction of a visual field.

120. The endoscope according to claim 116, wherein an opening portion is provided on a guide plane of said therapeutic instrument elevator base on which said therapeutic instrument is arranged, and said guide wire fixing elevator base is provided at said opening portion.

121. The endoscope according to claim 116, wherein said guide wire fixing elevator base is provided in such a manner that a guide plane of said guide wire fixing elevator base is smoothly connected to that of said therapeutic instrument elevator base when said guide wire fixing elevator base is lowered.

122. The endoscope according to claim 116, wherein a raised angle of said guide wire fixing elevator base exceeds that of said therapeutic instrument elevator base.

123. The endoscope according to claim 116, wherein an elastic member is provided at a guide wire contact position provided when said guide wire is fixed by said guide wire fixing elevator base.

124. The endoscope according to claim 116, wherein a protrusion is provided at a guide wire contact position of said elevator base provided when said guide wire is fixed by said guide wire fixing elevator base.

125. The endoscope according to claim 104, further comprising:
 a biasing member capable of moving in the direction which is substantially vertical to said therapeutic instrument insertion path at said distal end portion of said endoscope;
 guide wire fixing means constituted by a spring material assisting movement of said biasing member; and
 operation transmitting means enabling operation of fixation and release of said guide wire by said guide wire fixing means.

126. The endoscope according to claim 125, wherein said guide wire fixing means is constituted by providing a torque transmission member between said biasing member and said operation transmitting means.

127. The endoscope according to claim 104, wherein said guide wire fixing means is constituted by fixing an end portion of a fixing operation wire projecting from a guide pipe provided to said endoscope in the vicinity of said opening portion of said therapeutic instrument insertion channel on the end side.

128. The endoscope according to claim 127, wherein an end portion of said guide wire fixing means is fixed so as to be capable of swiveling.

129. The endoscope according to claim 103, wherein said guide wire fixing means is included in the vicinity of the distal end of said insertion portion.

130. The endoscope according to claim 103, wherein said guide wire fixing means is arranged in the vicinity of said opening.

131. The endoscope according to claim 130, wherein said guide wire fixing means is arranged at a position which is in contact with the vicinity of the surface of said insertion portion or a position in the vicinity of the surface and a position away from an observation window arranged at the end of said insertion portion.

132. The endoscope according to claim 103, further comprising operating means for operating said guide wire fixing means.

133. The endoscope according to claim 132, wherein said operating means is provided to said operation portion of said endoscope.

134. The endoscope according to claim 132, wherein a transmission mechanism for transmitting the operation of said operating means is provided between said operating means and said guide wire fixing means.

135. The endoscope according to claim 134, wherein said transmission mechanism is an operation wire arranged in said therapeutic instrument insertion channel.

136. The endoscope according to claim 134, wherein said transmission mechanism is arranged in an external channel provided between the vicinity of the distal end of said insertion portion and the front side along the side surface of said endoscope.

137. The endoscope according to claim 136, wherein said transmission mechanism is an operation wire arranged in said external channel.

138. The endoscope according to claim 132, wherein a member for fixing said operation wire is provided in the vicinity of the base end of a bending portion in said endoscope.

139. The endoscope according to claim 132, wherein said operating means and said endoscope operation portion are arranged so as to be distanced from each other.

140. An endoscope comprising:
   an elongated insertion portion;
   a therapeutic instrument insertion channel provided in the insertion portion;
   a therapeutic instrument elevator base for controlling directions of leading portions of a therapeutic instrument and a guide wire inserted in the therapeutic insertion channel, the leading portions of the therapeutic instrument and the guide wire being out from an opening of the therapeutic insertion channel at a distal end of the insertion portion; and
   guide wire fixing means that restricts relative movement of the guide wire with respect to the insertion portion in a longitudinal direction of the insertion portion, at a portion close to the opening of the therapeutic insertion channel.

141. The endoscope according to claim 140, wherein a part of the guide wire fixing means is provided at the therapeutic instrument elevator base, and the movement of the guide wire is restricted by the guide wire fixing means when the therapeutic instrument elevator base is raised.

142. The endoscope according to claim 140, wherein the guide wire fixing means is provided separately with the therapeutic instrument elevator base.

143. The endoscope according to claim 140, which further comprises brake means for maintaining the movement of the guide wire restricted.

144. The endoscope according to claim 140, wherein an object optical system is arranged at a position at which a part of the guide wire is shown in an observation image, when the relative movement of the guide wire is restricted.

* * * * *